US012637696B2

(12) United States Patent (10) Patent No.: US 12,637,696 B2
Kohn et al. (45) Date of Patent: May 26, 2026

(54) AUGMENTATIONS TO LENTIVIRAL VECTORS (CCLC-MGATA/ANK-CORE LCR-BETA-AS3-FB) TO INCREASE EXPRESSION

(71) Applicant: The Regents of the University of California, Oakland, CA (US)

(72) Inventors: Donald B. Kohn, Tarzana, CA (US); Richard A. Morgan, Santa Monica, CA (US); Roger Paul Hollis, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1142 days.

(21) Appl. No.: 17/433,577

(22) PCT Filed: Feb. 27, 2020

(86) PCT No.: PCT/US2020/020053
§ 371 (c)(1),
(2) Date: Aug. 24, 2021

(87) PCT Pub. No.: WO2020/176712
PCT Pub. Date: Sep. 3, 2020

(65) Prior Publication Data
US 2022/0170045 A1 Jun. 2, 2022

Related U.S. Application Data

(60) Provisional application No. 62/846,504, filed on May 10, 2019, provisional application No. 62/812,173, filed on Feb. 28, 2019.

(51) Int. Cl.
*C12N 15/86* (2006.01)
*C07K 14/805* (2006.01)
*C12N 15/867* (2006.01)

(52) U.S. Cl.
CPC .......... *C12N 15/867* (2013.01); *C07K 14/805* (2013.01); *C12N 15/86* (2013.01); *C12N 2740/16043* (2013.01); *C12N 2830/008* (2013.01); *C12N 2830/30* (2013.01)

(58) Field of Classification Search
CPC ................. C12N 15/86; C12N 15/867; C12N 2740/16043; A61P 7/00
See application file for complete search history.

(56) References Cited

U.S. PATENT DOCUMENTS

| | | | | |
|---|---|---|---|---|
| 2003/0022303 A1* | 1/2003 | Sadelain | .................. | A61P 7/06 |
| | | | | 435/235.1 |
| 2006/0057725 A1* | 3/2006 | Leboulch | ................. | A61P 7/06 |
| | | | | 435/456 |
| 2009/0156534 A1* | 6/2009 | Lisowski | ................. | A61P 7/06 |
| | | | | 435/320.1 |
| 2011/0294114 A1* | 12/2011 | Van Der Loo | ......... | C12N 15/85 |
| | | | | 435/320.1 |
| 2015/0133528 A1 | 5/2015 | Krieg et al. | | |
| 2017/0173185 A1* | 6/2017 | Sadelain | .................. | A61P 7/06 |
| 2020/0291433 A1* | 9/2020 | Sadelain | ............... | C12N 15/86 |
| 2021/0222200 A1* | 7/2021 | Rivella | ............... | C07K 14/805 |
| 2022/0136007 A1* | 5/2022 | Kohn | .................... | C12N 15/86 |
| | | | | 424/93.2 |
| 2023/0287449 A1* | 9/2023 | Rivella | ............... | C12N 15/867 |

FOREIGN PATENT DOCUMENTS

| | | |
|---|---|---|
| WO | WO-2014043131 A1 | 3/2014 |
| WO | WO-2016037138 A1 | 3/2016 |
| WO | WO-2018106724 A1 | 6/2018 |

OTHER PUBLICATIONS

Breda, L., et al., "Therapeutic Hemoglobin Levels After Gene Transfer in B-thalassemia Mice and in Hematopoietic Cells of B-thalassemia and Sickle Cells Disease Patients," PloS one, 2012, vol. 7(3), pp. 1-16.
Cante-Barrett, K., et al., "Lentiviral Gene Transfer Into Human and Murine Hematopoietic Stem Cells: Size Matters," BMC research notes, 2016, vol. 9(312), pp. 1-6.
Chakalova, L., et al., "The Corfu Deltabeta Thalassemia Deletion Disrupts Gamma-globin Gene Silencing and Reveals Post-transcriptional Regulation of Hbf Expression," Blood, vol. 105(5), pp. 2154-2160.
ENCODE Project Consortium. An integrated encyclopedia of DNA elements in the human genome. Nature. 2012;489:57-74.
Extended European search report dated Dec. 13, 2022, in Application No. EP20763728.1.

(Continued)

*Primary Examiner* — Marcia S Noble
(74) *Attorney, Agent, or Firm* — Mark S. Cohen; PEARL COHEN ZEDEK LATZER BARATZ LLP

(57) ABSTRACT

In certain embodiments a lentiviral vector having an LCR comprising HS1 ENCODE core (EC1) sequence (SEQ ID NO:1), and one or more of an HS2 core sequence (ecHS2), an HS3 core sequence (ecHS3), an HS4 core sequence (ecHS4), a full length HS2, a full length HS3, and/or a full length HS4 sequence is provided. In certain embodiments the vector comprises a modified βAS3-globin transgene, where transgene comprises a codon optimized exon 1, and/or a codon optimized exon 2, and/or a codon optimized exon 3.

12 Claims, 9 Drawing Sheets

Specification includes a Sequence Listing.

(56)                    References Cited

OTHER PUBLICATIONS

Hanawa, H., et al., "Extended beta-globin locus control region elements promote consistent therapeutic expression of a gamma-globin lentiviral vector in murine beta-thalassemia," Blood, 2004, vol. 104(8), pp. 2281-2290.

International Search Report and Written Opinion dated Jul. 23, 2020 in PCT Application No. PCT/US2020/020053.

Kumar, M., et al., "Systematic Determination of the Packaging Limit of Lentiviral Vectors," Human Gene Therapy, Oct. 2001, vol. 12(15), pp. 1893-1905.

Levasseur, D.N., et al., "Correction of a Mouse Model of Sickle Cell Disease: Lentiviral/antisickling Beta-globin Gene Transduction of Unmobilized, Purified Hematopoietic Stem Cells", Blood, 2003, vol. 102(13), pp. 4312-4319.

Lisowski, L., et al., "Locus Control Region Elements Hs1 and Hs4 Enhance the Therapeutic Efficacy of Globin Gene Transfer in Beta-thalassemic Mice," Blood, 2007, vol. 110(13), pp. 4175-4178.

May, C., et al., "Therapeutic haemoglobin synthesis in beta-thalassaemic mice expressing lentivirus-encoded human beta-globin," Nature, 2000, vol. 406(6791), pp. 82-86.

May, C., et al., "Successful Treatment Of Murine Beta-thalassemia Intermedia By Transfer Of The Human Beta-globin Gene," Blood, 2002, vol. 99(6), pp. 1902-1908.

Miccio, A., et al., "In vivo selection of genetically modified erythroblastic progenitors leads to long-term correction of beta-thalassemia," Proceedings of the National Academy of Sciences of the United States of America, 2008, vol. 105(30), pp. 10547-10552.

Morgan, R., et al., "Improved Titer and Gene Transfer by Lentiviral Vectors Using Novel, Small B-globin Locus Control Region Elements," Molecular therapy, 2020, vol. 28(1), pp. 328-340.

Navas, P., et al., "The 5'hs4 Core Element of the Human Beta-globin Locus Control Region is Required for High-level Globin Gene Expression in Definitive but Not in Primitive Erythropoiesis," Journal of molecular biology, 2001, vol. 12(1), pp. 17-26.

Negre, O., et al., "Preclinical Evaluation of Efficacy and Safety of an Improved Lentiviral Vector for the Treatment of B-thalassemia and Sickle Cell Disease," Current gene therapy, 2015, vol. 15(1), pp. 64-81.

Pawliuk, R., et al., "Correction of sickle cell disease in transgenic mouse models by gene therapy," Science, 2001, vol. 294(5550), pp. 2368-2371.

Persons, D., et al., "The Degree of Phenotypic Correction of Murine Beta-thalassemia Intermedia Following Lentiviral-mediated Transfer of a Human Gamma-globin Gene is Influenced by Chromosomal Position Effects and Vector Copy Number," Blood, vol. 101(6), pp. 2175-2183.

Perumbeti, A., et al., A Novel Human Gamma-globin Gene Vector for Genetic Correction of Sickle Cell Anemia in a Humanized Sickle Mouse Model: Critical Determinants for Successful Correction, Blood, 2009, vol. 114(6), pp. 1174-1185.

Pestina, T., et al., "Correction of Murine Sickle Cell Disease Using Gamma-globin Lentiviral Vectors to Mediate High-level Expression of Fetal Hemoglobin," 2009, vol. 17(2), pp. 245-252.

Puthenveetil, G., et al., "Successful correction of the human beta-thalassemia major phenotype using a lentiviral vector," Blood, 2004, vol. 104(12), pp. 3445-3453.

Romero, Z., et al., "B-globin Gene Transfer to Human Bone Marrow for Sickle Cell Disease," The Journal of Clinical Investigation, The Journal of clinical investigation, 2013, vol. 123(8), pp. 3317-3330.

Romero, Z., et al., "The Human Ankyrin 1 Promoter Insulator Sustains Gene Expression in a B-globin Lentiviral Vector in Hematopoietic Stem Cells," Molecular Therapy. Methods & Clinical Development, 2015, vol. 22(2), pp. 1-9.

Russell, J., et al., "A Post-transcriptional Process Contributes to Efficient Gamma-globin Gene Silencing in Definitive Erythroid Cells," European Journal of Haematology, 2007, vol. 79(6), pp. 516-525.

Urbinati, F., et al., "Gene Therapy for Sickle Cell Disease: a Lentiviral Vector Comparison Study," Human gene therapy, 2018, vol. 29(10), pp. 1153-1166.

WO International Preliminary Report on Patentability dated Sep. 10, 2021, in PCT/US2020/020053.

* cited by examiner

(A)

(B)

*(A)*

*(B)*

*A*

*B*

SEQUENCE LISTING

<160> NUMBER OF SEQ ID NOS: 16

<210> SEQ ID NO 1
<211> LENGTH: 634
<212> TYPE: DNA
<213> ORGANISM: Artificial
<220> FEATURE:
<223> OTHER INFORMATION: Reduced hypersensitivity site 1 (HS1)

<400> SEQUENCE: 1
catcaataat tctagcccca caggagtttg ttctgaaagt aaacttccac aaccgcaagc        60
ttattgaggc taaggcatct gtgaaggaaa gaaacatctc ctctaaacca ctatgctgct       120
agagcctctt ttctgtactc aagcctcatt cagacactag tgtcaccagt ctcctcatat       180
acctattgta ttttcttctt cttgctggtt tagtcatgtt ttctgggagc ttaggggctt       240
attttatttt gttttgtttt ctaatcaaca gagatgggca aacccattat ttttttcttt       300
agacttggga tggtgatagc tgggcagcgt cagaaactgt gtgtggatat agataagagc       360
tcaggactat gctgagctgt gatgagggag gggcctagct aaaggcagtg agagtcagaa       420
tgctcctgct attgccttct cagtccccac gcttggtttc tacacaagta gatacataga       480
aaaggctata ggttagtgtt tgagagtcct gcatgattag ttgctcagaa atgcccgata       540
aatatgttat gtgtgtttat gtatatatat gttttatatg tgtgtgtgtg tgtgttgtgt       600
ttacaaatat gtgattatca tcaaaacgtg aggg                                   634

<210> SEQ ID NO 2
<211> LENGTH: 425
<212> TYPE: DNA
<213> ORGANISM: Artificial
<220> FEATURE:
<223> OTHER INFORMATION: Reduced hypersensitivity site 2 (HS2)

<400> SEQUENCE: 2
tacgtatatg tgtatatata tatatatatt caggaaataa tatattctag aatatgtcac        60
attctgtctc aggcatccat tttctttatg atgccgtttg aggtggagtt ttagtcaggt       120
ggtcagcttc tccttttttt tgccatctgc cctgtaagca tcctgctggg gacccagata       180
ggagtcatca ctctaggctg agaacatctg ggcacacacc ctaagcctca gcatgactca       240
tcatgactca gcattgctgt gcttgagcca gaaggtttgc ttagaaggtt acacagaacc       300
agaaggcggg ggtggggcac tgaccccgac aggggcctgg ccagaactgc tcatgcttgg       360
actatgggag gtcactaatg gagacacaca gaaatgtaac aggaactaag gaaaaactga       420
agctt                                                                   425

<210> SEQ ID NO 3
<211> LENGTH: 344
<212> TYPE: DNA
<213> ORGANISM: Artificial
<220> FEATURE:
<223> OTHER INFORMATION: Reduced hypersensitivity site 3 (HS3)

<400> SEQUENCE: 3
tgggggtata ggggagcagt cccatgtagt agtagaatga aaaatgctgc tatgctgtgc        60
ctcccccacc tttcccatgt ctgccctcta ctcatggtct atctctcctg gctcctggga       120
gtcatggact ccacccagca ccaccaacct gacctaacca cctatctgag cctgccagcc       180
tataacccat ctgggccctg atagctggtg gccagccctg accccacccc accctccctg       240
gaacctctga tagacacatc tggcacacca gctcgcaaag tcaccgtgag ggtcttgtgt       300

-continued

```
ttgctgagtc aaaattcctt gaaatccaag tccttagaga ctcc                         344

<210> SEQ ID NO 4
<211> LENGTH: 410
<212> TYPE: DNA
<213> ORGANISM: Artificial
<220> FEATURE:
<223> OTHER INFORMATION: Reduced hypersensitivity site 4 (HS4)

<400> SEQUENCE: 4
caggcttgga ttcaaagctc ctgactttct gtctagtgta tgtgcagtga gccccttttc       60
ctctaactga aagaaggaaa aaaaaatgga acccaaaata ttctacatag tttccatgtc      120
acagccaggg ctgggcagtc tcctgttatt tcttttaaaa taaatatatc atttaaatgc      180
ataaataagc aaaccctgct cgggaatggg agggagagtc tctggagtcc accccttctc      240
ggccctggct ctgcagatag tgctatcaaa gccctgacag agccctgccc attgctgggc      300
cttggagtga gtcagcctag tagagaggca gggcaagcca tctcatagct gctgagtggg      360
agagagaaaa gggctcattg tctataaact caggtcatgg ctattcttat                  410

<210> SEQ ID NO 5
<211> LENGTH: 223
<212> TYPE: DNA
<213> ORGANISM: Artificial
<220> FEATURE:
<223> OTHER INFORMATION: Codon optimized exon 2

<400> SEQUENCE: 5
cctgaagttc tcaggatcca cgtgcagctt gtcgcagtgc agctcgctca gctgggcgaa       60
ggtgcccttc aggttgtcca ggtgggccag gccgtcgctg aaggcgccca gcaccttctt      120
gccgtgggcc ttcaccttgg ggttgcccat cacggcgtcg ggggtgctca ggtcgccgaa      180
gctctcgaag aagcgctggg tccaggggta caccaccagc agc                        223

<210> SEQ ID NO 6
<211> LENGTH: 11003
<212> TYPE: DNA
<213> ORGANISM: Artificial
<220> FEATURE:
<223> OTHER INFORMATION: Lentiviral vector

<400> SEQUENCE: 6
gcgcaacgca attaatgtga gttagctcac tcattaggca ccccaggctt tacactttat       60
gcttccggct cgtatgttgt gtggaattgt gagcggataa caatttcaca caggaaacag      120
ctatgaccat gattacgcca agcgcgcaat taaccctcac taaagggaac aaaagctgga      180
gctgcaagct tggccattgc atacgttgta tccatatcat aatatgtaca tttatattgg      240
ctcatgtcca acattaccgc catgttgaca ttgattattg actagttatt aatagtaatc      300
aattacgggg tcattagttc atagcccata tatggagttc cgcgttacat aacttacggt      360
aaatggcccg cctggctgac cgcccaacga ccccgccca ttgacgtcaa taatgacgta      420
tgttcccata gtaacgccaa tagggacttt ccattgacgt caatgggtgg agtatttacg      480
gtaaactgcc cacttggcag tacatcaagt gtatcatatg ccaagtacgc ccctattga      540 cgtcaatgac ggtaaatggc ccgcctggca ttatgcccag tacatgacct tatgggactt      600
tcctacttgg cagtacatct acgtattagt catcgctatt accatggtga tgcggttttg      660
gcagtacatc aatgggcgtg atagcggttt gactcacggg gatttccaa gtctccaccc      720
```

-continued

```
cattgacgtc aatgggagtt tgttttggca ccaaaatcaa cgggactttc caaaatgtcg      780
taacaactcc gccccattga cgcaaatggg cggtaggcgt gtacggtggg aggtctatat      840
aagcagagct cgtttagtga accgggggtct ctctggttag accagatctg agcctgggag     900
ctctctggct aactagggaa cccactgctt aagcctcaat aaagcttgcc ttgagtgctt      960
caagtagtgt gtgcccgtct gttgtgtgac tctggtaact agagatccct cagacccttt     1020
tagtcagtgt ggaaaatctc tagcagtggc gcccgaacag ggacttgaaa gcgaaaggga     1080
aaccagagga gctctctcga cgcaggactc ggcttgctga agcgcgcacg gcaagaggcg     1140
aggggcggcg actggtgagt acgccaaaaa ttttgactag cggaggctag aaggagagag     1200
atgggtgcga gagcgtcagt attaagcggg ggagaattag atcgcgatgg gaaaaaattc     1260
ggttaaggcc aggggggaaag aaaaaatata aattaaaaca tatagtatgg gcaagcaggg     1320
agctagaacg attcgcagtt aatcctggcc tgttagaaac atcagaaggc tgtagacaaa     1380
tactgggaca gctacaacca tcccttcaga caggatcaga agaacttaga tcattatata     1440
atacagtagc aaccctctat tgtgtgcatc aaaggataga gataaaagac accaaggaag     1500
ctttagacaa gatagaggaa gagcaaaaca aaagtaagac caccgcacag caagcggccg     1560
ctgatcttca gacctggagg aggagatatg agggacaatt ggagaagtga attatataaa     1620
tataaagtag taaaaattga accattagga gtagcaccca ccaaggcaaa gagaagagtg     1680
gtgcagagag aaaaaagagc agtgggaata ggagctttgt tccttgggtt cttgggagca     1740
gcaggaagca ctatgggcgc agcgtcaatg acgctgacgg tacaggccag acaattattg     1800
tctggtatag tgcagcagca gaacaatttg ctgagggcta ttgaggcgca acagcatctg     1860
ttgcaactca cagtctgggg catcaagcag ctccaggcaa gaatcctggc tgtggaaaga     1920
tacctaaagg atcaacagct cctggggatt tggggttgct ctggaaaact catttgcacc     1980
actgctgtgc cttggaatgc tagttggagt aataaatctc tggaacagat ttggaatcac     2040
acgacctgga tggagtggga cagagaaatt aacaattaca caagcttaat acactcctta     2100
attgaagaat cgcaaaacca gcaagaaaag aatgaacaag aattattgga attagataaa     2160
tgggcaagtt tgtggaattg gtttaacata acaaattggc tgtggtatat aaaattattc     2220
ataatgatag taggaggctt ggtaggttta agaatagttt ttgctgtact ttctatagtg     2280
aatagagtta ggcagggata ttcaccatta tcgtttcaga cccacctccc aaccccgagg     2340
ggacccgaca ggcccgaagg aatagaagaa gaaggtggag agagagacag agacagatcc     2400
attcgattag tgaacggatc tcgacggtat cgatctcgac acaaatggca gtattcatcc     2460
acaattttaa aagaaaaggg gggattgggg ggtacagtgc aggggaaaga atagtagaca     2520
taatagcaac agacatacaa actaaagaat tacaaaaaca aattacaaaa attcaaaatt     2580 ttcgggtttta ttacagggac agcagagatc cagtttgggt cgaggatatc ggatcggaat     2640
tctctagatg atcaggatcc ctcgagccct tatcgatcac gagactagcc tcgactacta     2700
gtggagatcc cccgggctgc agagccagaa gcaccataag ggacatgata agggagccag     2760
cagacctctg atctcttcct gaatgctaat cttaaacatc ctgaggaaga atgggacttc     2820
catttggggt gggcctatga tagggtaata agacagtagt gaatatcaag ctacaaaaag     2880 cccccttttca aattcttctc agtcctaact tttcatacta agcccagtcc ttccaaagca     2940
gactgtgaaa gagtgatagt tccgggagac tagcactgca gattccgggt cactgtgagt     3000
gggggaggca gggaagaagg gctcacagga cagtcaaacc atgcccccctg ttttttccttc    3060 ttcaagtaga cctctataag acaacagaga caactaaggc tgagtggcca ggcgaggaga     3120
```

-continued

```
aaccatctcg ccgtaaaaca tggaaggaac acttcagggg aaaggtggta tctctaagca    3180
agagaactga gtggagtcaa ggctgagaga tgcaggataa gcaaatgggt agtgaaaaga    3240
cattcatgag gacagctaaa acaataagta atgtaaaata cagcatagca aaactttaac    3300
ctccaaatca agcctctact tgaatccttt tctgagggat gaataaggca taggcatcag    3360
gggctgttgc caatgtgcat tagctgtttg cagcctcacc ttctttcatg gagtttaaga    3420
tatagtgtat tttcccaagg tttgaactag ctcttcattt ctttatgttt taaatgcact    3480
gacctcccac attccctttt tagtaaaata ttcagaaata atttaaatac atcattgcaa    3540
tgaaaataaa tgtttttttat taggcagaat ccagatgctc aaggcccttc ataatatccc    3600
ccagtttagt agttggactt agggaacaaa ggaaccttta atagaaattg gacagcaaga    3660
aagcgagctt agtgatactt gtgggccagg gcattagcca caccagccac cactttctga    3720
taggcagcct gcactggtgg ggtgaattct ttgccaaagt gatgggccag cacacagacc    3780
agcacgttgc ccaggagctg tgggaggaag ataagaggta tgaacatgat tagcaaaagg    3840
gcctagcttg gactcagaat aatccagcct tatcccaacc ataaaataaa agcagaatgg    3900
tagctggatt gtagctgcta ttagcaatat gaaacctctt acatcagtta caatttatat    3960
gcagaaatat ttatatgcag aaatattgct attgccttaa cccagaaatt atcactgtta    4020
ttctttagaa tggtgcaaag aggcatgata cattgtatca ttattgccct gaaagaaaga    4080
gattagggaa agtattagaa ataagataaa caaaaaagta tattaaaaga agaaagcatt    4140
ttttaaaatt acaaatgcaa aattaccctg atttggtcaa tatgtgtacc ctgttacttc    4200
tccccttcct atgacatgaa cttaaccata gaaaagaagg ggaaagaaaa catcaagggt    4260
cccatagact caccctgaag ttctcaggat ccacgtgcag cttgtcacag tgcagctcac    4320
tcagctgggc aaaggtgccc ttgaggttgt ccaggtgagc caggccatca ctaaaggcac    4380
cgagcacttt cttgccatga gccttcacct tagggttgcc cataacagca tcaggagtgg    4440
acagatcccc aaaggactca aagaacctct gggtccaagg gtagaccacc agcagcctaa    4500
gggtgggaaa atagaccaat aggcagagag agtcagtgcc tatcagaaac ccaagagtct    4560
tctctgtctc cacatgccca gtttctattg gtctccttaa acctgtcttg taaccttgat    4620
accaacctgc ccagggcctc accaccaacg gcatccacgt tcaccttgtc ccacagggca    4680
gtaacggcag acttctcctc aggagtcagg tgcaccatgg tgtctgtttg aggttgctag    4740
tgaacacagt tgtgtcagaa gcaaatgtaa gcaatagatg gctctgccct gactttttatg    4800 cccagccctg gctcctgccc tccctgctcc tgggagtaga ttggccaacc ctagggtgtg    4860
gctccacagg gtgaggtcta agtgatgaca gccgtacctg tccttggctc ttctggcact    4920
ggcttaggag ttggacttca aaccctcagc cctccctcta agatatatct cttggccca    4980 taccatcagt acaaattgct actaaaaaca tcctcctttg caagtgtatt tacccgacgc    5040
gtcggcgata agcttgatcc atcgatcatc aataattcta gccccacagg agtttgttct    5100
gaaagtaaac ttccacaacc gcaagcttat tgaggctaag gcatctgtga aggaaagaaa    5160
catctcctct aaaccactat gctgctagag cctcttttct gtactcaagc ctcattcaga    5220
cactagtgtc accagtctcc tcatatacct attgtatttt cttcttcttg ctggtttagt    5280 catgtttttct gggagcttag gggcttattt tattttgttt tgttttctaa tcaacagaga    5340
tgggcaaacc cattatttttt ttctttagac ttgggatggt gatagctggg cagcgtcaga    5400
aactgtgtgt ggatatagat aagagctcag gactatgctg agctgtgatg agggagggggc    5460
```

-continued

```
ctagctaaag gcagtgagag tcagaatgct cctgctattg ccttctcagt ccccacgctt    5520
ggtttctaca caagtagata catagaaaag gctataggtt agtgtttgag agtcctgcat    5580
gattagttgc tcagaaatgc ccgataaata tgttatgtgt gtttatgtat atatatgttt    5640
tatatgtgtg tgtgtgtgtg ttgtgtttac aaatatgtga ttatcatcaa aacgtgaggg    5700
tacgtatatg tgtatatata tatatatatt caggaaataa tatattctag aatatgtcac    5760
attctgtctc aggcatccat tttctttatg atgccgtttg aggtggagtt ttagtcaggt    5820
ggtcagcttc tccttttttt tgccatctgc cctgtaagca tcctgctggg gacccagata    5880
ggagtcatca ctctaggctg agaacatctg ggcacacacc ctaagcctca gcatgactca    5940
tcatgactca gcattgctgt gcttgagcca gaaggtttgc ttagaaggtt acacagaacc    6000
agaaggcggg ggtggggcac tgaccccgac aggggcctgg ccagaactgc tcatgcttgg    6060
actatgggag gtcactaatg gagacacaca gaaatgtaac aggaactaag gaaaaactga    6120
agctttgggg gtataggga gcagtcccat gtagtagtag aatgaaaaat gctgctatgc    6180
tgtgcctccc ccacctttcc catgtctgcc ctctactcat ggtctatctc tcctggctcc    6240
tgggagtcat ggactccacc cagcaccacc aacctgacct aaccacctat ctgagcctgc    6300
cagcctataa cccatctggg ccctgatagc tggtggccag ccctgacccc accccaccct    6360
ccctggaacc tctgatagac acatctggca caccagctcg caaagtcacc gtgagggtct    6420
tgtgtttgct gagtcaaaat tccttgaaat ccaagtcctt agagactccc aggcttggat    6480
tcaaagctcc tgactttctg tctagtgtat gtgcagtgag cccctttttcc tctaactgaa    6540 agaaggaaaa aaaaatggaa cccaaaatat tctacatagt ttccatgtca cagccagggc    6600
tgggcagtct cctgttattt cttttaaaat aaatatatca tttaaatgca taaataagca    6660
aaccctgctc gggaatggga gggagagtct ctggagtcca ccccttctcg gccctggctc    6720
tgcagatagt gctatcaaag ccctgacaga gccctgccca ttgctgggcc ttggagtgag    6780
tcagcctagt agagaggcag ggcaagccat ctcatagctg ctgagtggga gagagaaaag    6840
ggctcattgt ctataaactc aggtcatggc tattcttatg gcctactcga ccacgaggga    6900
attccgataa tcaacctctg gattacaaaa tttgtgaaag attgactggt attcttaact    6960
atgttgctcc ttttacgcta tgtggatacg ctgctttaat gcctttgtat catgctattg    7020
cttcccgtat ggctttcatt ttctcctcct tgtataaatc ctggttgctg tctctttatg    7080
aggagttgtg gcccgttgtc aggcaacgtg gcgtggtgtg cactgtgttt gctgacgcaa    7140
cccccactgg ttggggcatt gccaccacct gtcagctcct ttccgggact ttcgctttcc    7200
ccctccctat tgccacggcg gaactcatcg ccgcctgcct tgcccgctgc tggacagggg    7260
ctcggctgtt gggcactgac aattccgtgg tgttgtcggg gaaatcatcg tcctttcctt    7320
ggctgctcgc ctgtgttgcc acctggattc tgcgcgggac gtccttctgc tacgtccctt    7380
cggccctcaa tccagcggac cttccttccc gcggcctgct gccggctctg cggcctcttc    7440
cgcgtcttcg ccttcgccct cagacgagtc ggatctccct ttgggccgcc tccccgcatc    7500
gataccgtcg acctcgagac ctagaaaaac atggccaatt cgagctcggt acctttaaga    7560
ccaatgactt acaaggcagc tgtagatctt agccactttt taaaagaaaa ggggggactg    7620
gaagggctaa ttcactccca acgaagacaa gatcccaggg atgtacgtcc ctaacccgct    7680 aggggggcagc acccaggcct gcactgccgc ctgccggcag gggtccagtc ctgctttttg    7740
cttgtactgg gtctctctgg ttagaccaga tctgagcctg ggagctctct ggctaactag    7800
ggaacccact gcttaagcct caataaagct tgccttgagt gcttcaagta gtgtgtgccc    7860
```

-continued

```
gtctgttgtg tgactctggt aactagagat ccctcagacc cttttagtca gtgtggaaaa   7920
tctctagcag tagtagttca tgtcatctta ttattcagta tttataactt gcaaagaaat   7980
gaatatcaga gagtgagagg aacttgttta ttgcagctta taatggttac aaataaagca   8040
atagcatcac aaatttcaca aataaagcat ttttttcact gcattctagt tgtggtttgt   8100
ccaaactcat caatgtatct tatcatgtct ggctctagct atcccgcccc taactccgcc   8160
catcccgccc ctaactccgc ccagttccgc ccattctccg ccccatggct gactaatttt   8220
ttttatttat gcagaggccg aggccgcctc ggcctctgag ctattccaga agtagtgagg   8280
aggctttttt ggaggcctag gcttttgcgt cgagacgtac ccaattcgcc ctatagtgag   8340
tcgtattacg cgcgctcact ggccgtcgtt ttacaacgtc gtgactggga aaaccctggc   8400
gttacccaac ttaatcgcct tgcagcacat ccccctttcg ccagctggcg taatagcgaa   8460
gaggcccgca ccgatcgccc ttcccaacag ttgcgcagcc tgaatggcga atggcgcgac   8520
gcgccctgta gcggcgcatt aagcgcggcg ggtgtggtgg ttacgcgcag cgtgaccgct   8580
acacttgcca gcgccctagc gcccgctcct ttcgctttct cccttcctt tctcgccacg   8640 ttcgccggct ttccccgtca agctctaaat cggggctcc ctttaggt ccgatttagt   8700 gctttacggc acctcgaccc caaaaaactt gattagggtg atggttcacg tagtgggcca   8760
tcgccctgat agacggtttt tcgcccttg acgttggagt ccacgttctt taatagtgga   8820
ctcttgttcc aaactggaac aacactcaac cctatctcgg tctattcttt tgatttataa   8880
gggattttgc cgatttcggc ctattggtta aaaaatgagc tgatttaaca aaaatttaac   8940
gcgaatttta acaaaatatt aacgtttaca atttcccagg tggcactttt cggggaaatg   9000
tgcgcggaac ccctatttgt ttatttttct aaatacattc aaatatgtat ccgctcatga   9060
gacaataacc ctgataaatg cttcaataat attgaaaaag gaagagtatg agtattcaac   9120
atttccgtgt cgcccttatt cccttttttg cggcatttg ccttcctgtt tttgctcacc   9180
cagaaacgct ggtgaaagta aaagatgctg aagatcagtt gggtgcacga gtgggttaca   9240
tcgaactgga tctcaacagc ggtaagatcc ttgagagttt tcgccccgaa gaacgttttc   9300
caatgatgag cacttttaaa gttctgctat gtggcgcggt attatcccgt attgacgccg   9360
ggcaagagca actcggtcgc cgcatacact attctcagaa tgacttggtt gagtactcac   9420
cagtcacaga aaagcatctt acggatggca tgacagtaag agaattatgc agtgctgcca   9480
taaccatgag tgataacact gcggccaact tacttctgac aacgatcgga ggaccgaagg   9540
agctaaccgc ttttttgcac aacatggggg atcatgtaac tcgccttgat cgttgggaac   9600
cggagctgaa tgaagccata ccaaacgacg agcgtgacac cacgatgcct gtagcaatgg   9660
caacaacgtt gcgcaaacta ttaactggcg aactacttac tctagcttcc cggcaacaat   9720
taatagactg gatggaggcg gataaagttg caggaccact tctgcgctcg gcccttccgg   9780
ctggctggtt tattgctgat aaatctggag ccggtgagcg tgggtctcgc ggtatcattg   9840
cagcactggg gccagatggt aagccctccc gtatcgtagt tatctacacg acggggagtc   9900
aggcaactat ggatgaacga aatagacaga tcgctgagat aggtgcctca ctgattaagc   9960
attggtaact gtcagaccaa gtttactcat atatacttta gattgattta aaacttcatt  10020
tttaatttaa aaggatctag gtgaagatcc tttttgataa tctcatgacc aaaatccctt  10080
aacgtgagtt ttcgttccac tgagcgtcag accccgtaga aaagatcaaa ggatcttctt  10140
gagatccttt ttttctgcgc gtaatctgct gcttgcaaac aaaaaaacca ccgctaccag  10200
```

-continued

```
cggtggtttg tttgccggat caagagctac caactctttt tccgaaggta actggcttca    10260
gcagagcgca gataccaaat actgtccttc tagtgtagcc gtagttaggc caccacttca    10320
agaactctgt agcaccgcct acatacctcg ctctgctaat cctgttacca gtggctgctg    10380
ccagtggcga taagtcgtgt cttaccgggt tggactcaag acgatagtta ccggataagg    10440
cgcagcggtc gggctgaacg gggggttcgt gcacacagcc cagcttggag cgaacgacct    10500
acaccgaact gagataccta cagcgtgagc tatgagaaag cgccacgctt cccgaaggga    10560
gaaaggcgga caggtatccg gtaagcggca gggtcggaac aggagagcgc acgagggagc    10620
ttccaggggg aaacgcctgg tatctttata gtcctgtcgg gtttcgccac ctctgacttg    10680
agcgtcgatt tttgtgatgc tcgtcagggg ggcggagcct atggaaaaac gccagcaacg    10740
cggccatttt tacggttcct ggccttttgc tggccttttg ctcacatgtt ctttcctgcg    10800
ttatcccctg attctgtgga taaccgtatt accgcctttg agtgagctga taccgctcgc    10860
cgcagccgaa cgaccgagcg cagcgagtca gtgagcgagg aagcggaaga gcgcccaata    10920
cgcaaaccgc ctctccccgc gcgttggccg attcattaat gcagctggca cgacaggttt    10980
cccgactgga aagcgggcag tga                                           11003
```

```
<210> SEQ ID NO 7
<211> LENGTH: 92
<212> TYPE: DNA
<213> ORGANISM: Artificial
<220> FEATURE:
<223> OTHER INFORMATION: Codon optimized exon 1

<400> SEQUENCE: 7
atggtgcacc tgaccccga ggagaagagc gccgtgaccg ccctgtggga caaggtgaac    60
gtggacgccg tgggcggcga ggccctgggc ag                                 92
```

```
<210> SEQ ID NO 8
<211> LENGTH: 223
<212> TYPE: DNA
<213> ORGANISM: Artificial
<220> FEATURE:
<223> OTHER INFORMATION: Codon optimized exon 2

<400> SEQUENCE: 8
cctgaagttc tcggggtcca cgtgcagctt gtcgcagtgc agctcgctca gctgggcgaa    60 ggtgccttc aggttgtcca ggtgggccag gccgtcgctg aaggcgccca gcaccttctt    120
gccgtgggcc ttcaccttgg ggttgcccat cacggcgtcg ggggtgctca ggtcgccgaa    180
gctctcgaag aagcgctggg tccaggggta caccaccagc agc                     223
```

```
<210> SEQ ID NO 9
<211> LENGTH: 129
<212> TYPE: DNA
<213> ORGANISM: Artificial
<220> FEATURE:
<223> OTHER INFORMATION: Codon optimized exon 3

<400> SEQUENCE: 9
ctcctgggca acgtgctggt gtgcgtgctg gcccaccact cggcaagga gttcacccc     60 cccgtgcagg ccgcctacca gaaggtggtg gccggcgtgg ccaacgccct ggcccacaag    120
taccactaa                                                          129
```

```
<210> SEQ ID NO 10
<211> LENGTH: 10369
```

<212> TYPE: DNA
<213> ORGANISM: Artificial
<220> FEATURE:
<223> OTHER INFORMATION: Lentiviral vector

<400> SEQUENCE: 10

```
gcgcaacgca attaatgtga gttagctcac tcattaggca ccccaggctt tacactttat      60
gcttccggct cgtatgttgt gtggaattgt gagcggataa caatttcaca caggaaacag     120
ctatgaccat gattacgcca agcgcgcaat taaccctcac taaagggaac aaaagctgga     180
gctgcaagct tggccattgc atacgttgta tccatatcat aatatgtaca tttatattgg     240
ctcatgtcca acattaccgc catgttgaca ttgattattg actagttatt aatagtaatc     300
aattacgggg tcattagttc atagcccata tatggagttc cgcgttacat aacttacggt     360
aaatggcccg cctggctgac cgcccaacga ccccgccca ttgacgtcaa taatgacgta     420
tgttcccata gtaacgccaa tagggacttt ccattgacgt caatgggtgg agtatttacg     480
gtaaactgcc cacttggcag tacatcaagt gtatcatatg ccaagtacgc cccctattga     540
cgtcaatgac ggtaaatggc ccgcctggca ttatgcccag tacatgacct tatgggactt     600
tcctacttgg cagtacatct acgtattagt catcgctatt accatggtga tgcggttttg     660
gcagtacatc aatgggcgtg atagcggtt tgactcacgg ggatttccaa gtctccaccc     720
cattgacgtc aatgggagtt tgttttggca ccaaaatcaa cgggactttc caaaatgtcg     780
taacaactcc gccccattga cgcaaatggg cggtaggcgt gtacggtggg aggtctatat     840
aagcagagct cgtttagtga accggggtct ctctggttag accagatctg agcctgggag     900
ctctctggct aactagggaa cccactgctt aagcctcaat aaagcttgcc ttgagtgctt     960
caagtagtgt gtgcccgtct gttgtgtgac tctggtaact agagatccct cagacccttt    1020
tagtcagtgt ggaaaatctc tagcagtggc gcccgaacag ggacttgaaa gcgaaaggga    1080
aaccagagga gctctctcga cgcaggactc ggcttgctga agcgcgcacg gcaagaggcg    1140
aggggcggcg actggtgagt acgccaaaaa ttttgactag cggaggctag aaggagagag    1200
atgggtgcga gagcgtcagt attaagcggg ggagaattag atcgcgatgg gaaaaaattc    1260
ggttaaggcc agggggaaag aaaaaatata aattaaaaca tatagtatgg gcaagcaggg    1320
agctagaacg attcgcagtt aatcctggcc tgttagaaac atcagaaggc tgtagacaaa    1380
tactgggaca gctacaacca tcccttcaga caggatcaga agaacttaga tcattatata    1440
atacagtagc aaccctctat tgtgtgcatc aaaggataga gataaaagac accaaggaag    1500
ctttagacaa gatagaggaa gagcaaaaca aaagtaagac caccgcacag caagcggccg    1560
ctgatcttca gacctggagg aggagatatg agggacaatt ggagaagtga attatataaa    1620
tataaagtag taaaaattga accattagga gtagcaccca ccaaggcaaa gagaagagtg    1680
gtgcagagag aaaaaagagc agtgggaata ggagctttgt ccttgggttc ttgggagca     1740 gcaggaagca ctatgggcgc agcgtcaatg acgctgacgg tacaggccag acaattattg    1800
tctggtatag tgcagcagca gaacaatttg ctgagggcta ttgaggcgca acagcatctg    1860
ttgcaactca cagtctgggg catcaagcag ctccaggcaa gaatcctggc tgtggaaaga    1920
tacctaaagg atcaacagct cctggggatt tggggttgct ctggaaaact catttgcacc    1980
actgctgtgc cttggaatgc tagttggagt aataaatctc tggaacagat ttggaatcac    2040
acgacctgga tggagtggga cagagaaatt aacaattaca caagcttaat acactcctta    2100
attgaagaat cgcaaaacca gcaagaaaag aatgaacaag aattattgga attagataaa    2160
```

-continued

```
tgggcaagtt tgtggaattg gtttaacata acaaattggc tgtggtatat aaaattattc    2220
ataatgatag taggaggctt ggtaggttta agaatagttt ttgctgtact ttctatagtg    2280
aatagagtta ggcagggata ttcaccatta tcgtttcaga cccacctccc aaccccgagg    2340
ggacccgacg ggcccgaagg aatagaagaa gaaggtggag agagagacag agacagatcc    2400
attcgattag tgaacggatc tcgacggtat cgatctcgac acaaatggca gtattcatcc    2460
acaattttaa aagaaaaggg gggattgggg ggtacagtgc aggggaaaga atagtagaca    2520
taatagcaac agacatacaa actaaagaat tacaaaaaca aattacaaaa attcaaaatt    2580
ttcgggttta ttacagggac agcagagatc cagtttgggt cgaggatatc ggatcggaat    2640
tctctagatg atcaggatcc ctcgagccct tatcgatcac gagactagcc tcgactacta    2700
gtggagatcc cccgggctgc agagccagaa gcaccataag ggacatgata agggagccag    2760
cagacctctg atctcttcct gaatgctaat cttaaacatc ctgaggaaga atgggacttc    2820
catttggggt gggcctatga tagggtaata agacagtagt gaatatcaag ctacaaaaag    2880
ccccctttca aattcttctc agtcctaact tttcatacta agcccagtcc ttccaaagca    2940
gactgtgaaa gagtgatagt tccgggagac tagcactgca gattccgggt cactgtgagt    3000
gggggaggca gggaagaagg gctcacagga cagtcaaacc atgcccctg tttttccttc     3060 ttcaagtaga cctctataag acaacagaga caactaaggc tgagtggcca ggcgaggaga    3120
aaccatctcg ccgtaaaaca tggaaggaac acttcagggg aaaggtggta tctctaagca    3180
agagaactga gtggagtcaa ggctgagaga tgcaggataa gcaaatgggt agtgaaaaga    3240
cattcatgag gacagctaaa acaataagta atgtaaaata cagcatagca aaactttaac    3300
ctccaaatca agcctctact tgaatccttt tctgagggat gaataaggca taggcatcag    3360
gggctgttgc caatgtgcat tagctgtttg cagcctcacc ttctttcatg gagtttaaga    3420
tatagtgtat tttcccaagg tttgaactag ctcttcattt ctttatgttt taaatgcact    3480
gacctcccac attccctttt tagtaaaata ttcagaaata atttaaatac atcattgcaa    3540
tgaaaataaa tgttttttat taggcagaat ccagatgctc aaggcccttc ataatatccc    3600
ccagtttagt agttggactt agggaacaaa ggaacctta atagaaattg gacagcaaga     3660
aagcgagctt agtgatactt gtgggccagg gcattagcca caccagccac cactttctga    3720
taggcagcct gcactggtgg ggtgaattct ttgccaaagt gatgggccag cacacagacc    3780
agcacgttgc ccaggagctg tgggaggaag ataagaggta tgaacatgat tagcaaaagg    3840
gcctagcttg gactcagaat aatccagcct tatcccaacc ataaaataaa agcagaatgg    3900
tagctggatt gtagctgcta ttagcaatat gaaacctctt acatcagtta caatttatat    3960
gcagaaatat ttatatgcag aaatattgct attgccttaa cccagaaatt atcactgtta    4020
ttctttagaa tggtgcaaag aggcatgata cattgtatca ttattgccct gaaagaaaga    4080
gattagggaa agtattagaa ataagataaa caaaaaagta tattaaaaga agaaagcatt    4140
ttttaaaatt acaaatgcaa aattaccctg atttggtcaa tatgtgtacc ctgttacttc    4200
tccccttcct atgacatgaa cttaaccata gaaagaagg ggaaagaaaa catcaagggt      4260
cccatagact caccctgaag ttctcaggat ccacgtgcag cttgtcacag tgcagctcac    4320
tcagctgggc aaaggtgccc ttgaggttgt ccaggtgagc caggccatca ctaaaggcac    4380
cgagcacttt cttgccatga gccttcacct tagggttgcc cataacagca tcaggagtgg    4440
acagatcccc aaaggactca aagaacctct gggtccaagg gtagaccacc agcagcctaa    4500
gggtgggaaa atagaccaat aggcagagag agtcagtgcc tatcagaaac ccaagagtct    4560
```

-continued

```
tctctgtctc cacatgccca gtttctattg gtctccttaa acctgtcttg taaccttgat    4620
accaacctgc ccagggcctc gccgcccacg gcgtccacgt tcaccttgtc ccacagggcg    4680
gtcacggcgc tcttctcctc gggggtcagg tgcaccatgg tgtctgtttg aggttgctag    4740
tgaacacagt tgtgtcagaa gcaaatgtaa gcaatagatg gctctgccct gacttttatg    4800
cccagccctg gctcctgccc tccctgctcc tgggagtaga ttggccaacc ctagggtgtg    4860
gctccacagg gtgaggtcta agtgatgaca gccgtacctg tccttggctc ttctggcact    4920
ggcttaggag ttggacttca aaccctcagc cctccctcta agatatatct cttggcccca    4980
taccatcagt acaaattgct actaaaaaca tcctcctttg caagtgtatt tacccgacgc    5040
gtcggcgata agcttgatcc atcgattacg tatatgtgta tatatatata tatattcagg    5100
aaataatata ttctagaata tgtcacattc tgtctcaggc atccattttc tttatgatgc    5160
cgtttgaggt ggagttttag tcaggtggtc agcttctcct ttttttttgcc atctgccctg    5220 taagcatcct gctggggacc cagataggag tcatcactct aggctgagaa catctgggca    5280
cacaccctaa gcctcagcat gactcatcat gactcagcat tgctgtgctt gagccagaag    5340
gtttgcttag aaggttacac agaaccagaa ggcgggggtg gggcactgac cccgacaggg    5400
gcctggccag aactgctcat gcttggacta tgggaggtca ctaatggaga cacacagaaa    5460
tgtaacagga actaaggaaa aactgaagct ttgggggtat aggggagcag tcccatgtag    5520
tagtagaatg aaaaatgctg ctatgctgtg cctcccccac ctttcccatg tctgccctct    5580
actcatggtc tatctctcct ggctcctggg agtcatggac tccacccagc accaccaacc    5640
tgacctaacc acctatctga gcctgccagc ctataaccca tctgggccct gatagctggt    5700
ggccagccct gacccccaccc caccctccct ggaacctctg atagacacat ctggcacacc    5760
agctcgcaaa gtcaccgtga gggtcttgtg tttgctgagt caaaattcct tgaaatccaa    5820
gtccttagag actcccaggc ttggattcaa agctcctgac tttctgtcta gtgtatgtgc    5880
agtgagcccc ttttcctcta actgaaagaa ggaaaaaaaa atggaaccca aaatattcta    5940
catagtttcc atgtcacagc cagggctggg cagtctcctg ttatttcttt taaaataaat    6000
atatcattta aatgcataaa taagcaaacc ctgctcggga atgggaggga gagtctctgg    6060
agtccacccc ttctcggccc tggctctgca gatagtgcta tcaaagccct gacagagccc    6120
tgcccattgc tgggccttgg agtgagtcag cctagtagag aggcagggca agccatctca    6180
tagctgctga gtgggagaga gaaaagggct cattgtctat aaactcaggt catggctatt    6240
cttatggcct actcgaccac gagggaattc cgataatcaa cctctggatt acaaaatttg    6300
tgaaagattg actggtattc ttaactatgt tgctcctttt acgctatgtg gatacgctgc    6360
tttaatgcct ttgtatcatg ctattgcttc ccgtatggct ttcattttct cctccttgta    6420
taaatcctgg ttgctgtctc tttatgagga gttgtggccc gttgtcaggc aacgtggcgt    6480
ggtgtgcact gtgtttgctg acgcaacccc cactggttgg ggcattgcca ccacctgtca    6540
gctcctttcc gggactttcg ctttccccct ccctattgcc acggcggaac tcatcgccgc    6600
ctgccttgcc cgctgctgga caggggctcg gctgttgggc actgacaatt ccgtggtgtt    6660
gtcggggaaa tcatcgtcct ttccttggct gctcgcctgt gttgccacct ggattctgcg    6720
cgggacgtcc ttctgctacg tcccttcggc cctcaatcca gcggaccttc cttcccgcgg    6780
cctgctgccg gctctgcggc ctcttccgcg tcttcgcctt cgccctcaga cgagtcggat    6840
ctccctttgg gccgcctccc cgcatcgata ccgtcgacct cgagacctag aaaaacatgg    6900
```

-continued

```
ccaattcgag ctcggtacct ttaagaccaa tgacttacaa ggcagctgta gatcttagcc    6960 acttttttaaa agaaaagggg ggactggaag ggctaattca ctcccaacga agacaagatc    7020
ccagggatgt acgtccctaa cccgctaggg ggcagcaccc aggcctgcac tgccgcctgc    7080
cggcaggggg ccagtcctgc tttttgcttg tactgggtct ctctggttag accagatctg    7140
agcctgggag ctctctggct aactagggaa cccactgctt aagcctcaat aaagcttgcc    7200
ttgagtgctt caagtagtgt gtgcccgtct gttgtgtgac tctggtaact agagatccct    7260
cagacccttt tagtcagtgt ggaaaatctc tagcagtagt agttcatgtc atcttattat    7320
tcagtattta taacttgcaa agaaatgaat atcagagagt gagaggaact tgtttattgc    7380
agcttataat ggttacaaat aaagcaatag catcacaaat ttcacaaata aagcattttt    7440
ttcactgcat tctagttgtg gtttgtccaa actcatcaat gtatcttatc atgtctggct    7500
ctagctatcc cgcccctaac tccgcccatc ccgcccctaa ctccgcccag ttccgcccat    7560
tctccgcccc atggctgact aattttttt attttatgcag aggccgaggc cgcctcggcc    7620
tctgagctat tccagaagta gtgaggaggc ttttttggag gcctaggctt ttgcgtcgag    7680
acgtacccaa ttcgccctat agtgagtcgt attacgcgcg ctcactggcc gtcgttttac    7740
aacgtcgtga ctgggaaaac cctggcgtta cccaacttaa tcgccttgca gcacatcccc    7800
ctttcgccag ctggcgtaat agcgaagagg cccgcaccga tcgcccttcc caacagttgc    7860
gcagcctgaa tggcgaatgg cgcgacgcgc cctgtagcgg cgcattaagc gcggcgggtg    7920
tggtggttac gcgcagcgtg accgctacac ttgccagcgc cctagcgccc gctcctttcg    7980
ctttcttccc ttcctttctc gccacgttcg ccggctttcc ccgtcaagct ctaaatcggg    8040
ggctcccttt agggttccga tttagtgctt tacggcacct cgaccccaaa aaacttgatt    8100
agggtgatgg ttcacgtagt gggccatcgc cctgatagac ggtttttcgc cctttgacgt    8160
tggagtccac gttctttaat agtggactct tgttccaaac tggaacaaca ctcaacccta    8220
tctcggtcta ttcttttgat ttataaggga ttttgccgat ttcggcctat tggttaaaaa    8280
atgagctgat ttaacaaaaa tttaacgcga attttaacaa aatattaacg tttacaattt    8340
cccaggtggc acttttcggg gaaatgtgcg cggaacccct atttgtttat ttttctaaat    8400
acattcaaat atgtatccgc tcatgagaca ataaccctga taaatgcttc aataatattg    8460
aaaaaggaag agtatgagta ttcaacattt ccgtgtcgcc cttattccct ttttttgcggc    8520 attttgcctt cctgtttttttg ctcacccaga aacgctggtg aaagtaaaag atgctgaaga    8580
tcagttgggt gcacgagtgg gttacatcga actggatctc aacagcggta agatccttga    8640
gagttttcgc cccgaagaac gttttccaat gatgagcact tttaaagttc tgctatgtgg    8700
cgcggtatta tcccgtattg acgccgggca agagcaactc ggtcgccgca tacactattc    8760
tcagaatgac ttggttgagt actcaccagt cacagaaaag catcttacgg atggcatgac    8820
agtaagagaa ttatgcagtg ctgccataac catgagtgat aacactgcgg ccaacttact    8880
tctgacaacg atcggaggac cgaaggagct aaccgctttt ttgcacaaca tgggggatca    8940
tgtaactcgc cttgatcgtt gggaaccgga gctgaatgaa gccataccaa acgacgagcg    9000
tgacaccacg atgcctgtag caatggcaac aacgttgcgc aaactattaa ctggcgaact    9060
acttactcta gcttcccggc aacaattaat agactggatg gaggcggata agttgcagg    9120 accacttctg cgctcggccc ttccggctgg ctggtttatt gctgataaat ctggagccgg    9180
tgagcgtggg tctcgcggta tcattgcagc actggggcca gatggtaagc cctcccgtat    9240
cgtagttatc tacacgacgg ggagtcaggc aactatggat gaacgaaata gacagatcgc    9300
```

```
tgagataggt gcctcactga ttaagcattg gtaactgtca gaccaagttt actcatatat      9360
actttagatt gatttaaaac ttcattttta atttaaaagg atctaggtga agatcctttt      9420
tgataatctc atgaccaaaa tcccttaacg tgagttttcg ttccactgag cgtcagaccc      9480
cgtagaaaag atcaaaggat cttcttgaga tcctttttt ctgcgcgtaa tctgctgctt       9540
gcaaacaaaa aaaccaccgc taccagcggt ggtttgtttg ccggatcaag agctaccaac      9600 tcttttttccg aaggtaactg gcttcagcag agcgcagata ccaaatactg tccttctagt     9660
gtagccgtag ttaggccacc acttcaagaa ctctgtagca ccgcctacat acctcgctct      9720
gctaatcctg ttaccagtgg ctgctgccag tggcgataag tcgtgtctta ccgggttgga      9780
ctcaagacga tagttaccgg ataaggcgca gcggtcgggc tgaacggggg gttcgtgcac      9840
acagcccagc ttggagcgaa cgacctacac cgaactgaga tacctacagc gtgagctatg      9900
agaaagcgcc acgcttcccg aagggagaaa ggcggacagg tatccggtaa gcggcagggt      9960
cggaacagga gagcgcacga gggagcttcc agggggaaac gcctggtatc tttatagtcc     10020
tgtcgggttt cgccacctct gacttgagcg tcgatttttg tgatgctcgt caggggggcg     10080
gagcctatgg aaaaacgcca gcaacgcggc cattttttacg gttcctggcc ttttgctggc    10140
cttttgctca catgttcttt cctgcgttat cccctgattc tgtggataac cgtattaccg     10200
cctttgagtg agctgatacc gctcgccgca gccgaacgac cgagcgcagc gagtcagtga     10260
gcgaggaagc ggaagagcgc ccaatacgca aaccgcctct ccccgcgcgt tggccgattc     10320
attaatgcag ctggcacgac aggtttcccg actggaaagc gggcagtga                 10369
```

```
<210> SEQ ID NO 11
<211> LENGTH: 10369
<212> TYPE: DNA
<213> ORGANISM: Artificial
<220> FEATURE:
<223> OTHER INFORMATION: Lentiviral vector

<400> SEQUENCE: 11
gcgcaacgca attaatgtga gttagctcac tcattaggca ccccaggctt tacactttat        60
gcttccggct cgtatgttgt gtggaattgt gagcggataa caatttcaca caggaaacag       120
ctatgaccat gattacgcca agcgcgcaat taaccctcac taaagggaac aaaagctgga       180
gctgcaagct tggccattgc atacgttgta tccatatcat aatatgtaca tttatattgg       240
ctcatgtcca acattaccgc catgttgaca ttgattattg actagttatt aatagtaatc       300
aattacgggg tcattagttc atagcccata tatggagttc cgcgttacat aacttacggt       360
aaatggcccg cctggctgac cgcccaacga cccccgccca ttgacgtcaa taatgacgta       420
tgttcccata gtaacgccaa tagggacttt ccattgacgt caatgggtgg agtatttacg       480
gtaaactgcc cacttggcag tacatcaagt gtatcatatg ccaagtacgc cccctattga       540
cgtcaatgac ggtaaatggc ccgcctggca ttatgcccag tacatgacct tatgggactt       600
tcctacttgg cagtacatct acgtattagt catcgctatt accatggtga tgcggttttg       660
gcagtacatc aatgggcgtg gatagcggtt tgactcacgg ggatttccaa gtctccaccc       720
cattgacgtc aatgggagtt tgttttggca ccaaaatcaa cgggactttc caaaatgtcg       780
taacaactcc gccccattga cgcaaatggg cggtaggcgt gtacggtggg aggtctatat       840
aagcagagct cgtttagtga accggggtct ctctggttag accagatctg agcctgggag       900
ctctctggct aactagggaa cccactgctt aagcctcaat aaagcttgcc ttgagtgctt       960
```

-continued

```
caagtagtgt gtgcccgtct gttgtgtgac tctggtaact agagatccct cagacccttt      1020
tagtcagtgt ggaaaatctc tagcagtggc gcccgaacag ggacttgaaa gcgaaaggga      1080
aaccagagga gctctctcga cgcaggactc ggcttgctga agcgcgcacg gcaagaggcg      1140
aggggcggcg actggtgagt acgccaaaaa ttttgactag cggaggctag aaggagagag      1200
atgggtgcga gagcgtcagt attaagcggg ggagaattag atcgcgatgg gaaaaaattc      1260
ggttaaggcc aggggggaaag aaaaaatata aattaaaaca tatagtatgg gcaagcaggg      1320
agctagaacg attcgcagtt aatcctggcc tgttagaaac atcagaaggc tgtagacaaa      1380
tactgggaca gctacaacca tcccttcaga caggatcaga agaacttaga tcattatata      1440
atacagtagc aaccctctat tgtgtgcatc aaaggataga gataaaagac accaaggaag      1500
ctttagacaa gatagaggaa gagcaaaaca aaagtaagac caccgcacag caagcggccg      1560
ctgatcttca gacctggagg aggagatatg agggacaatt ggagaagtga attatataaa      1620
tataaagtag taaaaattga accattagga gtagcaccca ccaaggcaaa gagaagagtg      1680
gtgcagagag aaaaaagagc agtgggaata ggagctttgt tccttgggtt cttgggagca      1740
gcaggaagca ctatgggcgc agcgtcaatg acgctgacgg tacaggccag acaattattg      1800
tctggtatag tgcagcagca gaacaatttg ctgagggcta ttgaggcgca acagcatctg      1860
ttgcaactca cagtctgggg catcaagcag ctccaggcaa gaatcctggc tgtggaaaga      1920
tacctaaagg atcaacagct cctggggatt tggggttgct ctggaaaact catttgcacc      1980
actgctgtgc cttggaatgc tagttggagt aataaatctc tggaacagat ttggaatcac      2040
acgacctgga tggagtggga cagagaaatt aacaattaca caagcttaat acactcctta      2100
attgaagaat cgcaaaacca gcaagaaaag aatgaacaag aattattgga attagataaa      2160
tgggcaagtt tgtggaattg gtttaacata acaaattggc tgtggtatat aaaattattc      2220
ataatgatag taggaggctt ggtaggttta agaatagttt ttgctgtact ttctatagtg      2280
aatagagtta ggcagggata ttcaccatta tcgtttcaga cccacctccc aaccccgagg      2340
ggacccgacg ggcccgaagg aatagaagaa gaaggtggag agagagacag agacagatcc      2400
attcgattag tgaacggatc tcgacggtat cgatctcgac acaaatggca gtattcatcc      2460
acaattttaa aagaaaaggg gggattgggg ggtacagtgc aggggaaaga atagtagaca      2520
taatagcaac agacatacaa actaaagaat tacaaaaaca aattacaaaa attcaaaatt      2580
ttcgggttta ttacagggac agcagagatc cagtttgggt cgaggatatc ggatcggaat      2640
tctctagatg atcaggatcc ctcgagccct tatcgatcac gagactagcc tcgactacta      2700
gtggagatcc cccgggctgc agagccagaa gcaccataag ggacatgata agggagccag      2760
cagacctctg atctcttcct gaatgctaat cttaaacatc ctgaggaaga atgggacttc      2820
catttggggt gggcctatga tagggtaata agacagtagt gaatatcaag ctacaaaaag      2880 cccccttttca aattcttctc agtcctaact tttcatacta agcccagtcc ttccaaagca      2940
gactgtgaaa gagtgatagt tccgggagac tagcactgca gattccgggt cactgtgagt      3000 ggggaggca gggaagaagg gctcacagga cagtcaaacc atgcccctg tttttccttc      3060 ttcaagtaga cctctataag acaacagaga caactaaggc tgagtggcca ggcgaggaga      3120
aaccatctcg ccgtaaaaca tggaaggaac acttcagggg aaaggtggta tctctaagca      3180
agagaactga gtggagtcaa ggctgagaga tgcaggataa gcaaatgggt agtgaaaaga      3240
cattcatgag gacagctaaa acaataagta atgtaaaata cagcatagca aaactttaac      3300
ctccaaatca agcctctact tgaatccttt tctgagggat gaataaggca taggcatcag      3360
```

```
gggctgttgc caatgtgcat tagctgtttg cagcctcacc ttctttcatg gagtttaaga    3420
tatagtgtat tttcccaagg tttgaactag ctcttcattt ctttatgttt taaatgcact    3480
gacctcccac attccctttt tagtaaaata ttcagaaata atttaaatac atcattgcaa    3540
tgaaaataaa tgtttttttat taggcagaat ccagatgctc aaggcccttc ataatatccc    3600
ccagtttagt agttggactt agggaacaaa ggaacctta atagaaattg gacagcaaga    3660
aagcgagctt agtgatactt gtgggccagg gcattagcca caccagccac cactttctga    3720
taggcagcct gcactggtgg ggtgaattct ttgccaaagt gatgggccag cacacagacc    3780
agcacgttgc ccaggagctg tgggaggaag ataagaggta tgaacatgat tagcaaaagg    3840
gcctagcttg gactcagaat aatccagcct tatcccaacc ataaaataaa agcagaatgg    3900
tagctggatt gtagctgcta ttagcaatat gaaacctctt acatcagtta caatttatat    3960
gcagaaatat ttatatgcag aaatattgct attgccttaa cccagaaatt atcactgtta    4020
ttctttagaa tggtgcaaag aggcatgata cattgtatca ttattgccct gaaagaaaga    4080
gattagggaa agtattagaa ataagataaa caaaaaagta tattaaaaga agaaagcatt    4140
ttttaaaatt acaaatgcaa aattaccctg atttggtcaa tatgtgtacc ctgttacttc    4200
tccccttcct atgacatgaa cttaaccata gaaaagaagg ggaaagaaaa catcaagggt    4260
cccatagact caccctgaag ttctcaggat ccacgtgcag cttgtcgcag tgcagctcgc    4320
tcagctgggc gaaggtgccc ttcaggttgt ccaggtgggc caggccgtcg ctgaaggcgc    4380
ccagcacctt cttgccgtgg gccttcacct tggggttgcc catcacggcg tcggggtgc     4440 tcaggtcgcc gaagctctcg aagaagcgct gggtccaggg gtacaccacc agcagcctaa    4500
gggtgggaaa atagaccaat aggcagagag agtcagtgcc tatcagaaac ccaagagtct    4560
tctctgtctc cacatgccca gtttctattg gtctccttaa acctgtcttg taaccttgat    4620
accaacctgc ccagggcctc gccgcccacg gcgtccacgt tcaccttgtc ccacagggcg    4680
gtcacggcgc tcttctcctc gggggtcagg tgcaccatgg tgtctgtttg aggttgctag    4740
tgaacacagt tgtgtcagaa gcaaatgtaa gcaatagatg gctctgccct gacttttatg    4800
cccagccctg gctcctgccc tccctgctcc tgggagtaga ttggccaacc ctagggtgtg    4860
gctccacagg gtgaggtcta agtgatgaca gccgtacctg tccttggctc ttctggcact    4920
ggcttaggag ttggacttca aaccctcagc cctccctcta agatatatct cttggcccca    4980
taccatcagt acaaattgct actaaaaaca tcctcctttg caagtgtatt tacccgacgc    5040
gtcggcgata agcttgatcc atcgattacg tatatgtgta tatatatata tatattcagg    5100
aaataatata ttctagaata tgtcacattc tgtctcaggc atccattttc tttatgatgc    5160
cgtttgaggt ggagttttag tcaggtggtc agcttctcct ttttttttgcc atctgccctg    5220 taagcatcct gctggggacc cagataggag tcatcactct aggctgagaa catctgggca    5280
cacaccctaa gcctcagcat gactcatcat gactcagcat tgctgtgctt gagccagaag    5340
gtttgcttag aaggttacac agaaccagaa ggcggggggtg gggcactgac cccgacaggg    5400
gcctggccag aactgctcat gcttggacta tgggaggtca ctaatggaga cacacagaaa    5460
tgtaacagga actaaggaaa aactgaagct ttggggggtat aggggagcag tcccatgtag    5520
tagtagaatg aaaaatgctg ctatgctgtg cctcccccac ctttcccatg tctgccctct    5580
actcatggtc tatctctcct ggctcctggg agtcatggac tccacccagc accaccaacc    5640
tgacctaacc acctatctga gcctgccagc ctataaccca tctgggccct gatagctggt    5700
```

```
ggccagccct gacccccaccc caccctccct ggaacctctg atagacacat ctggcacacc    5760
agctcgcaaa gtcaccgtga gggtcttgtg tttgctgagt caaaattcct tgaaatccaa    5820
gtccttagag actcccaggc ttggattcaa agctcctgac tttctgtcta gtgtatgtgc    5880
agtgagcccc ttttcctcta actgaaagaa ggaaaaaaaa atggaaccca aaatattcta    5940
catagtttcc atgtcacagc cagggctggg cagtctcctg ttatttcttt taaaataaat    6000
atatcattta aatgcataaa taagcaaacc ctgctcggga atgggaggga gagtctctgg    6060
agtccacccc ttctcggccc tggctctgca gatagtgcta tcaaagccct gacagagccc    6120
tgcccattgc tgggccttgg agtgagtcag cctagtagag aggcagggca agccatctca    6180
tagctgctga gtgggagaga gaaaagggct cattgtctat aaactcaggt catggctatt    6240
cttatggcct actcgaccac gagggaattc cgataatcaa cctctggatt acaaaatttg    6300
tgaaagattg actggtattc ttaactatgt tgctcctttt acgctatgtg gatacgctgc    6360
tttaatgcct ttgtatcatg ctattgcttc ccgtatggct ttcattttct cctccttgta    6420
taaatcctgg ttgctgtctc tttatgagga gttgtggccc gttgtcaggc aacgtggcgt    6480
ggtgtgcact gtgtttgctg acgcaacccc cactggttgg ggcattgcca ccacctgtca    6540
gctcctttcc gggactttcg ctttccccct ccctattgcc acggcggaac tcatcgccgc    6600
ctgccttgcc cgctgctgga caggggctcg gctgttgggc actgacaatt ccgtggtgtt    6660 gtcgggggaaa tcatcgtcct ttccttggct gctcgcctgt gttgccacct ggattctgcg    6720
cgggacgtcc ttctgctacg tcccttcggc cctcaatcca gcggaccttc cttcccgcgg    6780
cctgctgccg gctctgcggc ctcttccgcg tcttcgcctt cgccctcaga cgagtcggat    6840
ctccctttgg ccgcctcccc cgcatcgata ccgtcgacct cgagacctag aaaaacatgg    6900
ccaattcgag ctcggtacct ttaagaccaa tgacttacaa ggcagctgta gatcttagcc    6960 acttttttaaa agaaaagggg ggactggaag ggctaattca ctcccaacga agacaagatc    7020
ccagggatgt acgtccctaa cccgctaggg ggcagcaccc aggcctgcac tgccgcctgc    7080 cggcagggggt ccagtcctgc tttttgcttg tactgggtct ctctggttag accagatctg    7140
agcctgggag ctctctggct aactagggaa cccactgctt aagcctcaat aaagcttgcc    7200
ttgagtgctt caagtagtgt gtgcccgtct gttgtgtgac tctggtaact agagatccct    7260
cagacccttt tagtcagtgt ggaaaatctc tagcagtagt agttcatgtc atcttattat    7320
tcagtattta taacttgcaa agaaatgaat atcagagagt gagaggaact tgtttattgc    7380
agcttataat ggttacaaat aaagcaatag catcacaaat ttcacaaata aagcattttt    7440
ttcactgcat tctagttgtg gtttgtccaa actcatcaat gtatcttatc atgtctggct    7500
ctagctatcc cgcccctaac tccgcccatc ccgcccctaa ctccgcccag ttccgcccat    7560
tctccgcccc atggctgact aatttttttt atttatgcag aggccgaggc cgcctcggcc    7620
tctgagctat tccagaagta gtgaggaggc ttttttggag gcctaggctt ttgcgtcgag    7680
acgtacccaa ttcgccctat agtgagtcgt attacgcgcg ctcactggcc gtcgttttac    7740
aacgtcgtga ctgggaaaac cctggcgtta cccaacttaa tcgccttgca gcacatcccc    7800
ctttcgccag ctggcgtaat agcgaagagg cccgcaccga tcgcccttcc caacagttgc    7860
gcagcctgaa tggcgaatgg cgcgacgcgc cctgtagcgg cgcattaagc gcggcgggtg    7920
tggtggttac gcgcagcgtg accgctacac ttgccagcgc cctagcgccc gctcctttcg    7980
ctttcttccc ttcctttctc gccacgttcg ccggctttcc ccgtcaagct ctaaatcggg    8040
ggctcccttt agggttccga tttagtgctt tacggcacct cgaccccaaa aaacttgatt    8100
```

```
agggtgatgg ttcacgtagt gggccatcgc cctgatagac ggtttttcgc cctttgacgt   8160
tggagtccac gttctttaat agtggactct tgttccaaac tggaacaaca ctcaacccta   8220
tctcggtcta ttcttttgat ttataaggga ttttgccgat ttcggcctat tggttaaaaa   8280
atgagctgat ttaacaaaaa tttaacgcga attttaacaa aatattaacg tttacaattt   8340
cccaggtggc acttttcggg gaaatgtgcg cggaacccct atttgtttat ttttctaaat   8400
acattcaaat atgtatccgc tcatgagaca ataaccctga taaatgcttc aataatattg   8460
aaaaaggaag agtatgagta ttcaacattt ccgtgtcgcc cttattccct tttttgcggc   8520
attttgcctt cctgtttttg ctcacccaga aacgctggtg aaagtaaaag atgctgaaga   8580
tcagttgggt gcacgagtgg gttacatcga actggatctc aacagcggta agatccttga   8640
gagttttcgc cccgaagaac gttttccaat gatgagcact tttaaagttc tgctatgtgg   8700
cgcggtatta tcccgtattg acgccgggca agagcaactc ggtcgccgca tacactattc   8760
tcagaatgac ttggttgagt actcaccagt cacagaaaag catcttacgg atggcatgac   8820
agtaagagaa ttatgcagtg ctgccataac catgagtgat aacactgcgg ccaacttact   8880
tctgacaacg atcggaggac cgaaggagct aaccgctttt ttgcacaaca tgggggatca   8940
tgtaactcgc cttgatcgtt gggaaccgga gctgaatgaa gccataccaa acgacgagcg   9000
tgacaccacg atgcctgtag caatggcaac aacgttgcgc aaactattaa ctggcgaact   9060
acttactcta gcttcccggc aacaattaat agactggatg gaggcggata agttgcagg   9120 accacttctg cgctcggccc ttccggctgg ctggtttatt gctgataaat ctggagccgg   9180
tgagcgtggg tctcgcggta tcattgcagc actggggcca gatggtaagc cctcccgtat   9240
cgtagttatc tacacgacgg ggagtcaggc aactatggat gaacgaaata gacagatcgc   9300
tgagataggt gcctcactga ttaagcattg gtaactgtca gaccaagttt actcatatat   9360
actttagatt gatttaaaac ttcattttta atttaaaagg atctaggtga agatcctttt   9420
tgataatctc atgaccaaaa tcccttaacg tgagttttcg ttccactgag cgtcagaccc   9480
cgtagaaaag atcaaaggat cttcttgaga tccttttttt ctgcgcgtaa tctgctgctt   9540
gcaaacaaaa aaaccaccgc taccagcggt ggtttgtttg ccggatcaag agctaccaac   9600 tcttttccg aaggtaactg gcttcagcag agcgcagata ccaaatactg tccttctagt    9660
gtagccgtag ttaggccacc acttcaagaa ctctgtagca ccgcctacat acctcgctct   9720
gctaatcctg ttaccagtgg ctgctgccag tggcgataag tcgtgtctta ccgggttgga   9780
ctcaagacga tagttaccgg ataaggcgca gcggtcgggc tgaacggggg gttcgtgcac   9840
acagcccagc ttggagcgaa cgacctacac cgaactgaga tacctacagc gtgagctatg   9900
agaaagcgcc acgcttcccg aagggagaaa ggcggacagg tatccggtaa gcggcagggt   9960
cggaacagga gagcgcacga gggagcttcc aggggggaaac gcctggtatc tttatagtcc   10020
tgtcgggttt cgccacctct gacttgagcg tcgattttg tgatgctcgt caggggggcg   10080
gagcctatgg aaaaacgcca gcaacgcggc cattttacg gttcctggcc ttttgctggc   10140
cttttgctca catgttcttt cctgcgttat cccctgattc tgtggataac cgtattaccg   10200
cctttgagtg agctgatacc gctcgccgca gccgaacgac cgagcgcagc gagtcagtga   10260
gcgaggaagc ggaagagcgc ccaatacgca aaccgcctct ccccgcgcgt tggccgattc   10320
attaatgcag ctggcacgac aggtttcccg actggaaagc gggcagtga              10369
```

<210> SEQ ID NO 12

```
<211> LENGTH: 10369
<212> TYPE: DNA
<213> ORGANISM: Artificial
<220> FEATURE:
<223> OTHER INFORMATION: Lentiviral vector

<400> SEQUENCE: 12
gcgcaacgca attaatgtga gttagctcac tcattaggca ccccaggctt tacactttat      60
gcttccggct cgtatgttgt gtggaattgt gagcggataa caatttcaca caggaaacag     120
ctatgaccat gattacgcca agcgcgcaat taaccctcac taaagggaac aaaagctgga     180
gctgcaagct tggccattgc atacgttgta tccatatcat aatatgtaca tttatattgg     240
ctcatgtcca acattaccgc catgttgaca ttgattattg actagttatt aatagtaatc     300
aattacgggg tcattagttc atagcccata tatggagttc cgcgttacat aacttacggt     360
aaatggcccg cctggctgac cgcccaacga cccccgccca ttgacgtcaa taatgacgta     420
tgttcccata gtaacgccaa tagggacttt ccattgacgt caatgggtgg agtatttacg     480
gtaaactgcc cacttggcag tacatcaagt gtatcatatg ccaagtacgc ccctattga     540 cgtcaatgac ggtaaatggc ccgcctggca ttatgcccag tacatgacct tatgggactt     600
tcctacttgg cagtacatct acgtattagt catcgctatt accatggtga tgcggttttg     660
gcagtacatc aatgggcgtg atagcggttt gactcacggg gatttccaa gtctccaccc     720 cattgacgtc aatgggagtt tgttttggca ccaaaatcaa cgggactttc caaaatgtcg     780
taacaactcc gccccattga cgcaaatggg cggtaggcgt gtacggtggg aggtctatat     840
aagcagagct cgtttagtga accggggtct ctctggttag accagatctg agcctgggag     900
ctctctggct aactagggaa cccactgctt aagcctcaat aaagcttgcc ttgagtgctt     960
caagtagtgt gtgcccgtct gttgtgtgac tctggtaact agagatccct cagacccttt    1020
tagtcagtgt ggaaaatctc tagcagtggc gcccgaacag ggacttgaaa gcgaaaggga    1080
aaccagagga gctctctcga cgcaggactc ggcttgctga agcgcgcacg caagaggcg    1140 aggggcggcg actggtgagt acgccaaaaa ttttgactag cggaggctag aaggagagag    1200
atgggtgcga gagcgtcagt attaagcggg ggagaattag atcgcgatgg gaaaaaattc    1260
ggttaaggcc agggggaaag aaaaaatata aattaaaaca tatagtatgg gcaagcaggg    1320
agctagaacg attcgcagtt aatcctggcc tgttagaaac atcagaaggc tgtagacaaa    1380
tactgggaca gctacaacca tcccttcaga caggatcaga agaacttaga tcattatata    1440
atacagtagc aaccctctat tgtgtgcatc aaaggataga gataaaagac accaaggaag    1500
ctttagacaa gatagaggaa gagcaaaaca aaagtaagac caccgcacag caagcggccg    1560
ctgatcttca gacctggagg aggagatatg agggacaatt ggagaagtga attatataaa    1620
tataaagtag taaaaattga accattagga gtagcaccca ccaaggcaaa gagaagagtg    1680
gtgcagagag aaaaaagagc agtgggaata ggagctttgt tccttgggtt cttgggagca    1740
gcaggaagca ctatgggcgc agcgtcaatg acgctgacgg tacaggccag acaattattg    1800
tctggtatag tgcagcagca gaacaatttg ctgagggcta ttgaggcgca acagcatctg    1860
ttgcaactca cagtctgggg catcaagcag ctccaggcaa gaatcctggc tgtggaaaga    1920
tacctaaagg atcaacagct cctggggatt tggggttgct ctggaaaact catttgcacc    1980
actgctgtgc cttggaatgc tagttggagt aataaatctc tggaacagat ttggaatcac    2040
acgacctgga tggagtggga cagagaaatt aacaattaca caagcttaat acactcctta    2100
attgaagaat cgcaaaacca gcaagaaaag aatgaacaag aattattgga attagataaa    2160
```

-continued

```
tgggcaagtt tgtggaattg gtttaacata acaaattggc tgtggtatat aaaattattc   2220
ataatgatag taggaggctt ggtaggttta agaatagttt ttgctgtact ttctatagtg   2280
aatagagtta ggcagggata ttcaccatta tcgtttcaga cccacctccc aacccgagg    2340 ggacccgaca ggcccgaagg aatagaagaa gaaggtggag agagagacag agacagatcc   2400
attcgattag tgaacggatc tcgacggtat cgatctcgac acaaatggca gtattcatcc   2460
acaattttaa aagaaaaggg gggattgggg ggtacagtgc aggggaaaga atagtagaca   2520
taatagcaac agacatacaa actaaagaat tacaaaaaca aattacaaaa attcaaaatt   2580
ttcgggttta ttacgggac agcagagatc cagtttgggt cgaggatatc ggatcggaat    2640
tctctagatg atcaggatcc ctcgagccct tatcgatcac gagactagcc tcgactacta   2700
gtggagatcc cccgggctgc agagccagaa gcaccataag ggacatgata agggagccag   2760
cagacctctg atctcttcct gaatgctaat cttaaacatc ctgaggaaga atgggacttc   2820
catttggggt gggcctatga tagggtaata agacagtagt gaatatcaag ctacaaaaag   2880
ccccctttca aattcttctc agtcctaact tttcatacta agcccagtcc ttccaaagca   2940
gactgtgaaa gagtgatagt tccgggagac tagcactgca gattccgggt cactgtgagt   3000 ggggaggca gggaagaagg gctcacagga cagtcaaacc atgcccctg tttttccttc      3060 ttcaagtaga cctctataag acaacagaga caactaaggc tgagtggcca ggcgaggaga   3120
aaccatctcg ccgtaaaaca tggaaggaac acttcagggg aaaggtggta tctctaagca   3180
agagaactga gtggagtcaa ggctgagaga tgcaggataa gcaaatgggt agtgaaaaga   3240
cattcatgag gacagctaaa acaataagta atgtaaaata cagcatagca aaactttaac   3300
ctccaaatca agcctctact tgaatccttt tctgagggat gaataaggca taggcatcag   3360
gggctgttgc caatgtgcat tagctgtttg cagcctcacc ttctttcatg gagtttaaga   3420
tatagtgtat tttcccaagg tttgaactag ctcttcattt ctttatgttt taaatgcact   3480
gacctcccac attcccttt tagtaaaata ttcagaaata atttaaatac atcattgcaa    3540
tgaaaataaa tgttttttat taggcagaat ccagatgctc aaggcccttc ataatatccc   3600
ccagtttagt agttggactt agggaacaaa ggaacctta atagaaattg gacagcaaga    3660
aagcgagctt agtggtactt gtgggccagg gcgttggcca cgccggccac caccttctgg   3720
taggcggcct gcacggggg ggtgaactcc ttgccgaagt ggtgggccag cacgcacacc    3780
agcacgttgc ccaggagctg tgggaggaag ataagaggta tgaacatgat tagcaaaagg   3840
gcctagcttg gactcagaat aatccagcct tatcccaacc ataaaataaa agcagaatgg   3900
tagctggatt gtagctgcta ttagcaatat gaaacctctt acatcagtta caatttatat   3960
gcagaaatat ttatatgcag aaatattgct attgccttaa cccagaaatt atcactgtta   4020
ttctttagaa tggtgcaaag aggcatgata cattgtatca ttattgccct gaaagaaaga   4080
gattagggaa agtattagaa ataagataaa caaaaaagta tattaaaaga agaaagcatt   4140
ttttaaaatt acaaatgcaa aattaccctg atttggtcaa tatgtgtacc ctgttacttc   4200
tccccttcct atgacatgaa cttaaccata gaaaagaagg ggaaagaaaa catcaagggt   4260
cccatagact caccctgaag ttctcggggt ccacgtgcag cttgtcgcag tgcagctcgc   4320
tcagctgggc gaaggtgccc ttcaggttgt ccaggtgggc caggccgtcg ctgaaggcgc   4380
ccagcacctt cttgccgtgg gccttcacct tggggttgcc catcacggcg tcggggtgc    4440 tcaggtcgcc gaagctctcg aagaagcgct gggtccaggg gtacaccacc agcagcctaa   4500
```

-continued

```
gggtgggaaa atagaccaat aggcagagag agtcagtgcc tatcagaaac ccaagagtct   4560
tctctgtctc cacatgccca gtttctattg gtctccttaa acctgtcttg taaccttgat   4620
accaacctgc ccagggcctc gccgcccacg gcgtccacgt tcaccttgtc ccacagggcg   4680
gtcacggcgc tcttctcctc gggggtcagg tgcaccatgg tgtctgtttg aggttgctag   4740
tgaacacagt tgtgtcagaa gcaaatgtaa gcaatagatg gctctgccct gacttttatg   4800
cccagccctg gctcctgccc tccctgctcc tgggagtaga ttggccaacc ctagggtgtg   4860
gctccacagg gtgaggtcta agtgatgaca gccgtacctg tccttggctc ttctggcact   4920
ggcttaggag ttggacttca aaccctcagc cctccctcta agatatatct cttggcccca   4980
taccatcagt acaaattgct actaaaaaca tcctcctttg caagtgtatt taccccgacgc   5040 gtcggcgata agcttgatcc atcgattacg tatatgtgta tatatatata tatattcagg   5100
aaataatata ttctagaata tgtcacattc tgtctcaggc atccattttc tttatgatgc   5160
cgtttgaggt ggagtttttag tcaggtggtc agcttctcct ttttttttgcc atctgccctg   5220 taagcatcct gctggggacc cagataggag tcatcactct aggctgagaa catctgggca   5280
cacaccctaa gcctcagcat gactcatcat gactcagcat tgctgtgctt gagccagaag   5340
gtttgcttag aaggttacac agaaccagaa ggcgggggtg gggcactgac cccgacaggg   5400
gcctggccag aactgctcat gcttggacta tgggaggtca ctaatggaga cacacagaaa   5460
tgtaacagga actaaggaaa aactgaagct ttggggggtat aggggagcag tcccatgtag   5520
tagtagaatg aaaaatgctg ctatgctgtg cctcccccac ctttcccatg tctgccctct   5580
actcatggtc tatctctcct ggctcctggg agtcatggac tccacccagc accaccaacc   5640
tgacctaacc acctatctga gcctgccagc ctataaccca tctgggccct gatagctggt   5700
ggccagccct gaccccaccc cacccctccct ggaacctctg atagacacat ctggcacacc   5760
agctcgcaaa gtcaccgtga gggtcttgtg tttgctgagt caaaattcct tgaaatccaa   5820
gtccttagag actcccaggc ttggattcaa agctcctgac tttctgtcta gtgtatgtgc   5880
agtgagcccc ttttcctcta actgaaagaa ggaaaaaaaa atggaaccca aaatattcta   5940
catagtttcc atgtcacagc cagggctggg cagtctcctg ttatttcttt taaaataaat   6000
atatcattta aatgcataaa taagcaaacc ctgctcggga atgggaggga gagtctctgg   6060
agtccacccc ttctcggccc tggctctgca gatagtgcta tcaaagccct gacagagccc   6120
tgcccattgc tgggccttgg agtgagtcag cctagtagag aggcagggca agccatctca   6180
tagctgctga gtgggagaga gaaaagggct cattgtctat aaactcaggt catggctatt   6240
cttatggcct actcgaccac gagggaattc cgataatcaa cctctggatt acaaaatttg   6300
tgaaagattg actggtattc ttaactatgt tgctcctttt acgctatgtg gatacgctgc   6360
tttaatgcct ttgtatcatg ctattgcttc ccgtatggct ttcattttct cctccttgta   6420
taaatcctgg ttgctgtctc tttatgagga gttgtggccc gttgtcaggc aacgtggcgt   6480
ggtgtgcact gtgtttgctg acgcaacccc cactggttgg ggcattgcca ccacctgtca   6540
gctcctttcc gggactttcg ctttccccct ccctattgcc acggcggaac tcatcgccgc   6600
ctgccttgcc cgctgctgga caggggctcg gctgttgggc actgacaatt ccgtggtgtt   6660
gtcggggaaa tcatcgtcct ttccttggct gctcgcctgt gttgccacct ggattctgcg   6720
cgggacgtcc ttctgctacg tcccttcggc cctcaatcca gcggaccttc cttcccgcgg   6780
cctgctgccg gctctgcggc ctcttccgcg tcttcgcctt cgccctcaga cgagtcggat   6840
ctccctttgg gccgcctccc cgcatcgata ccgtcgacct cgagacctag aaaaacatgg   6900
```

-continued

```
ccaattcgag ctcggtacct ttaagaccaa tgacttacaa ggcagctgta gatcttagcc    6960 acttttaaa agaaaagggg ggactggaag ggctaattca ctcccaacga agacaagatc    7020
ccagggatgt acgtccctaa cccgctaggg ggcagcaccc aggcctgcac tgccgcctgc    7080
cggcaggggt ccagtcctgc ttttttgcttg tactgggtct ctctggttag accagatctg    7140
agcctgggag ctctctggct aactagggaa cccactgctt aagcctcaat aaagcttgcc    7200
ttgagtgctt caagtagtgt gtgcccgtct gttgtgtgac tctggtaact agagatccct    7260
cagacccttt tagtcagtgt ggaaaatctc tagcagtagt agttcatgtc atcttattat    7320
tcagtattta taacttgcaa agaaatgaat atcagagagt gagaggaact tgtttattgc    7380
agcttataat ggttacaaat aaagcaatag catcacaaat ttcacaaata aagcattttt    7440
ttcactgcat tctagttgtg gtttgtccaa actcatcaat gtatcttatc atgtctggct    7500
ctagctatcc cgcccctaac tccgcccatc ccgcccctaa ctccgcccag ttccgcccat    7560
tctccgcccc atggctgact aattttttt atttatgcag aggccgaggc cgcctcggcc    7620
tctgagctat tccagaagta gtgaggaggc tttttttggag gcctaggctt ttgcgtcgag    7680
acgtacccaa ttcgccctat agtgagtcgt attacgcgcg ctcactggcc gtcgttttac    7740
aacgtcgtga ctgggaaaac cctggcgtta cccaacttaa tcgccttgca gcacatcccc    7800
ctttcgccag ctggcgtaat agcgaagagg cccgcaccga tcgcccttcc caacagttgc    7860
gcagcctgaa tggcgaatgg cgcgacgcgc cctgtagcgg cgcattaagc gcggcgggtg    7920
tggtggttac gcgcagcgtg accgctacac ttgccagcgc cctagcgccc gctcctttcg    7980
ctttcttccc ttcctttctc gccacgttcg ccggctttcc ccgtcaagct ctaaatcggg    8040
ggctcccttt agggttccga tttagtgctt tacggcacct cgaccccaaa aaacttgatt    8100
agggtgatgg ttcacgtagt gggccatcgc cctgatagac ggtttttcgc cctttgacgt    8160
tggagtccac gttctttaat agtggactct tgttccaaac tggaacaaca ctcaacccta    8220
tctcggtcta ttcttttgat ttataaggga ttttgccgat ttcggcctat tggttaaaaa    8280
atgagctgat ttaacaaaaa tttaacgcga attttaacaa aatattaacg tttacaattt    8340
cccaggtggc acttttcggg gaaatgtgcg cggaaccccct atttgtttat ttttctaaat    8400
acattcaaat atgtatccgc tcatgagaca ataaccctga taaatgcttc aataatattg    8460
aaaaaggaag agtatgagta ttcaacattt ccgtgtcgcc cttattccct tttttgcggc    8520
attttgcctt cctgtttttg ctcacccaga aacgctggtg aaagtaaaag atgctgaaga    8580
tcagttgggt gcacgagtgg gttacatcga actggatctc aacagcggta agatccttga    8640
gagttttcgc cccgaagaac gttttccaat gatgagcact tttaaagttc tgctatgtgg    8700
cgcggtatta tcccgtattg acgccgggca agagcaactc ggtcgccgca tacactattc    8760
tcagaatgac ttggttgagt actcaccagt cacagaaaag catcttacgg atggcatgac    8820
agtaagagaa ttatgcagtg ctgccataac catgagtgat aacactgcgg ccaacttact    8880
tctgacaacg atcggaggac cgaaggagct aaccgctttt ttgcacaaca tgggggatca    8940
tgtaactcgc cttgatcgtt gggaaccgga gctgaatgaa gccataccaa acgacgagcg    9000
tgacaccacg atgcctgtag caatggcaac aacgttgcgc aaactattaa ctggcgaact    9060
acttactcta gcttcccggc aacaattaat agactggatg gaggcggata agttgcagg    9120 accacttctg cgctcggccc ttccggctgg ctggtttatt gctgataaat ctggagccgg    9180
tgagcgtggg tctcgcggta tcattgcagc actggggcca gatggtaagc cctcccgtat    9240
```

-continued

```
cgtagttatc tacacgacgg ggagtcaggc aactatggat gaacgaaata gacagatcgc    9300
tgagataggt gcctcactga ttaagcattg gtaactgtca gaccaagttt actcatatat    9360
actttagatt gatttaaaac ttcattttta atttaaaagg atctaggtga agatccttt     9420 tgataatctc atgaccaaaa tcccttaacg tgagttttcg ttccactgag cgtcagaccc    9480
cgtagaaaag atcaaaggat cttcttgaga tccttttttt ctgcgcgtaa tctgctgctt    9540
gcaaacaaaa aaaccaccgc taccagcggt ggtttgtttg ccggatcaag agctaccaac    9600 tcttttttccg aaggtaactg gcttcagcag agcgcagata ccaaatactg tccttctagt    9660
gtagccgtag ttaggccacc acttcaagaa ctctgtagca ccgcctacat acctcgctct    9720
gctaatcctg ttaccagtgg ctgctgccag tggcgataag tcgtgtctta ccgggttgga    9780
ctcaagacga tagttaccgg ataaggcgca gcggtcgggc tgaacggggg gttcgtgcac    9840
acagcccagc ttggagcgaa cgacctacac cgaactgaga tacctacagc gtgagctatg    9900
agaaagcgcc acgcttcccg aagggagaaa ggcggacagg tatccggtaa gcggcagggt    9960
cggaacagga gagcgcacga gggagcttcc agggggaaac gcctggtatc tttatagtcc   10020
tgtcgggttt cgccacctct gacttgagcg tcgatttttg tgatgctcgt caggggggcg   10080
gagcctatgg aaaaacgcca gcaacgcggc cattttttacg gttcctggcc ttttgctggc   10140
cttttgctca catgttcttt cctgcgttat ccctgattc tgtggataac cgtattaccg    10200
cctttgagtg agctgatacc gctcgccgca gccgaacgac cgagcgcagc gagtcagtga   10260
gcgaggaagc ggaagagcgc ccaatacgca aaccgcctct ccccgcgcgt tggccgattc   10320
attaatgcag ctggcacgac aggtttcccg actggaaagc gggcagtga              10369
```

```
<210> SEQ ID NO 13
<211> LENGTH: 8728
<212> TYPE: DNA
<213> ORGANISM: Artificial
<220> FEATURE:
<223> OTHER INFORMATION: Lentiviral vector

<400> SEQUENCE: 13
acgcgccctg tagcggcgca ttaagcgcgg cgggtgtggt ggttacgcgc agcgtgaccg      60
ctacacttgc cagcgcccta gcgcccgctc ctttcgcttt cttcccttcc tttctcgcca    120
cgttcgccgg ctttccccgt caagctctaa atcggggggct cccttaaggg ttccgatttta  180 gtgctttacg gcacctcgac cccaaaaaac ttgattaggg tgatggttca cgtagtgggc    240 catcgcccctg atagacggtt tttcgcccctt tgacgttgga gtccacgttc tttaatagtg   300
gactcttgtt ccaaactgga acaacactca accctatctc ggtctattct tttgatttat    360
aagggatttt gccgatttcg gcctattggt taaaaaatga gctgatttaa caaaaattta    420
acgcgaattt taacaaaata ttaacgctta caatttaggt ggcacttttc ggggaaatgt    480
gcgcggaacc cctatttgtt tatttttcta aatacattca aatatgtatc cgctcatgag    540
acaataaccc tgataaatgc ttcaataata gcacctagat caagagacag gatgaggatc    600
gtttcgcatg attgaacaag atggattgca cgcaggttct ccggccgctt gggtggagag    660
gctattcggc tatgactggg cacaacagac aatcggctgc tctgatgccg ccgtgttccg    720
gctgtcagcg caggggcgcc cggttctttt tgtcaagacc gacctgtccg gtgccctgaa    780
tgaactgcaa gacgaggcag cgcggctatc gtggctggcc acgacgggcg ttccttgcgc    840
agctgtgctc gacgttgtca ctgaagcggg aagggactgg ctgctattgg gcgaagtgcc    900
ggggcaggat ctcctgtcat ctcaccttgc tcctgccgag aaagtatcca tcatggctga    960
```

-continued

```
tgcaatgcgg cggctgcata cgcttgatcc ggctacctgc ccattcgacc accaagcgaa      1020
acatcgcatc gagcgagcac gtactcggat ggaagccggt cttgtcgatc aggatgatct      1080
ggacgaagag catcaggggc tcgcgccagc cgaactgttc gccaggctca aggcgagcat      1140
gcccgacggc gaggatctcg tcgtgaccca tggcgatgcc tgcttgccga atatcatggt      1200
ggaaaatggc cgcttttctg gattcatcga ctgtggccgg ctgggtgtgg cggaccgcta      1260
tcaggacata gcgttggcta cccgtgatat tgctgaagag cttggcggcg aatgggctga      1320
ccgcttcctc gtgctttacg gtatcgccgc tcccgattcg cagcgcatcg ccttctatcg      1380
ccttcttgac gagttcttct gaattattaa cgcttacaat ttcctgatgc ggtattttct      1440
ccttacgcat ctgtgcggta tttcacaccg catcaggtgg cacttttcgg ggaaatgtgc      1500
gcggaacccc tatttgttta tttttctaaa tacattcaaa tatgtatccg ctcatgacca      1560
aaatccctta acgtgagttt tcgttccact gagcgtcaga ccccgtagaa aagatcaaag      1620
gatcttcttg agatcctttt tttctgcgcg taatctgctg cttgcaaaca aaaaaaccac      1680
cgctaccagc ggtggtttgt ttgccggatc aagagctacc aactcttttt ccgaaggtaa      1740
ctggcttcag cagagcgcag ataccaaata ctgttcttct agtgtagccg tagttaggcc      1800
accacttcaa gaactctgta gcaccgccta catacctcgc tctgctaatc ctgttaccag      1860
tggctgctgc cagtggcgat aagtcgtgtc ttaccgggtt ggactcaaga cgatagttac      1920
cggataaggc gcagcggtcg ggctgaacgg ggggtcgtg cacacagccc agcttggagc      1980
gaacgaccta caccgaactg agatacctac agcgtgagct atgagaaagc gccacgcttc      2040
ccgaagggag aaaggcggac aggtatccgg taagcggcag ggtcggaaca ggagagcgca      2100
cgagggagct ccagggggga aacgcctggt atctttatag tcctgtcggg tttcgccacc      2160
tctgacttga gcgtcgattt ttgtgatgct cgtcagggg gcggagccta tggaaaaacg      2220
ccagcaacgc ggcctttta cggttcctgg cctttttgctg gccttttgct cacatgttct      2280
ttcctgcgtt atccctgat tctgtggata accgtattac cgcctttgag tgagctgata      2340
ccgctcgccg cagccgaacg accgagcgca gcgagtcagt gagcgaggaa gcggaagagc      2400
gcccaatacg caaaccgcct ctccccgcgc gttggccgat tcattaatgc agctggcacg      2460
acaggtttcc cgactggaaa gcgggcagtg agcgcaacgc aattaatgtg agttagctca      2520
ctcattaggc accccaggct ttacacttta tgcttccggc tcgtatgttg tgtggaattg      2580
tgagcggata acaatttcac acaggaaaca gctatgacca tgattacgcc aagcgcgcaa      2640
ttaaccctca ctaaagggaa caaaagctgg agctgcaagc ttggccattg catacgttgt      2700
atccatatca taatatgtac atttatattg gctcatgtcc aacattaccg ccatgttgac      2760
attgattatt gactagttat taatagtaat caattacggg gtcattagtt catagcccat      2820
atatggagtt ccgcgttaca taacttacgg taaatggccc gcctggctga ccgcccaacg      2880
acccccgccc attgacgtca ataatgacgt atgttcccat agtaacgcca atagggactt      2940
tccattgacg tcaatgggtg gagtatttac ggtaaactgc ccacttggca gtacatcaag      3000
tgtatcatat gccaagtacg ccccctattg acgtcaatga cggtaaatgg cccgcctggc      3060
attatgccca gtacatgacc ttatgggact ttcctacttg gcagtacatc tacgtattag      3120
tcatcgctat taccatggtg atgcggtttt ggcagtacat caatgggcgt ggatagcggt      3180
ttgactcacg gggatttcca agtctccacc ccattgacgt caatgggagt ttgttttggc      3240
accaaaatca acgggacttt ccaaaatgtc gtaacaactc cgccccattg acgcaaatgg      3300
```

-continued

```
gcggtaggcg tgtacggtgg gaggtctata taagcagagc tcgtttagtg aaccgggggtc   3360 tctctggtta gaccagatct gagcctggga gctctctggc taactaggga acccactgct   3420
taagcctcaa taaagcttgc cttgagtgct tcaagtagtg tgtgcccgtc tgttgtgtga   3480
ctctggtaac tagagatccc tcagacccctt ttagtcagtg tggaaaatct ctagcagtgg   3540
cgcccgaaca gggacttgaa agcgaaaggg aaaccagagg agctctctcg acgcaggact   3600
cggcttgctg aagcgcgcac ggcaagaggc gaggggcggc gactggtgag tacgccaaaa   3660
attttgacta gcggaggcta gaggagaga gatgggtgcg agagcgtcag tattaagcgg   3720
gggagaatta gatcgcgatg ggaaaaaatt cggttaaggc caggggggaaa gaaaaaatat   3780 aaattaaaac atatagtatg ggcaagcagg gagctagaac gattcgcagt taatcctggc   3840
ctgttagaaa catcagaagg ctgtagacaa atactgggac agctacaacc atcccttcag   3900
acaggatcag aagaacttag atcattatat aatacagtag caaccctcta ttgtgtgcat   3960
caaaggatag agataaaaga caccaaggaa gctttagaca agatagagga agagcaaaac   4020
aaaagtaaga ccaccgcaca gcaagcggcc gctgatcttc agacctggag gaggagatat   4080
gagggacaat tggagaagtg aattatataa atataaagta gtaaaaattg aaccattagg   4140
agtagcaccc accaaggcaa agagaagagt ggtgcagaga gaaaaaagag cagtgggaat   4200
aggagctttg ttccttgggt tcttgggagc agcaggaagc actatgggcg cagcgtcaat   4260
gacgctgacg gtacaggcca gacaattatt gtctggtata gtgcagcagc agaacaattt   4320
gctgagggct attgaggcgc aacagcatct gttgcaactc acagtctggg gcatcaagca   4380
gctccaggca agaatcctgg ctgtggaaag atacctaaag gatcaacagc tcctggggat   4440
ttggggttgc tctggaaaac tcatttgcac cactgctgtg ccttggaatg ctagttggag   4500
taataaatct ctggaacaga tttggaatca cacgacctgg atggagtggg acagagaaat   4560
taacaattac acaagcttaa tacactcctt aattgaagaa tcgcaaaacc agcaagaaaa   4620
gaatgaacaa gaattattgg aattagataa atgggcaagt ttgtggaatt ggtttaacat   4680
aacaaattgg ctgtggtata taaaattatt cataatgata gtaggaggct tggtaggttt   4740
aagaatagtt tttgctgtac tttctatagt gaatagagtt aggcagggat attcaccatt   4800
atcgtttcag acccacctcc caaccccgag gggacccgac aggcccgaag gaatagaaga   4860
agaaggtgga gagagagaca gagacagatc cattcgatta gtgaacggat ctcgacggta   4920
tcgatctcga cacaaatggc agtattcatc cacaatttta aaagaaaagg ggggattggg   4980
gggtacagtg caggggaaag aatagtagac ataatagcaa cagacataca aactaaagaa   5040
ttacaaaaac aaattacaaa aattcaaaat tttcgggttt attacaggga cagcagacat   5100
gaggacagct aaaacaataa gtaatgtaaa atacagcata gcaaaacttt aacctccaaa   5160
tcaagcctct acttgaatcc ttttctgagg gatgaataag gcataggcat caggggctgt   5220
tgccaatgtg cattagctgt ttgcagcctc accttctttc atggagttta agatatagtg   5280
tattttccca aggtttgaac tagctcttca tttctttatg ttttaaatgc actgacctcc   5340
cacattccct ttttagtaaa atattcagaa ataatttaaa tacatcattg caatgaaaat   5400
aaatgttttt tattaggcag aatccagatg ctcaaggccc ttcataatat cccccagttt   5460
agtagttgga cttagggaac aaaggaacct ttaatagaaa ttggacagca agaaagcgag   5520
cttagtgata cttgtgggcc agggcattag ccacaccagc caccactttc tgataggcag   5580
cctgcactgg tggggtgaat tctttgccaa agtgatgggc cagcacacag accagcacgt   5640
tgcccaggag ctgtgggagg aagataagag gtatgaacat gattagcaaa agggcctagc   5700
```

-continued

```
ttggactcag aataatccag ccttatccca accataaaat aaaagcagaa tggtagctgg   5760
attgtagctg ctattagcaa tatgaaacct cttacatcag ttacaattta tatgcagaaa   5820
taccctgtta cttctcccct tcctatgaca tgaacttaac catagaaaag aaggggaaag   5880
aaaacatcaa gggtcccata gactcaccct gaagttctca ggatccacgt gcagcttgtc   5940
acagtgcagc tcactcagct gggcaaaggt gcccttgagg ttgtccaggt gagccaggcc   6000
atcactaaag gcaccgagca cttttcttgcc atgagccttc accttagggt tgcccataac   6060
agcatcagga gtggacagat ccccaaagga ctcaaagaac ctctgggtcc aagggtagac   6120
caccagcagc ctaagggtgg gaaaatagac caataggcag agagagtcag tgcctatcag   6180
aaacccaaga gtcttctctg tctccacatg cccagtttct attggtctcc ttaaacctgt   6240
cttgtaacct tgataccaac ctgcccaggg cctcaccacc aacggcatcc acgttcacct   6300
tgtcccacag ggcagtaacg gcagacttct cctcaggagt caggtgcacc atggtgtctg   6360
tttgaggttg ctagtgaaca cagttgtgtc agaagcaaat gtaagcaata gatggctctg   6420
ccctgacttt tatgcccagc cctggctcct gccctccctg ctcctgggag tagattggcc   6480
aaccctaggt gtggctcca cagggtgagg tctaagtgat gacagccgta cctgtccttg   6540
gctcttctgg cactggctta ggagttggac ttcaaaccct cagccctccc tctaagatat   6600
atctcttggc cccataccat cagtacaaat tgctactaaa aacatcctcc tttgcaagtg   6660
tatttactac gtatatgtgt atatatatat atatattcag gaaataatat attctagaat   6720
atgtcacatt ctgtctcagg catccatttt ctttatgatg ccgtttgagg tggagtttta   6780
gtcaggtggt cagcttctcc tttttttttgc catctgccct gtaagcatcc tgctggggac   6840
ccagatagga gtcatcactc taggctgaga acatctgggc acacacccta agcctcagca   6900
tgactcatca tgactcagca ttgctgtgct tgagccagaa ggtttgctta gaaggttaca   6960
cagaaccaga aggcgggggt ggggcactga ccccgacagg ggcctggcca gaactgctca   7020
tgcttggact atgggaggtc actaatggag acacacagaa atgtaacagg aactaaggaa   7080
aaactgaagc tttgggggta taggggagca gtcccatgta gtagtagaat gaaaaatgct   7140
gctatgctgt gcctccccca cctttcccat gtctgccctc tactcatggt ctatctctcc   7200
tggctcctgg gagtcatgga ctccacccag caccaccaac ctgacctaac cacctatctg   7260
agcctgccag cctataaccc atctgggccc tgatagctgg tggccagccc tgaccccacc   7320
ccaccctccc tggaacctct gatagacaca tctggcacac cagctcgcaa agtcaccgtg   7380
agggtcttgt gtttgctgag tcaaaattcc ttgaaatcca agtccttaga gactcccagg   7440
cttggattca aagctcctga ctttctgtct agtgtatgtg cagtgagccc cttttcctct   7500
aactgaaaga aggaaaaaaa aatggaaccc aaaatattct acatagtttc catgtcacag   7560
ccagggctgg gcagtctcct gttatttctt ttaaaataaa tatatcattt aaatgcataa   7620
ataagcaaac cctgctcggg aatgggaggg agagtctctg gagtccaccc cttctcggcc   7680
ctggctctgc agatagtgct atcaaagccc tgacagagcc ctgcccattg ctgggccttg   7740
gagtgagtca gcctagtaga gaggcagggc aagccatctc atagctgctg agtgggagag   7800
agaaaagggc tcattgtcta taaactcagg tcatggctat tcttattaaa agaaaagggg   7860
ggactggaag ggctaattca ctcccaacga agacaagatc tgcttttttgc ttgtactggg   7920 tctctctggt tagaccagat ctgagcctgg gagctctctg gctaactagg gaacccactg   7980
cttaagcctc aataaagctt gccttgagtg cttcaagtag tgtgttggtt ttttgtgtgt   8040
```

-continued

```
gcattgtctg agtaggtgtc attctattct ggggggtggg gtggggcagc acagcaaggg      8100
ggaggattgg gaagacaata gcaggcatgc tggggatgcg gtgggctcta tggagtagta      8160
gttcatgtca tcttattatt cagtatttat aacttgcaaa gaaatgaata tcagagagtg      8220
agaggaactt gtttattgca gcttataatg gttacaaata aagcaatagc atcacaaatt      8280
tcacaaataa agcatttttt tcactgcatt ctagttgtgg tttgtccaaa ctcatcaatg      8340
tatcttatca tgtctggctc tagctatccc gcccctaact ccgcccatcc cgcccctaac      8400
tccgcccagt tccgcccatt ctccgcccca tggctctcac tacttctgga atagctcaga      8460
ggccgaggcg gcctcggcct ctgcataaat aaaaaaaatt agtcgaggct tttttggagg      8520
cctagggacg tacccaattc gccctatagt gagtcgtatt acgcgcgctc actggccgtc      8580
gttttacaac gtcgtgactg ggaaaaccct ggcgttaccc aacttaatcg ccttgcagca      8640
catccccctt tcgccagctg gcgtaatagc gaagaggccc gcaccgatcg cccttcccaa      8700
cagttgcgca gcctgaatgg cgaatggg                                         8728
```

```
<210> SEQ ID NO 14
<211> LENGTH: 8728
<212> TYPE: DNA
<213> ORGANISM: Artificial
<220> FEATURE:
<223> OTHER INFORMATION: Lentiviral vector

<400> SEQUENCE: 14
acgcgccctg tagcggcgca ttaagcgcgg cgggtgtggt ggttacgcgc agcgtgaccg        60
ctacacttgc cagcgcccta gcgcccgctc ctttcgcttt cttcccttcc tttctcgcca       120
cgttcgccgg ctttccccgt caagctctaa atcggggget ccctttaggg ttccgattta       180
gtgctttacg gcacctcgac cccaaaaaac ttgattaggg tgatggttca cgtagtgggc       240
catcgccctg atagacggtt tttcgccctt tgacgttgga gtccacgttc tttaatagtg       300
gactcttgtt ccaaactgga acaacactca accctatctc ggtctattct tttgatttat       360
aagggatttt gccgatttcg gcctattggt taaaaaatga gctgatttaa caaaaattta       420
acgcgaattt aacaaaata ttaacgctta caatttaggt ggcactttc ggggaaatgt         480 gcgcggaacc cctatttgtt tatttttcta aatacattca aatatgtatc cgctcatgag       540
acaataaccc tgataaatgc ttcaataata gcacctagat caagagacag gatgaggatc       600
gtttcgcatg attgaacaag atggattgca cgcaggttct ccggccgctt gggtggagag       660
gctattcggc tatgactggg cacaacagac aatcggctgc tctgatgccg ccgtgttccg       720
gctgtcagcg caggggcgcc cggttctttt tgtcaagacc gacctgtccg gtgccctgaa       780
tgaactgcaa gacgaggcag cgcggctatc gtggctggcc acgacgggcg ttccttgcgc       840
agctgtgctc gacgttgtca ctgaagcggg aagggactgg ctgctattgg gcgaagtgcc       900
ggggcaggat ctcctgtcat ctcaccttgc tcctgccgag aaagtatcca tcatggctga      960
tgcaatgcgg cggctgcata cgcttgatcc ggctacctgc ccattcgacc accaagcgaa      1020
acatcgcatc gagcgagcac gtactcggat ggaagccggt cttgtcgatc aggatgatct      1080
ggacgaagag catcaggggc tcgcgccagc cgaactgttc gccaggctca aggcgagcat      1140
gcccgacggc gaggatctcg tcgtgaccca tggcgatgcc tgcttgccga atatcatggt      1200
ggaaaatggc cgcttttctg gattcatcga ctgtggccgg ctgggtgtgg cggaccgcta      1260
tcaggacata gcgttggcta cccgtgatat tgctgaagag cttggcggcg aatgggctga      1320
ccgcttcctc gtgctttacg gtatcgccgc tcccgattcg cagcgcatcg ccttctatcg      1380
```

-continued

```
ccttcttgac gagttcttct gaattattaa cgcttacaat ttcctgatgc ggtattttct      1440
ccttacgcat ctgtgcggta tttcacaccg catcaggtgg cacttttcgg ggaaatgtgc      1500
gcggaacccc tatttgttta tttttctaaa tacattcaaa tatgtatccg ctcatgacca      1560
aaatccctta acgtgagttt tcgttccact gagcgtcaga ccccgtagaa aagatcaaag      1620
gatcttcttg agatcctttt tttctgcgcg taatctgctg cttgcaaaca aaaaaaccac      1680
cgctaccagc ggtggtttgt ttgccggatc aagagctacc aactcttttt ccgaaggtaa      1740
ctggcttcag cagagcgcag ataccaaata ctgttcttct agtgtagccg tagttaggcc      1800
accacttcaa gaactctgta gcaccgccta catacctcgc tctgctaatc ctgttaccag      1860
tggctgctgc cagtggcgat aagtcgtgtc ttaccgggtt ggactcaaga cgatagttac      1920
cggataaggc gcagcggtcg ggctgaacgg ggggtcgtg cacacagccc agcttggagc      1980
gaacgaccta caccgaactg agatacctac agcgtgagct atgagaaagc gccacgcttc      2040
ccgaagggag aaaggcggac aggtatccgg taagcggcag ggtcggaaca ggagagcgca      2100
cgagggagct ccaggggga aacgcctggt atctttatag tcctgtcggg tttcgccacc      2160
tctgacttga gcgtcgattt ttgtgatgct cgtcagggg gcggagccta ggaaaaacg      2220 ccagcaacgc ggcctttta cggttcctgg ccttttgctg gccttttgct cacatgttct      2280
ttcctgcgtt atccctgat tctgtggata accgtattac cgcctttgag tgagctgata      2340
ccgctcgccg cagccgaacg accgagcgca gcgagtcagt gagcgaggaa gcggaagagc      2400
gcccaatacg caaaccgcct ctccccgcgc gttggccgat tcattaatgc agctggcacg      2460
acaggtttcc cgactggaaa gcgggcagtg agcgcaacgc aattaatgtg agttagctca      2520
ctcattaggc accccaggct ttacacttta tgcttccggc tcgtatgttg tgtggaattg      2580
tgagcggata acaatttcac acaggaaaca gctatgacca tgattacgcc aagcgcgcaa      2640
ttaaccctca ctaaagggaa caaaagctgg agctgcaagc ttggccattg catacgttgt      2700
atccatatca taatatgtac atttatattg gctcatgtcc aacattaccg ccatgttgac      2760
attgattatt gactagttat taatagtaat caattacggg gtcattagtt catagcccat      2820
atatggagtt ccgcgttaca taacttacgg taaatggccc gcctggctga ccgcccaacg      2880
acccccgccc attgacgtca ataatgacgt atgttcccat agtaacgcca atagggactt      2940
tccattgacg tcaatgggtg gagtatttac ggtaaactgc ccacttggca gtacatcaag      3000
tgtatcatat gccaagtacg ccccctattg acgtcaatga cggtaaatgg cccgcctggc      3060
attatgccca gtacatgacc ttatgggact ttcctacttg gcagtacatc tacgtattag      3120
tcatcgctat taccatggtg atgcggtttt ggcagtacat caatgggcgt ggatagcggt      3180
ttgactcacg gggatttcca gtctccacc ccattgacgt caatgggagt ttgttttggc      3240
accaaaatca acgggacttt ccaaaatgtc gtaacaactc cgccccattg acgcaaatgg      3300
gcggtaggcg tgtacggtgg gaggtctata taagcagagc tcgtttagtg aaccggggtc      3360
tctctggtta gaccagatct gagcctggga gctctctggc taactaggga acccactgct      3420
taagcctcaa taaagcttgc cttgagtgct tcaagtagtg tgtgcccgtc tgttgtgtga      3480
ctctggtaac tagagatccc tcagacccct ttagtcagtg tggaaaatct ctagcagtgg      3540
cgcccgaaca gggacttgaa agcgaaaggg aaaccagagg agctctctcg acgcaggact      3600
cggcttgctg aagcgcgcac ggcaagaggc gaggggcggc gactggtgag tacgccaaaa      3660
attttgacta gcggaggcta gaaggagaga gatgggtgcg agagcgtcag tattaagcgg      3720
```

-continued

```
gggagaatta gatcgcgatg ggaaaaaatt cggttaaggc cagggggaaa gaaaaaatat   3780
aaattaaaac atatagtatg ggcaagcagg gagctagaac gattcgcagt taatcctggc   3840
ctgttagaaa catcagaagg ctgtagacaa atactgggac agctacaacc atcccttcag   3900
acaggatcag aagaacttag atcattatat aatacagtag caaccctcta ttgtgtgcat   3960
caaaggatag agataaaaga caccaaggaa gctttagaca agatagagga agagcaaaac   4020
aaaagtaaga ccaccgcaca gcaagcggcc gctgatcttc agacctggag gaggagatat   4080
gagggacaat tggagaagtg aattatataa atataaagta gtaaaaattg aaccattagg   4140
agtagcaccc accaaggcaa agagaagagt ggtgcagaga gaaaaaagag cagtgggaat   4200
aggagctttg ttccttgggt tcttgggagc agcaggaagc actatgggcg cagcgtcaat   4260
gacgctgacg gtacaggcca gacaattatt gtctggtata gtgcagcagc agaacaattt   4320
gctgagggct attgaggcgc aacagcatct gttgcaactc acagtctggg gcatcaagca   4380
gctccaggca agaatcctgg ctgtggaaag atacctaaag gatcaacagc tcctggggat   4440
ttggggttgc tctggaaaac tcatttgcac cactgctgtg ccttggaatg ctagttggag   4500
taataaatct ctggaacaga tttggaatca cacgacctgg atggagtggg acagagaaat   4560
taacaattac acaagcttaa tacactcctt aattgaagaa tcgcaaaacc agcaagaaaa   4620
gaatgaacaa gaattattgg aattagataa atgggcaagt ttgtggaatt ggtttaacat   4680
aacaaattgg ctgtggtata taaaattatt cataatgata gtaggaggct tggtaggttt   4740
aagaatagtt tttgctgtac tttctatagt gaatagagtt aggcagggat attcaccatt   4800
atcgtttcag acccacctcc caaccccgag gggacccgac aggcccgaag gaatagaaga   4860
agaaggtgga gagagagaca gagacagatc cattcgatta gtgaacggat ctcgacggta   4920
tcgatctcga cacaaatggc agtattcatc cacaatttta aaagaaaagg ggggattggg   4980
gggtacagtg cagggggaaag aatagtagac ataatagcaa cagacataca aactaaagaa   5040
ttacaaaaac aaaattacaa aattcaaaat tttcgggttt attacaggga cagcagacat   5100
gaggacagct aaaacaataa gtaatgtaaa atacagcata gcaaaacttt aacctccaaa   5160
tcaagcctct acttgaatcc ttttctgagg gatgaataag gcataggcat caggggctgt   5220
tgccaatgtg cattagctgt ttgcagcctc accttctttc atggagttta agatatagtg   5280
tattttccca aggtttgaac tagctcttca tttctttatg ttttaaatgc actgacctcc   5340
cacattccct ttttagtaaa atattcagaa ataatttaaa tacatcattg caatgaaaat   5400
aaatgttttt tattaggcag aatccagatg ctcaaggccc ttcataatat cccccagttt   5460
agtagttgga cttagggaac aaaggaacct ttaatagaaa ttggacagca agaaagcgag   5520
cttagtgata cttgtgggcc agggcattag ccacaccagc caccactttc tgataggcag   5580
cctgcactgg tggggtgaat tctttgccaa agtgatgggc cagcacacag accagcacgt   5640
tgcccaggag ctgtgggagg aagataagag gtatgaacat gattagcaaa agggcctagc   5700
ttggactcag aataatccag ccttatccca accataaaat aaaagcagaa tggtagctgg   5760
attgtagctg ctattagcaa tatgaaacct cttacatcag ttacaattta tatgcagaaa   5820
taccctgtta cttctcccct tcctatgaca tgaacttaac catagaaaag aaggggaaag   5880
aaaacatcaa gggtcccata gactcaccct gaagttctca ggatccacgt gcagcttgtc   5940
gcagtgcagc tcgctcagct gggcgaaggt gcccttcagg ttgtccaggt gggccaggcc   6000
gtcgctgaag gcgcccagca ccttcttgcc gtggccttc accttggggt tgcccatcac   6060
ggcgtcgggg gtgctcaggt cgccgaagct ctcgaagaag cgctgggtcc aggggtacac   6120
```

-continued

```
caccagcagc ctaagggtgg gaaaatagac caataggcag agagagtcag tgcctatcag    6180
aaacccaaga gtcttctctg tctccacatg cccagtttct attggtctcc ttaaacctgt    6240
cttgtaacct tgataccaac ctgcccaggg cctcaccacc aacggcatcc acgttcacct    6300
tgtcccacag ggcagtaacg gcagacttct cctcaggagt caggtgcacc atggtgtctg    6360
tttgaggttg ctagtgaaca cagttgtgtc agaagcaaat gtaagcaata gatggctctg    6420
ccctgacttt tatgcccagc cctggctcct gccctccctg ctcctgggag tagattggcc    6480
aaccctaggg tgtggctcca cagggtgagg tctaagtgat gacagccgta cctgtccttg    6540
gctcttctgg cactggctta ggagttggac ttcaaaccct cagccctccc tctaagatat    6600
atctcttggc cccataccat cagtacaaat tgctactaaa aacatcctcc tttgcaagtg    6660
tatttactac gtatatgtgt atatatatat atatattcag gaaataatat attctagaat    6720
atgtcacatt ctgtctcagg catccatttt ctttatgatg ccgtttgagg tggagtttta    6780
gtcaggtggt cagcttctcc ttttttttgc catctgccct gtaagcatcc tgctggggac    6840
ccagatagga gtcatcactc taggctgaga acatctgggc acacaccctaa agcctcagca    6900 tgactcatca tgactcagca ttgctgtgct tgagccagaa ggtttgctta gaaggttaca    6960
cagaaccaga aggcgggggt ggggcactga ccccgacagg ggcctggcca gaactgctca    7020
tgcttggact atgggaggtc actaatggag acacacagaa atgtaacagg aactaaggaa    7080
aaactgaagc tttgggggta tagggagca gtcccatgta gtagtagaat gaaaaatgct    7140
gctatgctgt gcctcccca cctttcccat gtctgccctc tactcatggt ctatctctcc    7200
tggctcctgg gagtcatgga ctccacccag caccaccaac ctgacctaac cacctatctg    7260
agcctgccag cctataaccc atctgggccc tgatagctgg tggccagccc tgaccccacc    7320
ccaccctccc tggaacctct gatagacaca tctggcacac cagctcgcaa agtcaccgtg    7380
agggtcttgt gtttgctgag tcaaaattcc ttgaaatcca agtccttaga gactcccagg    7440
cttggattca aagctcctga ctttctgtct agtgtatgtg cagtgagccc cttttcctct    7500
aactgaaaga aggaaaaaaa aatggaaccc aaaatattct acatagtttc catgtcacag    7560
ccagggctgg gcagtctcct gttatttctt ttaaaataaa tatatcattt aaatgcataa    7620
ataagcaaac cctgctcggg aatgggaggg agagtctctg gagtccaccc cttctcggcc    7680
ctggctctgc agatagtgct atcaaagccc tgacagagcc ctgcccattg ctgggccttg    7740
gagtgagtca gcctagtaga gaggcagggc aagccatctc atagctgctg agtgggagag    7800
agaaaagggc tcattgtcta taaactcagg tcatggctat tcttattaaa agaaaagggg    7860
ggactggaag ggctaattca ctcccaacga agacaagatc tgcttttttgc ttgtactggg    7920 tctctctggt tagaccagat ctgagcctgg gagctctctg gctaactagg gaacccactg    7980
cttaagcctc aataaagctt gccttgagtg cttcaagtag tgtgttggtt ttttgtgtgt    8040
gcattgtctg agtaggtgtc attctattct ggggggtggg gtggggcagc acagcaaggg    8100
ggaggattgg gaagacaata gcaggcatgc tggggatgcg gtgggctcta tggagtagta    8160
gttcatgtca tcttattatt cagtatttat aacttgcaaa gaaatgaata tcagagagtg    8220
agaggaactt gtttattgca gcttataatg gttacaaata aagcaatagc atcacaaatt    8280
tcacaaataa agcatttttt tcactgcatt ctagttgtgg tttgtccaaa ctcatcaatg    8340
tatcttatca tgtctggctc tagctatccc gcccctaact ccgcccatcc cgcccctaac    8400
tccgcccagt tccgcccatt ctccgcccca tggctctcac tacttctgga atagctcaga    8460
```

-continued

```
ggccgaggcg gcctcggcct ctgcataaat aaaaaaaatt agtcgaggct tttttggagg    8520
cctagggacg tacccaattc gccctatagt gagtcgtatt acgcgcgctc actggccgtc    8580
gttttacaac gtcgtgactg ggaaaaccct ggcgttaccc aacttaatcg ccttgcagca    8640
catccccctt tcgccagctg gcgtaatagc gaagaggccc gcaccgatcg cccttcccaa    8700
cagttgcgca gcctgaatgg cgaatggg                                       8728
```

```
<210> SEQ ID NO 15
<211> LENGTH: 9362
<212> TYPE: DNA
<213> ORGANISM: Artificial
<220> FEATURE:
<223> OTHER INFORMATION: Lentiviral vector

<400> SEQUENCE: 15
acgcgccctg tagcggcgca ttaagcgcgg cgggtgtggt ggttacgcgc agcgtgaccg     60
ctacacttgc cagcgcccta gcgcccgctc ctttcgcttt cttcccttcc tttctcgcca    120
cgttcgccgg ctttccccgt caagctctaa atcggggggct ccctttaggg ttccgattta    180
gtgctttacg gcacctcgac cccaaaaaac ttgattaggg tgatggttca cgtagtgggc    240
catcgcccta tagacggtt tttcgccctt tgacgttgga gtccacgttc tttaatagtg    300
gactcttgtt ccaaactgga acaacactca accctatctc ggtctattct tttgatttat    360
aagggatttt gccgatttcg gcctattggt taaaaaatga gctgatttaa caaaaattta    420
acgcgaattt taacaaaata ttaacgctta caatttaggt ggcacttttc ggggaaatgt    480
gcgcggaacc cctatttgtt tatttttcta aatacattca aatatgtatc cgctcatgag    540
acaataaccc tgataaatgc ttcaataata gcacctagat caagagacag gatgaggatc    600
gtttcgcatg attgaacaag atggattgca cgcaggttct ccggccgctt gggtggagag    660
gctattcggc tatgactggg cacaacagac aatcggctgc tctgatgccg ccgtgttccg    720
gctgtcagcg caggggcgcc cggttctttt tgtcaagacc gacctgtccg gtgccctgaa    780
tgaactgcaa gacgaggcag cgcggctatc gtggctggcc acgacgggcg ttccttgcgc    840
agctgtgctc gacgttgtca ctgaagcggg aagggactgg ctgctattgg gcgaagtgcc    900
ggggcaggat ctcctgtcat ctcaccttgc tcctgccgag aaagtatcca tcatggctga    960
tgcaatgcgg cggctgcata cgcttgatcc ggctacctgc ccattcgacc accaagcgaa    1020
acatcgcatc gagcgagcac gtactcggat ggaagccggt cttgtcgatc aggatgatct    1080
ggacgaagag catcaggggc tcgcgccagc cgaactgttc gccaggctca aggcgagcat    1140
gcccgacggc gaggatctcg tcgtgaccca tggcgatgcc tgcttgccga atatcatggt    1200
ggaaaatggc cgcttttctg gattcatcga ctgtggccgg ctgggtgtgg cggaccgcta    1260
tcaggacata gcgttggcta cccgtgatat tgctgaagag cttggcggcg aatgggctga    1320
ccgcttcctc gtgctttacg gtatcgccgc tcccgattcg cagcgcatcg ccttctatcg    1380
ccttcttgac gagttcttct gaattattaa cgcttacaat ttcctgatgc ggtattttct    1440
ccttacgcat ctgtgcggta tttcacaccg catcaggtgg cactttcgg ggaaatgtgc     1500 gcggaacccc tatttgttta ttttctaaa tacattcaaa tatgtatccg ctcatgacca     1560
aaatccctta acgtgagttt tcgttccact gagcgtcaga ccccgtagaa aagatcaaag    1620
gatcttcttg agatcctttt tttctgcgcg taatctgctg cttgcaaaca aaaaaaccac    1680
cgctaccagc ggtggtttgt ttgccggatc aagagctacc aactcttttt ccgaaggtaa    1740
ctggcttcag cagagcgcag ataccaaata ctgttcttct agtgtagccg tagttaggcc    1800
```

-continued

```
accacttcaa gaactctgta gcaccgccta catacctcgc tctgctaatc ctgttaccag   1860
tggctgctgc cagtggcgat aagtcgtgtc ttaccgggtt ggactcaaga cgatagttac   1920
cggataaggc gcagcggtcg ggctgaacgg gggggtcgtg cacacagccc agcttggagc   1980
gaacgaccta caccgaactg agatacctac agcgtgagct atgagaaagc gccacgcttc   2040
ccgaagggag aaaggcggac aggtatccgg taagcggcag ggtcggaaca ggagagcgca   2100
cgagggagct tccagggggga aacgcctggt atctttatag tcctgtcggg tttcgccacc   2160
tctgacttga gcgtcgattt ttgtgatgct cgtcaggggg gcggagccta tggaaaaacg   2220
ccagcaacgc ggcctttta cggttcctgg ccttttgctg gccttttgct cacatgttct   2280
ttcctgcgtt atcccctgat tctgtggata accgtattac cgcctttgag tgagctgata   2340
ccgctcgccg cagccgaacg accgagcgca gcgagtcagt gagcgaggaa gcggaagagc   2400
gcccaatacg caaaccgcct ctccccgcgc gttggccgat tcattaatgc agctggcacg   2460
acaggtttcc cgactggaaa gcgggcagtg agcgcaacgc aattaatgtg agttagctca   2520
ctcattaggc accccaggct ttacacttta tgcttccggc tcgtatgttg tgtggaattg   2580
tgagcggata acaatttcac acaggaaaca gctatgacca tgattacgcc aagcgcgcaa   2640
ttaaccctca ctaaagggaa caaaagctgg agctgcaagc ttggccattg catacgttgt   2700
atccatatca taatatgtac atttatattg gctcatgtcc aacattaccg ccatgttgac   2760
attgattatt gactagttat taatagtaat caattacggg gtcattagtt catagcccat   2820
atatggagtt ccgcgttaca taacttacgg taaatggccc gcctggctga ccgcccaacg   2880
acccccgccc attgacgtca ataatgacgt atgttcccat agtaacgcca tagggactt   2940 tccattgacg tcaatgggtg gagtatttac ggtaaactgc ccacttggca gtacatcaag   3000
tgtatcatat gccaagtacg ccccctattg acgtcaatga cggtaaatgg cccgcctggc   3060
attatgccca gtacatgacc ttatgggact ttcctacttg gcagtacatc tacgtattag   3120
tcatcgctat taccatggtg atgcggtttt ggcagtacat caatgggcgt ggatagcggt   3180
ttgactcacg gggatttcca agtctccacc ccattgacgt caatgggagt ttgttttggc   3240
accaaaatca acgggacttt ccaaaatgtc gtaacaactc cgccccattg acgcaaatgg   3300
gcggtaggcg tgtacggtgg gaggtctata taagcagagc tcgtttagtg aaccggggtc   3360
tctctggtta gaccagatct gagcctggga gctctctggc taactaggga acccactgct   3420
taagcctcaa taaagcttgc cttgagtgct tcaagtagtg tgtgcccgtc tgttgtgtga   3480
ctctggtaac tagagatccc tcagacccct ttagtcagtg tggaaaatct ctagcagtgg   3540
cgcccgaaca gggacttgaa agcgaaaggg aaaccagagg agctctctcg acgcaggact   3600
cggcttgctg aagcgcgcac ggcaagaggc gaggggcggc gactggtgag tacgccaaaa   3660
attttgacta gcggaggcta gaaggagaga gatgggtgcg agagcgtcag tattaagcgg   3720
gggagaatta gatcgcgatg ggaaaaaatt cggttaaggc caggggggaaa gaaaaaatat   3780 aaattaaaac atatagtatg ggcaagcagg gagctagaac gattcgcagt taatcctggc   3840
ctgttagaaa catcagaagg ctgtagacaa atactgggac agctacaacc atcccttcag   3900
acaggatcag aagaacttag atcattatat aatacagtag caaccctcta ttgtgtgcat   3960
caaaggatag agataaaaga caccaaggaa gctttagaca agatagagga agagcaaaac   4020
aaaagtaaga ccaccgcaca gcaagcggcc gctgatcttc agacctggag gaggagatat   4080
gagggacaat tggagaagtg aattatataa atataaagta gtaaaaattg aaccattagg   4140
```

-continued

```
agtagcaccc accaaggcaa agagaagagt ggtgcagaga gaaaaaagag cagtgggaat   4200
aggagctttg ttccttgggt tcttgggagc agcaggaagc actatgggcg cagcgtcaat   4260
gacgctgacg gtacaggcca gacaattatt gtctggtata gtgcagcagc agaacaattt   4320
gctgagggct attgaggcgc aacagcatct gttgcaactc acagtctggg gcatcaagca   4380
gctccaggca agaatcctgg ctgtggaaag atacctaaag gatcaacagc tcctggggat   4440
ttggggttgc tctggaaaac tcatttgcac cactgctgtg ccttggaatg ctagttggag   4500
taataaatct ctggaacaga tttggaatca cacgacctgg atggagtggg acagagaaat   4560
taacaattac acaagcttaa tacactcctt aattgaagaa tcgcaaaacc agcaagaaaa   4620
gaatgaacaa gaattattgg aattagataa atgggcaagt ttgtggaatt ggtttaacat   4680
aacaaattgg ctgtggtata taaaattatt cataatgata gtaggaggct tggtaggttt   4740
aagaatagtt tttgctgtac tttctatagt gaatagagtt aggcagggat attcaccatt   4800
atcgtttcag acccacctcc caaccccgag gggacccgac aggcccgaag gaatagaaga   4860
agaaggtgga gagagagaca gagacagatc cattcgatta gtgaacggat ctcgacggta   4920
tcgatctcga cacaaatggc agtattcatc cacaatttta aaagaaaagg ggggattggg   4980
gggtacagtg caggggaaag aatagtgac ataatagcaa cagacataca aactaaagaa   5040
ttacaaaaac aaattacaaa aattcaaaat tttcgggttt attacaggga cagcagacat   5100
gaggacagct aaaacaataa gtaatgtaaa atacagcata gcaaactttt aacctccaaa   5160
tcaagcctct acttgaatcc ttttctgagg gatgaataag gcataggcat caggggctgt   5220
tgccaatgtg cattagctgt ttgcagcctc accttctttc atggagttta agatatagtg   5280
tattttccca aggtttgaac tagctcttca tttctttatg ttttaaatgc actgacctcc   5340
cacattccct ttttagtaaa atattcagaa ataatttaaa tacatcattg caatgaaaat   5400
aaatgttttt tattaggcag aatccagatg ctcaaggccc ttcataatat cccccagttt   5460
agtagttgga cttagggaac aaaggaacct ttaatagaaa ttggacagca agaaagcgag   5520
cttagtgata cttgtgggcc agggcattag ccacaccagc caccactttc tgataggcag   5580
cctgcactgg tggggtgaat tctttgccaa agtgatgggc cagcacacag accagcacgt   5640
tgcccaggag ctgtgggagg aagataagag gtatgaacat gattagcaaa agggcctagc   5700
ttggactcag aataatccag ccttatccca accataaaat aaaagcagaa tggtagctgg   5760
attgtagctg ctattagcaa tatgaaacct cttacatcag ttacaattta tatgcagaaa   5820
taccctgtta cttctcccct tcctatgaca tgaacttaac catagaaaag aaggggaaag   5880
aaaacatcaa gggtcccata gactcaccct gaagttctca ggatccacgt gcagcttgtc   5940
acagtgcagc tcactcagct gggcaaaggt gcccttgagg ttgtccaggt gagccaggcc   6000
atcactaaag gcaccgagca ctttcttgcc atgagccttc accttagggt tgcccataac   6060
agcatcagga gtggacagat ccccaaagga ctcaaagaac ctctgggtcc aagggtagac   6120
caccagcagc ctaagggtgg gaaaatagac caataggcag agagagtcag tgcctatcag   6180
aaacccaaga gtcttctctg tctccacatg cccagtttct attggtctcc ttaaacctgt   6240
cttgtaacct tgataccaac ctgcccaggg cctcaccacc aacggcatcc acgttcacct   6300
tgtcccacag ggcagtaacg gcagacttct cctcaggagt caggtgcacc atggtgtctg   6360
tttgaggttg ctagtgaaca cagttgtgtc agaagcaaat gtaagcaata gatggctctg   6420
ccctgacttt tatgcccagc cctggctcct gccctccctg ctcctgggag tagattggcc   6480
aaccctaggg tgtggctcca cagggtgagg tctaagtgat gacagccgta cctgtccttg   6540
```

-continued

```
gctcttctgg cactggctta ggagttggac ttcaaaccct cagccctccc tctaagatat   6600
atctcttggc cccataccat cagtacaaat tgctactaaa aacatcctcc tttgcaagtg   6660
tatttaccat caataattct agccccacag gagtttgttc tgaaagtaaa cttccacaac   6720
cgcaagctta ttgaggctaa ggcatctgtg aaggaaagaa acatctcctc taaaccacta   6780
tgctgctaga gcctcttttc tgtactcaag cctcattcag acactagtgt caccagtctc   6840
ctcatatacc tattgtattt tcttcttctt gctggtttag tcatgttttc tgggagctta   6900
ggggcttatt ttattttgtt ttgttttcta atcaacagag atgggcaaac ccattatttt   6960
tttctttaga cttgggatgg tgatagctgg gcagcgtcag aaactgtgtg tggatataga   7020
taagagctca ggactatgct gagctgtgat gagggagggg cctagctaaa ggcagtgaga   7080
gtcagaatgc tcctgctatt gccttctcag tccccacgct tggtttctac acaagtagat   7140
acatagaaaa ggctataggt tagtgtttga gagtcctgca tgattagttg ctcagaaatg   7200
cccgataaat atgttatgtg tgtttatgta tatatatgtt ttatatgtgt gtgtgtgtgt   7260
gttgtgttta caaatatgtg attatcatca aaacgtgagg gtacgtatat gtgtatatat   7320
atatatatat tcaggaaata atatattcta gaatatgtca cattctgtct caggcatcca   7380
ttttctttat gatgccgttt gaggtggagt tttagtcagg tggtcagctt ctcctttttt   7440
ttgccatctg ccctgtaagc atcctgctgg ggacccagat aggagtcatc actctaggct   7500
gagaacatct gggcacacac cctaagcctc agcatgactc atcatgactc agcattgctg   7560
tgcttgagcc agaaggtttg cttagaaggt tacacagaac cagaaggcgg gggtggggca   7620
ctgaccccga caggggcctg gccagaactg ctcatgcttg gactatggga ggtcactaat   7680
ggagacacac agaaatgtaa caggaactaa ggaaaaactg aagctttggg ggtataggggg   7740 agcagtccca tgtagtagta gaatgaaaaa tgctgctatg ctgtgcctcc cccacctttc   7800
ccatgtctgc cctctactca tggtctatct ctcctggctc ctgggagtca tggactccac   7860
ccagcaccac caacctgacc taaccaccta tctgagcctg ccagcctata acccatctgg   7920
gccctgatag ctggtggcca gccctgaccc caccccaccc tccctggaac ctctgataga   7980
cacatctggc acaccagctc gcaaagtcac cgtgagggtc ttgtgtttgc tgagtcaaaa   8040
ttccttgaaa tccaagtcct tagagactcc caggcttgga ttcaaagctc ctgactttct   8100
gtctagtgta tgtgcagtga gcccctttttc ctctaactga aagaaggaaa aaaaaatgga   8160
acccaaaata ttctacatag tttccatgtc acagccaggg ctgggcagtc tcctgttatt   8220
tcttttaaaa taaatatatc atttaaatgc ataaataagc aaaccctgct cgggaatggg   8280
agggagagtc tctggagtcc accccttctc ggccctggct ctgcagatag tgctatcaaa   8340
gccctgacag agccctgccc attgctgggc cttggagtga gtcagcctag tagagaggca   8400
gggcaagcca tctcatagct gctgagtggg agagagaaaa gggctcattg tctataaact   8460
caggtcatgg ctattcttat taaaagaaaa ggggggactg gaagggctaa ttcactccca   8520
acgaagacaa gatctgcttt ttgcttgtac tgggtctctc tggttagacc agatctgagc   8580
ctgggagctc tctggctaac tagggaaccc actgcttaag cctcaataaa gcttgccttg   8640
agtgcttcaa gtagtgtgtt ggtttttttgt gtgtgcattt tctgagtagg tgtcattcta   8700
ttctgggggg tggggtgggg cagcacagca aggggagga ttgggaagac aatagcaggc   8760
atgctgggga tgcggtgggc tctatggagt agtagttcat gtcatcttat tattcagtat   8820
ttataacttg caaagaaatg aatatcagag agtgagagga acttgtttat tgcagcttat   8880
```

-continued

```
aatggttaca aataaagcaa tagcatcaca aatttcacaa ataaagcatt tttttcactg    8940
cattctagtt gtggtttgtc caaactcatc aatgtatctt atcatgtctg gctctagcta    9000
tcccgcccct aactccgccc atcccgcccc taactccgcc cagttccgcc cattctccgc    9060
cccatggctc tcactacttc tggaatagct cagaggccga ggcggcctcg gcctctgcat    9120
aaataaaaaa aattagtcga ggcttttttg gaggcctagg gacgtaccca attcgcccta    9180
tagtgagtcg tattacgcgc gctcactggc cgtcgtttta caacgtcgtg actgggaaaa    9240
ccctggcgtt acccaactta atcgccttgc agcacatccc cctttcgcca gctggcgtaa    9300
tagcgaagag gcccgcaccg atcgcccttc ccaacagttg cgcagcctga atggcgaatg    9360
gg                                                                    9362
```

```
<210> SEQ ID NO 16
<211> LENGTH: 9362
<212> TYPE: DNA
<213> ORGANISM: Artificial
<220> FEATURE:
<223> OTHER INFORMATION: Lentiviral vector

<400> SEQUENCE: 16
```

```
acgcgccctg tagcggcgca ttaagcgcgg cgggtgtggt ggttacgcgc agcgtgaccg      60
ctacacttgc cagcgcccta gcgcccgctc ctttcgcttt cttcccttcc tttctcgcca     120
cgttcgccgg ctttccccgt caagctctaa atcggggggct ccctttaggg ttccgattta    180
gtgctttacg gcacctcgac cccaaaaaac ttgattaggg tgatggttca cgtagtgggc     240
catcgccctg atagacggtt tttcgccctt tgacgttgga gtccacgttc tttaatagtg     300
gactcttgtt ccaaactgga acaacactca accctatctc ggtctattct tttgatttat     360
aagggatttt gccgatttcg gcctattggt taaaaaatga gctgatttaa caaaaattta     420
acgcgaattt taacaaaata ttaacgctta catttaggt ggcacttttc ggggaaatgt      480
gcgcggaacc cctatttgtt tatttttcta aatacattca aatatgtatc cgctcatgag     540
acaataaccc tgataaatgc ttcaataata gcacctagat caagagacag gatgaggatc     600
gtttcgcatg attgaacaag atggattgca cgcaggttct ccggccgctt gggtggagag     660
gctattcggc tatgactggg cacaacagac aatcggctgc tctgatgccg ccgtgttccg     720
gctgtcagcg caggggcgcc cggttctttt tgtcaagacc gacctgtccg gtgccctgaa     780
tgaactgcaa gacgaggcag cgcggctatc gtggctggcc acgacgggcg ttccttgcgc     840
agctgtgctc gacgttgtca ctgaagcggg aagggactgg ctgctattgg gcgaagtgcc     900
ggggcaggat ctcctgtcat ctcaccttgc tcctgccgag aaagtatcca tcatggctga     960
tgcaatgcgg cggctgcata cgcttgatcc ggctacctgc ccattcgacc accaagcgaa    1020
acatcgcatc gagcgagcac gtactcggat ggaagccggt cttgtcgatc aggatgatct    1080
ggacgaagag catcaggggc tcgcgccagc cgaactgttc gccaggctca aggcgagcat    1140
gcccgacggc gaggatctcg tcgtgaccca tggcgatgcc tgcttgccga atatcatggt    1200
ggaaaatggc cgcttttctg gattcatcga ctgtggccgg ctgggtgtgg cggaccgcta    1260
tcaggacata gcgttggcta cccgtgatat tgctgaagag cttggcggcg aatgggctga    1320
ccgcttcctc gtgctttacg gtatcgccgc tcccgattcg cagcgcatcg ccttctatcg    1380
ccttcttgac gagttcttct gaattattaa cgcttacaat ttcctgatgc ggtattttct    1440
ccttacgcat ctgtgcggta tttcacaccg catcaggtgg cacttttcgg ggaaatgtgc    1500
gcggaacccc tatttgttta ttttttctaaa tacattcaaa tatgtatccg ctcatgacca    1560
```

```
aaatccctta acgtgagttt tcgttccact gagcgtcaga ccccgtagaa aagatcaaag    1620
gatcttcttg agatccttt tttctgcgcg taatctgctg cttgcaaaca aaaaaaccac    1680
cgctaccagc ggtggtttgt ttgccggatc aagagctacc aactctttt ccgaaggtaa    1740 ctggcttcag cagagcgcag ataccaaata ctgttcttct agtgtagccg tagttaggcc    1800
accacttcaa gaactctgta gcaccgccta catacctcgc tctgctaatc ctgttaccag    1860
tggctgctgc cagtggcgat aagtcgtgtc ttaccgggtt ggactcaaga cgatagttac    1920
cggataaggc gcagcggtcg gctgaacggg ggggtcgtg cacacagccc agcttggagc    1980
gaacgaccta caccgaactg agatacctac agcgtgagct atgagaaagc gccacgcttc    2040
ccgaagggag aaaggcggac aggtatccgg taagcggcag ggtcggaaca ggagagcgca    2100
cgagggagct tccaggggga aacgcctggt atctttatag tcctgtcggg tttcgccacc    2160
tctgacttga gcgtcgattt ttgtgatgct cgtcaggggg gcggagccta tggaaaaacg    2220
ccagcaacgc ggccttttta cggttcctgg ccttttgctg gccttttgct cacatgttct    2280
ttcctgcgtt atcccctgat tctgtggata accgtattac cgcctttgag tgagctgata    2340
ccgctcgccg cagccgaacg accgagcgca gcgagtcagt gagcgaggaa gcggaagagc    2400
gcccaatacg caaaccgcct ctccccgcgc gttggccgat tcattaatgc agctggcacg    2460
acaggtttcc cgactggaaa gcgggcagtg agcgcaacgc aattaatgtg agttagctca    2520
ctcattaggc accccaggct ttacacttta tgcttccggc tcgtatgttg tgtggaattg    2580
tgagcggata acaatttcac acaggaaaca gctatgacca tgattacgcc aagcgcgcaa    2640
ttaaccctca ctaaagggaa caaaagctgg agctgcaagc ttggccattg catacgttgt    2700
atccatatca taatatgtac atttatattg gctcatgtcc aacattaccg ccatgttgac    2760
attgattatt gactagttat taatagtaat caattacggg gtcattagtt catagcccat    2820
atatggagtt ccgcgttaca taacttacgg taaatggccc gcctggctga ccgcccaacg    2880
acccccgccc attgacgtca ataatgacgt atgttcccat agtaacgcca atagggactt    2940
tccattgacg tcaatgggtg gagtatttac ggtaaactgc ccacttggca gtacatcaag    3000
tgtatcatat gccaagtacg cccctattg acgtcaatga cggtaaatgg cccgcctggc    3060
attatgccca gtacatgacc ttatgggact ttcctacttg gcagtacatc tacgtattag    3120
tcatcgctat taccatggtg atgcggtttt ggcagtacat caatgggcgt ggatagcggt    3180
ttgactcacg gggatttcca agtctccacc ccattgacgt caatgggagt ttgttttggc    3240
accaaaatca acgggacttt ccaaaatgtc gtaacaactc cgccccattg acgcaaatgg    3300
gcggtaggcg tgtacggtgg gaggtctata taagcagagc tcgtttagtg aaccggggtc    3360
tctctggtta gaccagatct gagcctggga gctctctggc taactaggga acccactgct    3420
taagcctcaa taaagcttgc cttgagtgct tcaagtagtg tgtgcccgtc tgttgtgtga    3480
ctctggtaac tagagatccc tcagacccct ttagtcagtg tggaaaatct ctagcagtgg    3540
cgcccgaaca gggacttgaa agcgaaaggg aaaccagagg agctctctcg acgcaggact    3600
cggcttgctg aagcgcgcac ggcaagaggc gaggggcggc gactggtgag tacgccaaaa    3660
attttgacta gcggaggcta gaaggagaga gatgggtgcg agagcgtcag tattaagcgg    3720
gggagaatta gatcgcgatg ggaaaaaatt cggttaaggc caggggggaaa gaaaaaatat    3780 aaattaaaac atatagtatg ggcaagcagg gagctagaac gattcgcagt taatcctggc    3840
ctgttagaaa catcagaagg ctgtagacaa atactgggac agctacaacc atcccttcag    3900
```

```
acaggatcag aagaacttag atcattatat aatacagtag caaccctcta ttgtgtgcat    3960
caaaggatag agataaaaga caccaaggaa gctttagaca agatagagga agagcaaaac    4020
aaaagtaaga ccaccgcaca gcaagcggcc gctgatcttc agacctggag gaggagatat    4080
gagggacaat tggagaagtg aattatataa atataaagta gtaaaaattg aaccattagg    4140
agtagcaccc accaaggcaa agagaagagt ggtgcagaga gaaaaaagag cagtgggaat    4200
aggagctttg ttccttgggt tcttgggagc agcaggaagc actatgggcg cagcgtcaat    4260
gacgctgacg gtacaggcca gacaattatt gtctggtata gtgcagcagc agaacaattt    4320
gctgagggct attgaggcgc aacagcatct gttgcaactc acagtctggg gcatcaagca    4380
gctccaggca agaatcctgg ctgtggaaag atacctaaag gatcaacagc tcctggggat    4440
ttggggttgc tctggaaaac tcatttgcac cactgctgtg ccttggaatg ctagttggag    4500
taataaatct ctggaacaga tttggaatca cacgacctgg atggagtggg acagagaaat    4560
taacaattac acaagcttaa tacactcctt aattgaagaa tcgcaaaacc agcaagaaaa    4620
gaatgaacaa gaattattgg aattagataa atgggcaagt ttgtggaatt ggtttaacat    4680
aacaaattgg ctgtggtata taaaattatt cataatgata gtaggaggct tggtaggttt    4740
aagaatagtt tttgctgtac tttctatagt gaatagagtt aggcagggat attcaccatt    4800
atcgtttcag acccacctcc caaccccgag gggacccgac aggcccgaag gaatagaaga    4860
agaaggtgga gagagagaca gagacagatc cattcgatta gtgaacggat ctcgacggta    4920
tcgatctcga cacaaatggc agtattcatc cacaatttta aaagaaaagg ggggattggg    4980
gggtacagtg caggggaaag aatagtagac ataatagcaa cagacataca aactaaagaa    5040
ttacaaaaac aaattacaaa aattcaaaat tttcgggttt attacaggga cagcagacat    5100
gaggacagct aaaacaataa gtaatgtaaa atacagcata gcaaactttt aacctccaaa    5160
tcaagcctct acttgaatcc ttttctgagg gatgaataag gcataggcat caggggctgt    5220
tgccaatgtg cattagctgt ttgcagcctc accttctttc atggagttta agatatagtg    5280
tattttccca aggtttgaac tagctcttca tttctttatg ttttaaatgc actgacctcc    5340
cacattccct ttttagtaaa atattcagaa ataatttaaa tacatcattg caatgaaaat    5400
aaatgttttt tattaggcag aatccagatg ctcaaggccc ttcataatat cccccagttt    5460
agtagttgga cttagggaac aaaggaacct ttaatagaaa ttggacagca agaaagcgag    5520
cttagtgata cttgtgggcc agggcattag ccacaccagc caccactttc tgataggcag    5580
cctgcactgg tggggtgaat tctttgccaa agtgatgggc cagcacacag accagcacgt    5640
tgcccaggag ctgtgggagg aagataagag gtatgaacat gattagcaaa agggcctagc    5700
ttggactcag aataatccag ccttatccca accataaaat aaaagcagaa tggtagctgg    5760
attgtagctg ctattagcaa tatgaaacct cttacatcag ttacaattta tatgcagaaa    5820
taccctgtta cttctcccct tcctatgaca tgaacttaac catagaaaag aaggggaaag    5880
aaaacatcaa gggtcccata gactcaccct gaagttctca ggatccacgt gcagcttgtc    5940
gcagtgcagc tcgctcagct gggcgaaggt gcccttcagg ttgtccaggt gggccaggcc    6000
gtcgctgaag gcgcccagca ccttcttgcc gtgggccttc accttggggt tgcccatcac    6060
ggcgtcgggg gtgctcaggt cgccgaagct ctcgaagaag cgctgggtcc aggggtacac    6120
caccagcagc ctaagggtgg gaaaatagac caataggcag agagagtcag tgcctatcag    6180
aaacccaaga gtcttctctg tctccacatg cccagtttct attggtctcc ttaaacctgt    6240
cttgtaacct tgataccaac ctgcccaggg cctcaccacc aacggcatcc acgttcacct    6300
```

```
tgtcccacag ggcagtaacg gcagacttct cctcaggagt caggtgcacc atggtgtctg    6360
tttgaggttg ctagtgaaca cagttgtgtc agaagcaaat gtaagcaata gatggctctg    6420
ccctgacttt tatgcccagc cctggctcct gccctccctg ctcctgggag tagattggcc    6480
aaccctaggg tgtggctcca cagggtgagg tctaagtgat gacagccgta cctgtccttg    6540
gctcttctgg cactggctta ggagttggac ttcaaaccct cagccctccc tctaagatat    6600
atctcttggc cccataccat cagtacaaat tgctactaaa aacatcctcc tttgcaagtg    6660
tatttaccat caataattct agccccacag gagtttgttc tgaaagtaaa cttccacaac    6720
cgcaagctta ttgaggctaa ggcatctgtg aaggaaagaa acatctcctc taaaccacta    6780
tgctgctaga gcctcttttc tgtactcaag cctcattcag acactagtgt caccagtctc    6840
ctcatatacc tattgtattt tcttcttctt gctggtttag tcatgttttc tgggagctta    6900
ggggcttatt ttattttgtt ttgtttttcta atcaacagag atgggcaaac ccattatttt    6960
tttctttaga cttgggatgg tgatagctgg gcagcgtcag aaactgtgtg tggatataga    7020
taagagctca ggactatgct gagctgtgat gagggagggg cctagctaaa ggcagtgaga    7080
gtcagaatgc tcctgctatt gccttctcag tccccacgct tggtttctac acaagtagat    7140
acatagaaaa ggctataggt tagtgtttga gagtcctgca tgattagttg ctcagaaatg    7200
cccgataaat atgttatgtg tgtttatgta tatatatgtt ttatatgtgt gtgtgtgtgt    7260
gttgtgttta caaatatgtg attatcatca aaacgtgagg gtacgtatat gtgtatatat    7320
atatatatat tcaggaaata atatattcta gaatatgtca cattctgtct caggcatcca    7380
ttttctttat gatgccgttt gaggtggagt tttagtcagg tggtcagctt ctcctttttt    7440
ttgccatctg ccctgtaagc atcctgctgg ggacccagat aggagtcatc actctaggct    7500
gagaacatct gggcacacac cctaagcctc agcatgactc atcatgactc agcattgctg    7560
tgcttgagcc agaaggtttg cttagaaggt tacacagaac cagaaggcgg gggtggggca    7620
ctgaccccga caggggcctg gccagaactg ctcatgcttg gactatggga ggtcactaat    7680
ggagacacac agaaatgtaa caggaactaa ggaaaaactg aagctttggg ggtatagggg    7740
agcagtccca tgtagtagta gaatgaaaaa tgctgctatg ctgtgcctcc cccacctttc    7800
ccatgtctgc cctctactca tggtctatct ctcctggctc ctgggagtca tggactccac    7860
ccagcaccac caacctgacc taaccaccta tctgagcctg ccagcctata acccatctgg    7920
gccctgatag ctggtggcca gccctgaccc caccccaccc tccctggaac ctctgataga    7980
cacatctggc acaccagctc gcaaagtcac cgtgagggtc ttgtgtttgc tgagtcaaaa    8040
ttccttgaaa tccaagtcct tagagactcc caggcttgga ttcaaagctc ctgactttct    8100
gtctagtgta tgtgcagtga gccccttttc tctaactga aagaaggaaa aaaaaatgga    8160
acccaaaata ttctacatag tttccatgtc acagccaggg ctgggcagtc tcctgttatt    8220
tcttttaaaa taaatatatc atttaaatgc ataaataagc aaaccctgct cgggaatggg    8280
agggagagtc tctggagtcc accccttctc ggccctggct ctgcagatag tgctatcaaa    8340
gccctgacag agccctgccc attgctgggc cttggagtga gtcagcctag tagagaggca    8400
gggcaagcca tctcatagct gctgagtggg agagagaaaa gggctcattg tctataaact    8460
caggtcatgg ctattcttat taaaagaaaa gggggggactg gaagggctaa ttcactccca    8520
acgaagacaa gatctgcttt ttgcttgtac tgggtctctc tggttagacc agatctgagc    8580
ctgggagctc tctggctaac tagggaaccc actgcttaag cctcaataaa gcttgccttg    8640
```

-continued

```
agtgcttcaa gtagtgtgtt ggttttttgt gtgtgcattg tctgagtagg tgtcattcta   8700
ttctgggggg tggggtgggg cagcacagca aggggggagga ttgggaagac aatagcaggc  8760
atgctgggga tgcggtgggc tctatggagt agtagttcat gtcatcttat tattcagtat   8820
ttataacttg caaagaaatg aatatcagag agtgagagga acttgtttat tgcagcttat   8880
aatggttaca aataaagcaa tagcatcaca aatttcacaa ataaagcatt tttttcactg   8940
cattctagtt gtggtttgtc caaactcatc aatgtatctt atcatgtctg gctctagcta   9000 tcccgccccct aactccgccc atcccgcccc taactccgcc cagttccgcc cattctccgc   9060
cccatggctc tcactacttc tggaatagct cagaggccga ggcggcctcg gcctctgcat   9120
aaataaaaaa aattagtcga ggcttttttg gaggcctagg gacgtaccca attcgcccta   9180
tagtgagtcg tattacgcgc gctcactggc cgtcgtttta caacgtcgtg actgggaaaa   9240
ccctggcgtt acccaactta atcgccttgc agcacatccc cctttcgcca gctggcgtaa   9300
tagcgaagag gcccgcaccg atcgcccttc ccaacagttg cgcagcctga atggcgaatg   9360
gg                                                                  9362
```

AUGMENTATIONS TO LENTIVIRAL VECTORS (CCLC-MGATA/ANK-CORE LCR-BETA-AS3-FB) TO INCREASE EXPRESSION

CROSS-REFERENCE TO RELATED APPLICATIONS

This application is a National Phase Application of PCT International Application No. PCT/US2020/020053, International Filing Date Feb. 27, 2020, claiming the benefit of U.S. Patent Applications Nos. 62/812,173, filed on Feb. 28, 2019, and 62/846,504, filed on May 10, 2019, which are hereby incorporated by reference.

INCORPORATION BY REFERENCE OF SEQUENCE LISTING PROVIDED AS A TEXT FILE

A Sequence Listing is provided herewith as a text file, "UCLAP208P2US_ST25.txt" created on May 10, 2019 and having a size of 107,770 bytes. The contents of the text file are incorporated by reference herein in their entirety.

BACKGROUND

Sickle cell disease (SCD) is one of the most common monogenic disorders worldwide and is a major cause of morbidity and early mortality (Hoffman et al. (2009) Hematology: Basic Principles and Practice. 5th ed. London, United Kingdom, Churchill Livingstone). SCD affects approximately 80,000 Americans, and causes significant neurologic, pulmonary, and renal injury, as well as severe acute and chronic pain that adversely impacts quality of life. It is estimated that approximately 240,000 children are born annually in Africa with SCD and 80% die by their second birthday. The average lifespan of subjects with SCD in the United States is approximately 40 years and this has remained unchanged over the last 3-4 decades.

SCD is caused by a single amino acid change in β-globin (Glu 6 to Val 6) which leads to hemoglobin polymerization and red blood cell (rbc) sickling. SCD typically results in continual low-grade ischemia and episodic exacerbations or "crises" resulting in tissue ischemia, organ damage, and premature death.

Although SCD is well characterized, there is still no ideal long-term treatment. Current therapies are based on induction of fetal hemoglobin (HbF) to inhibit polymerization of sickle hemoglobin (HbS) (Voskaridou et al. (2010) Blood, 115(12): 2354-2363) and cell dehydration (Eaton and Hofrichter (1987) Blood, 70(5): 1245-1266) or reduction of the percentage of HbS by transfusions (Stamatoyannopoulos et al., eds. (2001) Molecular Basis of Blood Diseases. 3rd ed. Philadelphia, Pennsylvania, USA: WB Saunders). Allogeneic human stem cell transplantation (HSCT) from bone marrow (BM) or umbilical cord blood (UCB) or mobilized peripheral blood stem cells (mPBSC) is a potentially curative therapy, although only a small percentage of patients have undergone this procedure, mostly children with severe symptoms who had HLA-matched sibling donors (Bolaños-Meade and Brodsky (2009) Curr. Opin. Oncol. 21(2): 158-161; Rees et al. (2010) Lancet, 376(9757): 2018-2031; Shenoy (2011) Hematology Am Soc Hematol Educ Program. 2011: 273-279).

Transplantation of allogeneic cells carries the risk of graft-versus host disease (GvHD), which can be a cause of extensive morbidity. HSCT using UCB from matched unrelated donors holds reduced risk of acute or chronic GvHD compared with using BM; however, there is a higher probability of engraftment failure using UCB as a result of its lower cell dose and immunologic immaturity (Kamani et al. (2012) Biol. Blood Marrow Transplant. 18(8): 1265-1272; Locatelli and Pagliara (2012) Pediatr. Blood Cancer. 59(2): 372-376).

Gene therapy with autologous human stem cells (HSCs) is an alternative to allogeneic HSCT, since it avoids the limitations of finding a matched donor and the risks of GvHD and graft rejection. For gene therapy application in SCD patients, one source for autologous HSC would be BM, due to the complications previously described when G-CSF was used to collect autologous peripheral blood stem cells (PBSCs) in SCD patients (Abboud et al. (1998) Lancet 351(9107): 959; Adler et al. (2001) Blood, 97(10): 3313-3314; Fitzhugh et al. (2009) Cytotherapy, 11(4): 464-471). However, more recently, plerixafor, an immunostimulant, can be used to mobilize hematopoietic stem cells into the blood stream. The stem cells can then be extracted from the blood and use. Although general anesthesia imposes a risk for SCD patients as well, current best medical practices can minimize these (Neumayr et al. (1998) Am. J. Hematol. 57(2): 101-108).

The development of integrating vectors for β-globin gene transfer has been challenging due to the complex regulatory elements needed for high-level, erythroid-specific expression (Lisowski a& Sadelain (2008) Br. J. Haematol. 141(3): 335-345). γ-Retroviral vectors were unable to transfer these β-globin expression cassettes intact (Gelinas et al. (1989) Adv. Exp. Med. Biol. 271: 135-148; Gelinas et al. (1989) Prog. Clin. Biol. Res. 316B: 235-249). In contrast, lentiviral vectors (LV) can transfer β-globin cassettes intact with relatively high efficiency, although the titers of these vectors are reduced compared with those of vectors bearing simpler cassettes (see, e.g., May et al. (2000) Nature 406(6791): 82-86; Pawliuk et al. (2001) Science, 294(5550): 2368-2371). In the last decade, many groups have developed different β-globin LV for targeting β-hemoglobinopathies, with successful therapeutic results following transplantation of ex vivo-modified HSC in mouse models (May et al. (2000) Nature 406(6791): 82-86; Pawliuk et al. (2001) Science, 294(5550): 2368-2371; Levasseur et al. (2003) Blood, 102(13):4312-4319; Hanawa et al. (2004) Blood, 104(8): 2281-2290; Puthenveetil et al. (2004) Blood, 104 (12): 3445-3453; Miccio et al. (2008) Proc. Natl. Acad. Sci. USA, 105(30):10547-10552; Pestina et al. (2008) Mol. Ther. 17(2): 245-252). Recently, Bluebird Bio, updated trial results with longer follow-up from lentiviral vector treated patients with beta-thalassemia and sickle cell disease. Across three small studies testing the gene therapy in the two blood diseases, patients given LentiGlobin saw their levels of the crucial oxygen-carrying protein hemoglobin rise to approach normal, eliminating the need for blood transfusions in most over the studied period.

Sickle patients with hereditary persistence of fetal hemoglobin (HbF) (HPFH) have improved survival and amelioration of clinical symptoms, with maximal clinical benefits observed when the HbF is elevated above threshold values (e.g., 8%-15% of the total cellular Hb) (Voskaridou et al. (2010) Blood, 115(12): 2354-2363; Platt et al. (1994) N. Engl. J. Med. 330(23): 1639-1644). Therefore, some gene therapy strategies have employed viral vectors carrying the human γ-globin gene (HBG1/2). However, these constructs expressed HbF poorly in adult erythroid cells, since fetal-specific transcription factors are required for high-level expression of the γ-globin gene (Chakalova et al. (2005)

*Blood* 105(5): 2154-2160; Russell (2007) *Eur. J. Haematol.* 79(6): 516-525). These limitations have been overcome by embedding the exons encoding human γ-globin within the human β-globin gene 5' promoter and 3' enhancer elements (Hanawa et al. (2004) Blood, 104(8): 2281-2290; Persons et al. (2002) *Blood,* 101(6): 2175-2183; Perumbeti et al. (2009) *Blood,* 114(6): 1174-1185). Breda et al. (2012) *PLoS One,* 7(3): e32345 used an LV vector encoding the human hemoglobin (HBB) gene to increase the expression of normal HbA in CD34$^+$-derived erythroid cells from SCD patients, however, the expression level needed when the HBB gene is used would be higher than would be required for HBG1/2 gene expression to achieve therapeutic benefits in SCD patients.

Another approach is to modify β-globin genes to confer antisickling activity by substituting key amino acids from γ-globin. The modified β-globin cassette should yield the necessary high-level, erythroid-specific expression in adult erythroid cells. Pawliuk et al. (2001) *Science,* 294(5550): 2368-2371 designed an LV carrying a human β-globin gene with the amino acid modification T87Q. The glutamine at position 87 of γ-globin has been implicated in the anti-sickling activity of HbF (Nagel et al. (1979) *Proc. Natl. Acad. Sci., USA,* 76(2): 670-672). This anti-sickling construct corrected SCD in 2 murine models of the disease, and a similar LV has been used in a clinical trial for β-thalassemia and SCD in France (Cavazzana-Calvo et al. (2010) *Nature,* 467(7313): 318-322).

Townes and colleagues have taken a similar approach, developing a recombinant human anti-sickling β-globin gene (HBBAS3) encoding a β-globin protein (HbAS3) that has 3 amino substitutions compared with the original (HbA): T87Q for blocking the lateral contact with the canonical Val 6 of HbS, E22A to disrupt axial contacts (McCune et al. (1994) *Proc. Natl. Acad. Sci. USA,* 91(21): 9852-9856) and G16D, which confers a competitive advantage over sickle-β-globin chains for interaction with the α-globin polypeptide. Functional analysis of the purified HbAS3 protein demonstrated that this recombinant protein had potent activity to inhibit HbS tetramer polymerization (Levasseur et al. (2004) *J. Biol. Chem.* 279(26): 27518-27524.). Levasseur et al. (2003) *Blood,* 102(13): 4312-4319, showed efficient transduction of BM stem cells from a murine model of SCD with a self-inactivating (SIN) LV carrying the HBBAS3 transgene that resulted in normalized rbc physiology and prevented the pathological manifestations of SCD.

Unfortunately, current β-globin expression vectors, suffer from low vector titer and sub-optimal gene transfer to hematopoietic stem cells, representing a major barrier toward the effective implementation of this gene therapy strategy to the clinic.

SUMMARY

Various embodiments contemplated herein may include, but need not be limited to, one or more of the following:

Embodiment 1: A recombinant lentiviral vector (LV) comprising:

an expression cassette comprising a nucleic acid construct comprising:

a human β-globin locus control region (LCR) comprising an HS1 ENCODE core (EC1) sequence (SEQ ID NO:1), and one or more of an HS2 core sequence (ecHS2 (SEQ ID NO: 2)), an HS3 core sequence (ecHS3 (SEQ ID NO:3)), an HS4 core sequence (ecHS4 (SEQ ID NO:4)), a full length HS2, a full length HS3, and/or a full length HS4.

Embodiment 2: The vector of embodiment 1, wherein said human β-globin locus control region (LCR) comprises an HS2 core sequence (ecHS2 (SEQ ID NO: 2)).

Embodiment 3: The vector of embodiment 1, wherein said human β-globin locus control region (LCR) comprises a full length HS2 sequence.

Embodiment 4: The vector according to any one of embodiments 1-3, wherein said human β-globin locus control region (LCR) comprises an HS3 core sequence (ecHS3 (SEQ ID NO:3)).

Embodiment 5: The vector according to any one of embodiments 1-3, wherein said human β-globin locus control region (LCR) comprises a full length HS3 sequence.

Embodiment 6: The vector according to any one of embodiments 1-5, wherein said human β-globin locus control region (LCR) comprises an HS4 core sequence (ecHS4 (SEQ ID NO:4).

Embodiment 7: The vector according to any one of embodiments 1-5, wherein said human β-globin locus control region (LCR) comprises a full length HS4.

Embodiment 8: The vector of embodiment 1, wherein said vector comprises the LCR shown in SEQ ID NO:6.

Embodiment 9: The vector according to any one of embodiments 1-8, wherein said heterologous gene comprises a recombinant human beta globin gene encoding a beta globin polypeptide.

Embodiment 10: The vector of embodiment 9, wherein said human beta globin gene comprises a wild-type beta globin gene.

Embodiment 11: The vector of embodiment 9, wherein said human beta globin gene comprises an anti-sickling human beta globin gene encoding an anti-sickling beta globin polypeptide.

Embodiment 12: The vector of embodiment 11, wherein said anti-sickling human beta globin gene encoding an anti-sickling-beta globin polypeptide comprise one or more mutations selected from the group consisting of Gly16Asp, Glu22Ala and Thr87Gln.

Embodiment 13: The vector of embodiment 12, wherein said beta globin gene comprises the mutation Gly16Asp.

Embodiment 14: The vector according to any one of embodiments 12-13, wherein said beta globin gene comprises the mutation Glu22Ala.

Embodiment 15: The vector according to any one of embodiments 12-14, wherein said beta globin gene comprises the mutation Thr87Gln.

Embodiment 16: The vector of embodiment 12, wherein said anti-sickling human β-globin gene comprises about 2.3 kb of recombinant human β-globin gene including exons and introns under the control of said human β-globin locus control region.

Embodiment 17: The vector according to any one of embodiments 12-16, wherein said β-globin gene comprises β-globin intron 2 with a 375 bp RsaI deletion from IVS2.

Embodiment 18: The vector according to any one of embodiments 12-17, wherein said β-globin gene comprises an SspI (S) to RsaI (R) deletion (~220 bp).

Embodiment 19: The vector of embodiment 11, wherein said anti-sickling human beta globin gene comprises a modified βAS3-globin transgene, said transgene comprising a codon optimized exon 1 (SEQ ID NO:7) (as shown within SEQ ID NO:10), and/or a codon optimized exon 2 (SEQ ID NOs:5 or 8) (as shown within SEQ ID NO:11), and/or comprising a codon optimized exon 3 (SEQ ID NO:9) (as shown within SEQ ID NO:12).

Embodiment 20: The vector of embodiment 19, wherein said βAS3-globin transgene comprises a codon optimized exon 2 (SEQ ID NO:5).

Embodiment 21: The vector of embodiment 19, wherein said βAS3-globin transgene comprises a codon optimized exon 2 (SEQ ID NO:8).

Embodiment 22: The vector according to any one of embodiments 19-21, wherein said βAS3-globin transgene comprises a codon optimized exon 1 (SEQ ID NO:7).

Embodiment 23: The vector according to any one of embodiments 19-22, wherein said βAS3-globin transgene comprises a codon optimized exon 3 (SEQ ID NO:9).

Embodiment 24: The vector according to any one of embodiments 1-23, wherein said vector comprises a human Ankyrin insulator element.

Embodiment 25: The vector according to any one of embodiments 1-24, further comprising an insulator in the 3' LTR.

Embodiment 26: The vector of embodiment 25, wherein said insulator comprises FB (FII/BEAD-A), a 77 bp insulator element, which contains the minimal CTCF binding site enhancer-blocking components of the chicken β-globin 5' DnaseI-hypersensitive site 4 (5' HS4).

Embodiment 27: The vector according to any one of embodiments 1-26, wherein said vector comprises a ψ region vector genome packaging signal.

Embodiment 28: The vector according to any one of embodiments 1-27, wherein the 5' LTR comprises a CMV enhancer/promoter.

Embodiment 29: The vector according to any one of embodiments 1-28, wherein said vector comprises a Rev Responsive Element (RRE).

Embodiment 30: The vector according to any one of embodiments 1-29, wherein said vector comprises a central polypurine tract.

Embodiment 31: The vector according to any one of embodiments 1-30, wherein said vector comprises a post-translational regulatory element.

Embodiment 32: The vector of embodiment 31, wherein the posttranscriptional regulatory element is modified Woodchuck Post-transcriptional Regulatory Element (WPRE).

Embodiment 33: The vector of embodiment 1, wherein said vector comprises the nucleic acid sequence of SEQ ID NO:6.

Embodiment 34: The vector according to any one of embodiments 1-33, wherein said vector is incapable of reconstituting a wild-type lentivirus through recombination.

Embodiment 35: The vector according to any one of embodiments 1-33, wherein said vector is incapable of reconstituting a wild-type lentivirus through recombination.

Embodiment 36: The vector embodiment 1, wherein said vector comprises the features of pUV–AS3 (FIG. 3).

Embodiment 37: The vector embodiment 1, wherein said vector comprises the nucleotide sequence of pUV–AS3 (SEQ ID NO: 13).

Embodiment 38: The vector embodiment 1, wherein said vector comprises the features of pUV–AS3(coX2) (FIG. 4).

Embodiment 39: The vector embodiment 1, wherein said vector comprises the nucleotide sequence of pUV–AS3 (coX2) (SEQ ID NO:14).

Embodiment 40: The vector embodiment 1, wherein said vector comprises the features of pUV–HS1-AS3 (FIG. 5).

Embodiment 41: The vector embodiment 1, wherein said vector comprises the nucleotide sequence of pUV–HS1-AS3 (SEQ ID NO:15).

Embodiment 42: The vector embodiment 1, wherein said vector comprises the features of pUV+HS1-AS3(coX2) (FIG. 6).

Embodiment 43: The vector embodiment 1, wherein said vectors comprises the nucleotide sequence of pUV+HS1-AS3(coX2) (SEQ ID NO: 16).

Embodiment 44: A host cell transduced with a vector according to any one of embodiments 1-43.

Embodiment 45: The host cell of embodiment 44, wherein the cell is a stem cell.

Embodiment 46: The host cell of embodiment 45, wherein said cell is a stem cell derived from bone marrow, and/or from umbilical cord blood, and/or from peripheral blood.

Embodiment 47: The host cell of embodiment 44, wherein the cell is a 293T cell.

Embodiment 48: The host cell of embodiment 44, wherein the cell is a human hematopoietic progenitor cell.

Embodiment 49: The host cell of embodiment 48, wherein the human hematopoietic progenitor cell is a CD34+ cell.

Embodiment 50: A method of treating a hemoglobinopathy, in a subject, said method comprising:

transducing a stem cell and/or progenitor cell from said subject with a vector according to any one of embodiments 1-43; and transplanting said transduced cell or cells derived therefrom into said subject where said cells or derivatives therefrom express said anti-sickling human beta globin gene.

Embodiment 51: The method of embodiment 50, wherein the cell is a stem cell.

Embodiment 52: The host cell of embodiment 50, wherein said cell is a stem cell derived from bone marrow.

Embodiment 53: The method of embodiment 50, wherein the cell is a human hematopoietic stem and progenitor cell.

Embodiment 54: The method of embodiment 53, wherein the human hematopoietic progenitor cell is a CD34$^+$ cell.

Embodiment 55: The method according to any one of embodiments 50-54, wherein said hemoglobinopathy is sickle cell disease.

Embodiment 56: The method according to any one of embodiments 50-54, wherein said hemoglobinopathy is β-thalassemia.

Embodiment 57: A nucleic acid encoding a modified βAS3-globin transgene, said transgene comprising a codon optimized exon 1 (SEQ ID NO:7) (as shown within SEQ ID NO:10), and/or a codon optimized exon 2 (SEQ ID NOs:5 or 8), and/or comprising a codon optimized exon 3 (SEQ ID NO:9) (as shown within SEQ ID NO:12).

Embodiment 58: The nucleic acid of embodiment 57, wherein said βAS3-globin transgene comprises a codon optimized exon 2 (SEQ ID NO: 5).

Embodiment 59: The nucleic acid of embodiment 57, wherein said βAS3-globin transgene comprises a codon optimized exon 2 (SEQ ID NO: 8).

Embodiment 60: The nucleic acid according to any one of embodiments 57-59, wherein said βAS3-globin transgene comprises a codon optimized exon 1 (SEQ ID NO: 7).

Embodiment 61: The nucleic acid according to any one of embodiments 57-60, wherein said βAS3-globin transgene comprises a codon optimized exon 3 (SEQ ID NO:9).

Definitions.

An "HS core sequence" as used herein refers to a reduced β-globin locus control region (LCR) hypersensitivity site (HS) sequence as defined herein (e.g., (HS2 (~420 bp), HS3 (~340 bp), and/or HS4 (~410 bp)). Full-length HS sequences refers to LCR HS2, HS3, and HS4 as previously defined (e.g., HS2 (~1.20 kb), HS3 (~1.28 kb), and HS4 (~1.1 kb)) (see, e.g., Forrester et al. (1986) *Proc. Natl. Acad. Sci. USA,* 83: 1359-1363).

"Recombinant" is used consistently with its usage in the art to refer to a nucleic acid sequence that comprises portions that do not naturally occur together as part of a single sequence or that have been rearranged relative to a naturally occurring sequence. A recombinant nucleic acid is created by a process that involves the hand of man and/or is generated from a nucleic acid that was created by hand of man (e.g., by one or more cycles of replication, amplification, transcription, etc.). A recombinant virus is one that comprises a recombinant nucleic acid. A recombinant cell is one that comprises a recombinant nucleic acid.

As used herein, the term "recombinant lentiviral vector" or "recombinant LV" refers to an artificially created polynucleotide vector assembled from an LV and a plurality of additional segments as a result of human intervention and manipulation.

By "globin nucleic acid molecule" is meant a nucleic acid molecule that encodes a globin polypeptide. In various embodiments the globin nucleic acid molecule may include regulatory sequences upstream and/or downstream of the coding sequence.

By "globin polypeptide" is meant a protein having at least 85%, or at least 90%, or at least 95%, or at least 98% amino acid sequence identity to a human beta, delta or gamma globin.

The term "therapeutic functional globin gene" refers to a nucleotide sequence the expression of which leads to a globin that does not produce a hemoglobinopathy phenotype, and which is effective to provide therapeutic benefits to an individual with a defective globin gene. The functional globin gene may encode a wild-type globin appropriate for a mammalian individual to be treated, or it may be a mutant form of globin, preferably one which provides for superior properties, for example superior oxygen transport properties or anti-sickling properties. The functional globin gene includes both exons and introns, as well as globin promoters and splice donors/acceptors.

By "an effective amount" is meant the amount of a required agent or composition comprising the agent to ameliorate or eliminate symptoms of a disease relative to an untreated patient. The effective amount of composition(s) used to practice the methods described herein for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991); and the like.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is typically represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison).

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. In various embodiments "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™. (Version 10; Genetics Computer Group, Inc., Madison, Wis.). "Gap" utilizes the algorithm of Needleman and Wunsch (1970) *J. Mol. Biol.* 48: 443-453, to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (1981) *Adv. Appl. Math.,* 2: 482-489, Smith et al. (1983) *Nucleic Acids Res.* 11: 2205-2220. Useful methods for determining sequence identity are also disclosed in Guide to Huge Computers (Martin J. Bishop, ed., Academic Press, San Diego (1994)), and Carillo et al. (1988) *Appl. Math,* 48: 1073). Certain illustrative computer programs for determining sequence identity include, but are not limited to, the Basic Local Alignment Search Tool (BLAST) programs, that are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., J. Mol. Biol. 215:403-410 (1990)); version 2.0 or higher of BLAST programs allows the introduction of gaps (deletions and insertions) into alignments; for peptide sequence, BLASTX can be used to determine sequence identity; and for polynucleotide sequence, BLASTN can be used to determine sequence identity.

DETAILED DESCRIPTION

It is believed that autologous stem cell gene therapy for sickle cell disease (SCD) or other hemoglobinopathies (e.g., β-thalassemia, etc.) has the potential to treat these illnesses without the need for immune suppression of current allogeneic hematopoietic stem cell transplantation (HSCT) approaches. In particular, it is believed that autologous stem cell gene therapy that introduces, for example, anti-sickling human beta globin into hematopoietic cells (or progenitors thereof) can provide effective therapy for SCD (including, for example, normalized red blood cell (RBC) physiology and prevention of the manifestations of SCD) or certain other hemoglobinopathies.

Current β-globin expression vectors, however, suffer from low vector titer and sub-optimal gene transfer to hematopoietic stem cells, representing a major barrier toward the effective implementation of this gene therapy strategy to the clinic. Without being bound to a particular theory, it is believed that the predominant factor most likely affecting vector performance is overall vector length.

To address this concern, we previously developed a reduced length globin vectors that produced at ~3-fold higher titer with superior gene transfer to hematopoietic stem cells and comparable expression of BAS3 when compared to antecedent vectors. These vectors were characterized by the incorporation of reduced length β-globin locous control region (LCR) hypersensitivity site (HS) sequences (e.g., (HS2 (~420 bp), HS3 (~340 bp), and/or HS4 (~410 bp) as described in PCT Publication No: WO/2018/106724 (PCT/US17/64766) which is incorporated herein by reference for the sequence of the reduced length hypersensitivity sites and vectors describe therein.

Previous reports have demonstrated that the full length HS1 element could increase expression per vector genome when combined with the full length HS 2, 3, and 4 elements {Lisowski & Sadelain (2007) *Blood,* 110: 4175-4178). We hypothesized that the HS1 ENCODE core (EC1) could similarly improve expression. Thus, as an alternative strategy to increase normalized expression, we again deployed ENCODE to redefine the boundaries of the HS1 element and designed a derivative of Core-AS3-FB containing the HS Core 1 and HS Core 2, 3, and 4 (called +EC1 (encode core 1)) to determine the influence of EC1 on BASB-globin expression.

Figure 1:
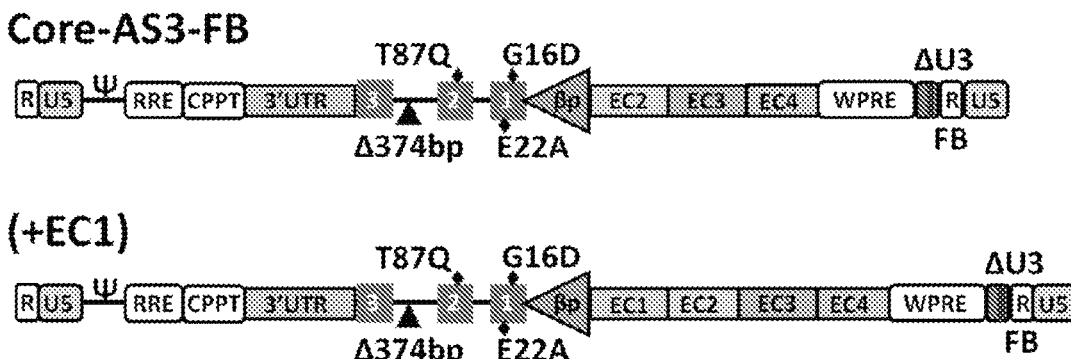
FIG. 1, panels A-B, illustrates the structure of a Core-ASB-FB and +EC1 lentiviral vectors (Panel A) and expression levels produced by each of these vectors when transfected into healthy donor hematopoietic stem and progenitor cells (HSPCs) panel B).
Figure 1:
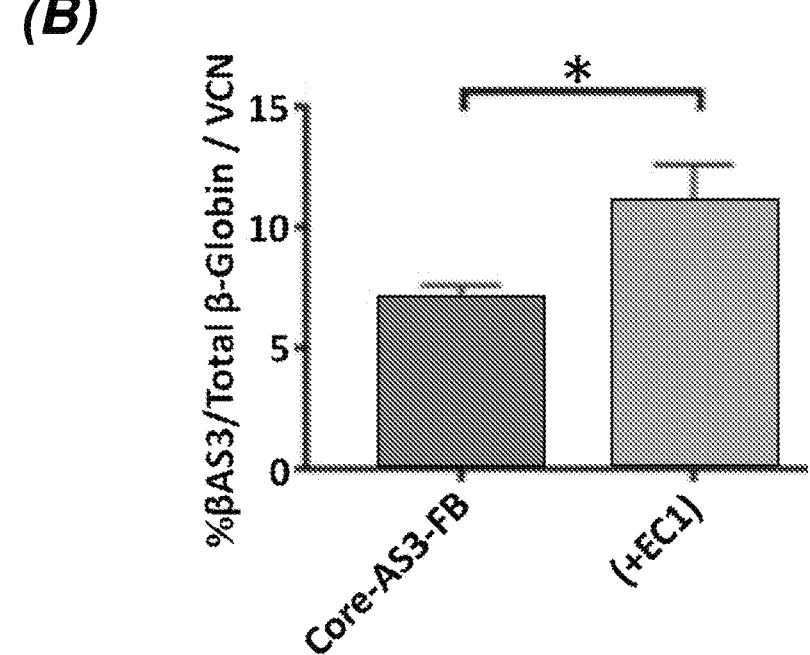

Healthy donor HSPCs were transduced with Core-ASB-FB and +EC1 (FIG. 1, Panel A) at equal MOI and cultured under erythroid culture conditions for 14 days. From three independent experiments, a 1.6-fold increase in expression per vector genome was observed when comparing Core-ASB-FB(+EC1) to its parental construct (p<0.05) (FIG. 1, Panel B).

Accordingly, in certain embodiments, a recombinant lentiviral vector (LV) is provided where the vector comprises an expression cassette comprising a human β-globin locus control region (LCR) comprising an HS1 ENCODE core (EC1) sequence (SEQ ID NO:1), and one or more of an HS2 core sequence (ecHS2 (SEQ ID NO: 2)), an HS3 core sequence (ecHS3 (SEQ ID NO:3)), an HS4 core sequence (ecHS4 (SEQ ID NO:4) (see, e.g., sequences in Table 1), a full length HS2, a full length HS3, and/or a full length HS4; and a heterologous gene to be expressed by the construct operably linked to the human β-globin locus control region.

In certain embodiments the human β-globin locus control region (LCR) comprises an HS2 core sequence (ecHS2 (SEQ ID NO: 2)). In certain embodiments the human β-globin locus control region (LCR) comprises a full length HS2 sequence. In certain embodiments the human β-globin locus control region (LCR) comprises an HS3 core sequence (ecHS3 (SEQ ID NO:3)). In certain embodiments the human β-globin locus control region (LCR) comprises a full length HS3 sequence. In certain embodiments the human β-globin locus control region (LCR) comprises an HS4 core sequence (ecHS4 (SEQ ID NO:4). In certain embodiments the human β-globin locus control region (LCR) comprises a full length HS4. In certain embodiments the vector comprises the LCR shown in SEQ ID NO:6.

TABLE 1

Nucleic acid sequences of ecHS1, ecHS2, ecHS3, ecHS4, a full vector with HS1, a vector comprising codon optimized exon 1, codon optimized exon 1, codon optimized exon 2, codon optimized exon 3, a vector comprising codon optimized exons 1 and 2, a vector comprising codon optimized exons 1, 2, and 3. In the codon optimized exons, the case letters are codon optimized sequence and the lower case match wildtype sequence

| | |
|---|---|
| ecHS1 (SEQ ID NO: 1) | Catcaataattctagccccacaggagtttgttctgaaagtaaacttccacaaccgcaagcttattgaggc taaggcatctgtgaaggaaagaaacatctcctctaaaccactatgctgctagagcctctttttctgtactc aagcctcattcagacactagtgtcaccagtctcctcatatacctattgtattttcttcttcttgctggtt tagtcatgtttctgggagcttaggggcttattttatttgttttgttttctaatcaacagagatgggca aacccattattttttctttagacttgggatggtgatagctgggcagcgtcagaaactgtgtgtggatat agataagagctcaggactatgctgagctgtgatgagggagggccctagctaaaggcagtgagagtcagaa tgctcctgctattgccttctcagtccccacgcttggtttctacacaagtagatacatagaaaaggctata ggttagtgtttgagagtcctgcatgattagttgctcagaaatgcccgataaatatgttatgtgtgtttat gtatatatatgtttttatatgtgtgtgtgtgtgtgttgtgtttacaaatatgtgattatcatcaaaacgtg aggg |
| ecHS2 (SEQ ID NO: 2) | Tacgtatatgtgtatatatatatatatattcaggaaataatatattctagaatatgtcacattctgtctc aggcatccattttctttatgatgccgttgaggtggagttttagtcaggtggtcagcttctcctttttt tgccatctgccctgtaagcatcctgctggggacccagataggagtcatcactctaggctgagaacatctg ggcacacaccctaagcctcagcatgactcatcatgactcagcattgctgtgcttgagccagaaggtttgc ttagaaggttacacagaaccagaaggcggggggtggggcactgaccccgacaggggcctggccagaactgc tcatgcttggactatgggaggtcactaatggagacacacagaaatgtaacaggaactaaggaaaaactga agctt |
| ecHS3 (ecCORE HS3) (SEQ ID NO: 3) | tgggggtataggggagcagtcccatgtagtagtagaatgaaaaatgctgctatgctgtgcctcccccacc tttcccatgtctgccctctactcatggtctatctctcctggctcctgggagtcatggactccacccagca ccaccaacctgacctaaccacctatctgagcctgccagcctataacccatctgggccctgatagctggtg gccagccctgaccccacccacccctccctggaacctctgatagacacatctggcacaccagctcgcaaag tcaccgtgagggtcttgtgtttgctgagtcaaaattccttgaaatccaagtccttagagactcc |
| ecHS4 (ecCORE HS4) (SEQ ID NO: 4) | caggcttggattcaaagctcctgactttctgtctagtgtatgtgcagtgagcccctttttcctctaactgaaaga aggaaaaaaaaatggaacccaaaatattctacatagtttccatgtcacagccagggctgggcagtctcctg ttatttcttttaaaataaatatatcatttaaatgcataaataagcaaaccctgctcgggaatgggagggaga gtctctggagtccaccccttctcggccctggctctgcagatagtgctatcaaagccctgacagagccctgccc attgctgggccttggagtgagtcagcctagtagagaggcagggcaagccatctcatagctgctgagtggga gagagaaaagggctcattgtctataaaactcaggtcatggctattcttat |
| coX2 (codon optimized exon 2) (SEQ ID NO: 5) | cctGAAGTTCTCaGGaTCCACGTGCAGCTTGTCGCAGTGCAGCTCGCTCAGCTGGG CGAAGGTGCCCTTCAGGTTGTCCAGGTGGGCCAGGCCGTCGCTGAAGGCGCCCA GCACCTTCTTGCCGTGGGCCTTCACCTTGGGGTTGCCCATCACGGCGTCGGGGGT GCTCAGGTCGCCGAAGCTCTCGAAGAAGCGCTGGGTCCAGGGGTACACCACCAG cagc |
| Fullvector with HS1 (SEQ ID NO: 6) | gcgcaacgcaattaatgtgagttagctcactcattaggcaccccaggctttacactttatgcttccggctcgt atgttgtgtggaattgtgagcggataacaatttcacacaggaaacagctatgaccatgattacgccaagcg cgcaattaaccctcactaaagggaacaaaagctggagctgcaagcttggccattgcatacgttgtatccat atcataatatgtacatttatattggctcatgtccaacattaccgccatgttgacattgattattgactagttatt aatagtaatcaattacggggtcattagttcatagcccatatatggagttccgcgttacataacttacggtaaa tggcccgcctggctgaccgcccaacgaccccgcccattgacgtcaataatgacgtatgttcccatagtaac gccaatagggactttccattgacgtcaatgggtggagtatttacggtaaactgcccacttggcagtacatca agtgtatcatatgccaagtacgccccctattgacgtcaatgacggtaaatggcccgcctggcattatgccca gtacatgaccttatgggactttcctacttggcagtacatctacgtattagtcatcgctattaccatggtgatgc ggttttggcagtacatcaatgggcgtggatagcggtttgactcacggggatttccaaagtctcccacccccattg acgtcaatgggagtttgttttggcaccaaaatcaacgggactttccaaaatgtcgtaacaactccgccccat tgacgcaaatgggcggtaggcgtgtacggtgggaggtctatataagcagagctcgtttagtgaaccggggt ctctctggttagaccagatctgagcctgggagctctctggctaactagggaacccactgcttaagcctcaat aaagcttgccttgagtgcttcaagtagtgtgtgcccgtctgttgtgtgactctggtaactagagatccctcag acccttttagtcagtgtggaaaatctctagcagtggcgcccgaacaggacttgaaagcgaaagggaaac cagaggagctctctcgacgcaggactcggcttgctgaagcgcgcacggcaagaggcgaggggcggcgac tggtgagtacgccaaaaattttgactagcggaggctagaaggagagagatgggtgcgagagcgtcagtat taagcggggggagaattagatcgcgatgggaaaaaattcggttaaggccaggggggaaagaaaaaatataa attaaaacatatagtatgggcaagcagggagctagaacgattcgcagttaatcctggcctgttagaaacat cagaaggctgtagacaaaatactgggacagctacaaccatcccttcagacaggatcagaagaacttagatc |

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
attatataatacagtagcaaccctctattgtgtgcatcaaaggatagagataaaagacaccaaggaagctt
tagacaagatagaggaagagcaaaacaaaagtaagaccaccgcacagcaagcggccgctgatcttcag
acctggaggaggagatatgagggacaattggagaagtgaattatataaatataaagtagtaaaaattgaa
ccattaggagtagcacccaccaaggcaaagagaagagtggtgcagagagagaaaaaagagcagtgggaat
aggagctttgttccttgggttcttgggagcagcaggaagcactatgggcgcagcgtcaatgacgctgacgg
tacaggccagacaattattgtctggtatagtgcagcagcagaacaatttgctgagggctattgaggcgcaa
cagcatctgttgcaactcacagtctggggcatcaagcagctccaggcaagaatcctggctgtggaaagata
cctaaaggatcaacagctcctggggatttggggttgctctggaaaactcatttgcaccactgctgtgccttgg
aatgctagttggagtaataaatctctggaacagatttggaatcacacgacctggatggagtgggacagag
aaattaacaattacacaagcttaatacactccttaattgaagaatcgcaaaaccagcaagaaaagaatga
acaagaattattggaattagataaatgggcaagtttgtggaattggtttaacataacaaattggctgtggta
tataaaattattcataatgatagtaggaggcttggtaggtttaagaatagttttttgctgtactttctatagtga
atagagttaggcagggatattcaccattatcgtttcagacccacctcccaaccccgagggggacccgacagg
cccgaaggaatagaagaagaaggtggagagagagacagagacagatccattcgattagtgaacggatct
cgacggtatcgatctcgacacaaatggcagtattcatccacaatttaaaagaaaaggggggattggggg
gtacagtgcaggggaaagaatagtagacataatagcaacagacatacaaactaaagaattacaaaaaca
aattacaaaaattcaaaattttcgggtttattacagggacagcagagatccagtttgggtcgaggatatcgg
atcggaattctctagatgatcaggatccctcgagcccttatcgatcacgagactagcctcgactactagtgg
agatccccggctgcagagcaggaagcaccataagggacatgataagggagccagcagacctctgatct
cttcctgaatgctaatcttaaacatcctgaggaagaatgggacttccatttggggtgggcctatgatagggt
aataagacagtagtgaatatcaagctacaaaaagcccctttcaaattcttctcagtcctaacttttcatact
aagcccagtccttccaaagcagactgtgaaagagtgatagttccgggagactagcactgcagattccgggt
cactgtgagtgggggaggcagggaagaagggctcacaggacagtcaaaccatgcccctgttttttccttct
tcaagtagacctctataagacaacagagacaactaaggctgagtggccaggcgaggagaaaccatctcg
ccgtaaaacatggaaggaacacttcaggggaaaggtggtatctctaagcaagagaactgagtggagtca
aggctgagagatgcaggataagcaaatgggtagtgaaaagacattcatgaggacagctaaaacaataag
taatgtaaaatacagcatagcaaaactttaacctccaaatcaagcctctacttgaatcctttttctgagggat
gaataaggcataggcatcaggggctgttgccaatgtgcattagctgtttgcagcctcaccttctttcatggag
tttaagatatagtgtattttcccaaggtttgaactagctcttcatttctttatgttttaaatgcactgacctccca
cattccctttttagtaaaatattcagaaataatttaaatacatcattgcaatgaaaataaatgttttttattag
gcagaatccagatgctcaaggccctcataatatccccagtttagtagttggacttagggaacaaaggaa
cctttaatagaaattggacagcaagaaagcgagcttagtacttgtgggccagggcattagccacacca
gccaccacttcctgataggcagcctgcactggtggggtgaattctttgccaaagtgatgggccagcacacag
accagcacgttgcccaggagctgtgggaggaagataagaggtatgaacatgattagcaaaagggcctag
cttggactcagaataatccagccttatcccaaccataaaataaaagcagaatggtagctggattgtagctg
ctattagcaatatgaaacctcttacatcagttacaatttatatgcagaaatatttatatgcagaaatattgct
attgccttaacccagaaattatcactgttattctttagaatggtgcaaagaggcatgatacattgtatcattat
tgccctgaaagaaagagattagggaaagtattagaaataagataaacaaaaaagtatattaaaagaaga
aagcatttttttaaaattacaaatgcaaaattaccctgatttggtcaatatgtgtaccctgttacttctccccttc
ctatgacatgaacttaaccatagaaaagaaggggaaagaaaacatcaagggtcccatagactcaccctg
aagttctcaggatccacgtgcagcttgtcacagtgcagctcactcagctgggcaaaggtgcccttgaggttg
tccaggtgagccaggccatcactaaaggcaccgagcactttcttgccatgagccttcaccttagggttgccc
ataacagcatcaggagtggacagatccccaaaggactcaaagaacctctgggtccaagggtagaccacc
agcagcctaagggtgggaaaatagaccaataggcagagagagtcagtgcctatcagaaaccaagagtc
ttctctgtctccacatgcccagtttctattggtctccttaaacctgtcttgtaaccttgataccaacctgcccag
ggcctcaccaccaacggcatccacgttcaccttgtcccacagggcagtaacggcagacttctcctcaggag
tcaggtgcaccatggtgtctgtttgaggttgctagtgaacacagttgtgtcagaagcaaatgtaagcaatag
atggctctgccctgacttttatgcccagccctggctcctgccctccctgctcctgggagtagattggccaaccc
tagggtgtggctccacagggtgaggtctaagtgatgacagccgtacctgtccttggctcttctggcactggct
taggagttggacttcaaaccctcagccctccctctaagatatatctcttggccccataccatcagtacaaatt
gctactaaaaacatcctcctttgcaagtgtatttacccgacgcgtcggcgataagcttgatccatcgatcatc
aataattctagccccacaggagtttgttctgaaagtaaacttccacaaccgcaagcttattgaggctaaggc
atctgtgaaggaaagaaacatctcctctaaaccactatgctgctagagcctcttttctgtactcaagcctcat
tcagacactagtgtcaccagtctcctcatatacctattgtattttcttcttcttgctggtttagtcatgtttctgg
gagcttaggggcttattttattttgttttgttttctaatcaacagagatgggcaaacccattattttttttctttag
acttgggatggtgatagctgggcagcgtcagaaactgtgtgtgtggatatagataagagctcaggactatgct
gagctgtgatgaggggaggggcctagctaaaggccagtgagagtcagaatgctcctgctattgccttctcagt
ccccacgcttggtttctacacaagtagatacatagaaaaggctataggttagtgtttgagagtcctgcatga
ttagttgctcagaaatgcccgataaatatgttatgtgtgtttatgtatatatatgtttttatatgtgtgtgtgtg
tgttgtgtttacaaatatgtgattatcatcaaaacgtgagggtacgtatatgtgtatatatatatatattca
ggaaataatattctagaatatgtcacattctgtctcaggcatccattttcttttgtgatgccgtttgaggtgg
agttttagtcaggtggtcagcttctcctttttttttgccatctgccctgtaagcatcctgctgggggaccagata
ggagtcatcactctaggctgagaacatctgggcacacaccctaagcctcagcatgactcatcatgactcag
cattgctgtgcttgagccagaaggtttgcttagaaggttacacagaaccagaaggcgggggtggggcactg
accccgacagggggcctggccagaagctgctcatgttggacttcactaatggagacacacagaatc tttggttt
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
ctgacagagccctgcccattgctgggccttggagtgagtcagcctagtagagaggcagggcaagccatctc
atagctgctgagtgggagagagaaaagggctcattgtctataaactcaggtcatggctattcttatggccta
ctcgaccacgagggaattccgataatcaacctctggattacaaaatttgtgaaagattgactggtattctta
actatgttgctcctttttacgctatgtggatacgctgctttaatgcctttgtatcatgctattgcttcccgtatggc
tttcattttctcctccttgtataaatcctggttgctgtctctttatgaggagttgtggcccgttgtcaggcaacgt
ggcgtggtgtgcactgtgtttgctgacgcaacccccactggttggggcattgccaccacctgtcagctccttt
ccgggactttcgctttcccccctccctattgccacggcggaactcatcgccgcctgccttgcccgctgctggac
aggggctcggctgttgggcactgacaattccgtggtgttgtcggggaaatcatcgtcctttccttggctgctc
gcctgtgttgccacctggattctgcgcgggacgtccttctgctacgtcccttcggccctcaatccagcggacc
ttccttcccgcggcctgctgccggctctgcggcctcttccgcgtcttcgccttcgccctcagacgagtcggatc
tccctttgggccgcctccccgcatcgataccgtcgacctcgagacctagaaaaacatggccaattcgagctc
ggtacctttaagaccaatgacttacaaggcagctgtagatcttagccactttttaaaagaaaaggggggac
tggaagggctaattcactcccaacgaagacaagatcccagggatgtacgtccctaacccgctaggggggca
gcacccaggcctgcactgccgcctgccggcaggggtccagtcctgcttttttgcttgtactgggtctctctggtt
agaccagatctgagcctgggagctctctggctaactagggaacccactgcttaagcctcaataaaagcttgc
cttgagtgcttcaagtagtgtgtgcccgtctgttgtgtgactctggtaactagagatccctcagacccttttag
tcagtgtggaaaatctctagcagtagtagttcatgtcatcttattattcagtatttataacttgcaaagaaatg
aatatcagagagtgagaggaacttgtttattgcagcttataatggttacaaataaagcaatagcatcacaa
atttcacaaataaagcatttttttcactgcattctagtgttgttgtccaaactcatcaatgtatcttatcatgt
ctggctctagctatcccgcccctaactccgcccatccgcccctaactccgcccagttccgcccattctccgc
cccatggctgactaattttttttatttatgcagaggccgaggccgcctcggcctctgagctattccagaagta
gtgaggaggcttttttggaggcctaggcttttgcgtcgagacgtacccaattcgccctatagtgagtcgtatt
acgcgcgctcactggccgtcgttttacaacgtcgtgactgggaaaacctggcgttacccaacttaatcgcc
ttgcagcacatcccccttttcgccagctggcgtaatagcgaagaggcccgcaccgatcgcccttcccaacagt
tgcgcagcctgaatggcgaatggcgcgacgcgccgtagcggcgcattaagcgcggcgggtgtggtggtt
acgcgcagcgtgaccgctacacttgccagcgccctagcgcccgctcctttcgctttcttcccttcctttctcgc
cacgttcgccggctttccccgtcaagctctaaatcgggggctccctttagggttccgatttagtgctttacggc
acctcgaccccaaaaaacttgattagggtgatggttcacgtagtgggccatcgccctgatagacggtttttc
gcccctttgacgttggagtccacgttctttaatagtggactcttgttccaaactggaacaacactcaaccctat
ctcggtctattcttttgatttataagggattttgccgatttcggcctattggttaaaaaatgagctgatttaaca
aaaatttaacgcgaattttaacaaaatattaacgtttacaatttcccaggtggcacttttcggggaaatgtgc
gcggaacccctatttgtttatttttctaaatacattcaaatatgtatccgctcatgagacaataaccctgataa
atgcttcaataatattgaaaaaggaagagtatgagtattcaacatttccgtgtcgcccttattccctttttttgc
ggcattttgccttcctgtttttgctcacccagaaacgctggtgaaagtaaaagatgctgaagatcagttgggt
gcacgagtgggttacatcgaactggatctcaacagcggtaagatccttgagagttttcgccccgaagaacg
ttttccaatgatgagcacttttaaagttctgctatgtggcgcggtattatcccgtattgacgccgggcaagag
caactcggtcgccgcatacactattctcagaatgacttggttgagtactcaccagtcacagaaaagcatctt
acggatggcatgacagtaagagaattatgcagtgctgccataaccatgagtgataacactgcggccaactt
acttctgacaacgatcggaggaccgaaggagctaaccgcttttttgcacaacatgggggatcatgtaactc
gccttgatcgttgggaaccggagctgaatgaagccataccaaacgacgagcgtgacaccacgatgcctgt
agcaatggcaacaacgttgcgcaaactattaactggcgaactacttactctagcttcccggcaacaattaat
agactggatggaggcggataaagttgcaggaccacttctgcgctcggcccttccggctggctggtttattgc
tgataaatctggagccggtgagcgtgggtctcgcggtatcattgcagcactggggccagatggtaagccct
cccgtatcgtagttatctacacgacggggagtcaggcaactatggatgaacgaaatagacagatcgctga
gataggtgcctcactgattaagcattggtaactgtcagaccaagtttactcatatatactttagattgatttaa
aacttcatttttaatttaaaaggatctaggtgaagatcctttttgataatctcatgaccaaaatcccttaacgt
gagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctacc
aactcttttttccgaaggtaactggcttcagcagagcgcagataccaaatactgtccttctagtgtagccgtag
ttaggccaccacttcaagaactctgtagcaccgcctacatacctcgctctgctaatcctgttaccagtggctg
ctgccagtggcgataagtcgtgtcttaccgggttggactcaagacgatagttaccggataaggcgcagcgg
tcgggctgaacggggggttcgtgcacacagcccagcttggagcgaacgacctacaccgaactgagatacc
tacagcgtgagctatgagaaagcgccacgcttcccgaagggagaaaggcggacaggtatccggtaagcg
gcagggtcggaacaggagagcgcacgagggagcttccaggggaaacgcctggtatctttatagtcctgt
cgggtttcgccacctctgacttgagcgtcgatttttgtgatgctcgtcaggggggcggagcctatggaaaaa
cgccagcaacgcggcctttttacggttcctggccttttgctggccttttgctcacatgttctttcctgcgttatc
ccctgattctgtggataaccgtattaccgcctttgagtgagctgataccgctcgccgcagccgaacgaccga
gcgcagcgagtcagtgagcgaggaagcggaagagcgcccaatacgcaaaccgcctctccccgcgcgttg
gccgattcattaatgcagctggcacgacaggtttcccgactggaaagcgggcagtga
```

| | |
|---|---|
| Codon optimized<br>exon 1 SEQ ID<br>NO: 7) | atgGTGCACCTGACCCCCGAGGAGAAGAGCGCCGTGACCGCCCTGT<br>GGGACAAGGTGAACGTGGACGCCGTGGGCGGCGAGGCCCTGggcag |
| Codon<br>optimized exon<br>2 SEQ ID NO: 8) | cctgaagttctcggggtccacgtgcagcttgtcgcagtgcagctcgctcagctgggcgaaggtgcccttcag<br>gttgtccaggtgggccaggccgtcgctgaaggcgcccagcaccttcttgccgtgggccttcaccttggggtt<br>gcccatcacggcgtcggggggtgctcaggtcgccgaagctctcgaagaagcgctgggtccaggggtacacc<br>accagcagc<br>Note - - - this optimization in vector with exons 1, 2, and 3 all codon<br>optimized. Other vectors use optimized exon 2 coEX2 (SEQ ID NO: 5) |
| Codon optimized<br>exon 3 SEQ ID<br>NO: 9) | ctcCTGGGCAACGTGCTGGTGTGCGTGCTGGCCCACCACTTCGGCA<br>AGGAGTTCACCCCCCCCGTGCAGGCCGCCTACCAGAAGGTGGTGG<br>CCGGCGTGGCCAACGCCCTGGCCCACAAGTACCACtaa |

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

| | |
|---|---|
| Codon<br>optimized exon<br>1 full vector<br>(SEQ ID NO: 10) | gcgcaacgcaattaatgtgagttagctcactcattaggcaccccaggctttacactttatgcttccggctcgt<br>atgttgtgtggaattgtgagcggataacaatttcacacaggaaacagctatgaccatgattacgccaagcg<br>cgcaattaaccctcactaaagggaacaaaagctggagctgcaagcttggccattgcatacgttgtatccat<br>atcataatatgtacatttatattggctcatgtccaacattaccgccatgttgacattgattattgactagttatt<br>aatagtaatcaattacggggtcattagttcatagcccatatatggagttccgcgttacataacttacggtaaa<br>tggcccgcctggctgaccgcccaacgacccccgcccattgacgtcaataatgacgtatgttcccatagtaac<br>gccaatagggactttccattgacgtcaatgggtggagtatttacggtaaactgcccacttggcagtacatca<br>agtgtatcatatgccaagtacgcccccctattgacgtcaatgacggtaaatggcccgcctggcattatgccca<br>gtacatgaccttatgggactttcctacttggcagtacatctacgtattagtcatcgctattaccatggtgatgc<br>ggttttggcagtacatcaatgggcgtggatagcggtttgactcacggggatttccaagtctccaccccattg<br>acgtcaatgggagtttgttttggcaccaaaatcaacgggactttccaaaatgtcgtaacaactccgccccat<br>tgacgcaaatgggcggtaggcgtgtacggtgggaggtctatataagcagagctcgtttagtgaaccggggt<br>ctctctggttagaccagatctgagcctgggagctctctggctaactagggaacccactgcttaagcctcaat<br>aaagcttgccttgagtgcttcaagtagtgtgtgcccgtctgttgtgtgactctggtaactagagatccctcag<br>acccttttagtcagtgtggaaaatctctagcagtggcgcccgaacagggacttgaaagcgaaagggaaac<br>cagaggagctctctcgacgcaggactcggcttgctgaagcgcgcacggcaagaggcgaggggcggcgac<br>tggtgagtacgccaaaaattttgactagcggaggctagaaggagagagatgggtgcgagagcgtcagtat<br>taagcgggggagaattagatcgcgatgggaaaaaattcggttaaggccaggggaaagaaaaaatataa<br>attaaaacatatagtatgggcaagcagggagctagaacgattcgcagttaatcctggccctgttagaaacat<br>cagaaggctgtagacaaatactgggacagctacaaccatcccttcagacaggatcagaagaacttagatc<br>attatataatacagtagcaaccctctattgtgtgcatcaaaggatagagataaaagacaccaaggaagctt<br>tagacaagatagaggaagagcaaaacaaaagtaagaccaccgcacagcaagcggccgctgaccttcag<br>acctggaggaggagatatgagggacaattggagaagtgaattatataaatataaagtagtaaaaattgaa<br>ccattaggagtagcacccaccaaggcaaagagaagagtggtgcagagagaaaaaagagcagtgggaat<br>aggagctttgttccttgggttcttgggagcagcaggaagcactatgggcgcagcgtcaatgacgctgacgg<br>tacaggccagacaattattgtctggtatagtgcagcagcagaacaatttgctgagggctattgaggcgcaa<br>cagcatctgttgcaactcacagtctggggcatcaagcagctccaggcaagaatcctggctgtggaaagata<br>cctaaaggatcaacagctcctggggatttggggttgctctggaaaactcatttgcaccactgctgtgccttgg<br>aatgctagttggagtaataaatctctggaacagatttggaatcacacgacctggatggagtgggacagag<br>aaattaacaattacacaagcttaatacactccttaattgaagaatcgcaaaaccagcaagaaaagaatga<br>acaagaattattggaattagataaatgggcaagtttgtggaattggtttaacataacaaattggctgtggta<br>tataaaattattcataatgatagtaggaggcttggtaggtttaagaatagtttttgctgtactttctatagtga<br>atagagttaggcagggatattcaccattatcgtttcagacccacctcccaaccccgaggggacccgacggg<br>cccgaaggaatagaagaagaaggtggagagagagacagagacagatccattcgattagtgaacggatct<br>cgacggtatcgatctcgacacaaatggcagtattcatccacaatttaaaagaaaaggggggattggggg<br>gtacagtgcaggggaaagaatagtagacataatagcaacagacatacaaactaaagaattacaaaaaca<br>aattacaaaaattcaaaattttcgggtttattacagggacagcagagatccagtttggggtcgaggatatcgg<br>atcggaattctctagatgatcaggatccctcgagcccttatcgatcacgagactagcctcgactactagtgg<br>agatcccccgggctgcagagccagaagcaccataagggacatgataagggagccagcagacctctgatct<br>cttcctgaatgctaatcttaaacatcctgaggaagaatgggacttccatttggggtgggcctatgatagggt<br>aataagacagtagtgaatatcaagctacaaaaagccccctttcaaattcttctcagtcctaacttttcatact<br>aagcccagtccttccaaagcagactgtgaaagagtgatagttccgggagactagcactgcagattccgggt<br>cactgtgagtggggggaggcagggaagaagggctcacaggacagtcaaaccatgcccccctgttttttccttct<br>tcaagtagacctctataagacaacagagacaactaaggctgagtggccaggcgaggagaaaccatctcg<br>ccgtaaaacatggaaggaacacttcaggggaaaggtggtatctctaagcaagagaactgagtggagtca<br>aggctgagagatgcaggataagcaaatgggtagtgaaaagacattcatgaggacagctaaaacaataag<br>taatgtaaaatacagcatagcaaaactttaacctccaaatcaagcctctacttgaatcctttttctgagggat<br>gaataaggcataggcatcaggggctgttgccaatgtgcattagctgtttgcagcctcaccttctttcatggag<br>tttaagatatagtgtattttcccaaggtttgaactagctcttcatttctttatgtttaaatgcactgacctccca<br>cattccctttttagtaaaatattcagaaataatttaaatacatcattgcaatgaaaataaatgttttttattag<br>gcagaatccagatgctcaaggcccttcataatatcccccagtttagtagttggacttagggaacaaaggaa<br>cctttaatagaaattggacagcaagaaagcgaggctacttgtgggcccagggcattagccacacca<br>gccaccacttctgataggcagcctgcactggtggggtgaattctttgccaaagtgatgggccagcacacag<br>accagcacgttgcccaggagctgtgggaggaagataagaggtatgaacatgattagcaaaagggcctag<br>cttggactcagaataatccagccttatcccaaccataaaataaaagcagaatggtagctggattgtagctg<br>ctattagcaatatgaaacctcttacatcagttacaatttatatgcagaaatatttatatgcagaaatattgct<br>attgccttaacccagaaattatcactgttattctttagaatggtgcaaagaggcatgatacattgtatcattat<br>tgccctgaaagaaagagattagggaaagtattagaaataagataaacaaaaaagtatattaaaagaaga<br>aagcatttttaaaattacaaatgcaaaattaccctgatttggtcaatatgtgtaccctgttacttctcccccttc<br>ctatgacatgaacttaaccatagaaaagaagggggaaaagaaaacatcaagggtcccatagactcaccctg<br>aagttctcaggatccacgtgcagcttgtcacagtgcagctcactcagctgggcaaaggtgcccttgaggttg<br>tccaggtgagccaggccatcactaaaggcaccgagcactttcttgccatgagccttcaccttagggttgccc<br>ataacagcatcaggagtggacagatccccaaaggactcaaagaacctctgggtccaagggtagaccacc<br>agcagcctaagggtgggaaaataggaccaataggcagagagagtcagtgcctatcagaaacccaagagtc<br>ttctctgtctccacatgcccagtttctattggtctccttaaacctgtcttgtaaccttgataccaacctgccag<br>ggcctcgccgcccacggcgtccacgttcaccttgtcccacagggcggtcacggcgctcttctcctcggggt<br>caggtgcaccatggtgtctgtttgaggttgctagtgaacacagttgtgtcagaagcaaatgtaagcaatag<br>atggctctgcactttatgcccagccctgccctgctcctgggagtagattggccaacc<br>tagggtgtggctccacagggtgaggtctaagtgatgacagccgtacctgtccttggctcttctggcactggct<br>taggagttggacttcaaaccctcagccctccctctaagatatatctcttggccccataccatcagtacaaatt<br>gctactaaaaacatcctccttttgcaagtgtatttacccgacgcgtcggcgataagcttgatccatcgattacg<br>tatatgtgtatatatatatatattcaggaaataatatattctagaatatgtcacattctgtctcaggcatcc<br>attttctttatgatgccgtttgaggtggagtttagtcaggtggtcagcttctctctcttttttttttgccatctgccctgt |

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
aagcatcctgctggggacccagataggagtcatcactctaggctgagaacatctgggcacacaccctaagc
ctcagcatgactcatcatgactcagcattgctgtgcttgagccagaaggtttgcttagaaggttacacagaa
ccagaaggcggggtgggcactgaccccgacaggggcctggccagaactgctcatgcttggactatggg
aggtcactaatggagacacacagaaatgtaacaggaactaaggaaaaactgaagctttgggggtatagg
ggagcagtcccatgtagtagtagaatgaaaaatgctgctatgctgtgcctcccccacctttcccatgtctgcc
ctctactcatggtctatctctcctggctcctgggagtcatggactccacccagcaccaccaacctgacctaac
cacctatctgagcctgccagcctataacccatctgggccctgatagctggtggccagccctgaccccaccc
accctccctggaacctctgatagacacatctggcacaccagctcgcaaagtcaccgtgagggtcttgtgttt
gctgagtcaaaattccttgaaatccaagtccttagagactcccaggcttggattcaaagctcctgactttctg
tctagtgtatgtgcagtgagcccctttcctctaactgaaagaaggaaaaaaaatggaacccaaaatatt
ctacatagtttccatgtcacagccaggggctgggcagtctcctgttatttcttttaaaataaatatatcatttaa
atgcataaataagcaaaccctgctcgggaatgggagggagagtctctggagtccacccccttctcggccctg
gctctgcagatagtgctatcaaagccctgacagagccctgcccattgctgggccttggagtgagtcagccta
gtagagaggcagggcaagccatctcatagctgctgagtgggagagagaaaagggctcattgtctataaac
tcaggtcatggctattcttatggcctactcgaccacgagggaattccgataatcaacctctggattacaaaa
tttgtgaaagattgactggtattcttaactatgttgctccttttacgctatgtggatacgctgcttaatgcctttt
gtatcatgctattgcttcccgtatggctttcatttttctcctccttgtataaatcctggttgctgtctctttatgagg
agttgtggcccgttgtcaggcaacgtggcgtggtgtgcactgtgtttgctgacgcaacccccactggttggg
gcattgccaccacctgtcagctcctttccgggactttcgctttccccctccctattgccacggcggaactcatc
gccgcctgccttgcccgctgctggacaggggctcggctgttgggcactgacaattccgtggtgttgtcgggg
aaatcatcgtcctttccttggctgctcgcctgtgttgccacctggattctgcgcgggacgtccttctgctacgtc
ccttcggccctcaatccagcggaccttccttcccgcggcctgctgccggctctgcggcctcttccgcgtcttcg
ccttcgccctcagacgagtcggatctccctttgggccgcctccccgcatcgataccgtcgacctcgagaccta
gaaaaacatggccaattcgagctcggtacctttaagaccaatgacttacaaggcagctgtagatcttagcc
acttttttaaaagaaaaggggggactggaagggctaattcactcccaacgaagacaagatcccagggatgt
acgtccctaacccgctaggggggcagcacccaggcctgcactgccgcctgccggcagggtccagtcctgct
ttttgcttgtactgggtctctctggttagaccagatctgagcctgggagctctctggctaactagggaaccca
ctgcttaagcctcaataaagcttgccttgagtgcttcaagtagtgtgtgcccgtctgttgtgtgactctggtaa
ctagagatccctcagacccttttagtcagtgtggaaaatctctagcagtagtagttcatgtcatcttattattc
agtatttataacttgcaaagaaatgaatatcagagagtgagaggaacttgtttattgcagcttataatggtt
acaaataaagcaatagcatcacaaatttcacaaataaagcatttttttcactgcattctagttgtggtttgtc
caaactcatcaatgtatcttatcatgtctggctctagctcatcgccccctaactccgcccatcccgcccctaac
tccgcccagttccgcccattctccgccccatggctgactaatttttttttatttatgcagaggccgaggccgcct
cggcctctgagctattccagaagtagtgaggaggcttttttggaggcctaggcttttgcgtcgagacgtaccc
aattcgccctatagtgagtcgtattacgcgcgctcactggccgtcgttttacaacgtcgtgactgggaaaac
cctggcgttacccaacttaatcgccttgcagcacatccccctttcgccagctggcgtaatagcgaagaggcc
cgcaccgatcgcccttcccaacagttgcgcagcctgaatggcgaatggcgcgacgcgccctgtagcggcgc
attaagcgcggcgggtgtggtggttacgcgcagcgtgaccgctacacttgccagcgccctagcgcccgctc
ctttcgctttcttcccttcctttctcgccacgttcgccggctttccccgtcaagctctaaatcggggctcccttt
agggttccgatttagtgctttacggcacctcgaccccaaaaaacttgattagggtgatggttcacgtagtgg
gccatcgccctgatagacggtttttcgcccttttgacgttggagtccacgttctttaatagtggactcttgttcca
aactggaacaacactcaaccctatctcggtctattcttttgatttataagggattttgccgatttcggcctatt
ggttaaaaaatgagctgatttaacaaaaatttaacgcgaattttaacaaaatattaacgtttacaatttccc
aggtggcacttttcggggaaatgtgcgcggaacccctatttgtttatttttctaaatacattcaaatatgtatc
cgctcatgagacaataaccctgataaatgcttcaataatattgaaaaaggaagagtatgagtattcaacat
ttccgtgtcgcccttattccctttttttgcggcattttgccttcctgtttttgctcacccagaaacgctggtgaaag
taaaagatgctgaagatcagttgggtgcacgagtgggttacatcgaactggatctcaacagcggtaagatc
cttgagagttttcgccccgaagaacgttttccaatgatgagcacttttaaagttctgctatgtggcgcggtatt
atcccgtattgacgccgggcaagagcaactcggtcgccgcatacactattctcagaatgacttggttgagta
ctcaccagtcacagaaaagcatcttacggatggcatgacagtaagagaattatgcagtgctgccataacca
tgagtgataacactgcggccaacttacttctgacaacgatcggaggaccgaaggagctaaccgcttttttgc
acaacatgggggatcatgtaactcgccttgatcgttgggaaccggagctgaatgaagccataccaaacga
cgagcgtgacaccacgatgcctgtagcaatggcaacaacgttgcgcaaactattaactggcgaactactta
ctctagcttcccggcaacaattaatagactggatggaggcggataaagttgcaggaccacttctgcgctcg
gcccttccggctggctggtttattgctgataaatctggagccggtgagcgtgggtctcgcggtatcattgcag
cactggggccagatggtaagccctcccgtatcgtagttatctacacgacggggagtcaggcaactatggat
gaacgaaatagacagatcgctgagataggtgcctcactgattaagcattggtaactgtcagaccaagttta
ctcatatatactttagattgatttaaaacttcatttttaatttaaaaggatctaggtgaagatcctttttgataa
tctcatgaccaaaatcccttaacgtgagttttcgttccactgagcgtcagaccccgtagaaaagatcaaagg
atcttcttgagatcctttttttctgcgcgtaatctgctgcttgcaaacaaaaaaaccaccgctaccagcggtg
gtttgtttgccggatcaagagctaccaactctttttccgaaggtaactggcttcagcagagcgcagatacca
aatactgtccttctagtgtagccgtagttaggccaccacttcaagaactctgtagcaccgcctacatacctcg
ctctgctaatcctgttaccagtggctgctgccagtggcgataagtcgtgtcttaccgggttggactcaagacg
atagttaccggataaggcgcagcggtcgggctgaacggggggttcgtgcacacagcccagcttggagcga
acgacctacaccgaactgagatacctacagcgtgagctatgagaaagcgccacgcttcccgaagggaga
aaggcggacaggtatccggtaagcggcagggtcggaacaggagagcgcacgagggagcttccagggg
aaacgcctggtatctttatagtcctgtcgggtttcgccacctctgacttgagcgtcgatttttgtgatgctcgtc
aggggggcggagcctatggaaaaacgccagcaacgcggcctttttacggttcctggccttttgctggcctt
ttgctcacatgttctttcctgcgttatcccctgattctgtggataaccgtattaccgcctttgagtgagctgata
ccgctcgccgcagccgaacgaccgagcgcagcgagtcagtgagcgaggaagcggaagagcgcccaata
cgcaaaccgcctctccccgcgcgttggccgattcattaatgcagctggcacgacaggtttcccgactggaaa
gcgggcagtga
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

| | |
|---|---|
| Codon optimized exon 1 and 2 full vector (SEQ ID NO: 11) | gcgcaacgcaattaatgtgagttagctcactcattaggcaccccaggctttacactttatgcttccggctcgt<br>atgttgtgtggaattgtgagcggataacaatttcacacaggaaacagctatgaccatgattacgccaagcg<br>cgcaattaaccctcactaaagggaacaaaagctggagctgcaagcttggccattgcatacgttgtatccat<br>atcataatatgtacatttatattggctcatgtccaacattaccgccatgttgacattgattattgactagttatt<br>aatagtaatcaattacggggtcattagttcatagcccatatatggagttccgcgttacataacttacggtaaa<br>tggcccgcctggctgaccgcccaacgaccccgcccattgacgtcaataatgacgtatgttcccatagtaac<br>gccaatagggactttccattgacgtcaatgggtggagtatttacggtaaactgcccacttggcagtacatca<br>agtgtatcatatgccaagtacgcccccctattgacgtcaatgacggtaaatggcccgcctggcattatgccca<br>gtacatgaccttatgggactttcctacttggcagtacatctacgtattagtcatcgctattaccatggtgatgc<br>ggttttggcagtacatcaatgggcgtggatagcggtttgactcacggggatttccaagtctccacccccattg<br>acgtcaatgggagtttgttttggcaccaaaatcaacgggactttccaaaatgtcgtaacaactccgccccat<br>tgacgcaaatgggcggtaggcgtgtacggtgggaggtctatataagcagagctcgtttagtgaaccggggt<br>ctctctggttagaccagatctgagcctgggagctctctggctaactagggaacccactgcttaagcctcaat<br>aaagcttgccttgagtgcttcaagtagtgtgtgcccgtctgttgtgtgactctggtaactagagatccctcag<br>accctttttagtcagtgtggaaaatctctagcagtggcgcccgaacagggacttgaaagcgaaagggaaac<br>cagaggagctctctcgacgcaggactcggcttgctgaagcgcgcacggcaagaggcgaggggcggcgac<br>tggtgagtacgccaaaaattttgactagcggaggctagaaggagagagatgggtgcgagagcgtcagtat<br>taagcgggggagaattagatcgcgatgggaaaaaattcggttaaggccagggggaaagaaaaaatataa<br>attaaaacatatagtatgggcaagcagggagctagaacgattcgcagttaatcctggcctgttagaaacat<br>cagaaggctgtagacaaatactgggacagctacaaccatcccttcagacaggatcagaagaacttagatc<br>attatataatacagtagcaaccctctattgtgtgcatcaaaggatagagataaaagacaccaaggaagctt<br>tagacaagatagaggaagagcaaaacaaaagtaagaccaccgcacagcaagcggccgcgtgatcttcag<br>acctgaggaggagagatatgagggacaattggagaagtgaattatataaatataaagtagtaaaaattgaa<br>ccattaggagtagcacccaccaaggcaaagagaagagtggtgcagagagaaaaaagagcagtgggaat<br>aggagctttgttccttgggttcttgggagcagcaggaagcactatgggcgcagcgtcaatgacgctgacgg<br>tacaggccagacaattattgtctggtatagtgcagcagcagaacaatttgctgagggctattgaggcgcaa<br>cagcatctgttgcaactcacagtctggggcatcaagcagctccaggcaagaatcctggctgtggaaagata<br>cctaaaggatcaacagctcctggggatttggggttgctctggaaaactcatttgcaccactgctgtgccttgg<br>aatgctagttggagtaataaatctctggaacagatttggaatcacacgacctggatggagtgggacagag<br>aaattaacaattacacaagcttaatacactccttaattgaagaatcgcaaaaccagcaagaaaagaatga<br>acaagaattattggaattagataaatgggcaagtttgtggaattggtttaacataacaaattggctgtggta<br>tataaaattattcataatgatagtaggaggcttggtaggtttaagaatagttttttgctgtactttctatagtga<br>atagagttaggcagggatattcaccattatcgtttcagacccacctcccaaccccgaggggacccgacggg<br>cccgaaggaatagaagaagaaggtggagagagagacagagacagatccattcgattagtgaacggatct<br>cgacggtatcgatctcgacacaaatggcagtattcatccacaatttaaaagaaaaggggggattggggg<br>gtacagtgcaggggaaagaatagtagacataatagcaacagacatacaaactaaagaattacaaaaaca<br>aattacaaaaattcaaaattttcgggtttattacagggacagcagagatccagtttggggtcgaggatatcgg<br>atcggaattctctagatgatcaggatccctcgagcccttatcgatcacgagactagcctcgactactagtgg<br>agatcccccgggctgcagagccagaagcaccataagggacatgataagggagccagcagacctctgatct<br>cttcctgaatgctaatcttaaacatcctgaggaagaatgggacttccatttggggtgggcctatgatagggt<br>aataagacagtagtgaatatcaagctacaaaaagcccccttttcaaattcttctcagtcctaacttttcatact<br>aagcccagtccttccaaagcagactgtgaaagagtgatagttccgggagactagcactgcagattccgggt<br>cactgtgagtggggggaggcagggaagaagggctcacaggacagtcaaaccatgcccccctgttttttccttct<br>tcaagtagacctctataagacaacagagacaactaaggctgagtggccaggcgaggagaaaccatctcg<br>ccgtaaaacatggaaggaacacttcaggggaaaggtggtatctctaagcaagagaactgagtggagtca<br>aggctgagagatgcaggataagcaaatgggtagtgaaaagacattcatgaggacagctaaaacaataag<br>taatgtaaaatacagcatagcaaaactttaacctccaaatcaagcctctacttgaatcctttttctgagggat<br>gaataagacataggcatcagggggctgttgccaatgtgcattagctgtttgcagcctcaccttcttttcatggag<br>tttaagatatagtgtattttcccaaggtttgaactagctcttcatttctttatgtttttaaatgcactgacctccca<br>cattccctttttagtaaaatattcagaaataatttaaatacatcattgcaatgaaaataaatgttttttattag<br>gcagaatccagatgctcaaggccctttcataatatccccccagtttagtagttggacttagggggaacaaaggaa<br>cctttaatagaaattggacagcaagaaagcgaggctttagtacttgtgggccagggcattagccacacca<br>gccaccacttctgataggcagcctgcactggtggggtgaattcttttgccaaagtgatgggccagcacacag<br>accagcacgttgcccaggagctgtgggaggaagataagaggtatgaacatgattagcaaaagggcctag<br>cttggactcagaataatccagccttatcccaaccataaaataaaagcagaatggtagctggattgtagctg<br>ctattagcaatatgaaacctcttacatcagttacaatttatatgcagaaatatttatgtgcagaaatattgct<br>attgccttaacccagaaattatcactgttattctttagaatggtgcaaagaggcatgatacattgtatcattat<br>tgccctgaaagaaagagattagggaaagtattagaaataagataaacaaaaaagtatattaaaagaaga<br>aagcattttttaaaattacaaatgcaaaattaccctgatttggtcaatatgtgtaccctgttacttctccccttc<br>ctatgacatgaacttaaccatagaaaaagagggggaaagaaaacatcaagggtcccatagactcac<u>cctg</u><br><u>aagttctcaggatccacgtgcagcttgtcgcagtgcagctcgctcagctgggcgaaggtgcccttcaggttg</u><br><u>tccaggtgggccaggccgtcgctgaaggcgcccagcaccttcttgccgtgggccttcaccttgggggttgccc</u><br><u>atcacggcgtcggggtgctcaggtcgccgaagctctcgaagaagcgctgggtccaggggtacaccacca</u><br><u>gcagcct</u>aagggtgggaaaatagccaataggcaggagggatcagtgcctatcagaaacccaagagtct<br>tctctgtctccacatgcccagtttctattggtctccttaaacctgtcttgtaaccttgataccaacctgcccagg<br>gcctcgccgcccacggcgtccacgttcaccttgtcccacagggcggtcacggcgctcttctcctcgggggtc<br>aggtgcaccatggtgtctgtttgaggttgctagtgaacacagttgtgtcagaagcaaatgtaagcaatagat<br>ggctcgccctgactttttatgcccagccctggctcgccctcctgcctcctgggagtagattggccaacccta<br>gggtgtggctccacagggtgaggtctaagtgatgacagccgtacctgtccttggctcttctggcactggctta<br>ggagtggacttcaaaccctcagccctccctcaagatatatctcttggccccataccatcagtacaaattgc<br>tactaaaaacatcctcctttgcaagtgtatttacccgacgcgtcggcgataagcttgatccatcgattacgta<br>tatgtgtatatatatatatattcaggaaataatatattctagaatatgtcacattctgtctcaggcatccat<br>tttctttatgatgccgtttgaggtggagttttagtcaggtggtcagcttctcctttttttttgccatctgccctgta |

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
agcatcctgctggggacccagataggagtcatcactctaggctgagaacatctgggcacacaccctaagcc
tcagcatgactcatcatgactcagcattgctgtgcttgagccagaaggtttgcttagaaggttacacagaac
cagaaggcgggggtggggcactgaccccgacaggggcctggccagaactgctcatgcttggactatggga
ggtcactaatggagacacacagaaatgtaacaggaactaaggaaaaactgaagctttgggggtataggg
gagcagtcccatgtagtagtagaatgaaaaatgctgctatgctgtgcctcccccacctttcccatgtctgccc
tctactcatggtctatctctcctggctcctgggagtcatggactccacccagcaccaccaacctgacctaacc
acctatctgagcctgccagcctataacccatctgggccctgatagctggtggccagccctgaccccacccca
ccctccctggaacctctgatagacacatctggcacaccagctcgcaaagtcaccgtgagggtcttgtgtttg
ctgagtcaaaattccttgaaatccaagtccttagagactcccaggcttggattcaaagctcctgactttctgt
ctagtgtatgtgcagtgagcccccttttcctctaactgaaagaaggaaaaaaaatggaacccaaaatattc
tacatagtttccatgtcacagcccaggggctgggcagtctcctgttattctctttaaaataaatatatcatttaaa
tgcataaataagcaaaccctgctcgggaatgggagggagagtctctggagtccaccccttctcggccctgg
ctctgcagatagtgctatcaaagccctgacagagccctgcccattgctgggccttggagtgagtcagcctag
tagagaggcagggcaagccatctcatagctgctgagtgggagagagaaaagggctcattgtctataaact
caggtcatggctattcttatggcctactcgaccacgagggaattccgataatcaacctctggattacaaaat
ttgtgaaagattgactggtattcttaactatgttgctccttttacgctatgtggatacgctgctttaatgcctttg
tatcatgctattgcttcccgtatggctttcattttctcctccttgtataaatcctggttgctgtctctttatgagga
gttgtggcccgttgtcaggcaacgtggcgtggtgtgcactgtgtttgctgacgcaaccccactggttggggc
attgccaccacctgtcagctcctttccgggactttcgctttccccctccctattgccacggcggaactcatcgc
cgccctgcctgcccgctgctggacaggggctcggctgttgggcactgacaattccgtggtgttgtcggggaa
atcatcgtcctttccttggctgctcgcctgtgttgccacctggattctgcgcgggacgtccttctgctacgtccc
ttcggccctcaatccagcggaccttccttcccgcggcctgctgccggctctgcgggcctcttccgcgtcttcgcc
ttcgccctcagacgagtcggatctcccttttgggccgcctcccccgcatcgataccgtcgacctcgagacctag
aaaaacatggccaattcgagctcggtacctttaagaccaatgacttacaaggcagctgtagatcttagcca
ctttttaaaagaaaaggggggactggaagggctaattcactcccaacgaagacaagatcccaggggatgta
cgtccctaacccgctaggggcagcacccaggcctgcactgccgcctgccggcaggggtccagtcctgcttt
ttgcttgtactgggtctctctggttagaccagatctgagcgtgggagctctctggctaactagggaacccact
gcttaagcctcaataaagcttgccttgagtgcttcaagtagtgtgtgcccgtctgttgtgtgactctggtaact
agagatccctcagacccttttagtcagtgtggaaaatctctagcagtagtagttcatgtcatcttattattcag
tatttataacttgcaaagaaatgaatatcagagagtgagaggaacttgtttattgcagcttataatggttac
aaataaagcaatagcatcacaaatttcacaaataaagcattttttttcactgcattctagttgtggtttgtcca
aactcatcaatgtatcttatcatgtctgtgctctagctatcccgcccctaactccgcccatccccgcccctaactc
cgcccagttccgcccattctccgccccatggctgactaatttttttatttatgcagaggccgaggccgcctcg
gcctctgagctattccagaagtagtgaggaggcttttttggaggcctaggcttttgcgtcgagacgtaccca
attcgccctatagtgagtcgtattacgcgcgctcactggccgtcgttttacaacgtcgtgactgggaaaaccc
tggcgttacccaacttaatcgccttgcagcacatccccctttcgccagctggcgtaatagcgaagaggcccg
caccgatcgcccttcccaacagttgcgcagcctgaatggcgaatggcgcgacgcgccctgtagcggcgcat
taagcgcggcgggtgtggtggttacgcgcagcgtgaccgctacacttgccagcgccctagcgcccgctcctt
tcgctttcttcccttcctttctcgccacgttcgccggctttccccgtcaagctctaaatcggggctccctttag
ggttccgatttagtgctttacggcacctcgaccccaaaaaacttgattagggtgatggttcacgtagtgggc
catcgccctgatagacggtttttcgccctttgacgttggagtccacgttctttaatagtggactcttgttccaa
actggaacaacactcaaccctatctcggtctattcttttgatttataagggattttgccgatttcggcctattg
gttaaaaaatgagctgatttaacaaaaatttaacgcgaattttaacaaaatattaacgtttacaatttccca
ggtggcacttttcggggaaatgtgcgcggaacccctatttgtttatttttctaaatacattcaaatatgtatcc
gctcatgagacaataaccctgataaatgcttcaataatattgaaaaaggaagagtatgagtattcaacattt
ccgtgtcgcccttattcccttttttgcggcattttgccttcctgtttttgctcacccagaaacgctggtgaaagt
aaaagatgctgaagatcagttgggtgcacgagtgggttacatcgaactggatctcaacagcggtaagatcc
ttgagagttttcgccccgaagaacgttttccaatgatgagcacttttaaagttctgctatgtggcgcggtatta
tcccgtattgacgccgggcaagagcaactcggtcgccgcatacactattctcagaatgacttggttgagtac
tcaccagtcacagaaaagcatcttacggatggcatgacagtaagagaattatgcagtgctgccataaccat
gagtgataacactgcggccaacttacttctgacaacgatcggaggaccgaaggagctaaccgcttttttgc
acaacatgggggatcatgtaactcgccttgatcgttgggaaccggagctgaatgaagccataccaaacga
cgagcgtgacaccacgatgcctgtagcaatggcaacaacgttgcgcaaactattaactggcgaactactta
ctctagcttcccggcaacaattaatagactggatggaggcggataaagttgcaggaccacttctgcgctcg
gcccttccggctggctggtttattgctgataaatctggagccggtgagcgtgggtctcgcggtatcattgcag
cactggggccagatggtaagccctcccgtatcgtagttatctacacgacggggagtcaggcaactatggat
gaacgaaatagacagatcgctgagataggtgcctcactgattaagcattggtaactgtcagaccaagttta
ctcatatatactttagattgatttaaaacttcatttttaatttaaaaggatctaggtgaagatcctttttgataa
tctcatgaccaaaatcccttaacgtgagttttcgttccactgagcgtcagaccccgtagaaaagatcaaagg
atcttcttgagatcctttttttctgcgcgtaatctgctgcttgcaaacaaaaaaaccaccgctaccagcggtg
gtttgtttgccggatcaagagctaccaactctttttccgaaggtaactggcttcagcagagcgcagatacca
aatactgtccttctagtgtagccgtagttaggccaccacttcaagaactctgtagcaccgcctacatacctcg
ctctgctaatcctgttaccagtggctgctgccagtggcgataagtcgtgtcttaccgggttggactcaagacg
atagttaccggataaggcgcagcggtcgggctgaacggggggttcgtgcacacagcccagcttggagcga
acgacctacaccgaactgagatacctacagcgtgagctatgagaaagcgccacgcttcccgaagggaga
aaggcggacaggtatccggtaagcggcagggtcggaacaggagagcgcacgagggagcttccaggggg
aaacgcctggtatctttatagtcctgtcgggtttcgccacctctgacttgagcgtcgatttttgtgatgctcgtc
aggggggcggagcctatggaaaaacgccagcaacgcggcctttttacggttcctggccttttgctggcctt
ttgctcacatgttctttcctgcgttatcccctgattctgtggataaccgtattaccgcctttgagtgagctgata
ccgctcgccgcagccgaacgaccgagcgcagcgagtcagtgagcgaggaagcggaagagcgcccaata
cgcaaaccgcctctccccgcgcgttggccgattcattaatgcagctggcacgacaggtttcccgactggaaa
gcgggcagtga
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

| | |
|---|---|
| Codon<br>optimized exon<br>1, 2, and 3 full<br>vector (SEQ ID<br>NO: 12) | gcgcaacgcaattaatgtgagttagctcactcattaggcaccccaggctttacactttatgcttccggctcgt<br>atgttgtgtggaattgtgagcggataacaatttcacacaggaaacagctatgaccatgattacgccaagcg<br>cgcaattaaccctcactaaagggaacaaaagctggagctgcaagcttggccattgcatacgttgtatccat<br>atcataatatgtacatttatattggctcatgtccaacattaccgccatgttgacattgattattgactagttatt<br>aatagtaatcaattacggggtcattagttcatagcccatatatggagttccgcgttacataacttacggtaaa<br>tggcccgcctggctgaccgcccaacgacccccgcccattgacgtcaataatgacgtatgttcccatagtaac<br>gccaatagggactttccattgacgtcaatgggtggagtatttacggtaaactgcccacttggcagtacatca<br>agtgtatcatatgccaagtacgcccccctattgacgtcaatgacggtaaatggcccgcctggcattatgccca<br>gtacatgaccttatgggactttcctacttggcagtacatctacgtattagtcatcgctattaccatggtgatgc<br>ggttttggcagtacatcaatgggcgtggatagcggtttgactcacggggatttccaagtctccaccccattg<br>acgtcaatgggagtttgttttggcaccaaaatcaacgggactttccaaaatgtcgtaacaactccgccccat<br>tgacgcaaatgggcggtaggcgtgtacggtgggaggtctatataagcagagctcgtttagtgaaccggggt<br>ctctctggttagaccagatctgagcctgggagctctctggctaactagggaacccactgcttaagcctcaat<br>aaagcttgccttgagtgcttcaagtagtgtgtgcccgtctgttgtgtgactctggtaactagagatccctcag<br>acccttttagtcagtgtggaaaatctctagcagtggcgcccgaacagggacttgaaagcgaaagggaaac<br>cagaggagctctctcgacgcaggactcggcttgctgaagcgcgcacggcaagaggcgaggggcggcgac<br>tggtgagtacgccaaaaattttgactagcggaggctagaaggagagagatgggtgcgagagcgtcagtat<br>taagcgggggagaattagatcgcgatgggaaaaaattcggttaaggccaggggggaaagaaaaaatataa<br>attaaaacatatagtatgggcaagcagggagctagaacgattcgcagttaatcctggcctgttagaaacat<br>cagaaggctgtagacaaatactgggacagctacaaccatcccttcagacaggatcagaagaacttagatc<br>attatataatacagtagcaaccctctattgtgtgcatcaaaggatagagataaaagacaccaaggaagctt<br>tagacaagatagaggaagagcaaaacaaaagtaagaccaccgcacagcaagcggccgctgtaagtcttcag<br>acctggaggaggagatatgagggacaattggagaagtgaattatataaatataaagtagtaaaaattgaa<br>ccattaggagtagcacccaccaaggcaaagagaagagtggtgcagagagaaaaaagagcagtgggaat<br>aggagctttgttccttgggttcttgggagcagcaggaagcactatgggcgcagcgtcaatgacgctgacgg<br>tacaggccagacaattattgtctggtatagtgcagcagcagaacaatttgctgagggctattgaggcgcaa<br>cagcatctgttgcaactcacagtctggggcatcaagcagctccaggcaagaatcctggctgtggaaagata<br>cctaaaggatcaacagctcctggggatttggggttgctctggaaaactcatttgcaccactgctgtgccttgg<br>aatgctagttggagtaataaatctctggaacagatttggaatcacacgacctggatggagtgggacagag<br>aaattaacaattacacaagcttaatacactccttaattgaagaatcgcaaaaccagcaagaaaagaatga<br>acaagaattattggaattagataaatgggcaagtttgtggaattggtttaacataacaaattggctgtggta<br>tataaaattattcataatgatagtaggaggcttggtaggtttaagaatagtttttgctgtactttctatagtga<br>atagagttaggcagggatattcaccattatcgtttcagacccacctcccaacccgaggggacccgacagg<br>cccgaaggaatagaagaagaaggtggagagagagacagagacagatccattcgattagtgaacggatct<br>cgacggtatcgatctcgacacaaatggcagtattcatccacaatttaaaagaaaaggggggattgggggg<br>tacagtgcaggggaaagaatagtagacataatagcaacagacatacaaactaaagaattacaaaaaca<br>aattacaaaaattcaaaattttcgggtttattacagggacagcagagatccagtttggggtcgaggatatcgg<br>atcggaattctctagatgatcaggatccctcgagccctatatcgatcacgagactagcctcgactactagtgg<br>agatccccgggctgcagagccagaagcaccataagggacatgataagggagccagcagacctctgatct<br>cttcctgaatgctaatcttaaacatcctgaggaagaatgggacttccatttggggtgggcctatgatagggt<br>aataagacagtagtgaatatcaagctacaaaaagccccctttcaaattcttctcagtcctaacttttcatact<br>aagcccagtccttccaaagcagactgtgaaagagtgatagttccgggagactagcactgcagattccgggt<br>cactgtgagtggggggaggcaggaagaagggctcacaggacagctcaaaccatgccccctgttttttccttct<br>tcaagtagacctctataagacaacagagacaactaaggctgagtggccaggcgaggagaaaccatctcg<br>ccgtaaaacatggaaggaacacttcaggggaaaggtggtatctctaagcaagagaactgagtggagtca<br>aggctgagagatgcaggataagcaaatgggtagtgaaaagacattcatgaggacagctaaaacaataag<br>taatgtaaaatacagcatagcaaaactttaacctccaaatcaagcctctacttgaatcctttttctgagggat<br>gaataaggcataggcatcagggggctgttgccaatgtgcattagctgtttgcagcctcacctttctttcatggag<br>tttaagatatagtgtattttcccaaggtttgaactagctcttcatttctttatgtttttaaatgcactgacctccca<br>cattcccttttttagtaaaatattcagaaataatttaaatacatcattgcaatgaaaataaatgttttttattag<br>gcagaatccagatgctcaaggcccttcataatatcccccagtttagtagttggacttagggaacaaaggaa<br>cctttaatagaaattggacagcaagaaagcgagcttagtggtacttgtgggccagggcgttggccacgccg<br>gccaccaccttctggtaggcggcctgcacggggggggtgaactccttgccgaagtggtgggccagcacgc<br>acaccagcacgttgcccaggagctgtgggaggaagataagaggtatgaacatgattagcaaaagggcct<br>agcttggactcagaataatccagccttatcccaaccataaaataaaagcagaatggtagctggattgtagc<br>tgctattagcaatatgaaacctcttacatcagttacaatttatatcagcgaaatatttatatgcagaaatattg<br>ctattgccttaacccagaaattatcactgttattctttagaatggtgcaaagaggcatgatacattgtatcatt<br>attgccctgaaagaaagagattagggaaagtattagaaataagataaacaaaaaagtatattaaaagaa<br>gaaagcatttttttaaaattacaaatgcaaaattaccctgatttggtcaatatgtgtaccctgttacttctcccc<br>ttcctatgacatgaacttaaccatagaaaagaagggggaaagaaaacatcaagggtcccatagactcaccc<br>tgaagttctcggggtccacgtgcagcttgtcgcagtgcagctcgctcagctgggcgaaggtgcccttcaggt<br>tgtccaggtgggccaggccgtcgctgaaggcgcccagcaccttcttgccgtgggccttcaccttgggttgc<br>ccatcacggcgtcggggggtgctcaggtcgccgaagctctcgaagaagcgctgggtccaggggtacaccac<br>cagcagcctaagggtgggaaaatagaccaataggcagagaggtcagtgcctatcagaaacccaagagt<br>cttctctgtctccacatgcccagtttctattggtctccttaaacctgtcttgtaaccttgataccaacctgccca<br>gggcctcgccgcccacggcgtccacgttcaccttgtcccacagggcggtcacggcggctcttctcctcggggg<br>tcaggtgcaccatggtgtctgtttgaggttgctagtgaacacagttgtgtcagaagcaaatgtaagcaatag<br>atggctctgccctgacttttatgcccagccctgagctcctgggactgctcctggggattggctggccaaccc<br>tagggtgtggtcccacagggtgaggtctaagtgatgacagccgtacctgtccttggctcttctggcactggct<br>taggagttggacttcaaaccctcagccctccctctaagatatatctcttggccccataccatcagtacaaatt<br>gctactaaaaacatcctcctttgcaagtgtatttacccgacgcgtcggcgataagcttgatccatcgattacg<br>tatatgtgtatatatatatatattcaggaaataatatattctagaatatgtcacattctgtctcaggcatcc<br>attttctttatgatgccgtttgaggtggagttttagtcaggtggtcagcttctctcctttttttttgccatctgccctgt |

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
aagcatcctgctgggggacccagataggagtcatcactctaggctgagaacatctgggcacacaccctaagc
ctcagcatgactcatcatgactcagcattgctgtgcttgagccagaaggtttgcttagaaggttacacagaa
ccagaaggcggggggtggggcactgaccccgacaggggcctggccagaactgctcatgcttggactatggg
aggtcactaatggagacacacagaaatgtaacaggaactaaggaaaaactgaagctttggggggtatagg
ggagcagtcccatgtagtagtagaatgaaaaatgctgctatgctgtgcctcccccaccttcccatgtctgcc
ctctactcatggtctatctctcctggctcctgggagtcatggactccacccagcaccaccaacctgacctaac
cacctatctgagcctgccagcctataacccatctgggccctgatagctggtggccagccctgaccccacccc
accctccctggaacctctgatagacacatctggcacaccagctcgcaaagtcaccgtgagggtcttgtgtttt
gctgagtcaaaattccttgaaatccaagtccttagagactcccaggcttggattcaaagctcctgactttctg
tctagtgtatgtgcagtgagcccctttcctctaactgaaagaaggaaaaaaaaatggaacccaaaatatt
ctacatagtttccatgtcacagccagggctgggcagtctcctgttatttcttttaaaataaatatatcatttaa
atgcataaataagcaaaccctgctcgggaatgggagggagagtctctggagtccaccccttctcggccctg
gctctgcagatagtgctatcaaagccctgacagagccctgcccattgctgggccttggagtgagtcagccta
gtagagaggcagggcaagccatctcatagctgctgagtgggagagagaaaagggctcattgtctataaac
tcaggtcatggctattcttatggcctactcgacccacgagggaattccgataatcaacctctggattacaaaa
tttgtgaaagattgactggtattcttaactatgttgctccttttacgctatgtggatacgctgcttaatgcctttt
gtatcatgctattgcttcccgtatggctttcattttctcctccttgtataaatcctggttgctgtctctttatgagg
agttgtggcccgttgtcaggcaacgtggcgtggtgtgcactgtgtttgctgacgcaacccccactggttggg
gcattgccaccacctgtcagctcctttccgggactttcgctttccccctccctattgccacggcggaactcatc
gccgcctgccttgcccgctgctggacaggggctcggctgttgggcactgacaattccgtggtgttgtcggggg
aaatcatcgtcctttccttggctgctcgcctgtgttgccacctggattctgcgcgggacgtccttctgctacgtc
ccttcggccctcaatccagcggaccttccttcccgcggcctgctgccggctctgcggcctcttccgcgtcttcg
ccttcgccctcagacgagtcggatctcccctttgggccgcctccccgcatcgataccgtcgacctcgagaccta
gaaaaacatggccaattcgagctcggtacctttaagaccaatgacttacaaggcagctgtagatcttagcc
actttttaaaagaaaaggggggactggaagggctaattcactcccaacgaagacaagatcccaggggatgt
acgtccctaacccgctaggggggcagcacccaggcctgcactgccgcctgccggcagggggtccagtcctgct
ttttgcttgtactgggtctctctggttagaccagatctgagcctgggagctctctggctaactagggaaccca
ctgcttaagcctcaataaagcttgccttgagtgcttcaagtagtgtgtgcccgtctgttgtgtgactctggtaa
ctagagatccctcagacccttMagtcagtgtggaaaatctctagcagtagtagttcatgtcatcttattattc
agtatttataacttgcaaagaaatgaatatcagagagtgagaggaacttgtttattgcagcttataatggtt
acaaataaagcaatagcatcacaaatttcacaaataaagcatttttttcactgcattctagttgtggtttgtc
caaactcatcaatgtatcttatcatgtctggctctagctatcccgcccttaactccgcccatcccgcccctaac
tccgcccagttccgcccattctccgcccccatggctgactaatttttttttatttatgcagaggccgaggccgcct
cggcctctgagctattccagaagtagtgaggaggcttttttggaggcctaggcttttgcgtcgagacgtaccc
aattcgccctatagtgagtcgtattacgcgcgctcactggccgtcgttttacaacgtcgtgactgggaaaac
cctggcgttacccaacttaatcgccttgcagcacatccccctttcgccagctggcgtaatagcgaagaggcc
cgcaccgatcgcccttcccaacagttgcgcagcctgaatggcgaatggcgcgacgcgccctagcgcccgctc
ctttcgctttcttcccttcctttctcgccacgttcgccggctttccccgtcaagctctaaatcggggggctcccttt
agggttccgatttagtgctttacggcacctcgaccccaaaaaacttgattagggtgatggttcacgtagtgg
gccatcgccctgatagacggtttttcgcccttgacgttggagtccacgttctttaatagtggactcttgttcca
aactggaacaacactcaaccctatctcggtctattcttttgatttataagggattttgccgatttcggcctatt
ggttaaaaaatgagctgatttaacaaaaatttaacgcgaattttaacaaaatattaacgtttacaatttccc
aggtggcacttttcggggaaatgtgcgcggaacccctatttgtttatttttctaaatacattcaaatatgtatc
cgctcatgagacaataaccctgataaatgcttcaataatattgaaaaaggaagagtatgagtattcaacat
ttccgtgtcgcccttattcccttttttgcggcattttgccttcctgtttttgctcacccagaaacgctggtgaaag
taaaagatgctgaagatcagttgggtgcacgagtgggttacatcgaactggatctcaacagcggtaagatc
cttgagagttttcgccccgaagaacgttttccaatgatgagcacttttaaagttctgctatgtggcgcggtatt
atcccgtattgacgccgggcaagagcaactcggtcgccgcatacactattctcagaatgacttggttgagta
ctcaccagtcacagaaaagcatcttacggatggcatgacagtaagagaattatgcagtgctgccataacca
tgagtgataacactgcggccaacttacttctgacaacgatcggaggaccgaaggagctaaccgcttttttgc
acaacatgggggatcatgtaactcgccttgatcgttgggaaccggagctgaatgaagccataccaaacga
cgagcgtgacaccacgatgcctgtagcaatggcaacaacgttgcgcaaactattaactggcgaactactta
ctctagcttcccggcaacaattaatagactggatggaggcggataaagttgcaggaccacttctgcgctcg
gcccttccggctggctggtttattgctgataaatctggagccggtgagcgtgggtctcgcggtatcattgcag
cactggggccagatggtaagccctcccgtatcgtagttatctacacgacggggagtcaggcaactatggat
gaacgaaatagacagatcgctgagataggtgcctcactgattaagcattggtaactgtcagaccaagttta
ctcatatatactttagattgatttaaaacttcattttaatttaaaaggatctaggtgaagatcctttttgataa
tctcatgaccaaaatcccttaacgtgagttttcgttccactgagcgtcagaccccgtagaaaagatcaaag
gatcttcttgagatcctttttttctgcgcgtaatctgctgcttgcaaacaaaaaaaccaccgctaccagcggtg
gtttgtttgccggatcaagagctaccaactctttttccgaaggtaactggcttcagcagagcgcagatacca
aatactgtccttctagtgtagccgtagttaggccaccacttcaagaactctgtagcaccgcctacatacctcg
ctctgctaatcctgttaccagtggctgctgccagtggcgataagtcgtgtcttaccgggttggactcaagacg
atagttaccggataaggcgcagcggtcgggctgaacggggggttcgtgcacacagcccagcttggagcga
acgacctacaccgaactgagatacctacagcgtgagctatgagaaagcgccacgcttcccgaagggaga
aaggcggacaggtatccggtaagcggcagggtcggaacaggagagcgcacgagggagcttccaggggg
aaacgcctggtatctttatagtcctgtcgggtttcgccacctctgacttgagcgtcgatttttgtgatgctcgtc
aggggggcggagcctatggaaaaacgccagcaacgcggcctttttacggttcctggccttttgctggcctt
ttgctcacatgttctttcctgcgttatcccctgattctgtggataaccgtattaccgcctttgagtgagctgata
ccgctcgccgcagccgaacgaccgagcgcagcgagtcagtgagcgaggaagcggaagagcgcccaata
cgcaaaccgcctctccccgcgcgttggccgattcattaatgcagctggcacgacaggtttcccgactggaaa
gcgggcagtga
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence pUV-AS3
from junction
marker (SEQ ID
NO: 13)

```
ACGCGCCCTGTAGCGGCGCATTAAGCGCGGCGGGTGTGGTGGTTACGCGCAGCGTGACCGCTACACTTGC
CAGCGCCCTAGCGCCCGCTCCTTTCGCTTTCTTCCCTTCCTTTCTCGCCACGTTCGCCGGCTTTCCCCGT
CAAGCTCTAAATCGGGGGCTCCCTTTAGGGTTCCGATTTAGTGCTTTACGGCACCTCGACCCCAAAAAAC
TTGATTAGGGTGATGGTTCACGTAGTGGGCCATCGCCCTGATAGACGGTTTTTCGCCCTTTGACGTTGGA
GTCCACGTTCTTTAATAGTGGACTCTTGTTCCAAACTGGAACAACACTCAACCCTATCTCGGTCTATTCT
TTTGATTTATAAGGGATTTTGCCGATTTCGGCCTATTGGTTAAAAAATGAGCTGATTTAACAAAAATTTA
ACGCGAATTTTAACAAAATATTAACGCTTACAATTTAGGTGGCACTTTTCGGGGAAATGTGCGCGGAACC
CCTATTTGTTTATTTTTCTAAATACATTCAAATATGTATCCGCTCATGAGACAATAACCCTGATAAATGC
TTCAATAATAGCACCTAGATCAAGAGACAGGATGAGGATCGTTTCGCATGATTGAACAAGATGGATTGCA
CGCAGGTTCTCCGGCCGCTTGGGTGGAGAGGCTATTCGGCTATGACTGGGCACAACAGACAATCGGCTGC
TCTGATGCCGCCGTGTTCCGGCTGTCAGCGCAGGGGCGCCCGGTTCTTTTTGTCAAGACCGACCTGTCCG
GTGCCCTGAATGAACTGCAAGACGAGGCAGCGCGGCTATCGTGGCTGGCCACGACGGGCGTTCCTTGCGC
AGCTGTGCTCGACGTTGTCACTGAAGCGGGAAGGGACTGGCTGCTATTGGGCGAAGTGCCGGGGCAGGAT
CTCCTGTCATCTCACCTTGCTCCTGCCGAGAAAGTATCCATCATGGCTGATGCAATGCGGCGGCTGCATA
CGCTTGATCCGGCTACCTGCCCATTCGACCACCAAGCGAAACATCGCATCGAGCGAGCACGTACTCGGAT
GGAAGCCGGTCTTGTCGATCAGGATGATCTGGACGAAGAGCATCAGGGGCTCGCGCCAGCCGAACTGTTC
GCCAGGCTCAAGGCGAGCATGCCCGACGGCGAGGATCTCGTCGTGACCCATGGCGATGCCTGCTTGCCGA
ATATCATGGTGGAAAATGGCCGCTTTTCTGGATTCATCGACTGTGGCCGGCTGGGTGTGGCGGACCGCTA
TCAGGACATAGCGTTGGCTACCCGTGATATTGCTGAAGAGCTTGGCGGCGAATGGGCTGACCGCTTCCTC
GTGCTTTACGGTATCGCCGCTCCCGATTCGCAGCGCATCGCCTTCTATCGCCTTCTTGACGAGTTCTTCT
GAATTATTAACGCTTACAATTTCCTGATGCGGTATTTTCTCCTTACGCATCTGTGCGGTATTTCACACCG
CATCAGGTGGCACTTTTCGGGGAAATGTGCGCGGAACCCCTATTTGTTTATTTTTCTAAATACATTCAAA
TATGTATCCGCTCATGACCAAAATCCCTTAACGTGAGTTTTCGTTCCACTGAGCGTCAGACCCCGTAGAA
AAGATCAAAGGATCTTCTTGAGATCCTTTTTTTCTGCGCGTAATCTGCTGCTTGCAAACAAAAAAACCAC
CGCTACCAGCGGTGGTTTGTTTGCCGGATCAAGAGCTACCAACTCTTTTTCCGAAGGTAACTGGCTTCAG
CAGAGCGCAGATACCAAATACTGTTCTTCTAGTGTAGCCGTAGTTAGGCCACCACTTCAAGAACTCTGTA
GCACCGCCTACATACCTCGCTCTGCTAATCCTGTTACCAGTGGCTGCTGCCAGTGGCGATAAGTCGTGTC
TTACCGGGTTGGACTCAAGACGATAGTTACCGGATAAGGCGCAGCGGTCGGGCTGAACGGGGGGTTCGTG
CACACAGCCCAGCTTGGAGCGAACGACCTACACCGAACTGAGATACCTACAGCGTGAGCTATGAGAAAGC
GCCACGCTTCCCGAAGGGAGAAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGGTTTCGCCACCTCTGACTTGA
GCGTCGATTTTTGTGATGCTCGTCAGGGGGGCGGAGCCTATGGAAAAACGCCAGCAACGCGGCCTTTTTA
CGGTTCCTGGCCTTTTGCTGGCCTTTTGCTCACATGTTCTTTCCTGCGTTATCCCCTGATTCTGTGGATA
ACCGTATTACCGCCTTTGAGTGAGCTGATACCGCTCGCCGCAGCCGAACGACCGAGCGCAGCGAGTCAGT
GAGCGAGGAAGCGGAAGAGCGCCCAATACGCAAACCGCCTCTCCCCGCGCGTTGGCCGATTCATTAATGC
AGCTGGCACGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGAGCGGATA
ACAATTTCACACAGGAAACAGCTATGACCATGATTACGCCAAGCGCGCAATTAACCCTCACTAAAGGGAA
CAAAAGCTGGAGCTGCAAGCTTGGCCATTGCATACGTTGTATCCATATCATAATATGTACATTTATATTG
GCTCATGTCCAACATTACCGCCATGTTGACATTGATTATTGACTAGTTATTAATAGTAATCAATTACGGG
GTCATTAGTTCATAGCCCATATATGGAGTTCCGCGTTACATAACTTACGGTAAATGGCCCGCCTGGCTGA
CCGCCCAACGACCCCCGCCCATTGACGTCAATAATGACGTATGTTCCCATAGTAACGCCAATAGGGACTT
TCCATTGACGTCAATGGGTGGAGTATTTACGGTAAACTGCCCACTTGGCAGTACATCAAGTGTATCATAT
GCCAAGTACGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGATGCGGTTTT
GGCAGTACATCAATGGGCGTGGATAGCGGTTTGACTCACGGGGATTTCCAAGTCTCCACCCCATTGACGT
CAATGGGAGTTTGTTTTGGCACCAAAATCAACGGGACTTTCCAAAATGTCGTAACAACTCCGCCCCATTG
ACGCAAATGGGCGGTAGGCGTGTACGGTGGGAGGTCTATATAAGCAGAGCTCGTTTAGTGAACCGGGGATC
TCTCTGGTTAGACCAGATCTGAGCCTGGGAGCTCTCTGGCTAACTAGGGAACCCACTGCTTAAGCCTCAA
TAAAGCTTGCCTTGAGTGCTTCAAGTAGTGTGTGCCCGTCTGTTGTGTGACTCTGGTAACTAGAGATCCC
TCAGACCCTTTTAGTCAGTGTGGAAAATCTCTAGCAGTGGCGCCCGAACAGGGACTTGAAAGCGAAAGGG
AAACCAGAGGAGCTCTCTCGACGCAGGACTCGGCTTGCTGAAGCGCGCACGGCAAGAGGCGAGGGGCGGC
GACTGGTGAGTACGCCAAAAATTTTGACTAGCGGAGGCTAGAAGGAGAGAGATGGGTGCGAGAGCGTCAG
TATTAAGCGGGGGAGAATTAGATCGCGATGGGAAAAAATTCGGTTAAGGCCAGGGGGAAAGAAAAAATAT
AAATTAAAACATATAGTATGGGCAAGCAGGGAGCTAGAACGATTCGCAGTTAATCCTGGCCTGTTAGAAA
CATCAGAAGGCTGTAGACAAATACTGGGACAGCTACAACCATCCCTTCAGACAGGATCAGAAGAACTTAG
ATCATTATATAATACAGTAGCAACCCTCTATTGTGTGCATCAAAGGATAGAGATAAAAGACACCAAGGAA
GCTTTAGACAAGATAGAGGAAGAGCAAAACAAAAGTAAGACCACCGCACAGCAAGCGGCCGCTGATCTTC
AGACCTGGAGGAGGAGATATGAGGGACAATTGGAGAAGTGAATTATATAAATATAAAGTAGTAAAAATTG
AACCATTAGGAGTAGCACCCACCAAGGCAAAGAGAAGAGTGGTGCAGAGAGAAAAAAGAGCAGTGGGAAT
AGGAGCTTTGTTCCTTGGGTTCTTGGGAGCAGCAGGAAGCACTATGGGCGCAGCGTCAATGACGCTGACG
GTACAGGCCAGACAATTATTGTCTGGTATAGTGCAGCAGCAGAACAATTTGCTGAGGGCTATTGAGGCGC
AACAGCATCTGTTGCAACTCACAGTCTGGGGCATCAAGCAGCTCCAGGCAAGAATCCTGGCTGTGGAAAG
ATACCTAAAGGATCAACAGCTCCTGGGGATTTGGGGTTGCTCTGGAAAACTCATTTGCACCACTGCTGTG
CCTTGGAATGCTAGTTGGAGTAATAAATCTCTGGAACAGATTTGGAATCACACGACCTGGATGGAGTGGG
ACAGAGAAATTAACAATTACACAAGCTTAATACACTCCTTAATTGAAGAATCGCAAAACCAGCAAGAAAA
GAATGAACAAGAATTATTGGAATTAGATAAATGGGCAAGTTTGTGGAATTGGTTTAACATAACAAATTGG
CTGTGGTATATAAAATTATTCATAATGATAGTAGGAGGCTTGGTAGGTTTAAGAATAGTTTTTGCTGTAC
TTTCTATAGTGAATAGAGTTAGGCAGGGATATTCACCATTATCGTTTCAGACCCACCTCCCAACCCCGAG
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
GGGACCCGACAGGCCCGAAGGAATAGAAGAAGAAGGTGGAGAGAGAGACAGAGACAGATCCATTCGATTA
GTGAACGGATCTCGACGGTATCGATCTCGACACAAATGGCAGTATTCATCCACAATTTTAAAAGAAAAGG
GGGGATTGGGGGGTACAGTGCAGGGGAAAGAATAGTAGACATAATAGCAACAGACATACAAACTAAAGAA
TTACAAAAACAAATTACAAAAATTCAAAATTTTCGGGTTTATTACAGGGACAGCAGACATGAGGACAGCT

AAAACAATAAGTAATGTAAAATACAGCATAGCAAAACTTTAACCTCCAAATCAAGCCTCTACTTGAATCC
TTTTCTGAGGGATGAATAAGGCATAGGCATCAGGGGCTGTTGCCAATGTGCATTAGCTGTTTGCAGCCTC
ACCTTCTTTCATGGAGTTTAAGATATAGTGTATTTTCCCAAGGTTTGAACTAGCTCTTCATTTCTTTATG
TTTTAAATGCACTGACCTCCCACATTCCCTTTTTAGTAAAATATTCAGAAATAATTTAAATACATCATTG
CAATGAAAATAAATGTTTTTTATTAGGCAGAATCCAGATGCTCAAGGCCCTTCATAATATCCCCCAGTTT
AGTAGTTGGACTTAGGGAACAAAGGAACCTTTAATAGAAATTGGACAGCAAGAAAGCGAGCTTAGTGATA
CTTGTGGGCCAGGGCATTAGCCACACCAGCCACCACTTTCTGATAGGCAGCCTGCACTGGTGGGGTGAAT
TCTTTGCCAAAGTGATGGGCCAGCACACAGACCAGCACGTTGCCCAGGAGCTGTGGGAGGAAGATAAGAG
GTATGAACATGATTAGCAAAAGGGCCTAGCTTGGACTCAGAATAATCCAGCCTTATCCCAACCATAAAAT
AAAAGCAGAATGGTAGCTGGATTGTAGCTGCTATTAGCAATATGAAACCTCTTACATCAGTTACAATTTA
TATGCAGAAATACCCTGTTACTTCTCCCCTTCCTATGACATGAACTTAACCATAGAAAGAAGGGGAAAG
AAAACATCAAGGGTCCCATAGACTCACCCTGAAGTTCTCAGGATCCACGTGCAGCTTGTCACAGTGCAGC
TCACTCAGCTGGGCAAAGGTGCCCTTGAGGTTGTCCAGGTGAGCCAGGCCATCACTAAAGGCACCGAGCA
CTTTCTTGCCATGAGCCTTCACCTTAGGGTTGCCCATAACAGCATCAGGAGTGGACAGATCCCCAAAGGA
CTCAAAGAACCTCTGGGTCCAAGGGTAGACCACCAGCAGCCTAAGGGTGGGAAAATAGACCAATAGGCAG
AGAGAGTCAGTGCCTATCAGAAACCCAAGAGTCTTCTCTGTCTCCACATGCCCAGTTTCTATTGGTCTCC
TTAAACCTGTCTTGTAACCTTGATACCAACCTGCCCAGGGCCTCACCACCAACGGCATCCACGTTCACCT
TGTCCCACAGGGCAGTAACGGCAGACTTCTCCTCAGGAGTCAGGTGCACCATGGTGTCTGTTTGAGGTTG
CTAGTGAACACAGTTGTGTCAGAAGCAAATGTAAGCAATAGATGGCTCTGCCCTGACTTTTATGCCCAGC
CCTGGCTCCTGCCCTCCCTGCTCCTGGGAGTAGATTGGCCAACCCTAGGGTGTGGCTCCACAGGGTGAGG
TCTAAGTGATGACAGCCGTACCTGTCCTTGGCTCTTCTGGCACTGGCTTAGGAGTTGGACTTCAAACCCT
CAGCCCTCCCTCTAAGATATATCTCTTGGCCCCATACCATCAGTACAAATTGCTACTAAAAACATCCTCC
TTTGCAAGTGTATTTACTACGTATATGTGTATATATATATATATATTCAGGAAATAATATATTCTAGAAT
ATGTCACATTCTGTCTCAGGCATCCATTTTCTTTATGATGCCGTTTGAGGTGGAGTTTTAGTCAGGTGGT
CAGCTTCTCCTTTTTTTTGCCATCTGCCCTGTAAGCATCCTGCTGGGGACCCAGATAGGAGTCATCACTC
TAGGCTGAGAACATCTGGGCACACACCCTAAGCCTCAGCATGACTCATCATGACTCAGCATTGCTGTGCT
TGAGCCAGAAGGTTTGCTTAGAAGGTTACACAGAACCAGAAGGCGGGGGTGGGGCACTGACCCCGACAGG
GGCCTGGCCAGAACTGCTCATGCTTGGACTATGGGAGGTCACTAATGGAGACACACAGAAATGTAACAGG
AACTAAGGAAAAACTGAAGCTTTGGGGGTATAGGGGAGCAGTCCCATGTAGTAGTAGAATGAAAAATGCT
GCTATGCTGTGCCTCCCCCACCTTTCCCATGTCTGCCCTCTACTCATGGTCTATCTCTCCTGGCTCCTGG
GAGTCATGGACTCCACCCAGCACCACCAACCTGACCTAACCACCTATCTGAGCCTGCCAGCCTATAACCC
ATCTGGGCCCTGATAGCTGGTGGCCAGCCCTGACCCCACCCCACCCTCCCTGGAACCTCTGATAGACACA
TCTGGCACACCAGCTCGCAAAGTCACCGTGAGGGTCTTGTGTTTGCTGAGTCAAAATTCCTTGAAATCCA
AGTCCTTAGAGACTCCCAGGCTTGGATTCAAAGCTCCTGACTTTCTGTCTAGTGTATGTGCAGTGAGCCC
CTTTTCCTCTAACTGAAAGAAGGAAAAAAAAATGGAACCCAAAATATTCTACATAGTTTCCATGTCACAG
CCAGGGCTGGGCAGTCTCCTGTTATTTCTTTTAAAATAAATATATCATTTAAATGCATAAATAAGCAAAC
CCTGCTCGGGAATGGGAGGGAGAGTCTCTGGAGTCCACCCCTTCTCGGCCCTGGCTCTGCAGATAGTGCT
ATCAAAGCCCTGACAGAGCCCTGCCCATTGCTGGGCCTTGGAGTGAGTCAGCCTAGTAGAGAGGCAGGGC
AAGCCATCTCATAGCTGCTGAGTGGGAGAGAGAAAAAGGGCTCATTGTCTATAAACTCAGGTCATGGCTAT
TCTTATTAAAAGAAAAGGGGGGACTGGAAGGGCTAATTCACTCCCAACGAAGACAAGATCTGCTTTTTGC
TTGTACTGGGTCTCTCTGGTTAGACCAGATCTGAGCCTGGGAGCTCTCGGCTAACTAGGGAACCCACTG
CTTAAGCCTCAATAAAGCTTGCCTTGAGTGCTTCAAGTAGTGTGTTGGTTTTTTGTGTGTGCATTGTCTG

AGTAGGTGTCATTCTATTCTGGGGGGTGGGGTGGGGCAGCACAGCAAGGGGGAGGATTGGGAAGACAATA

GCAGGCATGCTGGGGATGCGGTGGGCTCTATGGAGTAGTAGTTCATGTCATCTTATTATTCAGTATTTAT

AACTTGCAAAGAAATGAATATCAGAGAGTGAGAGGAACTTGTTTATTGCAGCTTATAATGGTTACAAATA
AAGCAATAGCATCACAAATTTCACAAATAAAGCATTTTTTTCACTGCATTCTAGTTGTGGTTTGTCCAAA
CTCATCAATGTATCTTATCATGTCTGGCTCTAGCTATCCCGCCCCTAACTCCGCCCATCCCGCCCCTAAC

TCCGCCCAGTTCCGCCCATTCTCCGCCCCATGGCTCTCACTACTTCTGGAATAGCTCAGAGGCCGAGGCG

GCCTCGGCCTCTGCATAAATAAAAAAAAATTAGTCGAGGCTTTTTTGGAGGCCTAGGGACGTACCCAATTC

GCCCTATAGTGAGTCGTATTACGCGCGCTCACTGGCCGTCGTTTTACAACGTCGTGACTGGGAAAACCCT
GGCGTTACCCAACTTAATCGCCTTGCAGCACATCCCCCTTTCGCCAGCTGGCGTAATAGCGAAGAGGCCC
GCACCGATCGCCCTTCCCAACAGTTGCGCAGCCTGAATGGCGAATGGG
``` pUV-
AS3(coX2)
from junction
marker (SEQ ID
NO: 14)

```
acgcgccctgtagcggcgcattaagcgcggcgggtgtggtggttacgcgcagcgtgaccgctacacttgcc
agcgccctagcgcccgctcctttcgctttcttcccttccttctcgccacgttcgccggctttccccgtcaagct
ctaaatcgggggctcccttttagggttccgatttagtgctttacggcacctcgacccaaaaaacttgattagg
gtgatggttcacgtagtgggccatcgccctgatagacggtttttcgcccttttgacgttggagtccacgttcttt
aatagtgggactcttgttccaaactggaacaacactcaaccctatctcggtctattcttttgatttataagggat
tttgccgatttcggcctattggttaaaaaatgagctgatttaacaaaaatttaacgcgaattttaacaaaata
ttaacgcttacaatttaggtggcacttttcggggaaatgtgcgcggaacccctatttgtttatttttctaaata
cattcaaatatgtatccgctcatgagacaataaccctgataaatgcttcaataatagcacctagatcaagag
acaggatgaggatcgtttcgcatgattgaacaagatggattgcacgcaggttctccggccgcttgggtgga
gaggctattcggctatgactgggcacaacagacaatcggctgctctgatgccgccgtgttccggctgtcagc
gcaggggcgcccggttctttttgtcaagaccgacctgtccggtgccctgaatgaactgcaagacgaggcag
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
cgcggctatcgtggctggccacgacgggcgttccttgcgcagctgtgctcgacgttgtcactgaagcgggaa
gggactggctgctattgggcgaagtgccggggcaggatctcctgtcatctcaccttgctcctgccgagaaag
tatccatcatggctgatgcaatgcggcggctgcatacgcttgatccggctacctgcccattcgaccaccaag
cgaaacatcgcatcgagcgagcacgtactcggatggaagccggtcttgtcgatcaggatgatctggacga
agagcatcaggggctcgcgccagccgaactgttcgccaggctcaaggcgagcatgcccgacggcgaggat
ctcgtcgtgacccatggcgatgcctgcttgccgaatatcatggtggaaaatggccgcttttctggattcatcg
actgtggccggctgggtgtggcggaccgctatcaggacatagcgttggctacccgtgatattgctgaagag
cttggcggcgaatgggctgaccgcttcctcgtgctttacggtatcgccgctcccgattcgcagcgcatcgcct
tctatcgccttcttgacgagttcttctgaattattaacgcttacaatttcctgatgcggtattttctccttacgca
tctgtgcggtatttcacaccgcatcaggtggcacttttcggggaaatgtgcgcggaacccctatttgtttattt
ttctaaatacattcaaatatgtatccgctcatgaccaaaatccttaacgtgagttttcgttccactgagcgtc
agaccccgtagaaaagatcaaaggatcttcttgagatcctttttttctgcgcgtaatctgctgcttgcaaaca
aaaaaaccaccgctaccagcggtggtttgtttgccggatcaagagctaccaactctttttccgaaggtaact
ggcttcagcagagcgcagataccaaatactgttcttctagtgtagccgtagttaggccaccacttcaagaac
tctgtagcaccgcctacatacctcgctctgctaatcctgttaccagtggctgctgccagtggcgataagtcgt
gtcttaccgggttggactcaagacgatagttaccggataaggcgcagcggtcgggctgaacggggggttc
gtgcacacagcccagcttggagcgaacgacctacaccgaactgagatacctacagcgtgagctatgagaa
agcgccacgcttcccgaagggagaaaggcggacaggtatccggtaagcggcagggtcggaacaggaga
gcgcacgagggagcttccaggggggaaacgcctggtatctttatagtcctgtcgggtttcgccacctctgactt
gagcgtcgatttttgtgatgctcgtcagggggggcggagcctatggaaaaacgccagcaacgcggccttttta
cggttcctggccttttgctggccttttgctcacatgttctttcctgcgttatcccctgattctgtggataaccgta
ttaccgcctttgagtgagctgataccgctcgccgcagccgaacgaccgagcgcagcgagtcagtgagcga
ggaagcggaagagcgcccaatacgcaaaccgcctctccccgcgcgttggccgattcattaatgcagctggc
acgacaggtttcccgactggaaagcgggcagtgagcgcaacgcaattaatgtgagttagctcactcattag
gcaccccaggctttacactttatgcttccggctcgtatgttgtgtggaattgtgagcggataacaatttcaca
caggaaacagctatgaccatgattacgccaagcgcgcaattaaccctcactaaagggaacaaaagctgg
agctgcaagcttggccattgcatacgttgtatccatatcataatatgtacatttatattggctcatgtccaaca
ttaccgccatgttgacattgattattgactagttattaataagtaatcaattacggggtcattagttcatagccc
atatatggagttccgcgttacataacttacggtaaatggcccgcctggctgaccgcccaacgacccccgccc
attgacgtcaataatgacgtatgttcccatagtaacgccaatagggactttccattgacgtcaatgggtgga
gtatttacggtaaactgcccacttggcagtacatcaagtgtatcatatgccaagtacgccccctattgacgtc
aatgacggtaaatggcccgcctggcattatgcccagtacatgaccttatgggactttcctacttggcagtac
atctacgtattagtcatcgctattaccatggtgatgcggttttggcagtacatcaatgggcgtggatagcggt
ttgactcacggggatttccaagtctccacccattgacgtcaatgggagtttgttttggcaccaaaatcaacg
ggactttccaaaatgtcgtaacaactccgccccattgacgcaaatgggcggtaggcgtgtacggtgggagg
tctatataagcagagctcgtttagtgaaccgGGGTCTCTCTGGTTAGACCAGATCTGAGCCT
GGGAGCTCTCTGGCTAACTAGGGAACCCACTGCTTAAGCCTCAATAAAGCTTGCC
TTGAGTGCTTCAAGTAGTGTGTGCCCGTCTGTTGTGTGACTCTGGTAACTAGAGA
TCCCTCAGACCCTTTTAGTCAGTGTGGAAAATCTCTAGCagtggcgcccgaacagggact
tgaaagcgaaagggaaaccagaggagctctcTCGACGCAGGACTCGGCTTGCTGAAGCGC
GCACGGCAAGAGGCGAGGGGCGGCGACTGGTGAGTACGCCAAAAATTTTGACT
AGCGGAGGCTAGAAGGAGAGAGATGGGTGCGAGAGCGTCAGTATTAAGCGGG
GGAGaattagatcgcgatgggaaaaaattcggttaaggccaggggggaaagaaaaaatataaattaaa
acatatagtatgggcaagcagggagctagaacgattcgcagttaatcctggcctgttagaaaacatcagaa
ggctgtagacaaaatactgggacagctacaaccatcccttcagacaggatcagaagaacttagatcattata
taatacagtagcaaccctctattgtgtgcatcaaaggatagagataaaagacaccaaggaagctttagac
aagatagaggaagagcaaaacaaaagtaagaccaccgcacagcaagcGGCCGCTgatcttcagacc
tggaggaggagatatgagggacaattggagaagtgaattatatataaaataaaagtagtaaaaattgaacca
ttaggagtagcacccaccaaggcaaagagaagagtggtgcagagagagaaaaaagaGCAGTGGGAAT
aggagctttgttccttgggttcttgggagcagcaggaagcactatgggcgcagcgtcaatgacgctgacgg
tacaggccagacaattattgtctggtatagtgcagcagcagaacaatttgctgagggctattgaggcgcaa
cagcatctgttgcaactcacagtctggggcatcaagcagctccaggcaagaatcctggctgtggaaagata
cctaaaggatcaacagctcctggggatttggggttgctctggaaaactcatttgcaccactgctgtgccttgg
aatgctagttggagtaataaatctctggaacagatttggaatcacacgacctggatggagtgggacagaa
aaattaacaattacacaagcttaatacactccttaattgaagaatcgcaaaaccagcaagaaaagaatga
acaagaattattggaattagataaatgggcaagtttgtggaattggtttaacataacaaattggctgtggta
tataaaattattcataatgatagtaggaggcttggtaggtttaagaatagtttttgctgtactttctatagtga
atagagttaggcagggatattcaccattatcgtttcagacccacctcccaacccgaggggacccgacagg
cccgaaggaatagaagaagaaggtggagagagagacagagacagatccattcgattagtgaacggatC
TCGACGGTATCGATCTCGAcacaaatggcagtattcatccacaattttaaaagaaaaggggggat
tgggggtacagtgcaggggaaagaatagtagacataatagcaacagacatacaaactaaagaattaca
aaaacaaattacaaaaattcaaaattttcgggtttattacagggacagcagacatgaggacagctaaaac
aataagtaatgtaaaatacagcatagcaaaactttaacctccaaatcaagcctctacttgaatcctttctg
agggatgaataaggcataggcatcaggggctgttgccaatgtgcattagctgtttgcagcctcaccttctttc
atggagtttaagatatagtgtattttcccaaggttgaactagctcttcattttctttatgtttaaatgcactga
cctcccacattcccttttttagtaaaatattcagaaataattttaaatacatcattgcaatgaaaataaatgtttt
ttattaggcagaatccagatgctcaaggcccttcataatatccccccagtttagtagttggacttagggaaca
aaggaacctttaatagaaattggacagcaagaaagcgagcttagtgatacttgtgggccagggcattagc
cacaccagccaccacttttctgataggcagcctgtggggtgggttgaattcttttgcaaagtgatgggccag
cacacagaccagcacgttgcccaggagctgtgggaggaagataagaggtatgaacatgattagcaaaag
ggcctagcttggactcagaataatccagccttatcccaaccataaaataaaagcagaatggtagctggatt
gtagctgctattagcaatatgaaacctcttacatcagttacaatttatatgcagaaataccctgttacttctcc
ccttcctatgacatgaacttaaccatagaaaagaagggggaaagaaaacatcaagggtcccatagactcac
cctGAAGTTCTCaGGaTCCACGTGCAGCTTGTCGCAGTGCAGCTCGCTCAGCTGGG
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
CGAAGGTGCCCTTCAGGTTGTCCAGGTGGGCCAGGCCGTCGCTGAAGGCGCCCA
GCACCTTCTTGCCGTGGGCCTTCACCTTGGGGTTGCCCATCACGGCGTCGGGGGT
GCTCAGGTCGCCGAAGCTCTCGAAGAAGCGCTGGGTCCAGGGGTACACCACCAG
cagcctaagggtgggaaaatagaccaataggcagagagagtcagtgcctatcagaaacccaagagtcttc
tctgtctccacatgcccagtttctattggtctccttaaacctgtcttgtaaccttgataccaacctgcccaggg
cctcaccaccaacggcatccacgttcaccttgtcccacagggcagtaacggcagacttctcctcaggagtca
ggtgcaccatggtgtctgtttgaggttgctagtgaacacagttgtgtcagaagcaaatgtaagcaatagatg
gctctgccctgacttttatgcccagccctggctcctgccctccctgctcctgggagtagattggccaaccctag
ggtgtggctccacagggtgaggtctaagtgatgacagccgtacctgtccttggctcttctggcactggcttag
gagttggacttcaaaccctcagccctccctctaagatatatctcttggccccataccatcagtacaaattgct
actaaaaacatcctcctttgcaagtgtatttacTACGTaTATGTGTATATATATATATATATTCA
GGAAATAATATATTCTAGAATATGTCACATTCTGTCTCAGGCATCCATTTTCTTTAT
GATGCCGTTTGAGGTGGAGTTTTAGTCAGGTGGTCAGCTTCTCCTTTTTTTTGCCA
TCTGCCCTGTAAGCATCCTGCTGGGGACCCAGATAGGAGTCATCACTCTAGGCTG
AGAACATCTGGGCACACACCCTAAGCCTCAGCATGACTCATCATGACTCAGCATT
GCTGTGCTTGAGCCAGAAGGTTTGCTTAGAAGGTTACACAGAACCAGAAGGCGG
GGGTGGGGCACTGACCCCGACAGGGGCCTGGCCAGAACTGCTCATGCTTGGACT
ATGGGAGGTCACTAATGGAGACACACAGAAATGTAACAGGAACTAAGGAAAAA
CTGAAGCTTgggggtatagggggagcagtcccatgtagtagtagaatgaaaaatgctgctatgctgtgc
ctcccccacctttcccatgtctgccctctactcatggtctatctctcctggctcctgggagtcatggactccacc
cagcaccaccaacctgacctaaccacctatctgagcctgccagcctataacccatctgggccctgatagctg
gtggccagccctgaccccacccaccctccctggaacctctgatagacacatctggcacaccagctcgcaa
agtcaccgtgagggtcttgtgtttgctgagtcaaaattccttgaaatccaagtccttagagactcccaggctt
ggattcaaagctcctgactttctgtctagtgtatgtgcagtgagcccctttcctctaactgaaagaaggaaa
aaaaaatggaacccaaaatattctacatagtttccatgtcacagccagggctgggcagtctcctgttatttct
tttaaaataaatatatcatttaaatgcataaataagcaaaccctgctcgggaatgggagggagagtctctg
gagtccacccccttctcggccctggctctgcagatagtgctatcaaagccctgacagagccctgcccattgct
gggccttggagtgagtcagcctagtagagaggcaggcaagccatctcatagctgctgctgagtgggagagag
aaaagggctcattgtctataaactcaggtcatggctattcttattaaaagaaaaggggggactggaagggc
taattcactcccaacgaagacaagatctgcttttttgcttgtactGGGTCTCTCTGGTTAGACCAGA
TCTGAGCCTGGGAGCTCTCTGGCTAACTAGGGAACCCACTGCTTAAGCCTCAATA
AAGCTTGCCTTGAGTGCTTCAAGTAGTGTGTTGGTTTTTTGTGTGTGCATTGTCTG
AGTAGGTGTCATTCTATTCTGGGGGGTGGGGTGGGGCAGCACAGCAAGGGGGA
GGATTGGGAAGACAATAGCAGGCATGCTGGGGATGCGGTGGGCTCTATGGagta
gtagttcatgtcatcttattattcagtatttataacttgcaaagaaatgaatatcagagagtgagaggaactt
gtttattgcagcttataatggttacaaataaagcaaatagcatcacaaatttcacaaataaagcattttttca
ctgcattctagttgtggtttgtccaaactcatcaatgtatcttatcatgtctggctctagctatcccgcccctaa
ctccgcccATCCCGCCCCTAACTCCGCCCAGTTCCGCCCATTCTCCGCCCCATGGCTC
TCACTACTTCTGGAATAGCTCAGAGGCCGAGGCGGCCTCGGCCTCTGCATAAATA
AAAAAAATTAGTCGAGGCTTTTTTGGAGGCCTAGGacgtacccaattcgccctatagtga
gtcgtattacgcgcgctcactggccgtcgtttacaacgtcgtgactgggaaaaccctggcgttacccaactt
aatcgccttgcagcacatccccctttcgccagctggcgtaatagcgaagaggcccgcaccgatcgcccttcc
caacagttgcgcagcctgaatggcgaatggg
``` pUV-HS1-AS3
from junction
marker
(SEQ ID NO: 15)

```
acgcgccctgtagcggcgcattaagcgcggcgggtgtggtggttacgcgcagcgtgaccgctacacttgcc
agcgccctagcgcccgctccttttcgctttcttcccttcctttctcgccacgttcgccggctttccccgtcaagct
ctaaatcgggggctccctttagggttccgatttagtgctttacggcacctcgaccccaaaaaacttgattagg
gtgatggttcacgtagtgggccatcgccctgatagacggtttttcgccctttgacgttggagtccacgttcttt
aatagtggactcttgttccaaactggaacaacactcaaccctatctcggtctattctttgatttataagggat
tttgccgatttcggcctattggttaaaaaatgagctgatttaacaaaaatttaacgcgaattttaacaaaata
ttaacgcttacaattaggtggcacttttcggggaaatgtgcgcggaacccctatttgtttatttttctaaata
cattcaaatatgtatccgctcatgagacaataaccctgataaatgcttcaataatagcacctagatcaagag
acaggatgaggatcgtttcgcatgattgaacaagatggattgcacgcaggttctccggccgcttgggtgga
gaggctattcggctatgactgggcacaacagacaatcggctgctctgatgccgccgtgttccggctgtcagc
gcaggggcgcccggttcttttttgtcaagaccgacctgtccggtgccctgaatgaactgcaagacgaggcag
cgcggctatcgtggctggccacgacgggcgttccttgcgcagctgtgctcgacgttgtcactgaagcgggaa
gggaccggctgctattgggcgaagtgccgggcaggatctcctgtcatctcaccttgctcctgccgagaaag
tatccatcatggctgatgcaatgcggcggctgcatacgcttgatccggctacctgcccattcgaccaccaag
cgaaacatcgcatcgagcgagcacgtactcggatggaagccggtcttgtcgatcaggatgatctggacga
agagcatcaggggctcgcgccagccgaactgttcgccaggctcaaggcgagcatgcccgacgcgaggat
ctcgtcgtgacccatggcgatgcctgcttgccgaatatcatggtggaaaatggccgcttttctggattcatcg
actgtggccggctgggtgtggcggaccgctatcaggacatagcgttggctacccgtgatattgctgaagag
cttggcggcgaatgggctgaccgcttcctcgtgctttacggtatcgccgctcccgattcgcagcgcatcgcct
tctatcgccttcttgacgagttcttctgaattattaacgcttacaatttcctgatgcggtattttctccttacgca
tctgtgcggtatttcacaccgcatcaggtggcactttttcggggaaatgtgcgcggaacccctatttgtttattt
ttctaaatacattcaaatatgtatccgctcatgaccaaaatcccttaacgtgagttttcgttccactgagcgtc
agaccccgtagaaaagatcaaaggatcttcttgagatcctttttttctgcgcgtaatctgctgcttgcaaaca
aaaaaaccaccgctaccagcggtggtttgtttgccggatcaagagctaccaactctttttccgaaggtaact
ggcttcagcagagcgcagataccaaatactgttcttctagtgtagccgtagttaggccaccacttcaagaac
tctgtagcaccgcctacatacctcgctctgctaatcctgttaccagtggctgctgccagtggcgataagtcgt
gtcttaccgggttggactcaagacgatagttaccggataaggcgcagcggtcgggctgaacggggggtc
gtgcacacagcccagcttggagcgaacgacctacaccgaactgagatacctacagcgtgagctatgagaa
agcgccacgcttcccgaagggagaaaggcggacaggtatccggtaagcggcagggtcggaacaggaga
gcgcacgagggagcttccaggggggaaacgcctggtatctttatagtcctgtcgggtttcgccacctctgactt
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
gagcgtcgattttttgtgatgctcgtcagggggggcggagcctatggaaaaacgccagcaacgcggcctttta
cggttcctggccttttgctggccttttgctcacatgttctttcctgcgttatcccctgattctgtggataaccgta
ttaccgcctttgagtgagctgataccgctcgccgcagccgaacgaccgagcgcagcgagtcagtgagcga
ggaagcggaagagcgcccaatacgcaaaccgcctctccccgcgcgttggccgattcattaatgcagctggc
acgacaggtttcccgactggaaagcgggcagtgagcgcaacgcaattaatgtgagttagctcactcattag
gcaccccaggctttacactttatgcttccggctcgtatgttgtgtggaattgtgagcggataacaatttcaca
caggaaacagctatgaccatgattacgccaagcgcgcaattaaccctcactaaagggaacaaaagctgg
agctgcaagcttggccattgcatacgttgtatccatatcataatatgtacatttatattggctcatgtccaaca
ttaccgccatgttgacattgattattgactagttattaatagtaatcaattacggggtcattagttcatagccc
atatatggagttccgcgttacataacttacggtaaatggcccgcctggctgaccgcccaacgacccccgccc
attgacgtcaataatgacgtatgttcccatagtaacgccaataggggactttccattgacgtcaatgggtgga
gtatttacggtaaactgcccacttggcagtacatcaagtgtatcatatgccaagtacgccccctattgacgtc
aatgacggtaaatggcccgcctggcattatgcccagtacatgaccttatgggactttcctacttggcagtac
atctacgtattagtcatcgctattaccatggtgatgcggttttggcagtacatcaatgggcgtggatagcggt
ttgactcacggggatttccaagtctccaccccattgacgtcaaatgggcgtggatagcggt
ttgactcacggggatttccaagtctccaccccattgacgtcaaatgggcgtggatagcggt
ttgactcacggggatttccaagtctccaccccattgacgtcaaatggcgaggtcgtgtacggtgggagg
tctatataagcagagctcgtttagtgaaccgGGGTCTCTCTGGTTAGACCAGATCTGAGCCT
GGGAGCTCTCTGGCTAACTAGGGAACCCACTGCTTAAGCCTCAATAAAGCTTGCC
TTGAGTGCTTCAAGTAGTGTGTGCCCGTCTGTTGTGTGACTCTGGTAACTAGAGA
TCCCTCAGACCCTTTTAGTCAGTGTGGAAAATCTCTAGCagtggcgcccgaacagggact
tgaaagcgaaagggaaaccagaggagctctcTCGACGCAGGACTCGGCTTGCTGAAGCGC
GCACGGCAAGAGGCGAGGGGCGGCGACTGGTGAGTACGCCAAAAATTTTGACT
AGCGGAGGCTAGAAGGAGAGAGATGGGTGCGAGAGCGTCAGTATTAAGCGGG
GGAGaattagatcgcgatgggaaaaaattcggttaaggccagggggaaagaaaaaatatattaaa
acatatagtatgggcaagcagggagctagaacgattcgcagttaatcctggcctgttagaaacatcagaa
ggctgtagacaaatactgggacagctacaaccatcccttcagacaggatcagaagaacttagatcattata
taatacagtagcaaccctctattgtgtgcatcaaaggatagagataaaagacaccaaggaagctttagac
aagatagaggaagagcaaaacaaaagtaagaccaccgcacagcaagcGGCCGCTgatcttcagacc
tggaggaggagatatgagggacaattggagaagtgaattatataaatataaagtagtaaaaattgaacca
ttaggagtagcacccaccaaggcaaagagaagagtggtgcagagagaaaaaagaGCAGTGGGAAT
aggagctttgttccttgggttcttgggagcagcaggaagcactatgggcgcagcgtcaatgacgctgacgg
tacaggccagacaattattgtctggtatagtgcagcagcagaacaatttgctgagggctattgaggcgcaa
cagcatctgttgcaactcacagtctggggcatcaagcagctccaggcaagaatcctggctgtggaaagata
cctaaaggatcaacagctcctggggatttggggttgctctggaaaactcatttgcaccactgctgtgccttgg
aatgctagttggagtaataaatctctggaacagatttggaatcacacgacctggatggagtgggacagag
aaattaacaattacacaagcttaatacactccttaattgaagaatcgcaaaaccagcaagaaaagaatga
acaagaattattggaattagataaatgggcaagtttgtggaattggtttaacataacaaattggctgtggta
tataaaattattcataatgatagtaggaggcttggtaggtttaagaatagtttttgctgtactttctatagtga
atagagttaggcagggatattcaccattatcgtttcagacccacctcccaaccccgaggggacccgacagg
cccgaaggaatagaagaagaaggtggagagagacagagacagatccattcgattagtgaacggatC
TCGACGGTATCGATCTCGAcacaaatggcagtattcatccacaattttaaaagaaaaggggggat
tggggggtacagtgcaggggaaagaatagtagacataatagcaacagacatacaaactaaagaattaca
aaaacaaattacaaaaattcaaaattttcgggtttattacagggacagcagacatgaggacagctaaaac
aataagtaatgtaaaatacagcatagcaaaactttaacctccaaatcaagcctctacttgaatccttttctg
agggatgaataaggcataggcatcaggggctgttgccaatgtgcattagctgtttgcagcctcaccttctttc
atggagtttaagatatagtgtatttcccaaggtttgaactagctcttcatttctttatgtttaaatgcactga
cctcccacattcccttttttagtaaaatattcagaaataatttaaatacatcattgcaatgaaaataaatgtttt
ttattaggcagaatccagatgctcaaggcccttcataatatccccccagtttagtagttggacttaggggaaca
aaggaacctttaatagaaattggacagcaagaaagcgagcttagtgatacttgtgggcccagggcattagc
cacaccagccaccactttctgataggcagcctgcactggtggggtgaattctttgccaaagtgatgggccag
cacacagaccagcacgttgcccaggagctgtgggaggaagataagaggtatgaacatgattagcaaaag
ggcctagcttggactcagaataatccagccttatcccaaccataaaataaaagcagaatggtagctggatt
gtagctgctattagcaatatgaaacctcttacatcagtttacaatttatatgcagaaatacctgttacttctcc
ccttcctatgacatgaacttaaccatagaaaagaaggggaaagaaaacatcaagggtcccatagactcac
cctgaagttctcaggatccacgtgcagcttgtcacagtgcagctcactcagctgggcaaaggtgcccttgag
gttgtccaggtgagccaggccatcactaaaggcaccgagcacttcttgccatgagccttcaccttagggtt
gcccataacagcatcaggagtggacagatccccaaaggactcaaagaacctctgggtccaagggtagac
caccagcagcctaagggtgggaaaatagaccaataggcagagagagtcagtgcctatcagaaacccaag
agtcttctctgtctccacatgcccagtttctattggtctccttaaacctgtcttgtaaccttgataccaacctgc
ccagggcctcaccaccaacggcatccacgttcaccttgtcccacagggcagtaacggcagacttctcctca
ggagtcaggtgcaccatggtgtctgtttgaggttgctagtgaacacagttgtgtcagaagcaaatgtaagca
atagatggctctgccctgactttttatgcccagccctggctcctgccctccctgctcctgggagtagattggcc
aacccctagggtgtggctccacagggtgaggtctaagtgatgacagccgtacctgtccttggctcttctggca
ctggcttaggagttggacttcaaaccctcagccctccctctaagatatatctcttggccccataccatcagta
caaattgctactaaaaacatcctcctttgcaagtgtatttaccatcaataatctctagccccacaggagtttgtt
ctgaaagtaaacttccacaaccgcaagcttattgaggctaaggcatctgtgaaggaaagaaacatctcctc
taaaccactatgctgctagagcctcttttctgtactcaagcctcattcagacactagtgtcaccagtctcctca
tatacctattgtattttcttcttcttgctggtttagtcatgttttctgggagcttaggggcttatttattttgtttg
tttctaatcaacagagatgggcaaacccattattttttctttagacttgggatggtgatagctgggcagcgt
cagaaactgtgtgtggatatagataagagctcaggactatgctgagctgtgatgaggggaggggcctagcta
aaggcagtgagagtcagaatgctcctgctattgccttctcagtccccacgcttggtttctacacaagtagata
catagaaaaggctataggttagtgtttgagagtcctgcatgattagttgctcagaaatgcccgataaatatg
ttatgtgtgtttatgtatatatatgtttatatgtgtgtgtgtgtgtgttgtgtttacaaatatgtgattatcatca
aaacgtgagggTACGTaTATGTGTATATATATATATATTCCAGGAAATAATATATTCT
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
                    AGAATATGTCACATTCTGTCTCAGGCATCCATTTTCTTTATGATGCCGTTTGAGGT
                    GGAGTTTTAGTCAGGTGGTCAGCTTCTCCTTTTTTTTGCCATCTGCCCTGTAAGCA
                    TCCTGCTGGGGACCCAGATAGGAGTCATCACTCTAGGCTGAGAACATCTGGGCA
                    CACACCCTAAGCCTCAGCATGACTCATCATGACTCAGCATTGCTGTGCTTGAGCCA
                    GAAGGTTTGCTTAGAAGGTTACACAGAACCAGAAGGCGGGGGTGGGGCACTGA
                    CCCCGACAGGGGCCTGGCCAGAACTGCTCATGCTTGGACTATGGGAGGTCACTA
                    ATGGAGACACACAGAAATGTAACAGGAACTAAGGAAAAACTGAAGCTTtgggggta
                    tagggggagcagtcccatgtagtagtagaatgaaaaatgctgctatgctgtgcctcccccacctttcccatgt
                    ctgccctctactcatggtctatctctcctggctcctgggagtcatggactccacccagcaccaccaacctgac
                    ctaaccacctatctgagcctgccagcctataacccatctgggccctgatagctggtggccagccctgacccc
                    accccaccctccctggaacctctgatagacacatctggcacaccagctcgcaaagtcaccgtgagggtctt
                    gtgtttgctgagtcaaaattccttgaaatccaagtccttagagactcccaggcttggattcaaagctcctgac
                    tttctgtctagtgtatgtgcagtgagccccttttcctctaactgaaagaaggaaaaaaaatggaacccaaa
                    atattctacatagtttccatgtcacagccagggctgggcagtctcctgttatttctttttaaaataaatatatca
                    tttaaatgcataaataagcaaaccctgctcgggaatgggagggagagtctctggagtccacccccttctcgg
                    ccctggctctgcagatagtgctatcaaagccctgacagagccctgcccattgctgggccttggagtgagtca
                    gcctagtagagaggcagggcaagccatctcatagctgctgagtgggagagagaaaagggctcattgtcta
                    taaactcaggtcatggctattcttattaaaagaaaagggggggactggaagggctaattcactcccaacgaa
                    gacaagatctgcttttttgcttgtactGGGTCTCTCTGGTTAGACCAGATCTGAGCCTGGGAG
                    CTCTCTGGCTAACTAGGGAACCCACTGCTTAAGCCTCAATAAAGCTTGCCTTGAGT
                    GCTTCAAGTAGTGIGTTGGTTTTTTGTGTGTGCATTGTCTGAGTAGGTGTCATTCT
                    ATTCTGGGGGGTGGGGTGGGGCAGCACAGCAAGGGGGAGGATTGGGAAGACA
                    ATAGCAGGCATGCTGGGGATGCGGIGGGCTCTATGGagtagtagttcatgtcatcttatta
                    ttcagtatttataacttgcaaagaaatgaatatcagagagtgagagggaacttgtttattgcagcttataatg
                    gttacaaataaagcaatagcatcacaaatttcacaaataaagcatttttttcactgcattctagttgtggtttg
                    tccaaactcatcaatgtatcttatcatgtctggctctagctatcccgcccctaactccgcccATCCCGCCC
                    CTAACTCCGCCCAGTTCCGCCCATTCTCCGCCCCATGGCTCTCACTACTTCTGGAAT
                    AGCTCAGAGGCCGAGGCGGCCTCGGCCTCTGCATAAATAAAAAAAAAATTAGTCGA
                    GGCTTTTTGGAGGCCTAGGgacgtacccaattcgccctatagtgagtcgtattacgcgcgctcac
                    tggccgtcgttttacaacgtcgtgactgggaaaaccctggcgttacccaacttaatcgccttgcagcacatcc
                    ccctttcgccagctggcgtaatagcgaagaggcccgcaccgatcgcccttcccaacagttgcgcagcctga
                    atggcgaatggg
``` pUV + HS1-               acgcgccctgtagcggcgcattaagcgcggcgggtgtggtggttacgcgcagcgtgaccgctacacttgcc
AS3(coX2)               agcgccctagcgcccgctcctttcgctttcttcccttcctttctcgccacgttcgccggctttccccgtcaagct
from junction           ctaaatcgggggctccctttagggttccgatttagtgctttacggcacctcgaccccaaaaaacttgattagg
marker (SEQ ID          gtgatggttcacgtagtgggccatcgccctgatagacggtttttcgccctttgacgttggagtccacgttcttt
NO: 16)                 aatagtggactcttgttccaaactggaacaacactcaaccctatctcggtctattcttttgatttataagggat
                        tttgccgatttcggcctattggttaaaaaatgagctgatttaacaaaaatttaacgcgaattttaacaaaata
                        ttaacgcttacaatttaggtggcacttttcggggaaatgtgcgcggaacccctatttgtttatttttctaaata
                        cattcaaatatgtatccgctcatgagacaataaccctgataaatgcttcaataatagcacctagatcaagag
                        acaggatgaggatcgtttcgcatgattgaacaagatggattgcacgcaggttctccggccgcttgggtgga
                        gaggctattcggctatgactgggcacaacagacaatcggctgctctgatgccgccgtgttccggctgtcagc
                        gcaggggcgcccggttcttttttgtcaagaccgacctgtccggtgccctgaatgaactgcaagacgaggcag
                        cgcggctatcgtggctggccacgacgggcgttccttgcgcagctgtgctcgacgttgtcactgaagcgggaa
                        gggactggctgctattgggcgaagtgccggggcaggatctcctgtcatctcaccttgctcctgccgagaaag
                        tatccatcatggctgatgcaatgcggcggctgcatacgcttgatccggctacctgcccattcgaccaccaag
                        cgaaacatcgcatcgagcgagcacgtactcggatggaagccggtcttgtcgatcaggatgatctggacga
                        agagcatcaggggctcgcgccagccgaactgttcgccaggctcaaggcgagcatgcccgacggcgaggat
                        ctcgtcgtgacccatggcgatgcctgcttgccgaatatcatggtggaaaatggccgcttttctggattcatcg
                        actgtggccggctgggtgtggcggaccgctatcaggacatagcgttggctacccgtgatattgctgaagag
                        cttggcggcgaatgggctgaccgcttcctcgtgctttacggtatcgccgctcccgattcgcagcgcatcgcct
                        tctatcgccttcttgacgagttcttctgaattattaacgcttacaatttcctgatgcggtattttctccttacgca
                        tctgtgcggtatttcacaccgcatcaggtggcacttttcggggaaatgtgcgcggaacccctatttgtttattt
                        ttctaaatacattcaaatatgtatccgctcatgaccaaaatcccttaacgtgagttttcgttccactgagcgtc
                        agaccccgtagaaaagatcaaaggatcttcttgagatcctttttttctgcgcgtaatctgctgcttgcaaaca
                        aaaaaaccaccgctaccagcggtggtttgtttgccggatcaagagctaccaactctttttccgaaggtaact
                        ggcttcagcagagcgcagataccaaatactgttcttctagtgtagccgtagttaggccaccacttcaagaac
                        tctgtagcaccgcctacatacctcgctctgctaatcctgttaccagtggctgctgccagtggcgataagtcgt
                        gtcttaccgggttggactcaagacgatagttaccggataaggcgcagcggtcgggctgaacggggggggtc
                        gtgcacacagcccagcttggagcgaacgacctacaccgaactgagatacctacagcgtgagctatgagaa
                        agcgccacgcttcccgaaggagaaaggcggacaggtatccggtaagcggcagggtcggaacaggaga
                        gcgcacgagggagcttccaggggaaacgcctggtatctttatagtcctgtcgggtttcgccacctctgactt
                        gagcgtcgatttttgtgatgctcgtcaggggggcggagcctatggaaaaacgccagcaacgcggcctttta
                        cggttcctggccttttgctggccttttgctcacatgttctttcctgcgttatcccctgattctgtggataaccgta
                        ttaccgcctttgagtgagctgataccgctcgccgcagccgaacgaccgagcgcagcgagtcagtgagcga
                        ggaagcggaagagcgcccaatacgcaaaccgcctctccccgcgcgttggccgattcattaatgcagctggc
                        acgacaggtttcccgactggaaagcgggcagtgagcgcaacgcaattaatgtgagttagctcactcattag
                        gcaccccaggctttacactttatgcttccggctcgtatgttgtgtggaattgtgagcggataacaatttcaca
                        caggaaacagctatgaccatgattacgccaagcgcgcaattaaccctcactaaagggaacaaaagctgg
                        agctgcaagcttggccattgcatacgttgtatccatatcataatatgtacatttatattggctcatgtccaaca
                        ttaccgccatgttgacattgattattgactagttattaatagtaatcaattacggggtcattagttcatagccc
                        atatatggagttccgcgttacataacttacggtaaatggcccgcctggctgaccgcccaacgacccccgccc
                        attgacgtcaataatgacgtatgttcccatagtaacgccaatagggactttccattgacgtcaatgggtgga TABLE 1-continued Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
gtatttacggtaaactgcccacttggcagtacatcaagtgtatcatatgccaagtacgcccctattgacgtc
aatgacggtaaatggcccgcctggcattatgcccagtacatgacccttatgggactttcctacttggcagtac
atctacgtattagtcatcgctattaccatggtgatgcggttttggcagtacatcaatgggcgtggatagcggt
ttgactcacggggatttccaagtctccaccccattgacgtcaatgggagtttgttttggcaccaaaatcaacg
ggactttccaaaatgtcgtaacaactccgccccattgacgcaaatgggcggtaggcgtgtacggtgggagg
tctatataagcagagctcgtttagtgaaccgGGGTCTCTCTGGTTAGACCAGATCTGAGCCT
GGGAGCTCTCTGGCTAACTAGGGAACCCACTGCTTAAGCCTCAATAAAGCTTGCC
TTGAGTGCTTCAAGTAGTGTGTGCCCGTCTGTTGTGTGACTCTGGTAACTAGAGA
TCCCTCAGACCCTTTTAGTCAGTGTGGAAAATCTCTAGCagtggcgcccgaacagggact
tgaaagcgaaagggaaaccagaggagctctcTCGACGCAGGACTCGGCTTGCTGAAGCGC
GCACGGCAAGAGGCGAGGGGCGGCGACTGGTGAGTACGCCAAAAATTTTGACT
AGCGGAGGCTAGAAGGAGAGAGATGGGTGCGAGAGCGTCAGTATTAAGCGGG
GGAGaattagatcgcgatgggaaaaaattcggttaaggccaggggggaaagaaaaaatataaattaaa
acatatagtatgggcaagcagggagctagaacgattcgcagttaatcctggcctgttagaaacatcagaa
ggctgtagacaaatactgggacagctacaaccatcccttcagacaggatcagaagaacttagatcattata
taatacagtagcaaccctctattgtgtgcatcaaaggatagagataaaagacaccaaggaagctttagac
aagatagaggaagagcaaaacaaaagtaagaccaccgcacagcaagcGGCCGCTgatcttcagacc
tggaggaggagatatgagggacaattggagaagtgaattatataaatataaagtagtaaaaattgaacca
ttaggagtagcacccaccaaggcaaagagaagagtggtgcagagagaaaaaagaGCAGTGGGAAT
aggagctttgttccttgggttcttgggagcagcaggaagcactatgggcgcagcgtcaatgacgctgacgg
tacaggccagacaattattgtctggtatagtgcagcagcagaacaatttgctgagggctattgaggcgcaa
cagcatctgttgcaactcacagtctggggcatcaagcagctccaggcaagaatcctggctgtggaaagata
cctaaaggatcaacagctcctggggatttggggttgctctggaaaactcatttgcaccactgctgtgccttgg
aatgctagttggagtaataaatctctggaacagatttggaatcacacgacctggatggagtgggacagag
aaattaacaattacacaagcttaatacactccttaattgaagaatcgcaaaaccagcaagaaaagaatga
acaagaattattggaattagataaatgggcaagtttgtggaattggttaacataacaaattggctgtggta
tataaaattattcataatgatagtaggaggcttggtaggtttaagaatagtttttgctgtactttctatagtga
atagagttaggcagggatattcaccattatcgtttcagacccacctcccaacccgaggggacccgacagg
cccgaaggaatagaagaagaaggtggagagagagacagagacagatccattcgattagtgaacggatC
TCGACGGTATCGATCTCGAcacaaatggcagtattcatccacaatttttaaaagaaaaggggggat
tggggggtacagtgcaggggaaagaatagtagacataatagcaacagacatacaaactaaagaattaca
aaaacaaattacaaaaattcaaaattttcgggtttattacaggcagcagacatgaggacagcagctaaaac
aataagtaatgtaaaatacagcatagcaaaactttaacctccaaatcaagcctctacttgaatccttttctg
agggatgaataaggcataggcatcagggggctgttgccaatgtgcattagctgtttgcagcctcaccttctttc
atggagtttaagatatagtgtattttcccaaggtttgaactagctcttcatttctttatgttttaaatgcactga
cctcccacattccctttttagtaaaatattcagaaataatttaaatacatcattgcaatgaaataaatgtttt
ttattaggcagaatccagatgctcaaggcccttcataatatcccccagtttagtagttggacttagggaaca
aaggaacctttaatagaaattggacagcaagaaagcgagcttagtgatacttgtgggccagggcattagc
cacaccagccaccactttctgataggcagcctgcactggtggggtgaattctttgccaaagtgatgggccag
cacacagaccagcacgttgcccaggagctgtgggaggaagataagaggtatgaacatgattagcaaaag
ggcctagcttggactcagaataatccagccttatcccaaccataaaataaaagcagaatggtagctggatt
gtagctgctattagcaatatgaaacctcttacatcagttacaatttatatgcagaaataccctgttacttctcc
ccttcctatgacatgaacttaaccatagaaaagaaggggaaagaaaacatcaagggtcccatagactcac
cctGAAGTTCTCAGGaTCCACGTGCAGCTTGTCGCAGTGCAGCTCGCTCAGCTGGG
CGAAGGTGCCCTTCAGGTTGTCCAGGTGGGCCAGGCCGTCGCTGAAGGCGCCCA
GCACCTTCTTGCCGTGGGCCTTCACCTTGGGGTTGCCCATCACGGCGTCGGGGGT
GCTCAGGTCGCCGAAGCTCTCGAAGAAGCGCTGGGTCCAGGGGTACACCACCAG
cagcctaagggtgggaaaatagaccaataggcagagagagtcagtgcctatcagaaacccaagagtcttc
tctgtctccacatgcccagtttctattggtctccttaaacctgtcttgtaaccttgataccaacctgcccaggg
cctcaccaccaacggcatccacgttcaccttgtcccacagggcagtaacggcagacttctcctcaggagtca
ggtgcaccatggtgtctgtttgaggttgctagtgaacacagttgtgtcagaagcaaatgtaagcaatagatg
gctctgccctgacttttatgcccagccctggctcctgccctccctgctcctgggagtagattggccaaccctag
ggtgtggctccacagggtgaggtctaagtgatgacagccgtacctgtccttggctcttctggcgactggcttag
gagttggacttcaaaccctcagccctccctctaagatatatctcttggcccataccatcagtacaaattgct
actaaaaacatcctcctttgcaagtgtatttaccatcaataattctagccccacaggagtttgttctgaaagt
aaacttccacaaccgcaagcttattgaggctaaggcatctgtgaaggaaagaaacatctcctctaaaccac
tatgctgctagagcctcttttctgtactcaagcctcattcagacactagtgtcaccagtctcctcatatacctat
tgtattttcttcttcttgctggtttagtcatgtttctgggagcttaggggcttattttattttgttttgttttctaat
caacagagatgggcaaacccattattttttttctttagacttgggatggtgatagctgggcagcgtcagaaac
tgtgtgtggatatagataagagctcaggactatgctgagctgtgatgagggagggcctagctaaaggca
gtggagctcagaatgctcctgctattgccttcctcagtccccacgcttggtttctacacaagtagatacataga
aaaggctataggttagtgtttgagagtcctgcatgattagttgctcagaaatgcccgataaatatgttatgtg
tgtttatgtatatatatgtttttatgtgtgtgtgtgtgtgttgtgtttacaaatatgtgattatcatcaaaacgt
gagggTACGTaTATGTGTATATATATATATATTCAGGAAATAATATATTCTAGAA
TATGTCACATTCTGTCTCAGGCATCCATTTTCTTTATGATGCCGTTTGAGGTGGAG
TTTTAGTCAGGTGGTCAGCTTCTCCTTTTTTTTGCCATCTGCCCTGTAAGCATCCTG
CTGGGGACCCAGATAGGAGTCATCACTCTAGGCTGAGAACATCTGGGCACACAC
CCTAAGCCTCAGCATGACTCATCATGACTCAGCATTGCTGTGCTTGAGCCAGAAG
GTTTGCTTAGAAGGTTACACAGAACCAGAAGGCGGGGGTGGGGCACTGACCCCG
ACAGGGGCCTGGCCAGAACTGCTCATGCTTGGACTATGGGAGGTCACTAATGGA
GACACACAGAAATGTAACAGGAACTAAGGAAAAACTGAAGCTTtggggggtataggggg
agcagtcccatgtagtagtagaatgaaaaatgctgctatgctgtgcctcccccacctttcccatgtctgccct
ctactcatggtctatctctcctggctcctgggagtcatggactccacccagcaccaccaacctgacctaacca
cctatctgagcctgccagcctataacccatctgggccctgatagctggtggccagccctgaccccacccac
```

TABLE 1-continued

Nucleic acid sequences of ecHS1, ecHS2, ecHS3, ecHS4, a full vector with HS1, a
vector comprising codon optimized exon 1, codon optimized exon 1, codon optimized exon
2, codon optimized exon 3, a vector comprising codon optimized exons 1 and 2, a vector
comprising codon optimized exons 1, 2, and 3. In the codon optimized exons, the case letters
are codon optimized sequence and the lower case match wildtype sequence

```
cctccctggaacctctgatagacacatctggcacaccagctcgcaaagtcaccgtgagggtcttgtgtttgct
gagtcaaaattccttgaaatccaagtccttagagactcccaggcttggattcaaagctcctgactttctgtct
agtgtatgtgcagtgagcccctttcctctaactgaaagaaggaaaaaaaaatggaacccaaaatattcta
catagtttccatgtcacagccagggctgggcagtctcctgttatttcttttaaaataaatatatcatttaaatg
cataaataagcaaaccctgctcgggaatgggagggagagtctctggagtccacccctctcggccctggct
ctgcagatagtgctatcaaagccctgacagagccctgcccattgctgggccttggagtgagtcagcctagta
gagaggcagggcaagccatctcatagctgctgagtgggagagagaaaagggctcattgtctataaactca
ggtcatggctattcttattaaaagaaaaggggggactggaagggctaattcactcccaacgaagacaaga
tctgcttttttgcttgtactGGGTCTCTCTGGTTAGACCAGATCTGAGCCTGGGAGCTCTCT
GGCTAACTAGGGAACCCACTGCTTAAGCCTCAATAAAGCTTGCCTTGAGTGCTTC
AAGTAGTGTGTTGGTTTTTTGTGTGTGCATTGTCTGAGTAGGTGTCATTCTATTCT
GGGGGGTGGGGTGGGGCAGCACAGCAAGGGGGAGGATTGGGAAGACAATAGC
AGGCATGCTGGGGATGCGGTGGGCTCTATGGagtagtagttcatgtcatcttattattcagta
tttataacttgcaaagaaatgaatatcagagagtgagaggaacttgtttattgcagcttataatggttacaa
ataaagcaatagcatcacaaatttcacaaataaagcatttttttcactgcattctagttgtggtttgtccaaa
ctcatcaatgtatcttatcatgtctggctctagctatcccgcccctaactccgcccATCCCGCCCCTAAC
TCCGCCCAGTTCCGCCCATTCTCCGCCCCATGGCTCTCACTACTTCTGGAATAGCTC
AGAGGCCGAGGCGGCCTCGGCCTCTGCATAAATAAAAAAAATTAGTCGAGGCTT
TTTTGGAGGCCTAGGgacgtacccaattcgccctatagtgagtcgtattacgcgcgctcactggccgt
cgttttacaacgtcgtgactgggaaaaccctggcgttacccaacttaatcgccttgcagcacatccccctttc
gccagctggcgtaatagcgaagaggcccgcaccgatcgcccttcccaacagttgcgcagcctgaatggcg
aatggg
```

In certain embodiments the human β-globin gene in the vectors contemplated herein comprises an anti-sickling human β-globin gene encoding an anti-sickling β-globin polypeptide. In certain embodiments the anti-sickling version of a human β-globin gene used in the vector comprises one, two, or three mutations selected from the group consisting of Gly16Asp, Glu22Ala and Thr87Gln (see, e.g., Levasseur (2004) *J. Biol. Chem.* 279(26): 27518-27524). Without being bound to a particular theory, it is believed the Glu22Ala mutation increases affinity to α-chain, the Thr87Gln mutation blocks lateral contact with Val6 of βS protein, and the Gly16Asp mutation decreases axial contact between globin chains.

Figure 2:
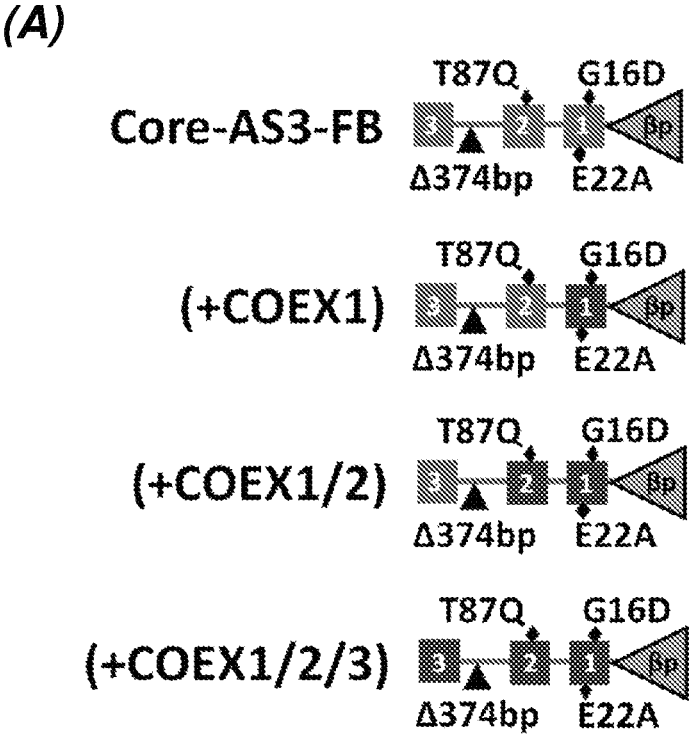
FIG. 2, panels A and B, illustrates the structure of a modified βAS3-globin transgene comprising a codon optimized exon 1, or a codon optimized exon 1 and 2, or a codon optimized exon 1, 2 and 3 (panel A) and levels of expression produced by each of these constructs compared to Core-AS3-FB (panel B).
Figure 2:
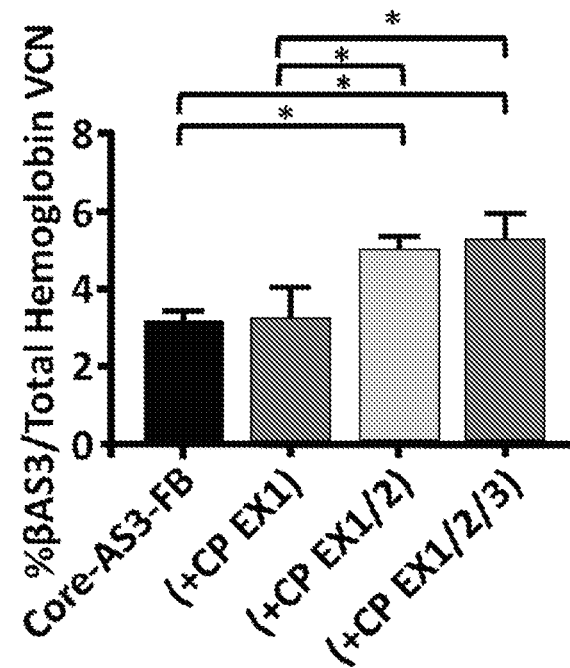
Figure 3:
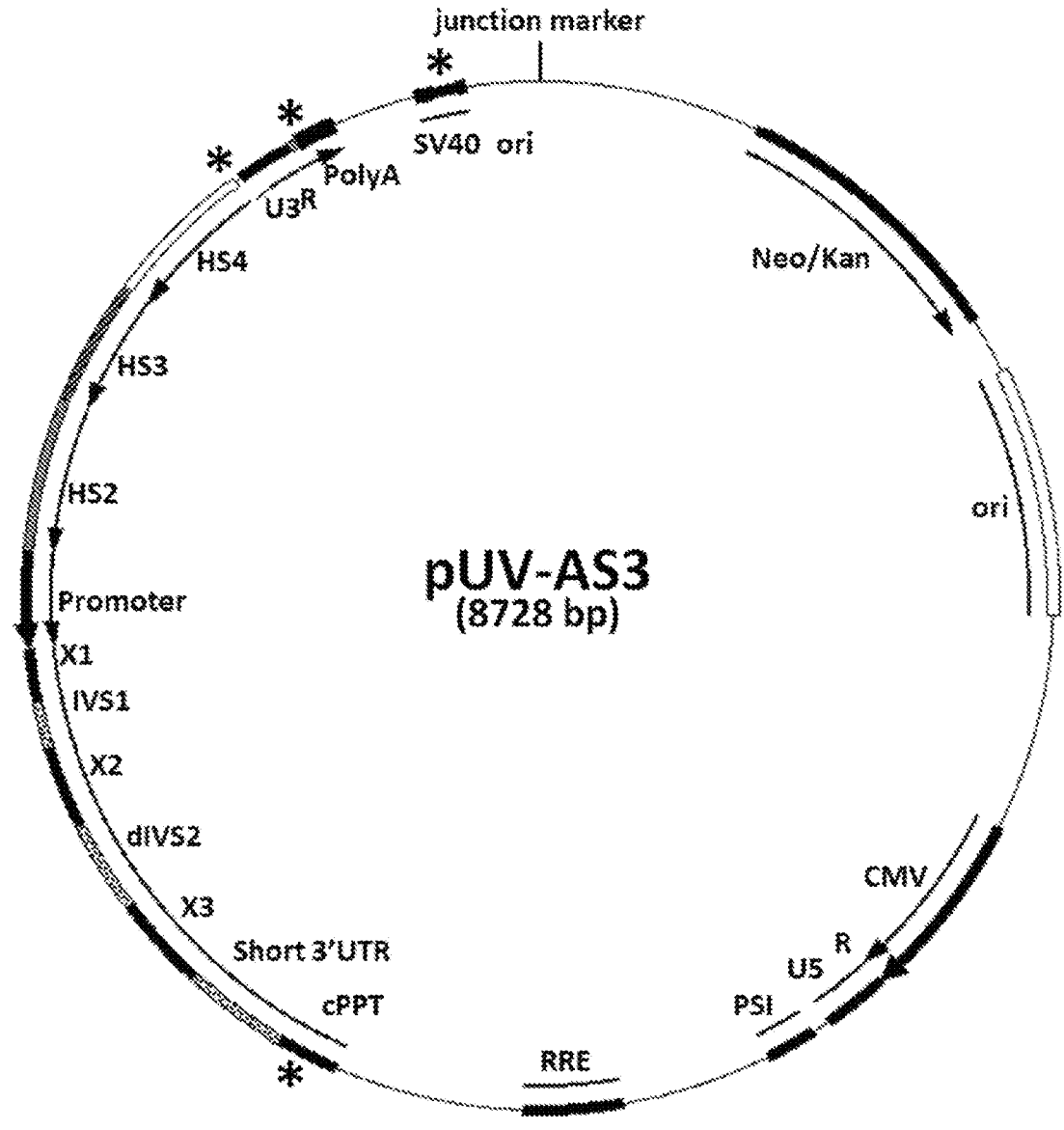
FIG. 3 illustrates the structure of the pUV–AS3 vector and "*" illustrates changes from the GLOBE1 vector. pUV–AS3 is shown as SEQ ID NO:13 in Table 1. The cPPT and surrounding modifications (from GLOBE1) include: 1) GTTAAC (SEQ ID NO:17) is now ATCTCGACACAAATGGCAGTATTCATCCACAA SEQ ID NO:18) (at position 4,924 in SEQ ID NO:13); 2) An additional A (at position 5,062 in SEQ ID NO:13); and 3) ATCGGTACGTAC (SEQ ID NO:18) is now CGGGTTTAT-TACAGGGACAGCAGA (SEQ ID NO:19) (at position 5,074 in SEQ ID NO:13). 3'PPT and surrounding modification: 4) GGGGGATCCACTAGTTCTAGAG CGGC-CAAATGGCGGCCGTACCTTTAAGACCAATGACTTA-CAAGGCAGCTGTAGA TCTTAGCCACTTTTTAAAAGAAAAGGGGGGAC (SEQ ID NO:20) is now TAAAAGAAAAGGGGGGAC (SEQ ID NO:21) (at position 7,847 in SEQ ID NO:13). 3'LTR modifications: 5) CAAGTAGTGTGTGCCCGTCTGTTG TGTGACTCTGGTAACTAGAGATCCCTCAGACCC TTTAGTCAGTGTGGAAAATCT CTAGC (SEQ ID NO:22) (U5 region) is replaced by CAAGTAGTGTGTTGGT TTTTGTGTGTGCATTGTCT-GAGTAGGTGTCATTCTAT-TCTGGGGGGTGGGGTGGG GCAGCACAGCAAGGGGGAGGATTGGGAA-GACAATAGCAGGCATGCTGGGGATG CGGTGGGCTCTATGG (SEQ ID NO:23) (rabbit beta globin DSE and bovine growth hormone polyA) at position 8,014 of SEQ ID NO:13. SV40 origin of replication modification. SV40 origin of replication modification: 6) ATCCCGCCCCTAACT CCGCCCAGTTCCGCCCAT-TCTCCGCCCCATGGCTGACTAAITTTTTTATTTATGC AGAGGCCGAGGCCGCCTCGGCCCTCTGAGCTAT-TCCAGAAGTAGTGAGGAGGCTT TTTG-GAGGCCTAGG (SEQ ID NO:24) is replaced by ATCCCGCCCCTAAC TCCGCCCAGTTCCGCCCAT-TCTCCGCCCCATGGCTCTCACTACTTCTG-GAATAGCT CAGAGGCCGAGGCGGCCTCGGCCTCTGCAT-AAATAAAAAAAATTAGTCGAGGCT TTTTTG-GAGGCCTAGG (SEQ ID NO:25) at position 8,387 of SEQ ID NO:13. In addition the antibiotic resistance gene was changed from ampicillin to kanamycin resistance.
Figure 4:
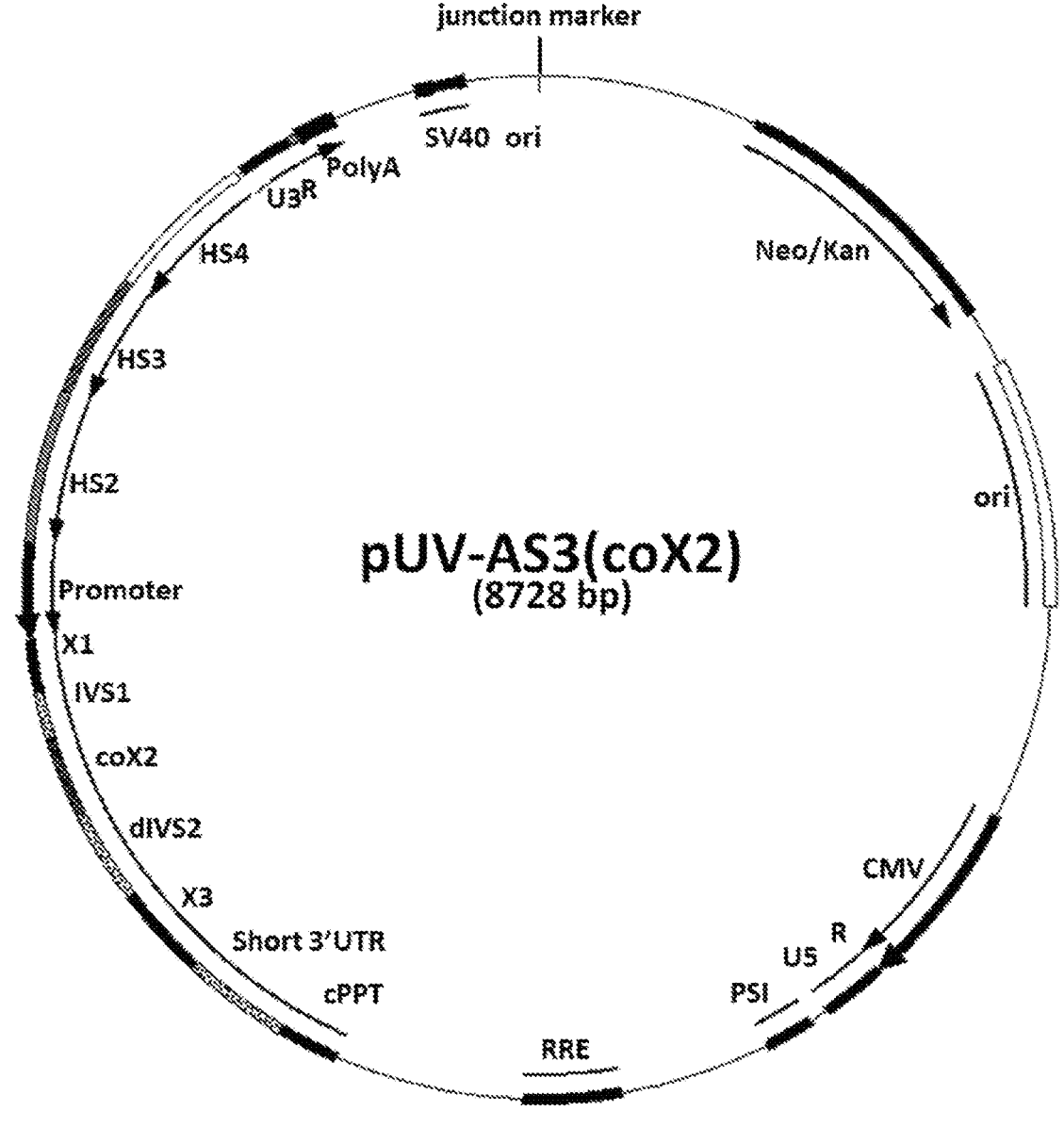
FIG. 4 illustrates the structure of the pUV–AS3(coX2) vector.
Figure 5:
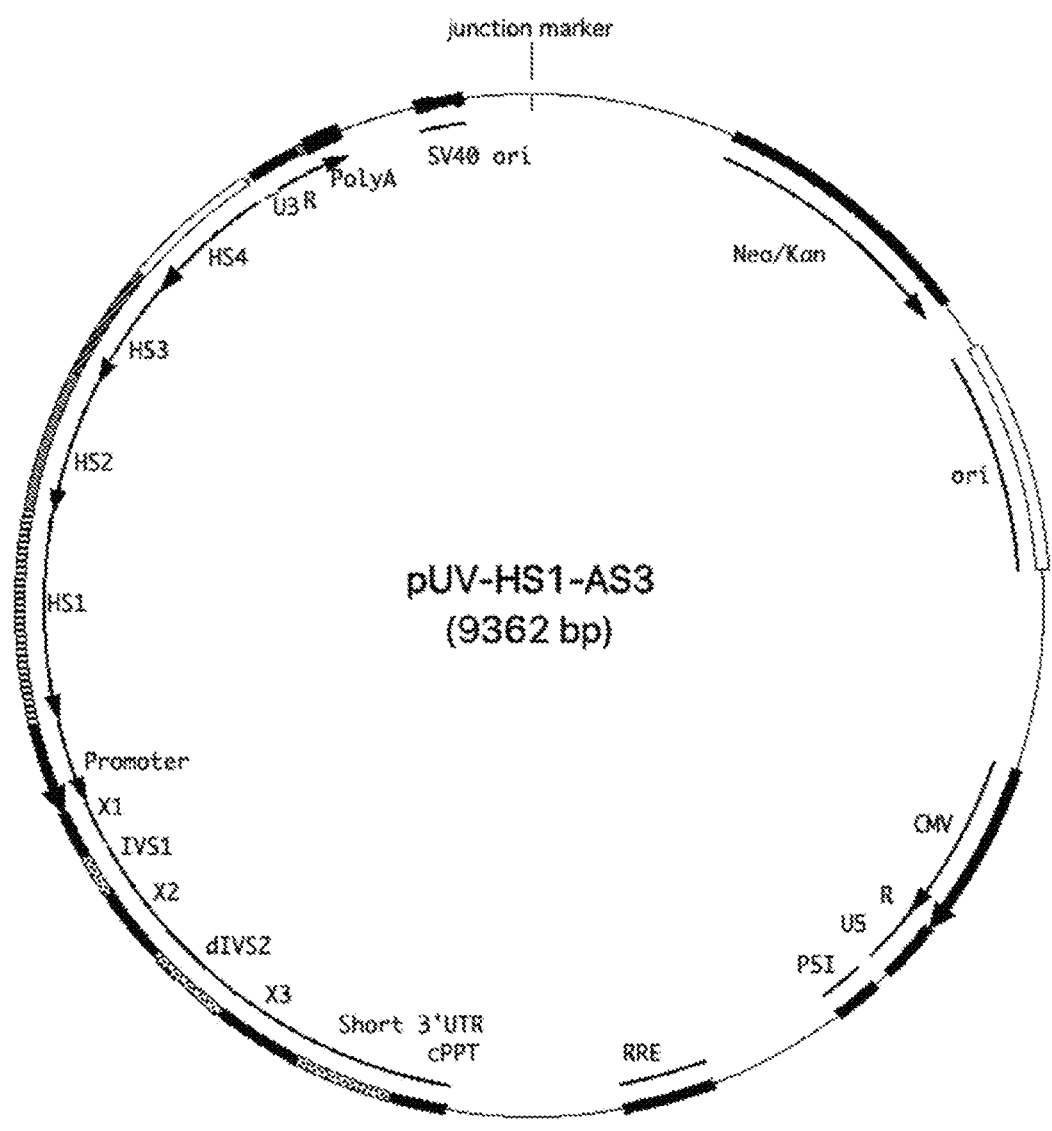
FIG. 5 illustrates the structure of the pUV–HS1-AS3 vector.

However, we also tested the usefulness of codon optimization on BASB-globin transgene expression. The BAS3-globin transgene was codon optimized for expression using the J-CAT software (Grote et al. (2005) *Nucleic Acids. Res.,* 33: 526-531) and care was taken to retain the three anti-sickling mutations (Gly16Asp, Glu22Ala, and Thr87Gln). The optimized BASB-globin exons had 84% sequence homology at the nucleotide level when compared to the original unmodified sequences. Three derivatives of Core-ASB-FB were made that contained, 1). Codon-optimized exon one with unmodified exons two and three, 2) codon-optimized exons one and two with unmodified exon three, and 3), codon-optimized exons one, two, and three with no unmodified exons (see, e.g., FIG. 2, panel A). To determine if codon optimization could enhance expression, HSPCs derived from multiple healthy donors were transduced with Core-AS3-FB derivatives at equal MOI and subjected to in vitro erythroid differentiation for 14 days. Enhancement of expression by about 1.6-fold was observed in derivatives that contained a codon optimized exon two (p<0.05) when compared to the parental construct (see, e.g., FIG. 2, panel B). The additional optimization of exons one or three did not result in increased expression per vector genome when compared to the appropriate control (see, e.g., FIG. 2, panel B). Taken together, these data provide strategies to increase expression per vector genome.

Accordingly in various embodiments the heterologous gene in the vector described above comprises an anti-sickling human beta globin gene comprises a modified βAS3-globin transgene, said transgene comprising a codon optimized exon 1 (SEQ ID NO:7) (as shown within SEQ ID NO:10), and/or a codon optimized exon 2 (SEQ ID NO:8) (as shown within SEQ ID NO:11), and/or comprising a codon optimized exon 3 (SEQ ID NO:9) (as shown within SEQ ID NO:12). In certain embodiments the βAS3-globin transgene comprises a codon optimized exon 2 (SEQ ID NO:8). In certain embodiments the βAS3-globin transgene comprises a codon optimized exon 1 (SEQ ID NO:7). In certain embodiments the βAS3-globin transgene comprises a codon optimized exon 3 (SEQ ID NO:9). See Table 1 for referenced sequences.

In certain embodiments the vectors described herein comprise a human Ankyrin insulator element In certain embodiments the vectors described herein comprise a murine GATA1.

In various embodiments, the LVs described herein can have additional safety features that can include, for example, the presence of an insulator (e.g., an FB insulator in the 3'LTR). Additionally, or alternatively, in certain embodiments, the HIV LTR has been substituted with an alternative promoter (e.g., a CMV) to yield a higher titer vector without the inclusion of the HIV TAT protein during packaging. Other strong promoters (e.g., RSV, and the like can also be used).

As shown above, the vectors described herein are effective to transduce cells at high titer and to also provide high levels of expression.

In view of these results, it is believed that LVs described herein, e.g., recombinant TAT-independent, SIN LVs that express a human beta-globin gene can be used to effectively treat hemoglobinopathies in subjects (e.g., human and non-human mammals). Such hemoglobinopathies include, but are not limited to sickle cell disease (SCD) and β-thalassemia. It is believed these vectors can be used for the modification of stem cells (e.g., hematopoietic stem and progenitor cells) that can be introduced into a subject in need thereof for the treatment of, e.g., SCD or β-thalassemia. Moreover, it appears that the resulting cells will produce enough of the transgenic β-globin protein to demonstrate significant improvement in subject health. It is also believed the vectors can be directly administered to a subject to achieve in vivo transduction of the target (e.g., hematopoietic stem or progenitor cells) and thereby also effect a treatment of subjects in need thereof.

As noted above, in various embodiments the LVs described herein can comprise various safety features. For example, the HIV LTR has been substituted with a CMV promoter to yield higher titer vector without the inclusion of the HIV TAT protein during packaging. In certain embodiments an insulator (e.g., the FB insulator) is introduced into the 3'LTR for safety. The LVs are also constructed to provide efficient transduction and high titer.

It will be appreciated that the foregoing elements are illustrative and need not be limiting. In view of the teachings provided herein, suitable substitutions for these elements will be recognized by one of skill in the art and are contemplated within the scope of the teachings provided herein.

Anti-Sickling β-Globin Gene and Expression Cassette.

As indicated above, in various embodiments the LV described herein comprise an expression cassette encoding a wild-type β-globin gene, or an anti-sickling human β-globin gene. On illustrative, but non-limiting cassette is βAS3 which comprises an ~2.3 kb recombinant human β-globin gene (exons and introns) with three amino acid substitutions (Thr87Gln; Gly16Asp; and Glu22Ala) under the control of transcriptional control elements (e.g., the human β-globin gene 5' promoter (e.g., ~266 bp), the human β-globin 3' enhancer (e.g., ~260 bp), β-globin intron 2 with a ~375 bp RsaI deletion from IVS2, and a ~3.4 kb composite human β-globin locus control region (e.g., HS2~1203 bp; HS3~1213 bp; HS4~954 bp). One embodiment of a βAS3 cassette is described by Levasseur (2003) *Blood* 102: 4312-4319.

In certain embodiments the β-globin gene comprises a SspI (S) to RsaI (R) deletion (~220 bp), e.g., as described by Antoniou et al. 1998) *Nucl. Acids Res.,* 26(3): 721-729.

The βAS3 cassette, however, is illustrative and need not be limiting. Using the teaching provided herein, numerous variations will be available to one of skill in the art. Such variations include, for example, use of a gene encoding a wild-type β-globin, use of a gene comprising one or two mutations selected from the group consisting of Thr87Gln, Gly16Asp, and Glu22Ala, and/or further or alternative mutations to the β-globin to further enhance non-sickling properties, alterations in the transcriptional control elements (e.g., promoter and/or enhancer), variations on the intron size/structure, and the like.

As noted above, in certain embodiments, the βAS3 cassette comprises a codon optimized exon 1, and/or a codon optimized exon 2, and/or a codon optimized exon 3. In certain embodiments only exon 2 is codon optimized.

TAT-Independent and Self Inactivating Lentiviral Vectors.

To further improve safety, in various embodiments, the lentiviral vectors described herein comprise a TAT-independent, self-inactivating (SIN) configuration. Thus, in various embodiments it is desirable to employ in the LVs described herein an LTR region that has reduced promoter activity relative to wild-type LTR. Such constructs can be provided that are effectively "self-inactivating" (SIN) which provides a biosafety feature. SIN vectors are ones in which the production of full-length vector RNA in transduced cells is greatly reduced or abolished altogether. This feature minimizes the risk that replication-competent recombinants (RCRs) will emerge. Furthermore, it reduces the risk that that cellular coding sequences located adjacent to the vector integration site will be aberrantly expressed.

Furthermore, a SIN design reduces the possibility of interference between the LTR and the promoter that is driving the expression of the transgene. SIN LVs can often permit full activity of the internal promoter.

The SIN design increases the biosafety of the LVs. The majority of the HIV LTR is comprised of the U3 sequences. The U3 region contains the enhancer and promoter elements that modulate basal and induced expression of the HIV genome in infected cells and in response to cell activation. Several of these promoter elements are essential for viral replication. Some of the enhancer elements are highly conserved among viral isolates and have been implicated as critical virulence factors in viral pathogenesis. The enhancer elements may act to influence replication rates in the different cellular target of the virus As viral transcription starts at the 3' end of the U3 region of the 5' LTR, those sequences are not part of the viral mRNA and a copy thereof from the 3' LTR acts as template for the generation of both LTR's in the integrated provirus. If the 3' copy of the U3 region is altered in a retroviral vector construct, the vector RNA is still produced from the intact 5' LTR in producer cells, but cannot be regenerated in target cells. Transduction of such a vector results in the inactivation of both LTR's in the progeny virus. Thus, the retrovirus is self-inactivating (SIN) and those vectors are known as SIN transfer vectors.

In certain embodiments self-inactivation is achieved through the introduction of a deletion in the U3 region of the 3' LTR of the vector DNA, i.e., the DNA used to produce the vector RNA. During RT, this deletion is transferred to the 5' LTR of the proviral DNA. Typically, it is desirable to eliminate enough of the U3 sequence to greatly diminish or abolish altogether the transcriptional activity of the LTR, thereby greatly diminishing or abolishing the production of full-length vector RNA in transduced cells. However, it is generally desirable to retain those elements of the LTR that are involved in polyadenylation of the viral RNA, a function typically spread out over U3, R and U5. Accordingly, in certain embodiments, it is desirable to eliminate as many of the transcriptionally important motifs from the LTR as possible while sparing the polyadenylation determinants.

The SIN design is described in detail in Zufferey et al. (1998) *J Virol.* 72(12): 9873-9880, and in U.S. Pat. No. 5,994,136. As described therein, there are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3'LTR may decrease polyadenylation of vector transcripts with adverse consequences both on the titer of the vector in producer cells and the transgene expression in target cells.

Additional SIN designs are described in U.S. Patent Publication No: 2003/0039636. As described therein, in certain embodiments, the lentiviral sequences removed from the LTRs are replaced with comparable sequences from a non-lentiviral retrovirus, thereby forming hybrid LTRs. In particular, the lentiviral R region within the LTR can be replaced in whole or in part by the R region from a non-lentiviral retrovirus. In certain embodiments, the lentiviral TAR sequence, a sequence which interacts with TAT protein to enhance viral replication, is removed, preferably in whole, from the R region. The TAR sequence is then replaced with a comparable portion of the R region from a non-lentiviral retrovirus, thereby forming a hybrid R region. The LTRs can be further modified to remove and/or replace with non-lentiviral sequences all or a portion of the lentiviral U3 and U5 regions.

Accordingly, in certain embodiments, the SIN configuration provides a retroviral LTR comprising a hybrid lentiviral R region that lacks all or a portion of its TAR sequence, thereby eliminating any possible activation by TAT, wherein the TAR sequence or portion thereof is replaced by a comparable portion of the R region from a non-lentiviral retrovirus, thereby forming a hybrid R region. In a particular embodiment, the retroviral LTR comprises a hybrid R region, wherein the hybrid R region comprises a portion of the HIV R region (e.g., a portion comprising or consisting of the nucleotide sequence shown in SEQ ID NO: 10 in US 2003/0039636) lacking the TAR sequence, and a portion of the MoMSV R region (e.g., a portion comprising or consisting of the nucleotide sequence shown in SEQ ID NO: 9 in 2003/0039636) comparable to the TAR sequence lacking from the HIV R region. In another particular embodiment, the entire hybrid R region comprises or consists of the nucleotide sequence shown in SEQ ID NO: 11 in 2003/0039636.

Suitable lentiviruses from which the R region can be derived include, for example, HIV (HIV-1 and HIV-2), EIV, SIV and FIV. Suitable retroviruses from which non-lentiviral sequences can be derived include, for example, MoMSV, MoMLV, Friend, MSCV, RSV and Spumaviruses. In one illustrative embodiment, the lentivirus is HIV and the non-lentiviral retrovirus is MoMSV.

In another embodiment described in US 2003/0039636, the LTR comprising a hybrid R region is a left (5') LTR and further comprises a promoter sequence upstream from the hybrid R region. Preferred promoters are non-lentiviral in origin and include, for example, the U3 region from a non-lentiviral retrovirus (e.g., the MoMSV U3 region). In one particular embodiment, the U3 region comprises the nucleotide sequence shown in SEQ ID NO: 12 in US 2003/0039636. In another embodiment, the left (5') LTR further comprises a lentiviral U5 region downstream from the hybrid R region. In one embodiment, the U5 region is the HIV U5 region including the HIV att site necessary for genomic integration. In another embodiment, the U5 region comprises the nucleotide sequence shown in SEQ ID NO: 13 in US 2003/0039636. In yet another embodiment, the entire left (5') hybrid LTR comprises the nucleotide sequence shown in SEQ ID NO: 1 in US 2003/0039636.

In another illustrative embodiment, the LTR comprising a hybrid R region is a right (3') LTR and further comprises a modified (e.g., truncated) lentiviral U3 region upstream from the hybrid R region. The modified lentiviral U3 region can include the att sequence, but lack any sequences having promoter activity, thereby causing the vector to be SIN in that viral transcription cannot go beyond the first round of replication following chromosomal integration. In a particular embodiment, the modified lentiviral U3 region upstream from the hybrid R region consists of the 3' end of a lentiviral (e.g., HIV) U3 region up to and including the lentiviral U3 att site. In one embodiment, the U3 region comprises the nucleotide sequence shown in SEQ ID NO: 15 in US 2003/0039636. In another embodiment, the right (3') LTR further comprises a polyadenylation sequence downstream from the hybrid R region. In another embodiment, the polyadenylation sequence comprises the nucleotide sequence shown in SEQ ID NO: 16 in US 2003/0039636. In yet another embodiment, the entire right (5') LTR comprises the nucleotide sequence shown in SEQ ID NO: 2 or 17 of US 2003/0039636.

Thus, in the case of HIV based LV, it has been discovered that such vectors tolerate significant U3 deletions, including the removal of the LTR TATA box (e.g., deletions from −418 to −18), without significant reductions in vector titers. These deletions render the LTR region substantially transcriptionally inactive in that the transcriptional ability of the LTR in reduced to about 90% or lower.

It has also been demonstrated that the trans-acting function of Tat becomes dispensable if part of the upstream LTR in the transfer vector construct is replaced by constitutively active promoter sequences (see, e.g., Dull et al. (1998) *J Virol.* 72(11): 8463-8471. Furthermore, we show that the expression of rev in trans allows the production of high-titer HIV-derived vector stocks from a packaging construct which contains only gag and pol. This design makes the expression of the packaging functions conditional on complementation available only in producer cells. The resulting gene delivery system, conserves only three of the nine genes of HIV-1 and relies on four separate transcriptional units for the production of transducing particles.

In one embodiments illustrated in Example 1, the cassette expressing an anti-sickling β-globin (e.g., βAS3) is placed in the pCCL LV backbone, which is a SIN vector with the CMV enhancer/promoter substituted in the 5' LTR.

It will be recognized that the CMV promoter typically provides a high level of non-tissue specific expression. Other promoters with similar constitutive activity include, but are not limited to the RSV promoter, and the SV40 promoter. Mammalian promoters such as the beta-actin promoter, ubiquitin C promoter, elongation factor 1αpromoter, tubulin promoter, etc., may also be used.

The foregoing SIN configurations are illustrative and non-limiting. Numerous SIN configurations are known to those of skill in the art. As indicated above, in certain embodiments, the LTR transcription is reduced by about 95% to about 99%. In certain embodiments LTR may be rendered at least about 90%, at least about 91%, at least about 92%, at least about 93%, at least about 94%, at least about 95% at least about 96%, at least about 97%, at least about 98%, or at least about 99% transcriptionally inactive.

Insulator Element

In certain embodiments, to further enhance biosafety, insulators are inserted into the lentiviral vectors described herein. Insulators are DNA sequence elements present throughout the genome. They bind proteins that modify chromatin and alter regional gene expression. The placement of insulators in the vectors described herein offer various potential benefits including, inter alia: 1) Shielding of the vector from positional effect variegation of expression by flanking chromosomes (i.e., barrier activity); and 2) Shielding flanking chromosomes from insertional trans-activation of gene expression by the vector (enhancer blocking). Thus, insulators can help to preserve the independent function of genes or transcription units embedded in a genome or genetic context in which their expression may otherwise be influenced by regulatory signals within the genome or genetic context (see, e.g., Burgess-Beusse et al. (2002) *Proc. Natl. Acad. Sci. USA,* 99: 16433; and Zhan et al. (2001) Hum. Genet., 109: 471). In the present context insulators may contribute to protecting lentivirus-expressed sequences from integration site effects, which may be mediated by cis-acting elements present in genomic DNA and lead to deregulated expression of transferred sequences. In various embodiments LVs are provided in which an insulator sequence is inserted into one or both LTRs or elsewhere in the region of the vector that integrates into the cellular genome.

The first and best characterized vertebrate chromatin insulator is located within the chicken β-globin locus control region. This element, which contains a DNase-I hypersensitive site-4 (cHS4), appears to constitute the 5' boundary of the chicken β-globin locus (Prioleau et al. (1999) *EMBO J.* 18: 4035-4048). A 1.2-kb fragment containing the cHS4 element displays classic insulator activities, including the ability to block the interaction of globin gene promoters and enhancers in cell lines (Chung et al. (1993) Cell, 74: 505-514), and the ability to protect expression cassettes in *Drosophila* (Id.), transformed cell lines (Pikaart et al. (1998) *Genes Dev.* 12: 2852-2862), and transgenic mammals (Wang et al. (1997) *Nat. Biotechnol.,* 15: 239-243; Taboit-Dameron et al. (1999) *Transgenic Res.,* 8: 223-235) from position effects. Much of this activity is contained in a 250-bp fragment. Within this stretch is a 49-bp cHS4 core (Chung et al. (1997) *Proc. Natl. Acad. Sci., USA,* 94: 575-580) that interacts with the zinc finger DNA binding protein CTCF implicated in enhancer-blocking assays (Bell et al. (1999) *Cell,* 98: 387-396).

One illustrative and suitable insulator is FB (FIT/BEAD-A), a 77 bp insulator element, that contains the minimal CTCF binding site enhancer-blocking components of the chicken β-globin 5' HS4 insulators and a homologous region from the human T-cell receptor alpha/delta blocking element alpha/delta I (BEAD-I) insulator described by Ramezani et al. (2008) *Stem Cell* 26: 3257-3266. The FB "synthetic" insulator has full enhancer blocking activity. This insulator is illustrative and non-limiting. Other suitable insulators may be used including, for example, the full-length chicken beta-globin HS4 or insulator sub-fragments thereof, the ankyrin gene insulator, and other synthetic insulator elements.

Packaging Signal.

In various embodiments the vectors described herein further comprise a packaging signal. A "packaging signal," "packaging sequence," or "psi sequence" is any nucleic acid sequence sufficient to direct packaging of a nucleic acid whose sequence comprises the packaging signal into a retroviral particle. The term includes naturally occurring packaging sequences and also engineered variants thereof. Packaging signals of a number of different retroviruses, including lentiviruses, are known in the art.

Rev Responsive Element (RRE).

In certain embodiments the lentiviral vectors described herein comprise a Rev response element (RRE) to enhance nuclear export of unspliced RNA. RREs are well known to those of skill in the art. Illustrative RREs include, but are not limited to RREs such as that located at positions 7622-8459 in the HIV NL4-3 genome (Genbank accession number AF003887) as well as RREs from other strains of HIV or other retroviruses. Such sequences are readily available from Genbank or from the database with URL hiv-web.lanl-.gov/content/index.

Central PolyPurine Tract (cPPT).

In various embodiments the lentiviral vectors described herein further include a central polypurine tract. Insertion of a fragment containing the central polypurine tract (cPPT) in lentiviral (e.g., HIV-1) vector constructs is known to enhance transduction efficiency drastically, reportedly by facilitating the nuclear import of viral cDNA through a central DNA flap.

Expression-Stimulating Posttranscriptional Regulatory Element (PRE)

In certain embodiments the lentiviral vectors (LVs) described herein may comprise any of a variety of posttranscriptional regulatory elements (PREs) whose presence within a transcript increases expression of the heterologous nucleic acid (e.g., βAS3) at the protein level. PREs may be particularly useful in certain embodiments, especially those that involve lentiviral constructs with modest promoters.

One type of PRE is an intron positioned within the expression cassette, which can stimulate gene expression. However, introns can be spliced out during the life cycle events of a lentivirus. Hence, if introns are used as PRE's they are typically placed in an opposite orientation to the vector genomic transcript.

Posttranscriptional regulatory elements that do not rely on splicing events offer the advantage of not being removed during the viral life cycle. Some examples are the posttranscriptional processing element of herpes simplex virus, the posttranscriptional regulatory element of the hepatitis B virus (HPRE) and the woodchuck hepatitis virus (WPRE). Of these the WPRE is typically preferred as it contains an additional cis-acting element not found in the HPRE. This regulatory element is typically positioned within the vector so as to be included in the RNA transcript of the transgene, but outside of stop codon of the transgene translational unit.

The WPRE is characterized and described in U.S. Pat. No. 6,136,597. As described therein, the WPRE is an RNA export element that mediates efficient transport of RNA from the nucleus to the cytoplasm. It enhances the expression of transgenes by insertion of a cis-acting nucleic acid sequence, such that the element and the transgene are contained within a single transcript. Presence of the WPRE in the sense orientation was shown to increase transgene expression by up to 7- to 10-fold. Retroviral vectors transfer sequences in the form of cDNAs instead of complete intron-containing genes as introns are generally spliced out during the sequence of events leading to the formation of the retroviral particle. Introns mediate the interaction of primary transcripts with the splicing machinery. Because the processing of RNAs by the splicing machinery facilitates their cytoplasmic export, due to a coupling between the splicing and transport machineries, cDNAs are often inefficiently expressed. Thus, the inclusion of the WPRE in a vector results in enhanced expression of transgenes.

Illustrative, but Non-Limiting Embodiments

Figure 6:
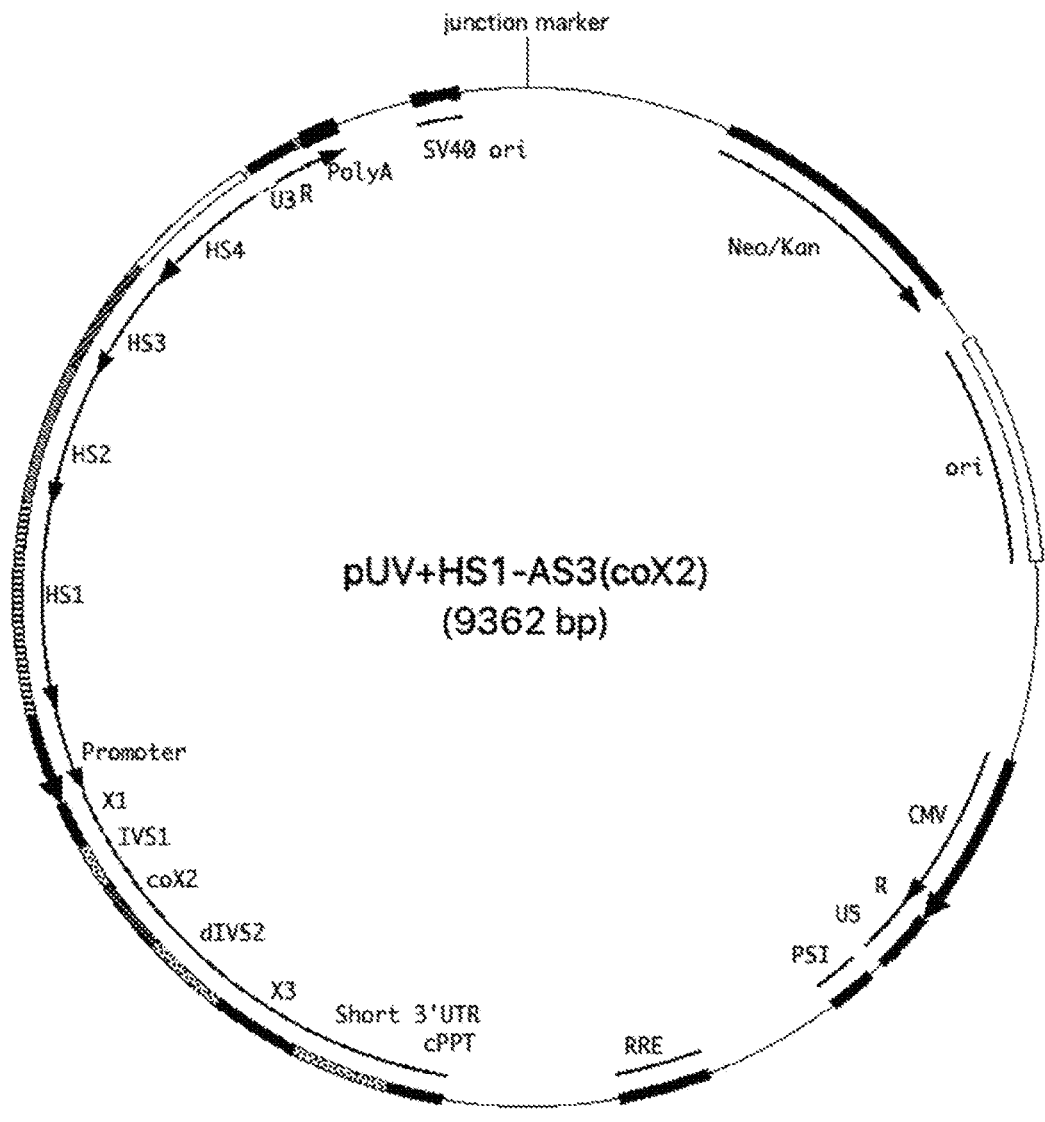
FIG. 6 illustrates the structure of the pUV+AS3(coX2) vector.

FIGS. 2-6 schematically illustrate various features certain illustrative embodiments of the vectors described herein. It is noted that in various embodiments the IVS2 sequence comprises a deletion. As shown in Table 2 the underlined region shows the entire deletion, bold and underlined shows the additional 371 bp deletion that was added in the pUV–AS3 (FIG. 3), pUV–AS3(coX2) (FIG. 4), pUV–HS1-AS3 (FIG. 5), and pUV+HS1-AS3(coX2) (FIG. 6). There was a smaller deletion in our older vectors and now there is an additional larger 371 bp deletion in our new vectors (591 bp total), the additional deleted region is the one in bold and underlined.

TABLE 2

Illustration of IVS2 deletion.

IVS2 Deletion

```
CTGTGGGAGGAAGATAAGAGGTATGAACATGATTAGCAAAAGGGCCTAG

CTTGGACTCAGAATAATCCAGCCTTATCCCAACCATAAAATAAAAGCAG

AATGGTAGCTGGATTGTAGCTGCTATTAGCAATATGAAACCTCTTACAT

CAGTTACAATTTATATGCAGAAATATTTATATGCAGAGATATTGCTATT

GCCTTAACCCAGAAATTATCACTGTTATTCTTTAGAATGGTGCAAAGAG

GCATGATACATTGTATCATTATTGCCCTGAAAGAAAGAGATTAGGGAAA

GTATTAGAAATAAGATAAACAAAAAAGTATATTAAAAGAAGAAAGCATT

TTTTAAAATTACAAATGCAAAATTACCCTGATTTGGTCAATATGTGTAC

ACATATTAAAACATTACACTTTAACCCATAAATATGTATAATGATTATG

TATCAATTAAAAATAAAAGAAAATAAAGTAGGGAGATTATGAATATGCA

AATAAGCACACATATATTCCAAATAGTAATGTACTAGGCAGACTGTGTA

AAGTTTTTTTTTAAGTTACTTAATGTATCTCAGAGATATTTCCTTTTGT

TATACACAATGTTAAGGCATTAAGTATAATAGTAAAAATTGCGGAGAAG

AAAAAAAAAGAAAGCAAGAATTAAACAAAAGAAAACAATTGTTATGAAC

AGCAAATAAAAGAAACTAAAACGATCCTGAGACTTCCACACTGATGCAA

TCATTCGTCTGTTTCCATTCTAAACTGTACCCTGTTACTTATCCCCTT

CCTATGACATGAACTTAACCATAGAAAAGAAGGGGAAAGAAAACATCAA

GCGTCCCATAGACTCAC
```

In certain embodiments the vectors contemplated herein comprises the features of pUV–AS3 (FIG. 3), pUV–AS3 (coX2) (FIG. 4), pUV–HS1-AS3 (FIG. 5), or pUV+HS1-AS3(coX2) (FIG. 6).

In certain embodiments the vectors contemplated herein comprise the nucleotide sequence of pUV–AS3 (SEQ ID NO: 13), pUV–AS3(coX2) (SEQ ID NO:14), pUV–HS1-AS3 (SEQ ID NO:15), and pUV+HS1-AS3(coX2) (SEQ ID NO: 16).

Improved Titer, Gene Transfer, and Increased Total Expression.

Figure 7:
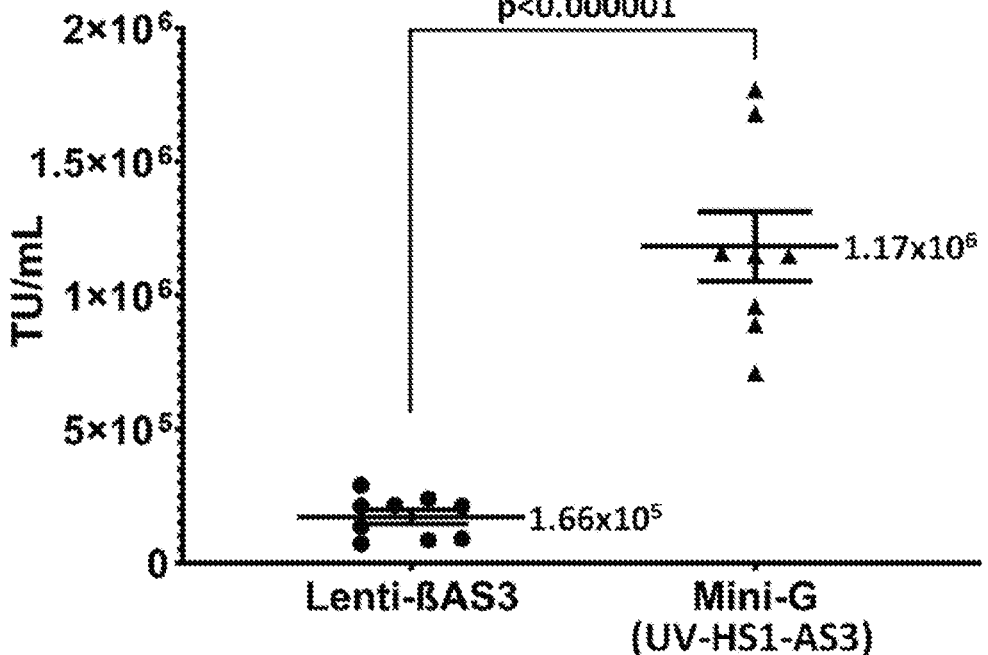
FIG. 7 shows that the unconcentrated vector titer of the pUV–HS1-AS3 (Mini-G) is ~10 fold higher than the parental vector. Titer was determined by the number of infectious particles, transducing units (TU), per ml on HT-29 cells. Readout is through detection of PSI sequences by ddPCR 3 days post transduction.

As shown in FIG. 7, unconcentrated vector titer of the pUV–HS1-AS3 (Mini-G) is ~10 fold higher than the parental vector. Titer was determined by the number of infectious particles, transducing units (TU), per ml on HT-29 cells.

Figure 8:
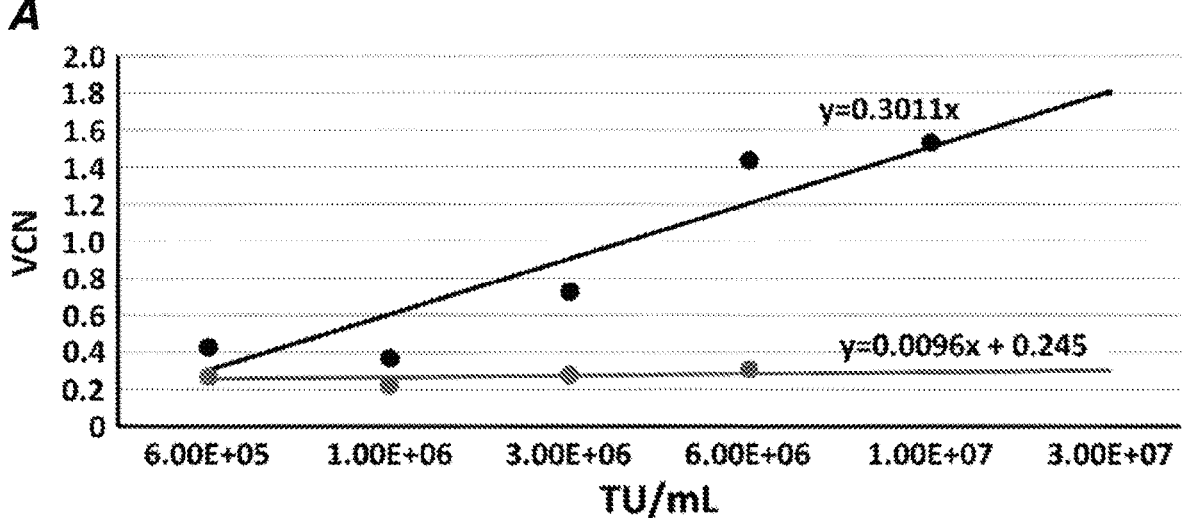
FIG. 8, panels A-B, shows that Gene transfer is significantly enhanced for the shorter globin vector Mini-G (UV-HS1-AS3) in primary human hematopoietic stem and progenitor (CD34[+]) cells (HSPCs). Panel A demonstrates how gene transfer continues to increase with Mini-G, compared to the parental vector that displays little increase in gene transfer. Panel B focusses on a single vector concentration ($2\times10^7$ TU/ml) that is typically used for clinical vector transductions, here the gene transfer is significantly improved and is ~10 fold higher than the parental vector.
Figure 8:
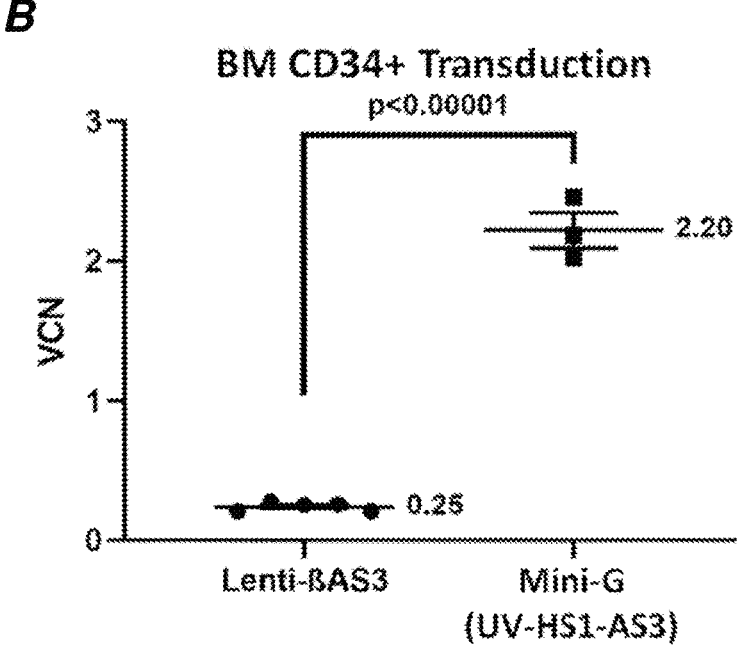

Gene transfer was significantly enhanced for the shorter globin vector Mini-G (pUV–HS1-AS3) in primary human hematopoietic stem and progenitor (CD34⁺) cells (HSPCs). FIG. 8, panel A demonstrates how gene transfer continues to increase with Mini-G, compared to the parental vector that displays little increase in gene transfer. FIG. 8, panel B focusses on a single vector concentration ($2\times10^7$ TU/ml) that is typically used for clinical vector transductions, here the gene transfer is significantly improved and is ~10 fold higher than the parental vector.

Figure 9:
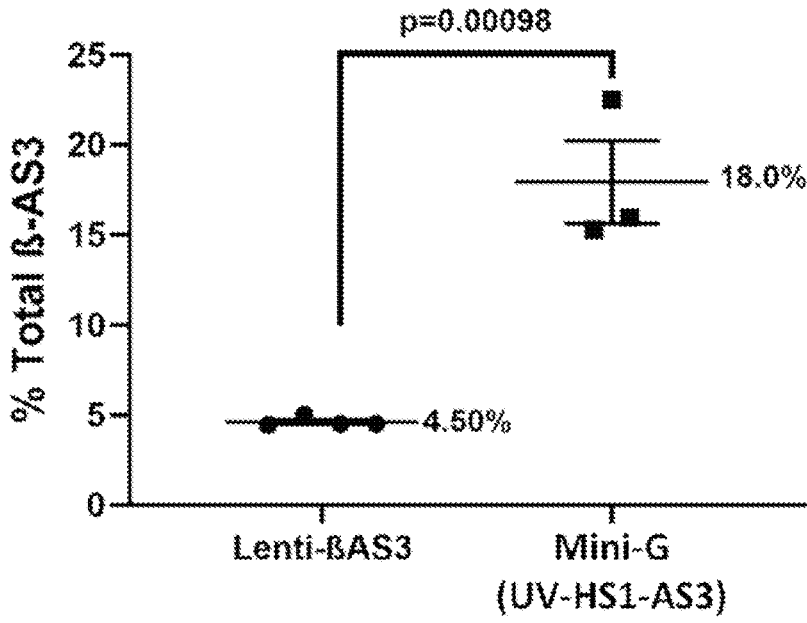
FIG. 9 shows that expression of AS3-globin is ~5-fold higher in erythrocytes differentiated in vitro from transduced HSPCs. Globin expression was assayed at the RNA level using ddPCR probe/primers. The difference in expression is caused by the enhanced gene transfer of Mini-G (UV-HS1-AS3).

Additionally, Mini-G provided increased total expression. FIG. 9 shows that expression of AS3-globin is ~5-fold higher in erythrocytes differentiated in vitro from transduced HSPCs. Globin expression was assayed at the RNA level using ddPCR probe/primers. Without being bound by a particular theory, it is believed the difference in expression is caused by the enhanced gene transfer of Mini-G.

Transduced Host Cells and Methods of Cell Transduction.

The recombinant lentiviral vectors (LV) and resulting virus described herein are capable of transferring a heterologous nucleic acid (e.g., a nucleic acid encoding an anti-sickling β-globin) sequence into a mammalian cell. In various embodiments, for delivery to cells, vectors described herein are preferably used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

The recombinant LVs and resulting virus described herein are capable of transferring a nucleic acid (e.g., a nucleic acid encoding an anti-sickling β-globin or other sequence) into a mammalian cell. For delivery to cells, various vectors described herein are preferably used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

In certain embodiments the vectors are introduced via transfection into the packaging cell line. The packaging cell line produces viral particles that contain the vector genome. Methods for transfection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with or without a dominant selectable marker, such as neomycin, DHFR, Glutamine synthetase, followed by selection in the presence of the appropriate drug and isolation of clones. In certain embodiments the selectable marker gene can be linked physically to the packaging genes in the construct.

Stable cell lines wherein the packaging functions are configured to be expressed by a suitable packaging cell are known (see, e.g., U.S. Pat. No. 5,686,279, which describes packaging cells). In general, for the production of virus particles, one may employ any cell that is compatible with the expression of lentiviral Gag and Pol genes, or any cell that can be engineered to support such expression. For example, producer cells such as 293T cells and HT1080 cells may be used.

The packaging cells with a lentiviral vector incorporated therein form producer cells. Producer cells are thus cells or cell-lines that can produce or release packaged infectious viral particles carrying the therapeutic gene of interest (e.g., modified β-globin). These cells can further be anchorage dependent which means that these cells will grow, survive, or maintain function optimally when attached to a surface such as glass or plastic. Some examples of anchorage dependent cell lines used as lentiviral vector packaging cell lines when the vector is replication competent are HeLa or 293 cells and PERC.6 cells.

Accordingly, in certain embodiments, methods are provided of delivering a gene to a cell which is then integrated into the genome of the cell, comprising contacting the cell with a virion containing a lentiviral vector described herein. The cell (e.g., in the form of tissue or an organ) can be contacted (e.g., infected) with the virion ex vivo and then delivered to a subject (e.g., a mammal, animal or human) in which the gene (e.g., anti-sickling β-globin) will be expressed. In various embodiments the cell can be autologous to the subject (i.e., from the subject) or it can be non-autologous (i.e., allogeneic or xenogenic) to the subject. Moreover, because the vectors described herein are capable of being delivered to both dividing and non-dividing cells, the cells can be from a wide variety including, for example, bone marrow cells, mesenchymal stem cells (e.g., obtained from adipose tissue), and other primary cells derived from human and animal sources. Alternatively, the virion can be directly administered in vivo to a subject or a localized area of a subject (e.g., bone marrow).

Of course, as noted above, the lentivectors described herein will be particularly useful in the transduction of human hematopoietic progenitor cells or a hematopoietic stem cells, obtained either from the bone marrow, the peripheral blood or the umbilical cord blood, as well as in the transduction of a CD4$^+$ T cell, a peripheral blood B or T lymphocyte cell, and the like. In certain embodiments particularly preferred targets are CD34$^+$ hematopoetic stem and progenitor cells.

Gene Therapy.

In still other embodiments, methods are provide for transducing a human hematopoietic stem cell. In certain embodiments the methods involve contacting a population of human cells that include hematopoietic stem cells with one of the foregoing lentivectors under conditions to effect the transduction of a human hematopoietic progenitor cell in said population by the vector. The stem cells may be transduced in vivo or in vitro, depending on the ultimate application. Even in the context of human gene therapy, such as gene therapy of human stem cells, one may transduce the stem cell in vivo or, alternatively, transduce in vitro followed by infusion of the transduced stem cell into a human subject. In one aspect of this embodiment, the human stem cell can be removed from a human, e.g., a human patient, using methods well known to those of skill in the art and transduced as noted above. The transduced stem cells are then reintroduced into the same or a different human.

Stem Cell/Progenitor Cell Gene Therapy.

In various embodiments the lentivectors described herein are particularly useful for the transduction of human hematopoietic progenitor cells or haematopoietic stem cells (HSCs), obtained either from the bone marrow, the peripheral blood or the umbilical cord blood, as well as in the transduction of a CD4$^+$ T cell, a peripheral blood B or T lymphocyte cell, and the like. In certain embodiments particularly preferred targets are CD34$^+$ hematopoietic stem and progenitor cells.

When cells, for instance CD34$^+$ cells, dendritic cells, peripheral blood cells or tumor cells are transduced ex vivo, the vector particles are incubated with the cells using a dose generally in the order of between 1 to 50 multiplicities of infection (MOI) which also corresponds to $1\times10^5$ to $50\times10^5$ transducing units of the viral vector per $10^5$ cells. This can include amounts of vector corresponding to 1, 2, 3, 4, 5, 6, 7, 8, 9, 10, 15, 20, 25, 30, 35, 40, 45, and 50 MOI. Typically, the amount of vector may be expressed in terms of HT-29 transducing units (TU).

In certain embodiments cell-based therapies involve providing stem cells and/or hematopoietic precursors, transduce the cells with the lentivirus encoding, e.g., an anti-sickling human β-globin, and then introduce the transformed cells into a subject in need thereof (e.g., a subject with the sickle cell mutation).

In certain embodiments the methods involve isolating population of cells, e.g., stem cells from a subject, optionally expand the cells in tissue culture, and administer the lentiviral vector whose presence within a cell results in production of an anti-sickling β-globin in the cells in vitro. The cells are then returned to the subject, where, for example, they may provide a population of red blood cells that produce the anti-sickling β globin.

In some illustrative, but non-limiting, embodiments, a population of cells, which may be cells from a cell line or from an individual other than the subject, can be used. Methods of isolating stem cells, immune system cells, etc., from a subject and returning them to the subject are well known in the art. Such methods are used, e.g., for bone marrow transplant, peripheral blood stem cell transplant, etc., in patients undergoing chemotherapy.

Where stem cells are to be used, it will be recognized that such cells can be derived from a number of sources including bone marrow (BM), cord blood (CB), mobilized peripheral blood stem cells (mPBSC), and the like. In certain embodiments the use of induced pluripotent stem cells (IPSCs) is contemplated. Methods of isolating hematopoietic stem cells (HSCs), transducing such cells and introducing them into a mammalian subject are well known to those of skill in the art.

In certain embodiments a lentiviral vector described herein (see, e.g., FIG. 4) is used in stem cell gene therapy for SCD by introducing the βAS3 anti-sickling β-globin gene into the bone marrow stem cells of patients with sickle cell disease followed by autologous transplantation.

Direct Introduction of Vector.

In certain embodiments direct treatment of a subject by direct introduction of the vector(s) described herein is contemplated. The lentiviral compositions may be formulated for delivery by any available route including, but not limited to parenteral (e.g., intravenous), intradermal, subcutaneous, oral (e.g., inhalation), transdermal (topical), transmucosal, rectal, and vaginal. Commonly used routes of delivery include inhalation, parenteral, and transmucosal.

In various embodiments pharmaceutical compositions can include an LV in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

In some embodiments, active agents, i.e., a lentiviral described herein and/or other agents to be administered together the vector, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. Suitable materials can also be obtained commercially from Alza Corporation and Nova Pharmaceuticals, Inc. Liposomes can also be used as pharmaceutically acceptable carriers. These can be prepared according to methods known to those skilled in the art, for example, as described in U.S. Pat. No. 4,522,811. In some embodiments the composition is targeted to particular cell types or to cells that are infected by a virus. For example, compositions can be targeted using monoclonal antibodies to cell surface markers, e.g., endogenous markers or viral antigens expressed on the surface of infected cells.

It is advantageous to formulate compositions in dosage unit form for ease of administration and uniformity of dosage. Dosage unit form as used herein refers to physically discrete units suited as unitary dosages for the subject to be treated; each unit comprising a predetermined quantity of a LV calculated to produce the desired therapeutic effect in association with a pharmaceutical carrier.

A unit dose need not be administered as a single injection but may comprise continuous infusion over a set period of time. Unit dose of the LV described herein may conveniently be described in terms of transducing units (T.U.) of lentivector, as defined by titering the vector on a cell line such as HeLa or 293. In certain embodiments unit doses can range from $10^3$, $10^4$, $10^5$, $10^6$, $10^7$, $10^8$, $10^9$, $10^{10}$, $10^{11}$, $10^{12}$, $10^{13}$ T.U. and higher.

Pharmaceutical compositions can be administered at various intervals and over different periods of time as required, e.g., one time per week for between about 1 to about 10 weeks; between about 2 to about 8 weeks; between about 3 to about 7 weeks; about 4 weeks; about 5 weeks; about 6 weeks, etc. It may be necessary to administer the therapeutic composition on an indefinite basis. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a LV can include a single treatment or, in many cases, can include a series of treatments.

Illustrative, but non-limiting, doses for administration of gene therapy vectors and methods for determining suitable doses are known in the art. It is furthermore understood that appropriate doses of a LV may depend upon the particular recipient and the mode of administration. The appropriate dose level for any particular subject may depend upon a variety of factors including the age, body weight, general health, gender, and diet of the subject, the time of administration, the route of administration, the rate: of excretion, other administered therapeutic agents, and the like.

In certain embodiments lentiviral gene therapy vectors described herein can be delivered to a subject by, for example, intravenous injection, local administration, or by stereotactic injection (see, e.g., Chen et al. (1994) *Proc. Natl. Acad. Sci. USA,* 91: 3054). In certain embodiments vectors may be delivered orally or inhalationally and may be encapsulated or otherwise manipulated to protect them from degradation, enhance uptake into tissues or cells, etc. Pharmaceutical preparations can include a LV in an acceptable diluent, or can comprise a slow release matrix in which a LV is imbedded. Alternatively or additionally, where a vector can be produced intact from recombinant cells, as is the case for retroviral or lentiviral vectors as described herein, a pharmaceutical preparation can include one or more cells which produce vectors. Pharmaceutical compositions comprising a LV described herein can be included in a container, pack, or dispenser, optionally together with instructions for administration.

The foregoing compositions, methods and uses are intended to be illustrative and not limiting. Using the teachings provided herein other variations on the compositions, methods and uses will be readily available to one of skill in the art.

The approach to generate reduced length enhance regions is superior to previous strategies for generating tissue-specific enhancers for, among other reasons: 1) The cost of goods is decreased due to a low number of outputs required to be tested, 2) Strength of synthetic enhancers may be superior to those produced with current methods, or they may be less active but more suitable for LV-mediated delivery, and 3). Enhancers can be of minimal length.

Additionally, without being bound to a particular theory, it is believed the enhancer mapping strategy described herein can be modified to generate genome-wide enhancer maps using a similar cloning strategy and sonicated human genomic DNA and that the mapping strategies can be used to generate synthetic enhancers responsive to an array of distinct cellular perturbations.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

SEQUENCE LISTING

---

SEQ ID NO: 1 ecHS1 catcaataattctagccccacaggagtttgttctgaaagtaaacttccacaaccgcaagcttattgaggctaaggcatctgtgaaggaaa
gaaacatctcctctaaaccactatgctgctagagcctcttttctgtactcaagcctcattcagacactagtgtcaccagtctcctcatat
acctattgtattttcttcttcttgctggtttagtcatgttttctgggagcttaggggcttattttattttgtttgttttctaatcaaca
gagatgggcaaacccattattttttttctttagacttgggatggtgatagctgggcagcgtcagaaactgtgtgtggatatagataagagc
tcaggactatgctgagctgtgatgagggagggggcctagctaaaggcagtgagagtcagaatgctcctgctattgccttctcagtccccac
gcttggtttctacacaagtagatacatagaaaaggctataggttagtgtttgagagtcctgcatgattagttgctcagaaatgcccgata
aatatgttatgtgtgtttatgtatatatatgttttatatgtgtgtgtgtgtgtgttgtgtttacaaatatgtgattatcatcaaaacgtg
aggg SEQ ID NO: 2 ecHS2 tacgtatatgtgtatatatatatatatattcaggaaataatatattctagaatatgtcacattctgtctcaggcatccattttctttatg
atgccgtttgaggtggagttttagtcaggtggtcagcttctccttttttttgccatctgccctgtaagcatcctgctggggacccagata
ggagtcatcactctaggctgagaacatctgggcacacaccctaagcctcagcatgactcatcatgactcagcattgctgtgcttgagcca
gaaggtttgcttagaaggttacacagaaccagaaggcggggggtggggcactgaccccgacaggggcctggccagaactgctcatgcttgg
actatgggaggtcactaatggagacacacagaaatgtaacaggaactaaggaaaaactgaagctt SEQ ID NO: 3 ecHS3 tgggggtatagggggagcagtcccatgtagtagtagaatgaaaaatgctgctatgctgtgcctcccccacctttcccatgtctgccctcta
ctcatggtctatctctcctggctcctgggagtcatggactccacccagcaccaccaacctgacctaaccacctatctgagcctgccagcc
tataacccatctgggccctgatagctggtggccagccctgaccccaccccacctccctggaacctctgatagacacatctggcacacca
gctcgcaaagtcaccgtgagggtcttgtgtttgctgagtcaaaattccttgaaatccaagtccttagagctcc -continued

---

SEQUENCE LISTING

---

SEQ ID NO: 4 ecHS4
Caggcttggattcaaagctcctgactttctgtctagtgtatgtgcagtgagcccctttcctctaactgaaagaaggaaaaaaaaatgga
acccaaaatattctacatagtttccatgtcacagccagggctgggcagtctcctgttatttcttttaaaataaatatatcatttaaatgc
ataaataagcaaaccctgctcgggaatgggagggagagtctctggagtccacccttctcggccctggctctgcagatagtgctatcaaa
gccctgacagagccctgcccattgctgggccttggagtgagtcagcctagtagagaggcagggcaagccatctcatagctgctgagtggg
agagagaaaagggctcattgtctataaactcaggtcatggctattcttat SEQ ID NO: 5 coX2 (codon optimized exon 2)
CCTGAAGTTCTCAGGATCCACGTGCAGCTTGTCGCAGTGCAGCTCGCTCAGCTGGGCGAAGGTGCCCTTCAGGTTGTCCAGGTGGGCCAG
GCCGTCGCTGAAGGCGCCCAGCACCTTCTTGCCGTGGGCCTTCACCTTGGGGTTGCCCATCACGGCGTCGGGGGTGCTCAGGTCGCCGAA
GCTCTCGAAGAAGCGCTGGGTCCAGGGGTACACCACCAGCAGC SEQ ID NO: 6 full vector with HS1
gcgcaacgcaattaatgtgagttagctcactcattaggcaccccaggctttacactttatgcttccggctcgtatgttgtgtggaattgt
gagcggataacaatttcacacaggaaacagctatgaccatgattacgccaagcgcgcaattaaccctcactaaagggaacaaaagctgga
gctgcaagcttggccattgcatactgttgtatccatatcataatatgtacatttatattggctcatgtccaacattaccgccatgttgac
attgattattgactagttattaatagtaatcaattacggggtcattagttcatagcccatatatggagttccgcgttacataacttacgg
taaatggcccgcctggctgaccgcccaacgacccccgcccattgacgtcaataatgacgtatgttcccatagtaacgccaatagggactt
tccattgacgtcaatgggtggagtatttacggtaaactgcccacttggcagtacatcaagtgtatcatatgccaagtacgccccctattg
acgtcaatgacggtaaatggcccgcctggcattatgcccagtacatgaccttatgggactttcctacttggcagtacatctacgtattag
tcatcgctattaccatggtgatgcggttttggcagtacatcaatgggcgtggatagcggtttgactcacggggatttccaagtctccacc
ccattgacgtcaatgggagtttgttttggcaccaaaatcaacgggactttccaaaatgtcgtaacaactccgccccattgacgcaatggg
cggtaggcgtgtacggtgggaggtctatataagcagagctcgtttagtgaaccgtctctctggttagccagatctgagcctgggag
ctctctggctaactcagggaacccactgcttaagcctcaataaagcttgccttgagtgcttcaagtagtgtgtgcccgtctgttgtgtga
ctctggtaactagagatccctcagacccttttagtcagtgtggaaaatctctagcagtggcgcccgaacagggacttgaaagcgaaaggg
aaaccagaggagctctctcgacgcaggactcggcttgctgaagcgcgcacggcaagaggcgaggggcggcgactggtgagtacgccaaa
attttgactagcggaggctagaaggagagagatgggtgcgagagcgtcagtattaagcgggggagaattagatcgcgatgggaaaaaatt
cggttaaggccagggggaaagaaaaaatataaattaaaacatatagtatgggcaagcagggagctagaacgattcgcagttaatcctggc
ctgttagaaacatcagaaggctgtagacaaatactgggacagctacaaccatcccttcagacaggatcagaagaacttagatcattatat
aatacagtagcaaccctctattgtgtgcatcaaaggatagagataaaagacaccaaggaagctttagacaagatagaggaagagcaaaac
aaaagtaagaccaccgcacagcaagcggccgctgatcttcagacctggaggaggagatatgagggacaattggagaagtgaattatataa
atataaagtagtaaaaattgaaccattaggagtagcaccccaccaaggcaaagaagaagtggtgcagagagaaaaaagacagtgggaat
aggagctttgttccttgggttcttgggagcagcaggaagcactatgggcgcagcgtcaatgacgctgacggtacaggccagacaattatt
gtctggtatagtgcagcagcagaacaatttgctgagggctattgaggcgcaacagcatctgttgcaactcacagtctggggcatcaagca
gctccaggcaagaatcctggctgtggaaagatacctaaaggatcaacagctcctggggatttggggttgctctggaaaactcatttgcac
cactgctgtgccttggaatgctagttggagtaataaatctctggaacagatttggaatcacacgacctggatggagtgggacagagagaat
taacaattacacaagcttaatacactccttaattgaagaatcgcaaaaccagcaagaaaagaatgaacaagaattattggaattagataa
atgggcaagtttgtggaattggtttaacataacaaattggctgtggtatataaaattattcataatgatagtaggaggcttggtaggttt
aagaatagtttttgctgtactttctatagtgaatagagttaggcagggatattcaccattatcgtttcagacccacctcccaaccccgag
gggacccgacaggcccgaaggaatagaagaagaaggtggagagagagacagagacagatctcattcgattagtgaacggatctcgacggta
tcgatctcgacacaaatggcagtattcatccacaattttaaaagaaaaggggggggggactggggggtacagtgcaggggaaagaatagtagac
ataatagcaacagacatacaaactaaagaattacaaaaacaaattacaaaaattcaaaattttcgggtttattacagggacagcagagat
ccagtttgggtcgaggatatcggatcggaattctctagatgatcaggatccctcgagcccttatcgatcacgagactagcctcgactact
agtggagatccccgggctgcagacccagaagagcaccataaggagcatgatagaagcagacctctgatctcttcctgaatgctaa
tcttaaacatcctgaggaagaatgggacttccatttggggtgggcctatgatagggtaataagacagtagtgaatatcaagctacaaaaa
gcccccttttcaaattcttctcagtcctaacttttcatactaagcccagtccttccaaagcagactgtgaaagagtgatagttccgggaga
ctagcactgcagattccgggtcactgtgagtgggggaggcagggaagaaggggctcacaggacagtcaaaccatgcccctgttttttcctt
cttcaagtagacctctataagacaacagagacaactaaggctgagtggctggccaggcgaggagaaaccatctcgccgtaaaacatggaaggaa
cacttcaggggaaaggtggtatctctaagcaagagaactgagtggagtcaaggctgagagatgcaggataagcaaatgggtagtgaaaag
acattcatgaggacagctaaaacaataagtaatgtaaaatacagcatagcaaaactttaacctccaaatcaagcctctacttgaatcctt
ttctgagggatgaataaggcataggcatcaggggctgttgccaatgtgcattagctgtttgcagcctcaccttctttcatggagtttaag
atatagtgtattttcccaaggtttgaactagctcttcatttctttatggttttaaatgcactgacctcccacattccctttttagtaaaat
attcagaaataatttaaatacatcattgcaatgaaataaatgttttttattaggcagaatccagatgctcaaggcccttcataatatcc
cccagtttagtagttggacttagggaacaaaggaacctttaatagaaattggacagcaagaaagcgagcttagtgatacttgtgggccag
ggcattagccacaccagccaccactttctgataggcagcctgcactggtggggtgaattcttgccaaagtgatgggccagcacacagac
cagcacgttgcccaggagctgtgggaggaagataagaggtatgaacatgattagcaaaagggctagcttggactcagaataatccagcc
ttatcccaaccataaaataaaagcagaatggtagctggattgtagctgctattagcaatatgaaacctcttacatcagttacaatttata
tgcagaaatatttatatgcagaaatattgctattgccttaacccagaaattatcactgttattctttagaatggtgcaaagaggcatgat
acattgtatcattattgccctgaaagaaagagattagggaaagtattagaaataagtaaacaaaaaagtatattaaagaagaaagcat
tttttaaaattacaaatgcaaaattaccctgatttggttcaatatgtgtaccctgttacttctccccttcctatgacatgaacttaaccat
agaaaagaagggaaagaaaacatcaaggggtcccatagactcaccctgaagttctccaggttctcaggatccacgtgcagctgcagctca
ctcagctgggcaaaggtgcccttgaggttgtccaggtgagccaggccatcactaaaggcaccgagcacttcttgccatgagccttcacc
ttagggttgcccataacagcatcaggagtggacagatccccaaaggactcaaagaacctctgggtccaagggtagaccaccagcagccta
agggtgggaaaatagaccaataggcagagagagtcagtgcctatcagaaacccaagagtcttctctgtctccacatgcccagttctattg
gtctccttaaacctgtcttgtaaccttgataccaacctgcccagggcctcaccaccaacggcatccacgttcaccttgtcccacagggca
gtaacggcagacttctcctcaggagtcaggtgcaccatggtgtcgttgaggttgctcagtgaacacagttgtgtcagagacaaatgtaa
gcaatagatggctctgccctgacttttatgcccagccctggctcctgccctccctgctcctgggagtagattggccaaccctagggtgtg
gctccacagggtgaggtctaagtgatgacagccgtacctgtccttggctcttctggcactggcttaggagttggacttcaaaccctcagc
cctccctctaagatatatctcttggccccataccatcagtacaaattgctactaaaaacatcctcctttgcaagtgtatttacccgacgc
gtcggcgataagcttgatccatcgatcatcaataattctagccccaccaggagtttgttctgaaagtaaacttccacaaccgcaagctta
ttgaggctaaggcatctgtgaaggaaagaaacatctcctctaaaccactatgctgctagagcctcttttctgtactcaaagcctcattcag
acactagtgtcaccagtctcctcatatacctattgtattttcttcttcttgctggtttagtcatgttttctgggagcttaggggcttatt
ttattttgtttgtttttctaatcaacagagatgggcaaacccattatttttttcttttagacttgggatggtgatagctgggcagcgtcag
aaactgtgtgtggatatagataagagctcaggactatgctgagctgtgatgagggagggggcctagctaaaggcagtgagagtcagaatgc
tcctgctattgccttctcagtccccacgcttggtttctacacaagtagatacatagaaaaggctataggttagtgtttgagagtcctgca
tgattagttgctcagaaatgcccgataaatatgttatgtgtgtgtttatgtatatatgttttatatgtgtgtgtgtgtgtttgtgtttaca

SEQUENCE LISTING

```
aatatgtgattatcatcaaaacgtgagggtacgtatatgtgtatatatatatattcaggaaataatatattctagaatatgtcacattct
gtctcaggcatccattttctttatgatgccgtttgaggtggagttttagtcaggtggtcagcttctcctttttttgccatctgccctgt
aagcatcctgctggggacccagataggagtcatcactctaggctgagaacatctgggcacacaccctaagcctcagcatgactcatcatg
actcagcattgctgtgcttgagccagaaggtttgcttagaaggttacacagaaccagaaggcggggtggggcactgaccccgacagggg
cctggccagaactgctcatgcttggactatgggaggtcactaatggagacacacagaaatgtaacaggaactaaggaaaaactgaagctt
tgggggtatagggggagcagtcccatgtagtagtagaatgaaaaatgctgctatgctgtgcctcccccacctttcccatgtctgccctcta
ctcatggtctatctctcctggctcctgggagtcatggactccacccagaccaccaacctgacctaaccacctatctgagcctgccagcct
ataacccatctgggccctgatagctggtggccagccctgaccccaccccaccctccctggaacctctgatagacatctggcacaccag
ctcgcaaagtcaccgtgagggtcttgtgtttgctgagtcaaaattccttgaaatccaagtcctagagactcccaggcttggattcaaag
ctcctgactttctgtctagtgtatgtgcagtgagcccctttcctctaactgaaagaaggaaaaaaaaatggaacccaaaatattctaca
tagtttccatgtcacagccagggctgggcagtctcctgttatttcttttaaaataaatatatcatttaaatgcataaataagcaaaccct
gctcgggaatgggagggagagtctctggagtccaccccttctcggccctggctctgcagatagtgctatcaaagccctgacagagccctg
cccattgctgggccttggagtgagtcagcctagtagagaggcagggcaagccatctcatagctgctgagtgggagagagaaaagggctca
ttgtctataaactcaggtcatggctattcttatggcctactcgaccacgagggaattccgataatcaacctctggattacaaaatttgtg
aaagattgactggtattcttaactatgttgctcctttacgctatgtggatacgctgctttaatgcctttgtatcatgctattgcttccc
gtatggctttcattttctcctccttgtataaatcctggttgctgtctctttatgaggagttgtggccccgttgtcaggcaacgtggcgtgg
tgtgcactgtgtttgctgacgcaaccccccactggttggggcattgccaccacctgtcagctcctttccggggacttttcgctttcccctcc
ctattgccacggcggaactcatcgccgcctgcctgcccgctgctggacaggggctcggctgttgggcactgacaattccgtggtgttgt
cggggaaatcatcgtcctttccttggctgctcgcctgtgttgccacctggattctgcgcgggacgtccttctgctacgtcccttcggccc
tcaatccagcggaccttccttcccgcggcctcttgccggctctgcggcctcttccgcgtcttcgccttcgccctcagacgagtcggatct
cccctttgggccgcctcccgcatcgataccgtcgacctcgagacctagaaaaacatggccaattcgagctcggtacctttaagaccaatg
acttacaaggcagctgtagatcttagccacttttaaaagaaaaggggggactggaagggctaattcactcccaacgaagacaagatccc
agggatgtacgtccctaaccccgctaggggggcagcacccaggcctgcactgccgcctgccggcaggggtccagtcctgcttttttgcttgta
ctgggtctctctggttagaccagatctgagcctgggagctctctggctaactagggaacccactgcttaagcctcaataaagcttgcctt
gagtgcttcaagtagtgtgtgcccgtctgttgtgtgactctggtaactagagatccctcagacccttttagtcagtgtggaaaatctcta
gcagtagtagttcatgtcatcttattattcagtatttataacttgcaaagaaatgaatatcagagagtgagaggaacttgtttattgcag
cttataatggttacaaataaagcaatagcatcacaaatttcacaaataaagcattttttttcactgcattctagttgtggtttgtccaaac
tcatcaatgtatcttatcatgtctggctctagctatcccgcccctaactccgcccatcccgcccctaactccgcccagttccgcccattc
tccgccccatggctgactaatttttttatttatgcagaggccgaggccgcctcggcctctgagctattccagaagtagtgaggaggctt
ttttggaggcctaggcttttgcgtcgagacgtacccaattcgccctatagtgagtcgtattacgcgcgctcactggccgtcgttttacaa
cgtcgtgactgggaaaaccctggcgttacccaacttaatcgccttgcagcacatccccctttcgccagctggcgtaatagcgaagaggcc
cgcaccgatcgcccttcccaacagttgcgcagcctgaatggcgaatggcgcgacgcgccctgtagcggcgcattaagcgcggcgggtgtg
gtggttacgcgcagcgtgaccgctacacttgccagcgccctagcgcccgctcctttcgctttcttcccttcctttctcgccacgttcgcc
ggctttccccgtcaagctctaaatcggggctccctttagggttccgatttagtgctttacggcacctcgaccccaaaaaacttgattag
ggtgatggttcacgtagtgggccatcgccctgatagacggtttttcgccctttgacgttggagtccacgttctttaatagtggactcttg
ttccaaactggaacaacactcaaccctatctcggtctattcttttgatttataagggattttgccgatttcggcctattggttaaaaaat
gagctgatttaacaaaatttaacgcgaattttaacaaaatattaacgtttacaatttcccaggtggcacttttcggggaaatgtgcgcgg
gaaccccctatttgtttatttttctaaatacattcaaatatgtatccgctcatgagacaataaccctgataaatgcttcaataatattgaa
aaaggaagagtatgagtattcaacatttccgtgtcgcccttattcccttttttgcggcatttttgccttcctgtttttgctcacccagaaa
cgctggtgaaagtaaaagatgctgaagatcagttgggtgcacgagtgggttacatcgaactggatctcaacagcggtaagatccttgaga
gttttcgccccgaagaacgttttccaatgatgagcacttttaaagttctgctatgtggcgcggtattatcccgtattgacgccgggcaag
agcaactcggtcgccgcatacactattctcagaatgacttggttgagtactcaccagtcacagaaaagcatcttacggatggcatgacag
taagagaattatgcagtgctgccataaccatgagtgataacactgcggccaacttacttctgacaacgatcggaggaccgaaggagctaa
ccgcttttttgcacaacatgggggatcatgtaactcgccttgatcgttgggaaccggagctgaatgaagccataccaaacgacgagcgtg
acaccacgatgcctgtagcaatggcaacaacgttgcgcaaactattaactggcgaactacttactctagcttcccggcaacaattaatag
actggatggaggcggataaagttgcaggaccacttctgcgctcggcccttccggctggctggtttattgctgataaatctggagccggtg
agcgtgggtctcgcggtatcattgcagcactggggccagatggtaagccctcccgtatcgtagttatctacacgacggggagtcaggcaa
ctatggatgaacgaaatagacagatcgctgagataggtgcctcactgattaagcattggtaactgtcagaccaagtttactcatatactt
tagattgatttaaaacttcattttttaatttaaaaggatctaggtgaagatcctttttgataatctcatgaccaaaatcccttaacgtgag
ttttcgttccactgagcgtcagaccccgtagaaaagatcaaaggatcttcttgagatcctttttttctgcgcgtaatctgctgcttgcaaa
caaaaaaaccaccgctaccagcggtggtttgtttgccggatcaagagctaccaactctttttccgaaggtaactggcttcagcagagcgc
agataccaaatactgtccttctagtgtagccgtagttaggccaccacttcaagaactctgtagcaccgcctacatacctcgctctgctaa
tcctgttaccagtggctgctgccagtggcgcataagtcgtgtcttaccgggttggactcaagacgatagttaccggataaggcgcagcgg
tcgggctgaacggggggttcgtgcacacagcccagcttggagcgaacgacctacaccgaactgagatacctacagcgtgagctatgagaa
agcgccacgcttcccgaagggagaaaggcggacaggtatccggtaagcggcaggtcggaacaggagagcgcacgagggagcttccaggg
ggaaacgcctggtatctttatagtcctgtcgggtttcgccacctctgacttgagcgtcgatttttgtgatgctcgtcaggggggcggagc
ctatggaaaaacgccagcaacgcggcctttttacggttcctggccttttgctggccttttgctcacatgttctttcctgcgttatcccc
tgattctgtggataaccgtattaccgcctttgagtgagctgataccgctcgccgcagccgaacgaccgagcgcagcgagtcagtgagcgag
gaagcggaagagcgcccaatacgcaaaccgcctctccccgcgcgttggccgattcattaatgcagctggcacgacaggtttcccgactgg
aaagcgggcagtga
```

SEQ ID NO: 7 codon optimized exon 1
atgGTGCACCTGACCCCCGAGGAGAAGAGCGCCGTGACCGCCCTGTGGGACAAGGTGAACGTGGACGCCGTGGGCGGCGAGGCCCTGggc
ag SEQ ID NO: 8 codon optimized exon 2 (in vector with optimized codons 1, 2, and 3)
cctgaagttctcggggtccacgtgcagcttgtcgcagtgcagctcgctcagctgggcgaaggtgcccttcaggttgtccaggtgggccag
gccgtcgctgaaggcgcccagcaccttcttgccgtgggccttcaccttggggttgcccatcacggcgtcggggggtgctcaggtcgccgaa
gctctcgaagaagcgctgggtccaggggtacaccaccagcagc SEQ ID NO: 9 codon optimized exon 3
ctcCTGGGCAACGTGCTGGTGTGCGTGCTGGCCCACCACTTCGGCAAGGAGTTCACCCCCCCCGTGCAGGCCGCCTACCAGAAGGTGGTG
GCCGGCGTGGCCAACGCCCTGGCCCACAAGTACCACtaa SEQ ID NO: 10 vector comprising codon optimized exon 1
gcgcaacgcaattaatgtgagttagctcactcattaggcaccccaggctttacactttatgcttccggctcgtatgttgtgtggaattgt
gagcggataacaatttcacacaggaaacagctatgaccatgattacgccaagcgcgcaattaaccctcactaaagggaacaaaagctgga -continued

```
SEQUENCE LISTING gctgcaagcttggccattgcatacgttgtatccatatcataatatgtacatttatattggctcatgtccaacattaccgccatgttgaca
ttgattattgactagttattaatagtaatcaattacggggtcattagttcatagcccatatatggagttccgcgttacataacttacggt
aaatggcccgcctggctgaccgcccaacgacccccgcccattgacgtcaataatgacgtatgttcccatagtaacgccaataagggacttt
ccattgacgtcaatgggtggagtatttacggtaaactgcccacttggcagtacatcaagtgtatcatatgccaagtacgccccctattga
cgtcaatgacggtaaatggcccgcctggcattatgcccagtacatgacctttatgggactttcctacttggcagtacatctacgtattagt
catcgctattaccatggtgatgcggttttggcagtacatcaatgggcgtggatagcggtttgactcacggggatttccaagtctccaccc
cattgacgtcaatgggagtttgttttggcaccaaaatcaacgggactttccaaaatgtcgtaacaactccgccccattgacgcaaatggg
cggtaggcgtgtacggtgggaggtctatataagcagagctcgtttagtgaaccggggtctctctggttagaccagatctgagcctgggag
ctctctggctaactagggaacccactgcttaagcctcaataaagcttgccttgagtgcttcaagtagtgtgtgcccgtctgttgtgtgac
tctggtaactagagatccctcagacccttttagtcagtgtggaaaatctctagcagtggcgcccgaacagggacttgaaagcgaaaggga
aaccagaggagctctctcgacgcaggactcggcttgctgaagcgcgcacggcaagaggcgaggggcggcgactggtgagtacgccaaaaa
ttttgactagcggaggctagaaggagagagatgggtgcgagagcgtcagtattaagcggggagaattagatcgcgatgggaaaaaattc
ggttaaggccaggggggaaagaaaaaatataaattaaaacatatagtatgggcaagcagggagctagaacgattcgcagttaatcctggcc
tgttagaaacatcagaaggctgtagacaaatactgggacagctacaaccatcccttcagacaggatcagaagaacttagatcattatata
atacagtagcaaccctctattgtgtgtcatcaaaggatagagatgaaagacaccaaggaagctttagacaagatgaggaagagcaaaaca
aaagtaagaccaccgcacagcaagcggccgctgatcttcaagacctcggaggaggagaattggattatataaggtataataataaa
tataaagtagtaaaaattgaaccattaggagtagcacccaccaaggcaaagagaagagtggtgcagagagaaaaaagagcagtgggaata
ggagctttgttccttgggttcttgggagcagcaggaagcactatgggcgcagcgtcaatgacgctgacggtacaggccagacaattattg
tctggtatagtgcagcagcagaacaatttgctgagggctattgaggcgcaacagcatctgttgcaactcacagtctggggcatcaagcag
ctccaggcaagaatcctggctgtggaaagatacctaaaggatcaacagctcctggggatttggggttgctctggaaaactcatttgcacc
actgctgtgccttggaatgctagttggagtaataaatctctggaacagatttggaatcacacgacctggatggagtgggacagagaaatt
aacaattacacaagcttaatacactccttaattgaagaatcgcaaaaccagcaagaaaagaatgaacaagaattattggaattagataaa
tgggcaagtttgtggaattggtttaacataacaaattggctgtggtatataaaattattcataatgatagtaggaggcttggtaggttta
agaatagtttttgctgtactttctatagtgaatagagttaggcagggatattcaccattatcgtttcagacccacctcccaacccccgagg
ggacccgacgggcccgaaggaatagaagaagaaggtggagagacagagacagatccattcgattagtgaacggatctcgacggtatcg
atctcgacacaaatggcagtattcatccacaattttaaaagaaaaggggggattgggggtacagtgcaggggaaagaatagtagacata
atagcaacagacatacaaactaaagaattacaaaaacaaattacaaaaattcaaaattttcgggtttattacagggacagcagagatcca
gtttgggtcgaggatatcggatcggaattctctagatgatcaggatccctcgagccctttatcgatcacgaggactagcctcgactactagt
ggagatcccccgggctgcagagcagaagcaccataaggacatgataaggggagccagcagacctctgatctcttcctgaatgctaatct
taaacatcctgaggaagaatgggacttccatttggggtgggcctatgatagggtaataagacagtagtgaatatcaagctacaaaaagcc
cccctttcaaattcttctcagtcctaacttttcatactaagcccagtccttccaaagcagactgtgaaagagtgatagttccgggagacta
gcactgcagattccgggtcactgtgagtggggggaggcagggaagaagggctcacaggacagtcaaaccatgcccccctgttttttccttctt
caagtagacctctataagacaacagagacaactaaggctgagtggccaggcgaggcagagaaaccatctcgccgtaaaacatggaaggaacac
ttcaggggaaaggtggtatctctaagcaagagaactgagtggagtcaaggctgagagatgcaggataagcaaatgggtagtgaaaagaca
ttcatgaggacagctaaaacaataagtaatgtaaaatacagcatagcaaaactttaacctccaaatcaagcctctacttgaatcctttc
tgagggatgaataaggcataggcatcagggctgttgccaatgtgcattagctgtttgcagcctcacctttctttcatggagtttaagatat
agtgtattttcccaaggtttgaactagctcttcatttcttttatgtttataaatgcactgacctcccacattcccttttttagtaaaaatatt
cagaaataattttaaatacatcattgcaatgaaaataaatgtttttttattaggcagaatccagatgctcaaggcccttcataatatccccc
agtttagtagttggacttaggggaacaaaggaacctttaatagaaattggacagcaagaaagcgagcttagtgatacttgtgggccagggc
attagccacaccagccaccacttctgataggcagcctgcactggtggggtgaattcttgccaaagtgatgggccagcacacagaccag
cacgttgcccaggagctgtggggaggaagatgaacatgattagcaaaaggcctagcttggactcagaataatccagccttta
tcccaaccataaaataaaagcagaatggtagctggattgtagctgctattagcaatatgaaacctcttacatcagttacaatttatatgc
agaaatatttatatgcagaaatattgctattgccttaacccagaaattatcactgttattctttagaatggtgcaaagaggcatgataca
ttgtatcattattgccctgaaagaaagagattagggaaagtattagaaataagataaacaaaaaagtatattaaaagaagaaagcattttt
ttaaaattacaaatgcaaaattaccctgatttggtcaatatgtgtaccctgttacttctcccctttcctatgacatgaacttaaccataga
aaagaagggggaaagaaaacatcaagggtcccatagactcaccctgaagttctcaggatccacgtgcagcttgtcacagtgcagctcactc
agctgggcaaaggtgcccttgaggtggtgcaggtgagccaggccatcactaaaggcaccgagcacttcttgccatgagccttcaccttta
gggttgcccataacagcatcaggagtggacagatccccaaaggactcaaagaacctctgggtccaagggtagaccaccagcagcctaagg
gtgggaaaatgaacaatggcagagagtcagtgcctatcagaaaccaagagtcttctctgtctcccacatgcccagtttctcattggtct
ccttaaacctgtcttgtaaccttgataccaacctgcccagggcctcgccgcccacgggcgtccacgttcaccttgtcccacagggcggtca
cggcgctcttctcctcgggggtcaggtgcaccatggtgtctgtttgaggttgctagtgaacacagttgtgtcagaagcaaatgtaagcaa
tagatggctctgccctgacttttatgcccagccctggctcctgccctccctgctcctgggagtagattggccaacccttagggtgtggctc
cacagggtgaggtctaagtgatgacagccgtacctgtccttggcttctgttaggagttggacttcaaaccctcagccctc
cctctaagatatatctcttggccccataccatcagtacaaattgctactaaaacatcctccttgcaagtgtatttacccgacgcgtcg
gcgataagcttgatccatcgattacgtatatgtgtatatatatatattcaggaaataatatattctagaatatgtcacattctgtctc
aggcatccattttctttatgatgccgtttgaggtggagttttagtcaggtggtcagcttctcctttttttttgccatctgccctgtaagca
tcctgctggggacccagataggagtcatcactctaggctgagaacatctgggcacacaccctaagcctcagcatgactcatcatgactca
gcattgctgtgcttgagccagaaggtttgcttagaaggttacagaaccagaaggcgggggtgggcactgacccccgacaggggcctggcc
agaactgctcatgcttggactatgggaggtcactaatggagacacagaaatgtaacaggaactaaggaaaaactgaagctttgggggtat
aggggagcagtcccatgtagtagtagaatgaaaaatgctgctatgctgtgcctccccccacctttcccatgtctgccctctactcatggtc
tatctctcctggctcctgggagtcatggactccaccagcaccaccaacctgacctaaccacctatctgagcctgccagcctataaccca
tctgggccctgatagctggtggccaacgcctgacccccacccccacctcccctgaactctgatagacacatctggcacaccagctcgcaaa
gtcaccgtgagggtcttgtgtttgctgagtcaaaattcctttgaaatccaagtccttagagactcccaggcttggattcaaagctcctgac
tttctgtctagtgatgtgcagtgagcccctttcctctaactgaaagaaggaaaaaaaatggaacccaaaatattctacatagtttcca
tgtcacagccagggctgggcagtctcctgttatttcttttaaaataaatatatcatttaaatgcataaataagcaaaccctgctcggaa
tgggagggagagtctctggagtccacccctctcggccctggctctgcagatagtgctatcaaagccctgacagagccctgcccattgct
gggccttggagtgagtcagcctagtagaggcagggcaagccatctcatagctgctgagtgggagagaagaaaggcgttgttctataaa
ctcaggtcatggctattcttatggcctactcgaccacgagggaattccgataatcaacctctggattacaaaatttgtgaaagattgact
ggtattcttaactatgttgctccttttacgctatgtggatacgctgctttaatgcctttgtatcatgctattgcttcccgtatggctttc
attttctcctccttgtataaatcctggttgctgtctctttatgaggagttgtggcccgttgtcaggcaacgtggcgtggtgtgcactgtg
tttgctgacgcaaccccccactggttggggcattgccaccacctgtcagctcctttccgggactttcgctttccccctccctattgccacg
gcggaactcatcgccgcctgccttgcccgctgctggacaggggctcggctgttgggcactgacaattccgtggtgttgtcggggaaatca
tcgtcctttccttggctgctcgcctgtgttgccacctggattctgcgcgggacgtccttctgctacgtccctcggccctcaatccagcg
gaccttccttcccgcggcctgctgccggctctgcggcctcttccgcgtcttcgcttcgccctcagacgagtcggatctccctttgggcc
gcctccccgcatcgataccgtcgacctcgagacctagaaaaacatggccaattcgagctcggtacctttaagaccaatgacttacaaggc
agctgtagatcttagccactttttaaaagaaaaggggggactggaagggctaattcactcccaacgaagacaagatcccagggatgtacg
tccctaacccgctaggggggcagcacccaggcctgcactgccgcctgccggcagggtccagtcctgcttttttgcttgtactgggtctctc
``` tggttagaccagatctgagcctgggagctctctggctaactagggaacccactgcttaagcctcaataaagcttgccttgagtgcttcaa
gtagtgtgtgcccgtctgttgtgtgactctggtaactagagatccctcagaccctttagtcagtgtggaaaatctctagcagtagtagt
tcatgtcatcttattattataacttgcaaagaaatgaatatcagagagtgagaggaacttgtttattgcagcttataatggt
tacaaataaagcaatagcatcacaaatttcacaaataaagcatttttttcactgcattctagttgtggttgtccaaactcatcaatgtat
cttatcatgtctggctctagctatcccgccctaactccgcccatcccgcccctaactccgcccagttccgcccattctccgcccatgg
ctgactaattttttttatttatgcagaggccgaggccgcctcggcctctgagctattccagaagtagtgaggaggctttttggaggcct
aggcttttgcgtcgagacgtacccaattcgccctatagtgagtcgtattacgcgcgctcactggccgtcgttttacaacgtcgtgactgg
gaaaaccctggcgttacccaacttaatcgccttgcagcacatccccctttcgccagctggcgtaatagcgaagaggcccgcaccgatcgc
ccttcccaacagttgcgcagcctgaatggcgaatggcgcgacgcgccctgtagcggcgcattaagcgcggcgggtgtggtggttacgcgc
agcgtgaccgctacacttgccagcgccctagcgcccgctcctttcgctttcttcccttccttctcgccacgttcgccggctttccccgt
caagctctaaatcggggggctcccctttagggttccgatttagtgcttacggcacctcgacccccaaaaaactttgattagggtgatggttca
cgtagtgggccatcgccctgatagacggttttttcgcccttttgacgttggagtccacgttctttaatagtggactcttgttccaaactgga
acaacactcaaccctatctcggtctattcttttgatttataaggggattttgccgatttcggcctattggttaaaaaatgagctgatttaa
caaaaatttaacgcgaatttttaacaaaatattaacgtttacaatttcccaggtggcacttttcggggaaatgtgcgcggaacccctattt
gtttattttttctaaatacattcaaatatgtatccgctcatgagacaataaccctgatataaatgcttcaataatattgaaaaaggaagagta
tgagtattcaacatttccgtgtcgcccttattcccttttttgcggcattttgccttcctgtttttgctcacccagaaacgctggtgaaag
taaaagatgctgaagatcagttgggtgcacgagtgggttacatcgaactggatctcaacagcggtaagatccttgagagttttcgccccg
aagaacgttttccaatgatgagcacttttaaagttctgctatgtggcgcggtattatcccgtattgacgccgggcaagagcaactcggtc
gccgcatacactattctcagaatgacttggttgagtactcaccagtcacagaaaagcatcttacggatggcatgacagtaagagaattat
gcagtgctgccataaccatgagtgataaacctgcggccaacttacttctgacaacgatcggaggaccgaaggagctaaccgcttttttgc
acaacatgggggatcatgtaactcgccttgatcgttgggaaccggagctgaatgaagccataccaaacgacgagcgtgacaccacgatgc
ctgtagcaatggcaacaacgttgcgcaaactattaactggcgaactacttactctagcttcccggcaacaattaatagactggatggagg
cggataaagttgcaggaccacttctgcgctcggcccttccggctggctggtttattgctgataaatctggagccggtgagcgtgggtctc
gcggtatcattgcagcactggggccagatggtaagccctcccgtatcgtagttatctacacgacggggagtcaggcaactatggatgaac
gaaatagacagatcgctgagataggtgcctcactgattaagcattggtaactgtcagaccaagtttactcatatatctttagtattgatt
taaaacttcattttttaatttaaaaggatctaggtgaagatcctttttgataatctcatgaccaaaatcccttaacgtgagttttcgttcc
actgagcgtcagaccccgtagaaaagatcaaaggatcttcttgagatcctttttttctgcgcgtaatctgctgcttgcaaacaaaaaaac
caccgctaccagcggtggtttgtttgccggatcaagagctaccaactctttttccgaaggtaactggcttcagcagagcgcagataccaa
atactgtccttctagtgtagccgtagttaggccaccacttcaagaactctgtagcaccgcctacatacctcgctctgctaatcctgttac
cagtggctgctgccagtggcgataagtcgtgtcttaccgggttggactcaagacgatagttaccggataaggcgcagcggtcgggctgaa
cggggggttcgtgcacacagcccagcttggagcgaacgacctacaccgaactgagatacctacagcgtgagctatgagaaagcgccacgc
ttcccgaagggagaaaggcggacaggtatccggtaagcggcagggtcggaacaggagagcgcacgagggagcttccaggggaaacgcct
ggtatctttatagtcctgtcgggtttcgccacctctgacttgagcgtcgatttttgtgatgctcgtcaggggggcggagcctatggaaaa
acgccagcaacgcggcctttttacggttcctggccttttgctggccttttgctcacatgttctttcctgcgttatccctgattctgtg
gataaccgtattaccgcctttgagtgagctgataccgctcgccgcagccgaacgaccgagcgcagcgagtcagtgagcgaggaagcggaa
gagcgcccaatacgcaaaccgcctctccccgcgcgttggccgattcattaatgcagctggcacgacaggtttcccgactggaaagcgggc
agtga SEQ ID NO: 11 codon optimized exon 1 and 2
gcgcaacgcaattaatgtgagttagctcactcattaggcaccccaggctttacactttatgcttccggctcgtatgttgtgtggaattgt
gagcggataacaatttcacacaggaaacagctatgaccatgattacgccaagcgcgcaattaaccctcactaaagggaacaaaagctgga
gctgcaagcttggccattgcatacgttgtatccatatcataatatgtacatttatattggctcatgtccaacattaccgccatgttgaca
ttgattattgactagttattaatagtaatcaattacggggtcattagttcatagcccatatatggagttccgcgttacataacttacggt
aaatggtccgcctggctgaccgcccaacgacccccgcccattgacgtcaataatgacgtatgttcccatagtaacgccaataggggactttt
ccattgacgtcaatgggtggagtatttacggtaaactgcccacttggcagtacatcaagtgtatcatatgccaagtacgccccctattga
cgtcaatgacggtaaatggcccgcctggcattatgcccagtacatgaccttatgggactttcctacttggcagtacatctacgtattagt
catcgctattaccatggtgatgcggttttggcagtacatcaatgggcgtggatagcggtttgactcacggggatttccaagtctccaccc
cattgacgtcaatgggagtttgttttggcaccaaaatcaacgggactttccaaaatgtcgtaacaactccgccccattgacgcaaatggg
cggtaggcgtgtacggtgggaggtctatataagcagagctcgtttagtgaaccgtgggctcttggaccagatctgagcctgggagct
ctctggctaactagggaacccactgcttaagcctcaataaagcttgccttgagtgcttcaagtagtgtgtgcccgtctgttgtgtgactc
tggtaactagagatccctcagacccttttagtcagtgtggaaaatctctagcagtggcgcccgaacagggacttgaaagcgaaagggaaa
ccagaggagctctctcgacgcaggactcggcttgctgaagcgcgcacggcaagaggcgaggggcggcgactggtgagtacgccaaaaatt
ttgactagcggaggctagaaggagagagatgggtgcgagagcgtcagtattaagcgggggagaattagatcgcgatggaaaaaattcggt
taaggccagggggaaagaaaaaatataaattaaaacatatagtatgggcaagcagggagctagaacgattcgcagttaatcctggcctgt
tagaaacatcagaaggctgtagacaaatactgggacagctacaaccatcccttcagacaggatcagaagaacttagatcattatataata
cagtagcaacctctattgtgtgcatcaaaggatagagataaaagacaccaaggaagctttagacaagatagaggaagagcaaaacaaaa
gtaagaccaccgcacagcaagcggccgctgatcttcagacctggaggaggagatagatgagggacaattggagaagtgaattatataatat
aaagtagtaaaattgaaccattaggagtagcacccaccaaggcaaagagaagagtggtgcagagagaaaaaagagcagtgggaatagga
gctttgttccttgggttcttgggagcagcaggaagcactatgggcgcagcgtcaatgacgctgacggtacaggccagacaattattgtct
ggtatagtgcagcagcagaacaatttgctgagggctattgaggcgcaacagcatctgttgcaactcacagtctggggcatcaagcagctc
caggcaagaatcctggctgtggaaagatacctaaaggatcaacagctcctggggatttggggttgctctggaaaactcatttgcaccact
gctgtgccttggaatgctagttggagtaataaatctctggaacagatttggaatcacacgacctggatggagtgggacagagaaattaac
aattacacaagcttaatacactccttaattgaagaatcgcaaaaccagcaagaaaagaatgaacaagaattattggaattagtataaatg
ggcaagtttgtggaattggtttaacataacaaattggctgtggtatataaaattattcataatgatagtaggaggcttggtaggtttaag
aatagtttttgctgtactttctatagtgaatagagttaggcagggatattcaccattatcgtttcagacccacctcccaaccccgagggg
acccgacgggcccgaaggaatagaagaagaaggtggagagagagacagagacagatccattcgattagtgaacggatctcgacggtatcg
atctcgacacaaatggcagtattcatccacaattttaaaagaaaaggggggattggggggtacagtgcaggggaaagaatagtagacata
atagcaacagacatacaaactaaagaattacaaaaacaaattacaaaattcaaaattttcgggtttattacagggacagcagagatcca
gtttgggtcgaggatatcggatcggaattctctagatgatcaggatccctcgagcccttatcgatcacgagactagcctcgactactagt
ggagatcccccgggctgcagagccagaagcaccataagggacatgataagggagccagcagacctctgatctcttcctgaatgctaatct
taaacatcctgaggaagaatgggacttccatttggggtgggcctatgatagggtaataagacagtagtgaatatcaagctacaaaaagcc
cccttttcaaattcttctcagtcctaacttttcatactaagcccagtccttccaaagcagactgtgaaagagtgatagttccgggagacta
gcactgcagattccgggtcactgtgagtggggaggcagggaagaagggctcacaggacagtcaaaccatgcccctgttttttccttctt
caagtagacctctataagcaacagagacaactaaggctgagtggccaggcgaggagaaaccatctcgccgtaaaacatggaaggaacac
ttcaggggaaaggtggtatctctaagcaagagaactgagtggagtcaaggctgagagatgcaggataagcaaatgggtagtgaaaagaca
ttcatgaggacagctaaaacaataagtaatgtaaaatacagcatagcaaaactttaacctccaaatcaagcctctacttgaatccttttc
tgagggatgaataaggcataggcatcagggggctgttgccaatgtgcattagctgtttgcagcctcaccttcttttcatggagtttaagata

SEQUENCE LISTING

```
tagtgtattttcccaaggtttgaactagctcttcatttctttatgttttaaatgcactgacctcccacattccctttttagtaaaatatt
cagaaataatttaaatacatcattgcaatgaaaataaatgttttttattaggcagaatccagatgctcaaggcccttcataatatccccc
agtttagtagttggacttagggaacaaaggaacctttaatagaaattggacagcaaggaaagcgagcttagtgatacttgtgggccagggc
attagccacaccagccaccactttctgataggcagcctgcactgtggggtgaattctttgccaaagtgatgggccagcacacagaccagc
acgttgcccaggagctgtgggaggaagataagaggtatgaacatgattagcaaaagggcctagcttggactcagaataatccagccttat
cccaaccataaaataaaagcagaatggtagctggattgtagctgctattagcaatatgaaacctcttacatcagttacaatttatatgca
gaaatatttatatgcagaaatattgctattgccttaacccagaaattatcactgttattctttagaatggtgcaaagaggcatgatacat
tgtatcattattgccctgaaagaaagagattagggaaagtattagaaataagataaacaaaaaagtatattaaaagaagaaagcattttt
taaaattacaaatgcaaaattaccctgatttggtcaatatgtgtaccctgttacttctccccttcctatgacatgaacttaaccatagaa
aagaaggggaaagaaaacatcaagggtcccatagactcaccctgaagttctcaggatccacgtgcagcttgtcgcagtgcagctcgctca
gctgggcgaaggtgcccttcaggttgtccaggtgggccaggccgtcgctgaaggcgcccagcaccttcttgccgtgggccttcaccttgg
ggttgcccatcacggcgtcgggggtgctcaggtcgccgaagctctcgaagaagcgctgggtccagggggtacaccaccagcagcctaaggg
tgggaaaatagaccaataggcagagagagtcagtgcctatcagaaacccaagagtcttctctgtctccacatgcccagtttctattggtc
tccttaaacctgtcttgtaaccttgataccaacctgcccagggcctcgccgcccacggcgtccacgttcaccttgtcccacagggcggtc
acggcgctcttctcctcggggggtcaggtgcaccatggtgtctgtttgaggttgctagtgaacacagttgtgtcagaagcaaatgtaagca
atagatggctctgccctgacttttatgcccagccctggctcctgccctccctgctcctgggagtagattggccaaccctagggtgtggct
ccacagggtgaggtctaagtgatgacagccgtacctgtccttggctcttctggcactggcttaggagttggacttcaaaccctcagccct
ccctctaagatatatctcttggccccataccatcagtacaaattgctactaaaaacatcctcctttgcaagtgtatttacccgacgcgtc
ggcgataagcttgatccatcgattacgtatatgtgtatatatatatattcaggaaataatatattctagaatatgtcacattctgtct
caggcatccattttctttatgatgccgtttgaggtggagtttttagtcaggtggtcagcttctcctttttttttgccatctgccctgtaagc
atcctgctggggacccagataggagtcatcactctaggctgagaacatctgggcacacaccctaagcctcagcatgactcatcatgactc
agcattgctgtgcttgagccagaaggtttgcttagaaggttacacagaaccagaaggcggggggtggggcactgaccccgacaggggcctg
gccagaactgctcatgcttggactatgggaggtcactaatggagacacacagaaatgtaacaggaactaaggaaaaactgaagctttggg
ggtataggggagcagtcccatgtagtagtagaatgaaaaatgctgctatgctgtgcctcccccacctttcccatgtctgccctctactca
tggtctatctctcctggctcctgggagtcatggactccacccagcaccaccaacctgacctaaccacctatctgagcctgccagcctata
acccatctgggccctgatagctggtggccagccctgaccccaccccaccctccctggaacctctgatagacacatctggcacaccagctc
gcaaagtcaccgtgagggtcttgtgtttgctgagtcaaaattccttgaaatccaagtccttagagactcccaggcttggattcaaagctc
ctgactttctgtctagtgtatgtgcagtgagccccttttcctctaactgaaagaaggaaaaaaaaatggaacccaaaatattctacatag
tttccatgtcacagccagggctgggcagtctcctgttatttcttttaaaataaatatatcatttaaatgcataaataagcaaaccctgct
cgggaatgggagggagagtctctggagtccacccccttctcggccctggctctgcagatagtgctatcaaagccctgacagagccctgccc
attgctgggccttggagftgagtcagcctagtagagaggcagggcaagccatctcatagctgctgagtgggagagagaaaagggctcatt
gtctataaactcaggtcatggctattcttatggcctactcgaccacgagggaattccgataatcaacctctggattacaaaatttgtgaa
agattgactggtgattcttaactatgttgctccttttacgctatgtggatacgctgcttttaatgccttttgtatcatgctattgcttcccgt
atggctttcattttctcctccttgtataaatcctggttgctgtctctttatgaggagttgtggcccgttgtcaggcaacgtggcgtggtg
tgcactgtgtttgctgacgcaaccccccactggttggggcattgccaccacctgtcagctcctttccgggactttcgctttccccctccct
attgccacggcggaactcatcgccgcctgccttgcccgctgctggacaggggctcggctgttgggcactgacaattccgtggtgttgtcg
gggaaatcatcgtcctttccttggctgctcgcctgtgttgccacctggattctgcgcgggacgtccttctgctacgtcccttcggccctc
aatccagcggaccttccttcccgcgtcgctgccggctctgccggcctcttccgcgtcttcgccttcgccctcagacgagtcggatctcc
ctttgggccgctccccgcatcgataccgtcgacctcgagacctagaaaaacatggccattcgagctcggtacctttaagaccaatgact
tacaaggcagctgtagatcttagccacttttttaaaagaaaaggggggactggaagggctaattcactcccaacgaagacaagatcccagg
gatgtacgtccctaacccgctaggggggcagcacccaggcctgcactgccgcctgccggcaggggtccagtcctgcttttttgcttgtactg
ggtctctctggttagaccagatctgagcctgggagctctctggctaactagggaaccccactgcttaagcctcaataaagcttgccttgag
tgcttcaagtagtgtgtgcccgtctgttgtgtgactctggtaactagagatccctcagacccctttttagtcagtgtggaaaatctctagca
gtagtagttcatgtcatcttattattcagtatttataacttgcaaagaaatgaatatcagagagtgagaggaacttgtttattgcagctt
ataatggttacaaataaagcaatagcatcacaaatttcacaaataaagcattttttttcactgcattctagttgtggtttgtccaaactca
tcaatgtatcttatcatgtctggctctagctatcccgcccctaactccgcccatcccgcccctaactccgcccagttccgcccattctcc
gccccatggctgactaatttttttttatttatgcagaggccgaggccgcctcggcctctgagctattccagaagtagtgaggaggcttttt
tggaggcctaggcttttgcgtcgagacgtacccaattcgccctatagtgagtcgtattacgcgcgctcactggccgtcttcttttacaacgt
cgtgactgggaaaaccctggcgttacccaacttaatcgccttgcagcacatccccctttcgccagctggcgtaatagcgaagaggcccgc
accgatcgcccttcccaacagttgcgcagcctgaatggcgaatggcgcgacgcgccctgtagcggcgcattaagcgcggcgggtgtggtg
gttacgcgcagcgtgaccgctacacttgccagcgccctagcgcccgctcctttcgctttcttcccttcctttctcgccacgttcgccggc
tttccccgtcaagctctaaatcgggggctcccttagggttccgatttagtgctttacggcacctcgaccccaaaaaacttgattagggt
gatggttcacgtagtgggccatcgccctgatagacggtttttcgccctttgacgttggagtccacgttctttaatagtggactcttgttc
caaactggaacaacactcaaccctatctcggtctattcttttgatttataaggggattttgccgatttcggcctattggttaaaaaatgag
ctgatttaacaaaaatttaacgcgattttaacaaaatattaacgtttacaatttcccaggtggcacttttcggggaaatgtgcgcggaac
ccctatttgtttatttttctaaatacattcaaatatgtatccgctcatgagacaataaccctgataaatgcttaataatattgaaaaagg
aagagtatgagtattcaacatttccgtgtcgcccttattcccttttttgcggcatttttgccttcctgtttttgctcacccagaaacgctg
gtgaaagtaaaagatgctgaagatcagttgggtgcacgagtgggttacatcgaactggatctcaacagcggtaagatccttgagagttttt
cgccccgaagaacgttttccaatgatgagcacttttaaagttctgctatgtggcgcggtattatcccgtattgacgccgggcaagagcaa
ctcggtcgccgcatacactattctcagaatgacttggttgagtactcaccagtcacagaaaagcatcttacggatggcatgacagtaaga
gaattatgcagtgctgccataaccatgagtgataacactgcggccaacttacttctgacaacgatcggaggaccgaaggagctaaccgct
tttttgcacaacatgggggatcatgtaactcgccttgatcgttgggaaccggagctgaatgaagccataccaaacgacgagcgtgacacc
acgatgcctgtagcaatggcaacaacgttgcgcaaactattaactggcgaactacttactctagcttcccggcaacaattaatagactgg
atggaggcggataaagttgcaggaccacttctgcgctcggcccttccggctggctggtttattgctgataaatctggagccggtgagcgt
gggtctcgcggtatcattgcagcactggggccagatggtaagccctcccgtatcgtagttatctacacgacggggagtcaggcaactatg
gatgaacgaaatagacagatcgctgagataggtgcctcactgattaagcattggtaactgtcagaccaagtttactcatatactttagat
tgatttaaaacttcatttttaatttaaaaggatctaggtgaagatcctttttgataatctcatgaccaaaatcccttaacgtgagttttc
gttccactgagcgtcagaccccgtagaaaagatcaaaggatcttcttgagatcctttttttctgcgcgtaatctgctgcttgcaaacaaa
aaaaccaccgctaccagcggtggtttgtttgccggatcaagagctaccaactctttttccgaaggtaactggcttcagcagagcgcagat
accaaatactgtccttctagtgtagccgtagttaggccaccacttcaagaactctgtagcaccgcctacatacctcgctctgctaatcct
gttaccagtggctgctgccagtggcgataagtcgtgtcttaccgggttggactcaagacgatagttaccggataaggcgcagcggtcggg
ctgaacggggggttcgtgcacacagcccagcttggagcgaacgacctacaccgaactgagatacctacagcgtgagctatgagaaagcgc
cacgcttcccgaagggagaaaggcggacaggtatccggtaagcggcagggtcggaacaggagagcgcacgagggagcttccaggggggaaa
cgcctggtatctttatagtcctgtcgggtttcgccacctctgacttgagcgtcgatttttgtgatgctcgtcagggggggcggagcctatg
```

-continued

SEQUENCE LISTING

```
gaaaaacgccagcaacgcggccattttttacggttcctggcctttttgctggcctttttgctcacatgttctttcctgcgttatcccctgatt
ctgtggataaccgtattaccgcctttgagtgagctgataccgctcgccgcagccgaacgaccgagcgcagcgagtcagtgagcgaggaag
cggaagagcgcccaatacgcaaaccgcctctccccgcgcgttggccgattcattaatgcagctggcacgacaggtttcccgactggaaag
cgggcagtga
```

SEQ ID NO: 12 codon optimized exon 1, 2 and 3
```
gcgcaacgcaattaatgtgagttagctcactcattaggcaccccaggctttacactttatgcttccggctcgtatgttgtgtggaattgt
gagcggataacaatttcacacaggaaacagctatgaccatgattacgccaagcgcgcaattaaccctcactaaagggaacaaaagctgga
gctgcaagcttggccattgcatacgttgtatccatatcataatatgtacatttatattggctcatgtccaacattaccgccatgttgaca
ttgattattgactagttattaatagtaatcaattacggggtcattagttcatagcccatatatggagttccgcgttacataacttacggt
aaatggcccgcctggctgaccgcccaacgacccccgcccattgacgtcaataatgacgtatgttcccatagtaacgccaatagggactt
ccattgacgtcaatgggtggagtatttacggtaaactgcccacttggcagtacatcaagtgtatcatatgccaagtacgccccctattga
cgtcaatgacggtaaatggcccgcctggcattatgcccagtacatgaccttatgggactttcctacttggcagtacatctacgtattagt
catcgctattaccatggtgatgcggttttggcagtacatcaatgggcgtggatagcggtttgactcacggggatttccaagtctccaccc
cattgacgtcaatgggagtttgttttggcaccaaaatcaacgggactttccaaaatgtcgtaacaactccgccccattgacgcaaatggg
cggtaggcgtgtacggtgggaggtctatataagcagagctcgtttagtgaaccgtcctctctggctagaccagatctgagcctgggag
ctctctggctaactagggaacccactgcttaagcctcaataaagcttgccttgagtgcttcaagtagtgtgtgcccgtctgttgtgtgac
tctggtaactagagatccctcagacccttttagtcagtgtggaaaatctctagcagtggcgcccgaacagggacttgaaagcgaaaggga
aaccagaggagctctctcgacgcaggactcggcttgctgaagcgcgcacggcaagaggcgaggggcggcgactggtgagtacgccaaaaa
ttttgactagcggaggctagaaggagagagatgggtgcgagacgtcggtggctaacaaggccaggagagaagcaattggagaagtgaattatataaa
tataaagtagtaaaaattgaaccattaggagtagcacccaccaaggcaaagaagaagtggtgcagagagaaaaagagcagtgggaata
ggagctttgttcctgggttcttgggagcagcaggaagcactatgggcgcagcgtcaatgacgctgacggtacaggccagacaattattg
tctggtatagtgcagcagcagaacaatttgctgagggctattgaggcgcaacagcatctgttgcaactcacagtctggggcatcaagcag
ctccaggcaagaatcctggctgtggaaagatacctaaaggatcaacagctcctggggatttggggttgctctggaaaactcatttgcacc
actgctgtgccttggaatgctagttggagtaataaatctctggaacagatttggaatcacacgacctggatggagtgggacagagaaatt
aacaattacacaagcttaatacactccttaattgaagaatcgcaaaaccagcaagaaaagaatgaacaagaattattggaattagataaa
tgggcaagtttgtggaattggtttaacataacaaattggctgtggtatataaaattattcataatgatagtaggaggcttggtaggttta
agaatagtttttgctgtgacttttctatagtgaatagagttaggcagggatattcaccattatcgtttcagacccacctcccaacccccgagg
ggacccgacaggcccgaaggaatagaagaagaaggtggagagagagacagagacaggtccattcgattagtgaacggatctcgacggtat
cgatctcgacacaaatggcagtattcatccacaatttttaaaagaaaaggggggattggggggtacagtgcaggggaaagaatagtagaca
taatagcaacagacatacaaactaaagaattacaaaaacaaattacaaaaattcaaaatttcggggtttattacagggacagcagagatc
cagtttgggtcgaggatatcggatcggaattctctagatgatcaggatccctcgagccctatcgatcacgagactagcctcgactacta
gtggagatcccccgggctgcagagccagaagcaccataagggacatgataaggggaggaagctggaggaagagaagagatgcaggataagcaaatgggtagtgaaaaga
cttcaggggaaaggtggtatctctaagcaagagaactgagtggagtcaaggctgagagatgcaggataagcaaatgggtagtgaaaaga
cattcatgaggacagctaaaacaataagtaatgtaaaatacagcatagcaaaactttaacctccaaatcaagcctctacttgaatccttt
tctgagggatgaataaggcataggcatcagggctgttgccaatgtgcattagctgtttgcagcctcaccttctttcatggagtttaaga
tatagtgtattttcccaaggtttgaactagctcttcatttcttttatgtttaaatgcactgacctttcctccacattccctttttagtaaaata
ttcagaaataatttaaatacatcattgcaatgaaaataaaatgttttttattaggcagaatccagatgctcaaggcccttcataatatccc
ccagtttagtagttggacttagggaacaaaggaacctttaatagaaattggacagcaagaaagcgagcttagtggtacttgtgggccagg
gcgttggccacgccggccaccaccttctggtaggcggcctgcacgggggggggtgaactccttgccgaagtggtgggccagcacgcacacc
agcacgttgcccaggagctgtgggaggaagataagaggtatgaacatgattagcaaaaggtgctactaaaaacatcctccttttgcaagtggactcagaataatccagcct
tatcccaaccataaaataaaagcagaatggtagctggattgtagctgctattagcaatatgaaacctcttacatcagttacaatttatat
gcagaaatatttatatgcagaaatattgctattgccttaacccagaaattatcactgttattctttagaatggtgcaaagaggcatgata
cattgtatcattattgccctgaaagaaagagattagggaaagtattagaaataagataaacaaaaaagtatattaaaagaagaaagcatt
ttttaaaattacaaatgcaaatgacctgattggtcaatatgtgtcaacatatggtacctgttacttctcccttcctatgacatgaacttaaccata
gaaaagaaggggaaagaaaacatcaagggtcccatagactcaccctgaagttctcggggtccacgtgcagcttgtcgcagtgcagctcgc
tcagctgggcgaaggtgcccttcaggttgtccaggtgggccaggccgtcgctgaaggcgcccagcacctcttgccgtgggccttcacct
tggggttgcccatcacggccgtgcgggggtgctcaggtcgccgaagctctcgaagaagcgctgggtccaggggtacaccaccagcagccta
agggtgggaaaatagaccaataggcagagaggtcagtgcctatcagaaacccaagagtctctctgtctccacatgcccagtttctatt
ggtctccttaaacctgtcttgtaacctttgataccaacctgcccagggcctcgccgcccacggcgtccacgttcacctttgtcccacaggc
ggtcacggcgctcttctcctcgggggtcaggtgcaccatggtgtctgtttgaggttgctagtgaacacagttgtgtcagaagcaaatgta
agcaatagatggctctgccctgactttttatgcccagccctggctcctgcctccctgctcctgggagtagattggcaacccctagggtgt
ggctccacagggtgaggtctaagtgatgacagccgtacctgtccttggctcttctggcactggcttaggagttggacttcaaaccctcag
ccctccctctaagatatatctcttgccccatacatcagtacaaactgctactaaaaacatcctcctttgcaagtgtatttacccgacg
cgtcggcgataagcttgatccatcgattacgtatatgtgtatatatatatatattcaggaaataatatattctagaatatgtcacattct
gtctcaggcatccattttcttttatgatgccgttggaggtggagtttttagtcaggtggtcagcttctcctttttttttgccatctgccctgt
aagcatcctgctggggaccccagataggagtcatcactctaggctgagaacatctgggcacacaccctaagcctcagcatgactcatcatg
actcagcattgctgtgcttgagccagaaggtttgcttagaaggttacacagaaccagaaggcggggggtggggcactgaccccgacaggg
cctggccagaactgctcatgcttggacctatgggaggtcactaatgggaggtcactaaaggttaacaggaactaaggaaaaactgaagctt
tgggggtataggggagcagtcccatgtagtagtagaatgaaaaatgctgctatgctgtgcctccccacctttcccatgtctgccctcta
ctcatggtctatctctcctggctcctgggagtcatggactccacccagcaccaccaacctgacctaaccacctatctgagcctgccagcc
tataacccatctgggccctgatagctggtggccagccctgaccccacccacctcctggaacctctgatagacacatctggcacacca
gctcgcaaagtcaccgtgagggtcttgtgtttgctgagtcaaattccttgaaatccaagtccttagagactcccaggcttggattcaaag
ctcctgacttctgtctagtgtgtcaggtgtgggcagtctcctgttatttctttttaaaataaaatatatcatttaaatgcataaataagcaaaccct
gctcgggaatgggagggagagtctctggagtccacccttctcggccctggctctgcagatagtgctatcaaagccctgacagagccctg
cccattgctgggccttggagtgagtcagcctagtagagaggcagggcaagccatctcatagctgctgagtgggagagagaaagggctcat
tgtctataaaactcaggtcatggctattcttatggcctactcgaccacgagggaattccgataatcaacctctggattacaaaatttgtga
aagattgactggtattcttaactatgttgctccttttacgctatgtggatacgctgctttaatgcctttgatcatgctattgcttcccgt
```

SEQUENCE LISTING

```
atggctttcattttctcctccttgtataaatcctggttgctgtctctttatgaggagttgtggcccgttgtcaggcaacgtggcgtggtg
tgcactgtgtttgctgacgcaaccccccactggttggggcattgccaccacctgtcagctcctttccgggactttcgctttcccctccct
attgccacggcggaactcatcgccgcctgccttgcccgctgctggacaggggctcggctgttgggcactgacaattccgtggtgttgtcg
gggaaatcatcgtcctttccttggctgctcgcctgtgttgccacctggattctgcgcgggacgtccttctgctacgtcccttcggccctc
aatccagcggaccttccttcccgcggcctgctgccggctctgcggcctcttccgcgtcttcgccttcgccctcagacgagtcggatctcc
ctttgggccgcctccccgcatcgataccgtcgacctcgagacctagaaaaacatggccaattcgagctcggtacctttaagaccaatgac
ttacaaggcagctgtagatcttagccacttttttaaaagaaaaggggggactggaagggctaattcactcccaacgaagacaagatcccag
ggatgtacgtccctaacccgctaggggggcagcacccaggcctgcactgcctgctccggcaggggtccagtcctgcttttttgcttgtact
gggtctctctggttagaccagatctgagcctgggagctctctggctaactagggggaacccactgcttaagcctcaataaagcttgccttga
gtgcttcaagtagtgtgtgcccgtctgttgtgtgactctggtaactagagatccctcagacccttttagtcagtgtggaaaatctctagc
agtagtagttcatgtcatcttattattcagtatttataacttgcaaagaaatgaatatcagagagtgagaggaacttgtttattgcagct
tataatggttacaaataaagcaatagcatcacaaatttcacaaataaagcatttttttcactgcattctagttgtggtttgtccaaactc
atcaatgtatcttatcatgtctggctctagctatcccgcccctaactccgcccatcccgcccctaactccgcccagttccgcccattctc
cgccccatggctgactaatttttttttattatgcagaggccgaggccgcctcggcctctgagctattccagaagtagtgaggaggctttt
ttggaggcctaggcttttgcgtcgagacgtacccaattcgccctatagtgagtcgtattacgcgcgctcactggccgtcgttttacaacg
tcgtgactgggaaaaccctggcgttacccaacttaatcgccttgcagcacatccccctttcgccagctggcgtaatagcgaagaggcccg
caccgatcgcccttcccaacagttgcgcagcctgaatggcgaatggcgcgacgcgccctgtagcggcgcattaagcgcggcgggtgtggt
ggttacgcgcagcgtgaccgctacacttgccagcgccctagcgcccgctcctttcgctttcttcccttcctttctcgccacgttcgccgg
ctttccccgtcaagctctaaatcgggggctccctttagggttccgatttagtgctttacggcacctcgaccccaaaaaacttgattaggg
tgatggttcacgtagtgggccatcgccctgatagacggtttttcgcccttttgacgttggagtccacgttctttaatagtggactcttgtt
ccaaactggaacaacactcaacccctatctcggtctattcttttgatttataagggattttgccgatttcggcctattggttaaaaaatga
gctgatttaacaaaaatttaacgcgaattttaacaaaatattaacgtttacaatttcccaggtggcacttttcggggaaatgtgcgcgga
acccctatttgtttatttttctaaatacattcaaatatgtatccgctcatgagacaataaccctgataaatgcttcaataatattgaaaa
aggaagagtatgagtattcaacatttccgtgtcgcccttattcccttttttgcggcattttgccttcctgtttttgctcacccagaaacg
ctggtgaaagtaaaagatgctgaagatcagttgggtgcacgagtgggttacatcgaactggatctcaacagcggtaagatccttgagagt
tttcgccccgaagaacgttttccaatgatgagcacttttaaagttctgctatgtggcgcggtattatcccgtattgacgccgggcaagag
caactcggtcgccgcatacactattctcagaatgacttggttgagtactcaccagtcacagaaaagcatcttacggatggcatgacagta
agagaattatgcagtgctgccataaccatgagtgataacactgcggccaacttacttctgacaacgatcggaggaccgaaggagctaacc
gcttttttgcacaacatgggggatcatgtaactcgccttgatcgttgggaaccggagctgaatgaagccataccaaacgacgagcgtgac
accacgatgcctgtagcaatggcaacaacgttgcgcaaactattaactggcgaactacttactctagcttcccggcaacaattaatagac
tggatggaggcggataaagttgcaggaccacttctgcgctcggcccttccggctggctggtttattgctgataaatctggagccggtgag
cgtgggtctcgcggtatcattgcagcactggggccagatggtaagccctcccgtatcgtagttatctacacgacggggagtcaggcaact
atggatgaacgaaatagacagatcgctgagataggtgcctcactgattaagcattggtaactgtcagaccaagtttactcatatatactt
tagattgatttaaaacttcattttttaatttaaaaaggatctaggtgaagatcctttttgataatctcatgaccaaaatcccttaacgtgag
ttttcgttccactgagcgtcagacccctgtaaaagatcaaaggatcttcttgagatcctttttttctgcgcgtaactgctgcttgcaaac
aaaaaaaccaccgctaccagcggtggtttgtttgccggatcaagagctaccaactctttttccgaaggtaactggcttcagcagagcgca
gataccaaatactgtccttctagtgtagccgtagttaggccaccacttcaagaactctgtagcaccgcctacatacctcgctctgctaat
cctgttaccagtggctgctgccagtggcgataagtcgtgtcttaccgggttggactcaagacgatagttaccggataaggcgcagcggtc
gggctgaacggggggttcgtgcacacagcccagcttggagcgaacgacctacaccgaactgagatacctacagcgtgagctatgagaaag
cgccacgcttcccgaagggagaaaggcggacaggtatccggtaagcggcagggtcggaacaggagagcgcacgagggagcttccaggggg
aaacgcctggtatctttatagtcctgtcgggtttcgccacctctgacttgagcgtcgatttttgtgatgctcgtcaggggggcggagcct
atggaaaaacgccagcaacgcggcctttttacggttcctggccttttgctggccttttgctcacatgttctttcctgcgttatcccctg
attctgtggataaccgtattaccgcctttgagtgagctgataccgctgccgcagccgaacgaccgagcgcagcgagtcagtgagcgagga
agcggaagagcgcccaatacgcaaaccgcctctccccgcgcgttggccgattcattaatgcagctggcacgacaggtttcccgactggaa
agcgggcagtga
```

SEQ ID NO: 13 pUV-AS3 from junction marker
```
ACGCGCCCTGTAGCGGCGCATTAAGCGCGGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAATCGGGGGCTCCCTTTAGGGTTCCGATTTA
GTGCTTTACGGCACCTCGACCCCAAAAAACTTGATTAGGGTGATGGTTCACGTAGTGGGCCATCGCCCTGATAGACGGTTTTTCGCCCTT
TGACGTTGGAGTCCACGTTCTTTAATAGTGGACTCTTGTTCCAAACTGGAACAACACTCAACCCTATCTCGGTCTATTCTTTTGATTTAT
AAGGGATTTTGCCGATTTCGGCCTATTGGTTAAAAAATGAGCTGATTTAACAAAAATTTAACGCGAATTTTAACAAAATATTAACGCTTA
CAATTTAGGTGGCACTTTTCGGGGAAATGTGCGCGGAACCCCTATTTGTTTATTTTTCTAAATACATTCAAATATGTATCCGCTCATGAG
ACAATAACCCTGATAAATGCTTCAATAATAGCACCTAGATCAAGAGACAGGATGAGGATCGTTTCGCATGATTGAACAAGATGGATTGCA
CGCAGGTTCTCCGGCCGCTTGGGTGGAGAGGCTATTCGGCTATGACTGGGCACAACAGACAATCGGCTGCTCTGATGCCGCCGTGTTCCG
GCTGTCAGCGCAGGGGCGCCCGGTTCTTTTTGTCAAGACCGACCTGTCCGGTGCCCTGAATGAACTGCAAGACGAGGCAGCGCGGCTATC
GTGGCTGGCCACGACGGGCGTTCCTTGCGCAGCTGTGCTCGACGTTGTCACTGAAGCGGGAAGGGACTGGCTGCTATTGGGCGAAGTGCC
GGGGCAGGATCTCCTGTCATCTCACCTTGCTCCTGCCGAGAAAGTATCCATCATGGCTGATGCAATGCGGCGGCTGCATACGCTTGATCC
GGCTACCTGCCCATTCGACCACCAAGCGAAACATCGCATCGAGCGAGCACGTACTCGGATGGAAGCCGGTCTTGTCGATCAGGATGATCT
GGACGAAGAGCATCAGGGGCTCGCGCCAGCCGAACTGTTCGCCAGGCTCAAGGCGAGCATGCCCGACGGCGAGGATCTCGTCGTGACCCA
TGGCGATGCCTGCTTGCCGAATATCATGGTGGAAAATGGCCGCTTTTCTGGATTCATCGACTGTGGCCGGCTGGGTGTGGCGGACCGCTA
TCAGGACATAGCGTTGGCTACCCGTGATATTGCTGAAGAGCTTGGCGGCGAATGGGCTGACCGCTTCCTCGTGCTTTACGGTATCGCCGC
TCCCGATTCGCAGCGCATCGCCTTCTATCGCCTTCTTGACGAGTTCTTCTGAATTATTAACGCTTACAATTTCCTGATGCGGTATTTTCT
CCTTACGCATCTGTGCGGTATTTCACACCGCATCAGGTGGCACTTTTCGGGGAAATGTGCGCGGAACCCCTATTTGTTTATTTTTCTAAA
TACATTCAAATATGTATCCGCTCATGACCAAAATCCCTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATACCAAATACTGTTCTTCTAGTGTAGCCGTAGTTAGGCC
ACCACTTCAAGAACTCTGTAGCACCGCCTACATACCTCGCTCTGCTAATCCTGTTACCAGTGGCTGCTGCCAGTGGCGATAAGTCGTGTC
TTACCGGGTTGGACTCAAGACGATAGTTACCGGATAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGAAACGCCTGGTATCTTTATAGTCCTGTCGGGTTTCGCCACC
TCTGACTTGAGCGTCGATTTTTGTGATGCTCGTCAGGGGGGCGGAGCCTATGGAAAAACGCCAGCAACGCGGCCTTTTTACGGTTCCTGG
CCTTTTGCTGGCCTTTTGCTCACATGTTCTTTCCTGCGTTATCCCCTGATTCTGTGGATAACCGTATTACCGCCTTTGAGTGAGCTGATA
CCGCTCGCCGCAGCCGAACGACCGAGCGCAGCGAGTCAGTGAGCGAGGAAGCGGAAGAGCGCCCAATACGCAAACCGCCTCTCCCCGCGC
GTTGGCCGATTCATTAATGCAGCTGGCACGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGAGCGGATAACAATTTCACACAGGAAACA
GCTATGACCATGATTACGCCAAGCGCGCAATTAACCCTCACTAAAGGGAACAAAAGCTGGAGCTGCAAGCTTGGCCATTGCATACGTTGT
```

SEQUENCE LISTING

```
ATCCATATCATAATATGTACATTTATATTGGCTCATGTCCAACATTACCGCCATGTTGACATTGATTATTGACTAGTTATTAATAGTAAT
CAATTACGGGGTCATTAGTTCATAGCCCATATATGGAGTTCCGCGTTACATAACTTACGGTAAATGGCCCGCCTGGCTGACCGCCCAACG
ACCCCCGCCCATTGACGTCAATAATGACGTATGTTCCCATAGTAACGCCAATAGGGACTTTCCATTGACGTCAATGGGTGGAGTATTTAC
GGTAAACTGCCCACTTGGCAGTACATCAAGTGTATCATATGCCAAGTACGCCCCCTATTGACGTCAATGACGGTAAATGGCCCGCCTGGC
ATTATGCCCAGTACATGACCTTATGGGACTTTCCTACTTGGCAGTACATCTACGTATTAGTCATCGCTATTACCATGGTGATGCGGTTTT
GGCAGTACATCAATGGGCGTGGATAGCGGTTTGACTCACGGGGATTTCCAAGTCTCCACCCCATTGACGTCAATGGGAGTTTGTTTTGGC
ACCAAAATCAACGGGACTTTCCAAAATGTCGTAACAACTCCGCCCCATTGACGCAAATGGGCGGTAGGCGTGTACGGTGGGAGGTCTATA
TAAGCAGAGCTCGTTTAGTGAACCGGGGTCTCTCTGGTTAGACCAGATCTGAGCCTGGGAGCTCTCTGGCTAACTAGGGAACCCACTGCT
TAAGCCTCAATAAAGCTTGCCTTGAGTGCTTCAAGTAGTGTGTGCCCGTCTGTTGTGTGACTCTGGTAACTAGAGATCCCTCAGACCCTT
TTAGTCAGTGTGGAAAATCTCTAGCAGTGGCGCCCGAACAGGGACTTGAAAGCGAAAGGGAAACCAGAGGAGCTCTCTCGACGCAGGACT
CGGCTTGCTGAAGCGCGCACGGCAAGAGGCGAGGGGCGGCGACTGGTGAGTACGCCAAAAATTTTGACTAGCGGAGGCTAGAAGGAGAGA
GATGGGTGCGAGAGCGTCAGTATTAAGCGGGGGAGAATTAGATCGCGATGGGAAAAAATTCGGTTAAGGCCAGGGGGAAAGAAAAAATAT
AAATTAAAACATATAGTATGGGCAAGCAGGGAGCTAGAACGATTCGCAGTTAATCCTGGCCTGTTAGAAACATCAGAAGGCTGTAGACAA
ATACTGGGACAGCTACAACCATCCCTTCAGCACAGGATCAGAAGAACTTAGATCATTATATAATACAGTAGCAACCCTCTATTGTGTGCAT
CAAAGGATAGAGATAAAAGACACCAAGGAAGCTTTAGACAAGATAGAGGAAGGCAAAACAAAAGTAAGACCACCGCACAGCAAGCGGCC
GCTGATCTTCAGACCTGGAGGAGGAGATATGAGGGACAATTGGAGAAGTGAATTATATAAATATAAAGTAGTAAAAATTGAACCATTAGG
AGTAGCACCCACCAAGGCAAAGAGAAGAGTGGTGCAGAGAGAAAAAAGAGCAGTGGGAATAGGAGCTTTGTTCCTTGGGTTCTTGGGAGC
AGCAGGAAGCACTATGGGCGCAGCGTCAATGACGCTGACGGTACAGGCCAGACAATTATTGTCTGGTATAGTGCAGCAGCAGAACAATTT
GCTGAGGGCTATTGAGGCGCAACAGCATCTGTTGCAACTCACAGTCTGGGGCATCAAGCAGCTCCAGGCAAGAATCCTGGCTGTGGAAAG
ATACCTAAAGGATCAACAGCTCCTGGGGATTTGGGGTTGCTCTGGAAAACTCATTTGCACCACTGCTGTGCCTTGGAATGCTAGTTGGAG
TAATAAATCTCTGGAACAGATTTGGAATCACACGACCTGGATGGAGTGGGACAGAGAAATTAACAATTACACAAGCTTAATACACTCCTT
AATTGAAGAATCGCAAAACCAGCAAGAAAGAATGAACAAGAATTATTGGAATTAGATAAATGGGCAAGTTTGTGGAATTGGTTTAACAT
AACAAATTGGCTGTGGTATATAAAATTATTCATAATGATAGTAGGAGGCTTGGTAGGTTTAAGAATAGTTTTTGCTGTACTTTCTATAGT
GAATAGAGTTAGGCAGGGATATTCACCATTATCGTTTCAGACCCACCTCCCAACCCCGAGGGGACCCGACAGGCCCGAAGGAATAGAAGA
AGAAGGTGGAGAGAGAGACAGAGACAGATCCATTCGATTAGTGAACGGATCTCGACGGTATCGATCTCGACACAAATGGCAGTATTCATC
CACAATTTTAAAAGAAAAGGGGGGATTGGGGGGTACAGTGCAGGGGAAAGAATAGTAGACATAATAGCAACAGACATACAAACTAAAGAA
TTACAAAAACAAATTACAAAAATTCAAAATTTTCGGGTTTATTACAGGGACAGCAGACATGAGGACAGCTAAAACAATAAGTAATGTAAA
ATACAGCATAGCAAAACTTTAACCTCCAAATCAAGCCTCTACTTGAATCCTTTTCTGAGGGATGAATAAGGCATAGGCATCAGGGGCTGT
TGCCAATGTGCATTAGCTGTTTGCAGCCTCACCTTCTTTCATGGAGTTTAAGATATAGTGTATTTTCCCAAGGTTTGAACTAGCTCTTCA
TTTCTTTATGTTTTAAATGCACTGACCTCCCACATTCCCTTTTTAGTAAAATATTCAGAAATAATTTAAATACATCATTGCAATGAAAAT
AAATGTTTTTTATTAGGCAGAATCCAGATGCTCAAGGCCCTTCATAATATCCCCCAGTTTAGTAGTTGGACTTAGGGAACAAAGGAACCT
TTAATAGAAATTGGACAGCAGAAAGCGAGCTTAGTGATACTTGTGGGCATTAGCCACACAGCCACCGGCCACCACTTTCTGATAGGCAG
CCTGCACTGGTGGGGTGAATTCTTTGCCAAAGTGATGGGCCAGCACACAGACCAGCACGTTGCCCAGGAGCTGTGGGAGGAAGATAAGAG
GTATGAACATGATTAGCAAAAGGGCCTAGCTTGGACTCAGAATAATCCAGCCTTATCCCAACCATAAAATAAAAGCAGAATGGTAGCTGG
ATTGTAGCTGCTATTAGCAATATGAAACCTCTTACATCAGTTACAATTTATATGCAGAAATACCCTGTTACTTCTCCCCTTCCTATGACA
TGAACTTAACCATAGAAAAGAAGGGGAAGAAAAACATCAAGGGTCCCATAGACTCACCCTGAAGTTCTCAGGATCCACGTGCAGCTTGTC
ACAGTGCAGCTCACTCAGCTGGGCAAAGGTGCCCTTGAGGTTGTCCAGGTGAGCCAGGCCATCACTAAAGGCACCGAGCACTTTCTTGCC
ATGAGCCTTCACCTTAGGGTTGCCCATAACAGCATCAGGAGTGGACAGATCCCCAAAGGACTCAAAGAACCTCTGGGTCCAAGGGTAGAC
CACCAGCAGCCTAAGGGTGGGAAAATAGACCAATAGGCAGAGAGAGTCAGTGCCTATCAGAAACCCAAGAGTCTTCTCTGTCTCCACATG
CCCAGTTTCTATTGGTCTCCTTAAACCTGTCTTGTAACCTTGATACCAACCTGCCCAGGGCCTCACCACCAACGGCATCCACGTTCACCT
TGTCCCACAGGGCAGTAACGGCAGACTTCTCCTCAGGAGTCAGGTGCACCATGGTGTCTGTTTGAGGTTGCTAGTGAACACAGTTGTGTC
AGAAGCAAATGTAAGCAATAGATGGCTCTGCCCTGACTTTTATGCCCAGCCCTGGCTCCTGCCCTCCCTGCTCCTGGGAGTAGATTGGCC
AACCCTAGGGTGTGGCTCCACAGGGTGAGGTCTAAGTGATGACAGCCGTACCTGTCCTTGGCTCTTCTGGCACTGGCTTAGGAGTTGGAC
TTCAAACCCTCAGCCCTCCCTCTAAGATATATCTCTTGGCCCCATACCATCAGTACAAATTGCTACTAAAAACATCCTCCTTTGCAAGTG
TATTTACTACGTATATGTGTATATATATATATATTCAGGAAATAATATATTCTAGAATATGTCACATTCTGTCTCAGGCATCCATTTT
CTTTATGATGCCGTTTGAGGTGGAGTTTTAGTCAGGTGGTCAGCTTCTCCTTTTTTTTTGCCATCTGCCCTGTAAGCATCCTGCTGGGGAC
CCAGATAGGAGTCATCACTCTAGGCTGAGAACATCTGGGCACACACCCTAAGCCTCAGCATGACTCATCATGACTCAGCATTGCTGTGCT
TGAGCCAGAAGGTTTGCTTAGAAGGTTACACAGAACCAGAAGGCGGGGGTGGGGCACTGACCCCGACAGGGGCCTGGCCAGAACTGCTCA
TGCTTGGACTATGGGAGGTCACTAATGGAGACACACAGAAATGTAACAGGAACTAAGGAAAAACTGAAGCTTTGGGGGTATAGGGGAGCA
GTCCCATGTAGTAGTAGAATGAAAAATGCTGCTATGCTGTGCCTCCCCCACCTTTCCCATGTCTGCCCTCTACTCATGGTCTATCTCTCC
TGGCTCCTGGGAGTCATGGACTCCACCCAGCACCACCAACCTGACCTAACCACCTATCTGAGCCTGCCAGCCTATAACCCATCTGGGCCC
TGATAGCTGGTGGCCAGCCCTGACCCCACCCCACCCTCCCTGGAACCTCTGATAGACACATCTGGCACACCAGCTCGCAAAGTCACCGTG
AGGGTCTTGTGTTTGCTGAGTCAAAATTCCTTGAAATCCAAGTCCTTAGAGACTCCCAGGCTTGGATTCAAAGCTCCTGACTTTCTGTCT
AGTGTATGTGCAGTGAGCCCCTTTTCCTCTAACTGAAAGAAGGAAAAAAAAATGGAACCCAAAATATTCTACATAGTTTCCATGTCACAG
CCAGGGCTGGGCAGTCTCCTGTTATTTCTTTTAAAATAAATATATCATTTAAATGCATAAATAAGCAAACCCTGCTCGGGAATGGGAGGG
AGAGTCTCTGGAGTCCACCCCTTCTCGGCCCTGGCTCTGCAGATAGTGCTATCAAAGCCCTGACAGAGCCCTGCCCATTGCTGGGCCTTG
GAGTGAGTCAGCCTAGTAGAGAGGCAGGGCAAGCCATCTCATAGCTGCTGAGTGGGGAGAGAAAAGGGCTCATTGTCTATAAACTCAGG
TCATGGCTATTCTTATTAAAAGAAAAGGGGGGACTGGAAGGGCTAATTCACTCCCAACGAAGACAAGATCTGCTTTTTGCTTGTACTGGG
TCTCTCTGGTTAGACCAGATCTGAGCCTGGGAGCTCTCTGGCTAACTAGGGAACCCACTGCTTAAGCCTCAATAAAGCTTGCCTTGAGTG
CTTCAAGTAGTGTGTTGGTTTTTTGTGTGTGCATTGTCTGAGTAGGTGTCATTCTATTCTGGGGGGTGGGTGGGGCAGCACAGCAAGGG
GGAGGATTGGGAAGACAATAGCAGGCATGCTGGGGATGCGGTGGGCTCTATGGAGTAGTAGTTCATGTCATCTTATTATTCAGTATTTAT
AACTTGCAAAGAAATGAATATCAGAGAGTGAGAGGAACTTGTTTATTGCAGCTTATAATGGTTACAAATAAAGCAATAGCATCACAAATT
TCACAAATAAAGCATTTTTTTCACTGCATTCTAGTTGTGGTTTGTCCAAACTCATCAATGTATCTTATCATGTCTGGCTCTAGCTATCCC
GCCCCTAACTCCGCCCATCCCGCCCCTAACTCCGCCCAGTTCCGCCCATTCTCCGCCCCATGGCTCTCACTACTTCTGGAATAGCTCAGA
GGCCGAGGCGGCCTCGGCCTCTGCATAAATAAAAAAAATTAGTCGAGGCTTTTTGGAGGCCTAGGGACGTACCCAATTCGCCCTATAGT
GAGTCGTATTACGCGCGCTCACTGGCCGTCGTTTTACAACGTCGTGACTGGGAAAACCCTGGCGTTACCCAACTTAATCGCCTTGCAGCA
CATCCCCCTTTCGCCAGCTGGCGTAATAGCGAAGAGGCCCGCACCGATCGCCCTTCCCAACAGTTGCGCAGCCTGAATGGCGAATGGG
```

SEQ ID NO: 14 pUV-A53(coX2) from junction marker

```
ACGCGCCCTGTAGCGGCGCATTAAGCGCGGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAATCGGGGGCTCCCTTTAGGGTTCCGATTTA
GTGCTTTACGGCACCTCGACCCCAAAAAACTTGATTAGGGTGATGGTTCACGTAGTGGGCCATCGCCCTGATAGACGGTTTTTCGCCCTT
TGACGTTGGAGTCCACGTTCTTTAATAGTGGACTCTTGTTCCAAACTGGAACAACACTCAACCCTATCTCGGTCTATTCTTTTGATTTAT
AAGGGATTTTGCCGATTTCGGCCTATTGGTTAAAAAATGAGCTGATTTAACAAAAATTTAACGCGAATTTTAACAAAATATTAACGCTTA
CAATTTAGGTGGCACTTTTCGGGGAAATGTGCGCGGAACCCCTATTTGTTTATTTTTCTAAATACATTCAAATATGTATCCGCTCATGAG
ACAATAACCCTGATAAATGCTTCAATAATAGCACCTAGATCAAGAGACAGGATGAGGATCGTTTCGCATGATTGAACAAGATGGATTGCA
CGCAGGTTCTCCGGCCGCTTGGGTGGAGAGGCTATTCGGCTATGACTGGGCACAACAGACAATCGGCTGCTCTGATGCCGCCGTGTTCCG
```

SEQUENCE LISTING

```
GCTGTCAGCGCAGGGGCGCCCGGTTCTTTTTGTCAAGACCGACCTGTCCGGTGCCCTGAATGAACTGCAAGACGAGGCAGCGCGGCTATC
GTGGCTGGCCACGACGGGCGTTCCTTGCGCAGCTGTGCTCGACGTTGTCACTGAAGCGGGAAGGGACTGGCTGCTATTGGGCGAAGTGCC
GGGGCAGGATCTCCTGTCATCTCACCTTGCTCCTGCCGAGAAAGTATCCATCATGGCTGATGCAATGCGGCGGCTGCATACGCTTGATCC
GGCTACCTGCCCATTCGACCACCAAGCGAAACATCGCATCGAGCGAGCACGTACTCGGATGGAAGCCGGTCTTGTCGATCAGGATGATCT
GGACGAAGAGCATCAGGGGCTCGCGCCAGCCGAACTGTTCGCCAGGCTCAAGGCGAGCATGCCCGACGGCGAGGATCTCGTCGTGACCCA
TGGCGATGCCTGCTTGCCGAATATCATGGTGGAAAATGGCCGCTTTTCTGGATTCATCGACTGTGGCCGGCTGGGTGTGGCGGACCGCTA
TCAGGACATAGCGTTGGCTACCCGTGATATTGCTGAAGAGCTTGGCGGCGAATGGGCTGACCGCTTCCTCGTGCTTTACGGTATCGCCGC
TCCCGATTCGCAGCGCATCGCCTTCTATCGCCTTCTTGACGAGTTCTTCTGAATTATTAACGCTTACAATTTCCTGATGCGGTATTTTCT
CCTTACGCATCTGTGCGGTATTTCACACCGCATCAGGTGGCACTTTTCGGGGAAATGTGCGCGGAACCCCTATTTGTTTATTTTTCTAAA
TACATTCAAATATGTATCCGCTCATGACCAAAATCCCTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATACCAAATACTGTTCTTCTAGTGTAGCCGTAGTTAGGCC
ACCACTTCAAGAACTCTGTAGCACCGCCTACATACCTCGCTCTGCTAATCCTGTTACCAGTGGCTGCTGCCAGTGGCGATAAGTCGTGTC
TTACCGGGTTGGACTCAAGACGATAGTTACCGGATAAGGCGCAGCGGTCGGGCTGAACGGGGGGTCGTGCACACAGCCCAGCTTGGAGC
GAACGACCTACACCGAACTGAGATACCTACAGCGTGAGCTATGAGAAAGCGCCACGCTTCCCGAAGGGAGAAAGGCGGACAGGTATCCGG
TAAGCGGCAGGGTCGGAACAGGAGAGCGCACGAGGGAGCTTCACAGGGGAAACGCCTGGTATCTTTATAGTCCTGTCGGGTTTCGCCACC
TCTGACTTGAGCGTCGATTTTTGTGATGCTCGTCAGGGGGGCGGAGCCTATGGAAAAACGCCAGCAACGCGGCCTTTTTACGGTTCCTGG
CCTTTTGCTGGCCTTTTGCTCACATGTTCTTTCCTGCGTTATCCCCTGATTCTGTGGATAACCGTATTACCGCCTTTGAGTGAGCTGATA
CCGCTCGCCGCAGCCGAACGACCGAGCGCAGCGAGTCAGTGAGCGAGGAAGCGGAAGAGCGCCCAATACGCAAACCGCCTCTCCCCGCGC
GTTGGCCGATTCATTAATGCAGCTGGCACGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGAGCGGATAACAATTTCACACAGGAAACA
GCTATGACCATGATTACGCCAAGCGCGCAATTAACCCTCACTAAAGGGAACAAAAGCTGGAGCTGCAAGCTTGGCCATTGCATACGTTGT
ATCCATATCATAATATGTACATTTATATTGGCTCATGTCCAACATTACCGCCATGTTGACATTGATTATTGACTAGTTATTAATAGTAAT
CAATTACGGGGTCATTAGTTCATAGCCCATATATGGAGTTCCGCGTTACATAACTTACGGTAAATGGCCCGCCTGGCTGACCGCCCAACG
ACCCCCGCCCATTGACGTCAATAATGACGTATGTTCCCATAGTAACGCCAATAGGGACTTTCCATTGACGTCAATGGGTGGAGTATTTAC
GGTAAACTGCCCACTTGGCAGTACATCAAGTGTATCATATGCCAAGTACGCCCCCTATTGACGTCAATGACGGTAAATGGCCCGCCTGGC
ATTATGCCCAGTACATGACCTTATGGGACTTTCCTACTTGGCAGTACATCTACGTATTAGTCATCGCTATTACCATGGTGATGCGGTTTT
GGCAGTACATCAATGGGCGTGGATAGCGGTTTGACTCACGGGGATTTCCAAGTCTCCACCCCATTGACGTCAATGGGAGTTTGTTTTGGC
ACCAAAATCAACGGGACTTTCCAAAATGTCGTAACAACTCCGCCCCATTGACGCAAATGGGCGGTAGGCGTGTACGGTGGGAGGTCTATA
TAAGCAGAGCTCGTTTAGTGAACCGGGGTCTCTCTGGTTAGACCAGATCTGAGCCTGGGAGCTCTCTGGCTAACTAGGGAACCCACTGCT
TAAGCCTCAATAAAGCTTGCCTTGAGTGCTTCAAGTAGTGTGTGCCCGTCTGTTGTGTGACTCTGGTAACTAGAGATCCCTCAGACCCTT
TTAGTCAGTGTGGAAAATCTCTAGCAGTGGCGCCCGAACAGGGACTTGAAAGCGAAAGGGAAACCAGAGGAGCTCTCTCGACGCAGGACT
CGGCTTGCTGAAGCGCGCACGGCAAGAGGCGAGGGGCGGCGACTGGTGAGTACGCCAAAAATTTTGACTAGCGGAGGCTAGAAGGAGAGA
GATGGGTGCGAGAGCGTCAGTATTAAGCGGGGGAGAATTAGATCGCGATGGGAAAAAATTCGGTTAAGGCCAGGGGGAAAGAAAAAATAT
AAATTAAAACATATAGTATGGGCAAGCAGGGAGCTAGAACGATTCGCAGTTAATCCTGGCCTGTTAGAAACATCAGAAGGCTGTAGACAA
ATACTGGGACAGCTACAACCATCCCTTCAGACAGGATCAGAAGAACTTAGATCATTATATAATACAGTAGCAACCCTCTATTGTGTGCAT
CAAAGGATAGAGATAAAAGACACCAAGGAAGCTTTAGACAAGATAGAGGAAGAGCAAAACAAAAGTAAGACCACCGCACAGCAAGCGGCC
GCTGATCTTCAGACCTGGAGGAGGAGATATGAGGGACAATTGGAGAAGTGAATTATATAAATATAAAGTAGTAAAAATTGAACCATTAGG
AGTAGCACCCACCAAGGCAAAGAGAAGAGTGGTGCAGAGAGAAAAAAGAGCAGTGGGAATAGGAGCTTTGTTCCTTGGGTTCTTGGGAGC
AGCAGGAAGCACTATGGGCGCAGCGTCAATGACGCTGACGGTACAGGCCAGACAATTATTGTCTGGTATAGTGCAGCAGCAGAACAATTT
GCTGAGGGCTATTGAGGCGCAACAGCATCTGTTGCAACTCACAGTCTGGGGCATCAAGCAGCTCCAGGCAAGAATCCTGGCTGTGGAAAG
ATACCTAAAGGATCAACAGCTCCTGGGGATTTGGGGTTGCTCTGGAAAACTCATTTGCACCACTGCTGTGCCTTGGAATGCTAGTTGGAG
TAATAAATCTCTGGAACAGATTTGGAATCACACGACCTGGATGGAGTGGGACAGAGAAATTAACAATTACACAAGCTTAATACACTCCTT
AATTGAAGAATCGCAAAACCAGCAAGAAAGAATGAACAAGAATTATTGGAATTAGATAAATGGGCAAGTTTGTGGAATTGGTTTAACAT
AACAAATTGGCTGTGGTATATAAAATTATTCATAATGATAGTAGGAGGCTTGGTAGGTTTAAGAATAGTTTTTGCTGTACTTTCTATAGT
GAATAGAGTTAGGCAGGGATATTCACCATTATCGTTTCAGACCCACCTCCCAACCCCGAGGGGACCCGACAGGCCCGAAGGAATAGAAGA
AGAAGGTGGAGAGAGAGACAGAGACAGATCCATTCGATTAGTGAACGGATCTCGACGGTATCGATCTCGACACAAATGGCAGTATTCATC
CACAATTTTAAAAGAAAAGGGGGGATTGGGGGGTACAGTGCAGGGGAAAGAATAGTAGACATAATAGCAACAGACATACAAACTAAAGAA
TTACAAAAACAAATTACAAAAATTCAAAATTTTCGGGTTTATTACAGGGACAGCAGTAGATCAGGACAGCTAAAACAATAAGTAATGTAAA
ATACAGCATAGCAAAACTTTAACCTCCAAATCAAGCCTCTACTTGAATCCTTTTCTGAGGGATGAATAAGGCATAGGCATCAGGGGCTGT
TGCCAATGTGCATTAGCTGTTTGCAGCCTCACCTTCTTTCATGGAGTTTAAGATATAGTGTATTTTCCCAAGGTTTGAACTAGCTCTTCA
TTTCTTTATGTTTTAAATGCACTGACCTCCCACATTCCCTTTTTAGTAAAATATTCAGAAATAATTTAAATACATCATTGCAATGAAAAT
AAATGTTTTTTATTAGGCAGAATCCAGATGCTCAAGGCCCTTCATAATATCCCCCAGTTTAGTAGTTGGACTTAGGGAACAAAGGAACCT
TTAATAGAAATTGGACAGCAAGAAAGCGAGCTTAGTGATACTTGTGGGCCAGGGCATTAGCCACACCAGCCACCACTTTCTGATAGGCAG
CCTGCACTGGTGGGGTGAATTCTTTGCCAAAGTGATGGGCCAGCACACAGACCAGCACGTTGCCCAGGAGCTGTGGGAGGAAGATAAGAG
GTATGAACATGATTAGCAAAAGGGCCTAGCTTGGACTCAGAATAATCCAGCCTTATCCCAACCATAAAATAAAAGCAGAATGGTAGCTGG
ATTGTAGCTGCTATTAGCAATATGAAACCTCTTACATCAGTTACAATTTATATGCAGAATCTCTGTTACTTCTCCCCTTCCTATGACA
TGAACTTAACCATAGAAAAAGAAGGGGAAAGAAAACATCAAGGGTCCCATAGACTCACCCTGAAGTTCTCAGGATCCACGTGCAGCTTGTC
GCAGTGCAGCTCGCTCAGCTGGGCGAAGGTGCCCTTCAGGTTGTCCAGGTGGGCAGGCCGTCGCTGAAGGCGCCCAGCACCTTCTTGCC
GTGGGCCTTCACCTTGGGGTTGCCCATCACGGCGTCGGGGGTGCTCAGGTCGCCGAAGCTCTCGAAGAAGCGCTGGGTCCAGGGGTACAC
CACCAGCAGCCTAAGGGTGGGAAAATAGACCAATAGGCAGAGAGAGTCAGTGCCTATCAGAAACCCAAGAGTCTTCTCTGTCTCCACATG
CCCAGTTTCTATTGGTCTCCTTAAACCTGTCTTGTAACCTTGATACCAACCTGCCCAGGGCCTCACCACCAACGGCATCCACGTTCACCT
TGTCCCACAGGGCAGTAACGGCAGACTTCTCCTCAGGAGTCAGGTGCACCATGGTGTCTGTTTGAGGTTGCTAGTGAACACAGTTGTGTC
AGAAGCAAATGTAAGCAATAGATGGCTCTGCCCTGACTTTTATGCCCAGCCCTGGCTCCTGCCCTCCCTGCTCCTGGGAGTAGATTGGCC
AACCCTAGGGTGTGGCTCCACAGGGTGAGGTCTAAGTGATGACAGCCGTACCTGTCCTTGGCTCTTCTGGCACTGGCTTAGGAGTTGGAC
TTCAAACCCTCAGCCCTCCCTCTAAGATATATCTCTTGGCCCCATACCATCAGTACAAATTGCTACTAAAAACATCCTCCTTTGCAAGTG
TATTTACTACGTATATGTGTATATATATATATATATTCAGGAAATAATATATTCTAGAATATGTCACATTTCGTCTCAGGCATCCATTTT
CTTTATGATGCCGTTTGAGGTGGAGTTTTTAGTCAGGTGGTCAGCTTCTCCTTTTTTTTTGCCATCTGCCCTGTAAGCATCCTGCTGGGGAC
CCAGATAGGAGTCATCACTCTAGGCTGAGAACATCTGGGCACACACCCTAAGCCTCAGCATGACTCATCATGACTCAGCATTGCTGTGCT
TGAGCCAGAAGGTTTGCTTAGAAGGTTACACAGAACCAGAAGGCGGGGGTGGGGCACTGACCCCGACAGGGGCCTGGCCAGAACTGCTCA
TGCTTGGACTATGGGAGGTCACTAATGGAGACACACAGAAATGTAACAGGAACTAAGGAAAAACTGAAGCTTTGGGGGTATAGGGGGAGCA
GTCCCATGTAGTAGTAGAATGAAAAATGCTGCTATGCTGTGCCTCCCCCACCTTTCCCATGTCTGCCCTCTACTCATGGTCTATCTCTCC
TGGCTCCTGGGAGTCATGGACTCCACCCAGCACCACCAACCTGACCTAACCACCTATCTGAGCCTGCCAGCCTATAACCCATCTGGGCCC
TGATAGCTGGTGGCCAGCCCTGACCCCACCCCACCCTCCCTGGAACCTCTGATAGACACATCTGGCACACCAGCTCGCAAAGTCACCGTG
AGGGTCTTGTGTTTGCTGAGTCAAAATTCCTTGAAATCCAAGTCCTTAGAGACTCCCAGGCTTGGATTCAAAGCTCCTGACTTTCTGTCT
AGTGTATGTGCAGTGAGCCCCTTTTCCTCTAACTGAAAGAAGGAAAAAAAATGGAACCCAAAATATTCTACATAGTTTCCATGTCACAG
CCAGGGCTGGGCAGTCTCCTGTTATTTCTTTTAAAATAAATATATCATTTAAATGCATAAATAAGCAAACCCTGCTCGGGAATGGGAGGG
```

SEQUENCE LISTING

```
AGAGTCTCTGGAGTCCACCCCTTCTCGGCCCTGGCTCTGCAGATAGTGCTATCAAAGCCCTGACAGAGCCCTGCCCATTGCTGGGCCTTG
GAGTGAGTCAGCCTAGTAGAGAGGCAGGGCAAGCCATCTCATAGCTGCTGAGTGGGAGAGAGAAAAGGGCTCATTGTCTATAAACTCAGG
TCATGGCTATTCTTATTAAAAGAAAAGGGGGGACTGGAAGGGCTAATTCACTCCCAACGAAGACAAGATCTGCTTTTTGCTTGTACTGGG
TCTCTCTGGTTAGACCAGATCTGAGCCTGGGAGCTCTCTGGCTAACTAGGGAACCCACTGCTTAAGCCTCAATAAAGCTTGCCTTGAGTG
CTTCAAGTAGTGTGTTGGTTTTTTGTGTGTGCATTGTCTGAGTAGGTGTCATTCTATTCTGGGGGGTGGGGTGGGGCAGCACAGCAAGGG
GGAGGATTGGGAAGACAATAGCAGGCATGCTGGGGATGCGGTGGGCTCTATGGAGTAGTAGTTCATGTCATCTTATTATTCAGTATTTAT
AACTTGCAAAGAAATGAATATCAGAGAGTGAGAGGAACTTGTTTATTGCAGCTTATAATGGTTACAAATAAAGCAATAGCATCACAAATT
TCACAAATAAAGCATTTTTTTCACTGCATTCTAGTTGTGGTTTGTCCAAACTCATCAATGTATCTTATCATGTCTGGCTCTAGCTATCCC
GCCCCTAACTCCGCCCATCCCGCCCCTAACTCCGCCCAGTTCCGCCCATTCTCCGCCCCATGGCTCTCACTACTTCTGGAATAGCTCAGA
GGCCGAGGCGGCCTCGGCCTCTGCATAAATAAAAAAAAATTAGTGCGAGGCTTTTTTGGAGGCCTAGGGACGTACCCAATTCGCCCTATAGT
GAGTCGTATTACGCGCGCTCACTGGCCGTCGTTTTACAACGTCGTGACTGGGAAAACCCTGGCGTTACCCAACTTAATCGCCTTGCAGCA
CATCCCCCTTTCGCCAGCTGGCGTAATAGCGAAGAGGCCCGCACCGATCGCCCTTCCCAACAGTTGCGCAGCCTGAATGGCGAATGGG
```

SEQ ID NO: 15 pUV-HS1-AS3 from junction marker

```
ACGCGCCCTGTAGCGGCGCATTAAGCGCGGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAATCGGGGGCTCCCTTTAGGGTTCCGATTTA
GTGCTTTACGGCACCTCGACCCCAAAAAACTTGATTAGGGTGATGGTTCACGTAGTGGGCCATCGCCCTGATAGACGGTTTTTCGCCCTT
TGACGTTGGAGTCCACGTTCTTTAATAGTGGACTCTTGTTCCAAACTGGAACAACACTCAACCCTATCTCGGTCTATTCTTTTGATTTAT
AAGGGATTTTGCCGATTTCGGCCTATTGGTTAAAAAATGAGCTGATTTAACAAAAATTTAACGCGAATTTTAACAAAATATTAACGCTTA
CAATTTAGGTGGCACTTTTCGGGGAAATGTGCGCGGAACCCCTATTTGTTTATTTTTCTAAATACATTCAAATATGTATCCCGCTCATGAG
ACAATAACCCTGATAAATGCTTCAATAATAGCACCTAGATCAAGAGACAGGATGAGGATCGTTTCGCATGATTGAACAAGATGGATTGCA
CGCAGGTTCTCCGGCCGCTTGGGTGGAGAGGCTATTCGGCTATGACTGGGCACAACAGACAATCGGCTGCTCTGATGCCGCCGTGTTCCG
GCTGTCAGCGCAGGGGCGCCCGGTTCTTTTTGTCAAGACCGACCTGTCCGGTGCCCTGAATGAACTGCAAGACGAGGCAGCGCGGCTATC
GTGGCTGGCCACGACGGGCGTTCCTTGCGCAGCTGTGCTCAGCGTTGTCACTGAAGCGGGAAGGGACTGGCTGCTATTGGGCGAAGTGCC
GGGGCAGGATCTCCTGTCATCTCACCTTGCTCCTGCCGAGAAAGTATCCATCATGGCTGATGCAATGCGGCGGCTGCATACGCTTGATCC
GGCTACCTGCCCATTCGACCACCAAGCGAAACATCGCATCGAGCGAGCACGTACTCGGATGGAAGCCGGTCTTGTCGATCAGGATGATCT
GGACGAAGAGCATCAGGGGCTCGCGCCAGCCGAACTGTTCGCCAGGCTCAAGGCGAGCATGCCCGACGGCGAGGATCTCGTCGTGACCCA
TGGCGATGCCTGCTTGCCGAATATCATGGTGGAAAATGGCCGCTTTTCTGGATTCATCGACTGTGGCCGGCTGGGTGTGGCGGACCGCTA
TCAGGACATAGCGTTGGCTACCCGTGATATTGCTGAAGAGCTTGGCGGCGAATGGGCTGACCGCTTCCTCGTGCTTTACGGTATCGCCGC
TCCCGATTCGCAGCGCATCGCCTTCTATCGCCTTCTTGACGAGTTCTTCTGAATTATTAACGCTTACAATTTCCTGATGCGGTATTTTCT
CCTTACGCATCTGTGCGGTATTTCACACCGCATCAGGTGGCACTTTTCGGGGAAATGTGCGCGGAACCCCTATTTGTTTATTTTTCTAAA
TACATTCAAATATGTATCCGCTCATGAGACAATAACCCTTAACGTGAGTTTTCGTTCCACTGAGCGTCAGACCCCGTAGAAAAGATCAAAG
GATCTTCTTGAGATCCTTTTTTTTCTGCGCGTAATCTGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATACCAAATACTGTTCTTCTAGTGTAGCCGTAGTTAGGCC
ACCACTTCAAGAACTCTGTAGCACCGCCTACATACCTCGCTCTGCTAATCCTGTTACCAGTGGCTGCTGCCAGTGGCGATAAGTCGTGTC
TTACCGGGTTGGACTCAAGACGATAGTTACCGGATAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGAAACGCCTGGTATCTTTATAGTCCTGTCGGGTTTCGCCACC
TCTGACTTGAGCGTCGATTTTTGTGATGCTCGTCAGGGGGGCGGAGCCTATGGAAAAACGCCAGCAACGCGGCCTTTTTACGGTTCCTGG
CCTTTTGCTGGCCTTTTGCTCACATGTTCTTTCCTGCGTTATCCCCTGATTCTGTGGATAACCGTATTACCGCCTTTGAGTGAGCTGATA
CCGCTCGCCGCAGCCGAACGACCGAGCGCAGCGAGTCAGTGAGCGAGGAAGCGGAAGAGCGCCCAATACGCAAACCGCCTCTCCCCGCGC
GTTGGCCGATTCATTAATGCAGCTGGCACGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGAGCGGATAACAATTTCACACAGGAAACA
GCTATGACCATGATTACGCCAAGCGCGCAATTAACCCTCACTAAAGGGAACAAAAGCTGGAGCTGCAAGCTTGGCCATTGCATACGTTGT
ATCCATATCATAATATGTACATTTATATTGGCTCATGTCCAACATTACCGCCATGTTGACATTGATTATTGACTAGTTATTAATAGTAAT
CAATTACGGGGTCATTAGTTCATAGCCCATATATGGAGTTCCGCGTTACATAACTTACGGTAAATGGCCCGCCTGGCTGACCGCCCAACG
ACCCCCGCCCATTGACGTCAATAATGACGTATGTTCCCATAGTAACGCCAATAGGGACTTTCCATTGACGTCAATGGGTGGAGTATTTAC
GGTAAACTGCCCACTTGGCAGTACATCAAGTGTATCATATGCCAAGTACGCCCCCTATTGACGTCAATGACGGTAAATGGCCCGCCTGGC
ATTATGCCCAGTACATGACCTTATGGGACTTTCCTACTTGGCAGTACATCTACGTATTAGTCATCGCTATTACCATGGTGATGCGGTTTT
GGCAGTACATCAATGGGCGTGGATAGCGGTTTGACTCACGGGGATTTCCAAGTCTCCACCCCATTGACGTCAATGGGAGTTTGTTTTGGC
ACCAAATCAACGGGACTTTCCAAAATGTCGTAACAACTCCGCCCCATTGACGCAAATGGGCGGTAGGCGTGTACGGTGGGAGGTCTATA
TAAGCAGAGCTCGTTTAGTGAACCGGGGTCTCTCTGGTTAGACCAGATCTGAGCCTGGGAGCTCTCTGGCTAACTAGGGAACCCACTGCT
TAAGCCTCAATAAAGCTTGCCTTGAGTGCTTCAAGTAGTGTGTGCCCGTCTGTTGTGTGACTCTGGTAACTAGAGATCCCTCAGACCCTT
TTAGTCAGTGTGGAAAATCTCTAGCAGTGGCGCCCGAACAGGGACTTGAAAGCGAAAGGGAAACCAGAGGAGCTCTCTCGACGCAGGACT
CGGCTTGCTGAAGCGCGCACGGCAAGAGGCGAGGGGCGGCGACTGGTGAGTACGCCAAAAATTTTGACTAGCGGAGGCTAGAAGGAGAGA
GATGGGTGCGAGAGCGTCAGTATTAAGCGGGGGAGAATTAGATCGCGATGGGAAAAAATTCGGTTAAGGCCAGGGGGAAAGAAAAAATAT
AAATTAAAACATATAGTATGGGCAAGCAGGGAGCTAGAACGATTCGCAGTTAATCCTGGCCTGTTAGAAACATCAGAAGGCTGTAGACAA
ATACTGGGACAGCTACAACCATCCCTTCAGCACAGGATCAGAAGAACTTAGATCATTATATAATACAGTAGCAACCCTCTATTGTGTGCAT
CAAAGGATAGAGATAAAAGACACCAAGGAAGCTTTAGACAAGATAGAGGAAGAGCAAAACAAAAGTAAGACCACCGCACAGCAAGCGGCC
GCTGATCTTCAGACCTGGAGGAGGAGATATGAGGGACAATTGGAGAAGTGAATTATATAAATATAAAGTAGTAAAAATTGAACCATTAGG
AGTAGCACCCACCAAGGCAAAGAGAAGAGTGGTGCAGAGAGAAAAAAGAGCAGTGGGAATAGGAGCTTTGTTCCTTGGGTTCTTGGGAGC
AGCAGGAAGCACTATGGGCGCAGCGTCAATGACGCTGACGGTACAGGCCAGACAATTATTGTCTGGTATAGTGCAGCAGCAGAACAATTT
GCTGAGGGCTATTGAGGCGCAACAGCATCTGTTGCAACTCACAGTCTGGGGCATCAAGCAGCTCCAGGCAAGAATCCTGGCTGTGGAAAG
ATACCTAAAGGATCAACAGCTCCTGGGGATTTGGGGTTGCTCTGGAAAACTCATTTGCACCACTGCTGTGCCTTGGAATGCTAGTTGGAG
TAATAAATCTCTGGAACAGATTTGGAATCACACGACCTGGATGGAGTGGGACAGAGAAATTAACAATTACACAAGCTTAATACACTCCTT
AATTGAAGAATCGCAAAACCGCAAGAAAGGAATGAACAAGAATTATTGGAATTAGATAAATGGGCAAGTTTGTGGAATTGGTTTAACAT
AACAAATTGGCTGTGGTATATAAAATTATTCATAATGATAGTAGGAGGCTTGGTAGGTTTAAGAATAGTTTTTGCTGTACTTTCTATAGT
GAATAGAGTTAGGCAGGGATATTCACCATTATCGTTTCAGACCCACCTCCCAACCCCGAGGGGACCCGACAGGCCCGAAGGAATAGAAGA
AGAAGGTGGAGAGAGAGACAGAGACAGATCCATTCGATTAGTGAACGGATCTCGACGGTATCGATCTCGACACAAATGGCAGTATTCATC
CACAATTTTAAAAGAAAAGGGGGGATTGGGGGGTACAGTGCAGGGGAAAGAATAGTAGACATAATAGCAACAGACATACAAACTAAAGAA
TTACAAAAACAAATTACAAAAATTCAAAATTTTCGGGTTTATTACAGGGACAGCAGCAGATGGAGCAGCATGAAGGCGTAAAACAATAAGTAATGTAAA
ATACAGCATAGCAAACTTTAACCTCCAAATCAAGCCTCTACTTGAATCCTTTTCTGAGGGATGAATAAGGCATAGGCATCAGGGGCTGT
TGCCAATGTGCATTAGCTGTTTGCAGCCTCACCTTCTTTCATGGAGTTTAAGATATAGTGTATTTTCCCAAGGTTTGAACTAGCTCTTCA
TTTCTTTATGTTTTAAATGCACTGACCTCCCACATTCCCTTTTTAGTAAAATATTCAGAAATAATTTAAATACATCATTGCAATGAAAAT
AAATGTTTTTTATTAGGCAGAATCCAGATGCTCAAGGCCCTTCATAAATATCCCCCAGTTTAGTAGTTGGACTTAGGGAACAAAGGAACCT
TTAATAGAAATTGGACAGCAAGAAAGCGAGCTTAGTGATACTTGTGGGCCAGGGCATTAGCCACACCAGCCACCACTTTCTGATAGGCAG
CCTGCACTGGTGGGGTGAATTCTTTGCCAAAGTGATGGGCCAGCACACAGACCAGCACGTTGCCCAGGAGCTGTGGGAGGAAGATAAGAG
```

-continued

SEQUENCE LISTING

```
GTATGAACATGATTAGCAAAAGGGCCTAGCTTGGACTCAGAATAATCCAGCCTTATCCCAACCATAAAATAAAAGCAGAATGGTAGCTGG
ATTGTAGCTGCTATTAGCAATATGAAACCTCTTACATCAGTTACAATTTATATGCAGAAATACCCTGTTACTTCTCCCCTTCCTATGACA
TGAACTTAACCATAGAAAAGAAGGGGAAAGAAAACATCAAGGGTCCCATAGACTCACCCTGAAGTTCTCAGGATCCACGTGCAGCTTGTC
ACAGTGCAGCTCACTCAGCTGGGCAAAGGTGCCCTTGAGGTTGTCCAGGTGAGCCAGGCCATCACTAAAGGCACCGAGCACTTTCTTGCC
ATGAGCCTTCACCTTAGGGTTGCCCATAACAGCATCAGGAGTGGACAGATCCCCAAAGGACTCAAAGAACCTCTGGGTCCAAGGGTAGAC
CACCAGCAGCCTAAGGGTGGGAAAATAGACCAATAGGCAGAGAGAGTCAGTGCCTATCAGAAACCCAAGAGTCTTCTCTGTCTCCACATG
CCCAGTTTCTATTGGTCTCCTTAAACCTGTCTTGTAACCTTGATACCAACCTGCCCAGGGCCTCACCACCAACGGCATCCACGTTCACCT
TGTCCCACAGGGCAGTAACGGCAGACTTCTCCTCAGGAGTCAGGTGCACCATGGTGTCTGTTTGAGGTTGCTAGTGAACACAGTTGTGTC
AGAAGCAAATGTAAGCAATAGATGGCTCTGCCCTGACTTTTATGCCCAGCCCTGGCTCCTGCCCTCCCTGCTCCTGGGAGTAGATTGGCC
AACCCTAGGGTGTGGCTCCACAGGGTGAGGTCTAAGTGATGACAGCCGTACCTGTCCTTGGCTCTTCTGGCACTGGCTTAGGAGTTGGAC
TTCAAACCCTCAGCCCTCCCTCTAAGATATATCTCTTGGCCCCATACCATCAGTACAAATTGCTACTAAAAACATCCTCCTTTGCAAGTG
TATTTACCATCAATAATTCTAGCCCCACAGGAGTTTGTTCTGAAAGTAAACTTCCACAACCGCAAGCTTATTGAGGCTAAGGCATCTGTG
AAGGAAAGAAACATCTCCTCTAAACCACTATGCTGCTAGAGCCTCTTTTCTGTACTCAAGCCTCATTCAGACACTAGTGTCACCAGTCTC
CTCATATACCTATTGTATTTTCTTCTTCTTGCTGGTTTAGTCATGTTTTCTGGGAGCTTAGGGGCTTATTTTATTTTGTTTTGTTTTCTA
ATCAACAGAGATGGGCAAACCCATTATTTTTTTCTTTAGACTTGGGATGGTGATAGCTGGGCAGCGTCAGAAACTGTGTGTGGATATAGA
TAAGAGCTCAGGACTATGCTGAGCTGTGATGAGGGAGGGGCCTAGCTAAAGGCAGTGAGAGTCAGAATGCTCCTGCTATTGCCTTCTCAG
TCCCCACGCTTGGTTTCTACACAAGTAGATACATAGAAAAGGCTATAGGTTAGTGTTTGAGAGTCCTGCATGATTAGTTGCTCAGAAATG
CCCGATAAATATGTTATGTGTGTTTATGTATATATATGTTTTATATGTGTGTGTGTGTGTTGTGTTTACAAATATGTGATTATCATCA
AAACGTGAGGGTACGTATATGTGTATATATATATATATTCAGGAAATAATATATTCTAGAATATGTCACATTCTGTCTCAGGCATCCA
TTTTCTTTATGATGCCGTTTGAGGTGGAGTTTTAGTCAGGTGGTCAGCTTCTCCTTTTTTTTGCCATCTGCCCTGTAAGCATCCTGCTGG
GGACCCAGATAGGAGTCATCACTCTAGGCTGAGAACATCTGGGCACACACCCTAAGCCTCAGCATGACTCATCATGACTCAGCATTGCTG
TGCTTGAGCCAGAAGGTTTGCTTAGAAGGTTACACAGAACCAGAAGGCGGGGGTGGGGCACTGACCCCGACAGGGGCCTGGCCAGAACTG
CTCATGCTTGGACTATGGGAGGTCACTAATGGAGACACACAGAAATGTAACAGGAACTAAGGAAAAACTGAAGCTTTGGGGGTATAGGGG
AGCAGTCCCATGTAGTAGTAGAATGAAAAATGCTGCTATGCTGTGCCTCCCCCACCTTTCCCATGTCTGCCCTCTACTCATGGTCTATCT
CTCCTGGCTCCTGGGAGTCATGGACTCCACCCAGCACCACCAACCTGACCTAACCACCTATCTGAGCCTGCCAGCCTATAACCCATCTGG
GCCCTGATAGCTGGTGGCCAGCCCTGACCCCACCCCACCCTCCCTGGAACCTCTGATAGACACATCTGGCACACCAGCTCGCAAAGTCAC
CGTGAGGGTCTTGTGTTTGCTGAGTCAAAATTCCTTGAAATCCAAGTCCTTAGAGACTCCCAGGCTTGGATTCAAAGCTCCTGACTTTCT
GTCTAGTGTATGTGCAGTGAGCCCCTTTTCCTCTAACTGAAAGAAGGAAAAAAAATGAACCCCCAAAATATTCTACATAGTTTCCATGTC
ACAGCCAGGGCTGGGCAGTCTCCTGTTATTTCTTTTAAAATAAATATATCATTTAAATGCATAAATAAGCAAACCCTGCTCGGGAATGGG
AGGGAGAGTCTCTGGAGTCCACCCCTTCTCGGCCCTGGCTCTGCAGATAGTGCTATCAAAGCCCTGACAGAGCCCTGCCCATTGCTGGGC
CTTGGAGTGAGTCAGCCTAGTAGAGAGGCAGGGCAAGCCATCTCATAGCTGCTGAGTGGGAGAGAGAAAAGGGCTCATTGTCTATAAACT
CAGGTCATGGCTATTCTTATTAAAAGAAAAGGGGGGACTGGAAGGGCTAATTCACTCCCAACGAAGACAAGATCTGCTTTTTGCTTGTAC
TGGGTCTCTCTGGTTAGACACAGATCTGAGCCTGGGAGCTCTCTGGCTAACTAGGGAACCCACTGCTTAAGCCTCAATAAAGCTTGCCTTG
AGTGCTTCAAGTAGTGTGTTGGTTTTTGTGTGTGCATTGTCTGAGTAGGTGTCATTCTATTCTGGGGGGTGGGGTGGGGCAGCACAGCA
AGGGGGAGGATTGGGAAGACAATAGCAGGCATGCTGGGGATGCGGTGGGCTCATGGAGTAGTAGTTCATGTCATCTTATTATTCAGTAT
TTATAACTTGCAAAGAAATGAATATCAGAGAGTGAGAGGAACTTGTTTATTGCAGCTTATAATGGTTACAAATAAAGCAATAGCATCACA
AATTTCACAAATAAAGCATTTTTTTCACTGCATTCTAGTTGTGGTTTGTCCAAACTCATCAATGTATCTTATCATGTCTGGCTCTAGCTA
TCCCGCCCCTAACTCCGCCCATCCCGCCCCTAACTCCGCCCAGTTCCGCCCATTCTCCGCCCCATGGCTCTCACTACTTCTGGAATAGCT
CAGAGGCCGAGGCGGCCTCGGCCTCTGCATAAATAAAAAAAATTAGTCGAGGCTTTTTTGGAGGCCTAGGGACGTACCCAATTCGCCCTA
TAGTGAGTCGTATTACGCGCGCTCACTGGCCGTCGTTTTACAACGTCGTGACTGGGAAAACCCTGGCGTTACCCAACTTAATCGCCTTGC
AGCACATCCCCCTTTCGCCAGCTGGCGTAATAGCGAAGAGGCCCGCACCGATCGCCCTTCCCAACAGTTGCGCAGCCTGAATGGCGAATG
GG

SEQ ID NO: 16 pUV + HS1-AS3(coX2) from junction marker
ACGCGCCCTGTAGCGGCGCATTAAGCGCGGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAATCGGGGGCTCCCTTTAGGGTTCCGATTTA
GTGCTTTACGGCACCTCGACCCCAAAAAACTTGATTAGGGTGATGGTTCACGTAGTGGGCATCGCCCTGATAGACGGTTTTTCGCCCTT
TGACGTTGGAGTCCACGTTCTTTAATAGTGGACTCTTGTTCCAAACTGGAACAACACTCAACCCTATCTCGGTCTATTCTTTTGATTTAT
AAGGGATTTTGCCGATTTCGGCCTATTGGTTAAAAAATGAGCTATTTAACAAAAATTTAACAAAATATTAACGCTTA
CAATTTAGGTGGCACTTTTCGGGGAAATGTGCGCGGAACCCCTATTTGTTTATTTTTCTAAATACATTCAAATATGTATCCGCTCATGAG
ACAATAACCCTGATAAATGCTTCAATAATAGCACCTAGATCAAGAGACAGGATGAGGATCGTTTCGCATGATTGAACAAGATGGATTGCA
CGCAGGTTCTCCGGCCGCTTGGGTGGAGAGGCTATTCGGCTATGACTGGGCACAACAGACAATCGGCTGCTCTGATGCCGCCGTGTTCCG
GCTGTCAGCGCAGGGGCGCCCGGTTCTTTTTGTCAAGACCGACCTGTCCGGTGCCCTGAATGAACTGCAAGACGAGGCAGCGCGGCTATC
GTGGCTGGCCACGACGGGCGTTCCTTGCGCAGCTGTGCTCGACGTTGTCACTGAAGCGGGAAGGGACTGGCTGCTATTGGGCGAAGTGCC
GGGGCAGGATCTCCTGTCATCTCACCTTGCTCCTGCCGAGAAAGTATCCATCATGGCTGATGCAATGCGGCGGCTGCATACGCTTGATCC
GGCTACCTGCCCATTCGACCACCAAGCGAAACATCGCATCGAGCGAGCACGTACTCGGATGGAAGCCGGTCTTGTCGATCAGGATGATCT
GGACGAAGAGCATCAGGGGCTCGCGCCAGCCGAACTGTTCGCCAGGCTCAAGGCGAGCATGCCCGACGGCGAGGATCTCGTCGTGACCCA
TGGCGATGCCTGCTTGCCGAATATCATGGTGGAAAATGGCCGCTTTTCTGGATTCATCGACTGTGGCCGGCTGGGTGTGGCGGACCGCTA
TCAGGACATAGCGTTGGCTACCCGTGATATTGCTGAAGAGCTTGGCGGCGAATGGGCTGACCGCTTCCTCGTGCTTTACGGTATCGCCGC
TCCCGATTCGCAGCGCATCGCCTTCTATCGCCTTCTTGACGAGTTCTTCTGAATTATTAACGCTTACAATTTCCTGATGCGGTATTTTCT
CCTTACGCATCTGTGCGGTATTTCACACCGCATCAGGTGGCACTTTTCGGGGAAATGTGCGCGGAACCCCTATTTGTTTATTTTTCTAAA
TACATTCAAATATGTATCCGCTCATGACCAAAATCCCTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATACCAAATACTGTTCTTCTAGTGTAGCCGTAGTTAGGCC
ACCACTTCAAGAACTCTGTAGCACCGCCTACATACCTCGCTCTGCTAATCCTGTTACCAGTGGCTGCTGCCAGTGGCGATAAGTCGTGTC
TTACCGGGTTGGACTCAAGACGATAGTTACCGGATAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGAAACGCCTGGTATCTTTATAGTCCTGTCGGGTTTCGCCACC
TCTGACTTGAGCGTCGATTTTTGTGATGCTCGTCAGGGGGGCGGAGCCTATGGAAAAACGCCAGCAACGCGGCCTTTTTACGGTTCCTGG
CCTTTTGCTGGCCTTTTGCTCACATGTTCTTTCCTGCGTTATCCCCTGATTCTGTGGATAACCGTATTACCGCCTTTGAGTGAGCTGATA
CCGCTCGCCGCAGCCGAACGACCGAGCGCAGCGAGTCAGTGAGCGAGGAAGCGGAAGAGCGCCCAATACGCAAACCGCCTCTCCCCGCGC
GTTGGCCGATTCATTAATGCAGCTGGCACGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGAGCGGATAACAATTTCACACAGGAAACA
GCTATGACCATGATTACGCCAAGCGCGCAATTAACCCTCACTAAAGGGAACAAAAGCTGGAGCTGCAAGCTTGGCATTGCATACGTTGT
ATCCATATCATAATATGTACATTTATATTGGCTCATGTCCAACATTACCGCCATGTTGACATTGATTATTGACTAGTTATTAATAGTAAT
CAATTACGGGGTCATTAGTTCATAGCCCATATATGGAGTTCCGCGTTACATAACTTACGGTAAATGGCCCGCCTGGCTGACCGCCCAACG
ACCCCCGCCCATTGACGTCAATAATGACGTATGTTCCCATAGTAACGCCAATAGGGACTTTCCATTGACGTCAATGGGTGGAGTATTTAC
```

SEQUENCE LISTING

```
GGTAAACTGCCCACTTGGCAGTACATCAAGTGTATCATATGCCAAGTACGCCCCCTATTGACGTCAATGACGGTAAATGGCCCGCCTGGC
ATTATGCCCAGTACATGACCTTATGGGACTTTCCTACTTGGCAGTACATCTACGTATTAGTCATCGCTATTACCATGGTGATGCGGTTTT
GGCAGTACATCAATGGGCGTGGATAGCGGTTTGACTCACGGGGATTTCCAAGTCTCCACCCCATTGACGTCAATGGGAGTTTGTTTTGGC
ACCAAAATCAACGGGACTTTCCAAAATGTCGTAACAACTCCGCCCCATTGACGCAAATGGGCGGTAGGCGTGTACGGTGGGAGGTCTATA
TAAGCAGAGCTCGTTTAGTGAACCGGGGTCTCTCTGGTTAGACCAGATCTGAGCCTGGGAGCTCTCTGGCTAACTAGGGAACCCACTGCT
TAAGCCTCAATAAAGCTTGCCTTGAGTGCTTCAAGTAGTGTGTGCCCGTCTGTTGTGTGACTCTGGTAACTAGAGATCCCTCAGACCCTT
TTAGTCAGTGTGGAAAATCTCTAGCAGTGGCGCCCGAACAGGGACTTGAAAGCGAAAGGGAAACCAGAGGAGCTCTCTCGACGCAGGACT
CGGCTTGCTGAAGCGCGCACGGCAAGAGGCGAGGGGCGGCGACTGGTGAGTACGCCCAAAAATTTTGACTAGCGGAGGCTAGAAGGAGAGA
GATGGGTGCGAGAGCGTCAGTATTAAGCGGGGGAGAATTAGATCGCGATGGGAAAAAATTCGGTTAAGGCCAGGGGGAAAGAAAAAATAT
AAATTAAAACATATAGTATGGGCAAGCAGGGAGCTAGAACGATTCGCAGTTAATCCTGGCCTGTTAGAAACATCAGAAGGCTGTAGACAA
ATACTGGGACAGCTACAACCATCCCTTCAGACAGGATCAGAAGAACTTAGATCATTATATAATACAGTAGCAACCCTCTATTGTGTGCAT
CAAAGGATAGAGATAAAAGACACCAAGGAAGCTTTAGACAAGATAGAGGAAGAGCAAAACAAAAGTAAGACCACCGCACAGCAAGCGGCC
GCTGATCTTCAGACCTGGAGGAGGAGATATGAGGGACAATTGGAGAAGTGAATTATATAAATATAAAGTAGTAAAAATTGAACCATTAGG
AGTAGCACCCACCAAGGCAAAGAGAAGAGTGGTGCAGAGAGAAAAAAGAGCAGTGGGAATAGGAGCTTTGTTCCTTGGGTTCTTGGGAGC
AGCAGGAAGCACTATGGGCGCAGCGTCAATGACGCTGACGGTACAGGCCAGACAATTATTGTCTGGTATAGTGCAGCAGCAGAACAATTT
GCTGAGGGCTATTGAGGCGCAACAGCATCTGTTGCAACTCACAGTCTGGGGCATCAAGCAGCTCCAGGCAAGAATCCTGGCTGTGGAAAG
ATACCTAAAGGATCAACAGCTCCTGGGGATTTGGGGTTGCTCTGGAAAACTCATTTGCACCACTGCTGTGCCTTGGAATGCTAGTTGGAG
TAATAAATCTCTGGAACAGATTTGGAATCACACGACCTGGATGGAGTGGGACAGAGAAATTAACAATTACACAAGCTTAATACACTCCTT
AATTGAAGAATCGCAAAACCAGCAAGAAAAGAATGAACAAGAATTATTGGAATTAGATAAATGGGCAAGTTTGTGGAATTGGTTTAACAT
AACAAATTGGCTGTGGTATATAAAATTATTCATAATGATAGTAGGAGGCTTGGTAGGTTTAAGAATAGTTTTTGCTGTACTTTCTATAGT
GAATAGAGTTAGGCAGGGATATTCACCATTATCGTTTCAGACCCACCTCCCAACCCCGAGGGGACCCGACAGGCCCGAAGGAATAGAAGA
AGAAGGTGGAGAGAGAGACAGAGACAGATCCATTCGATTAGTGAACGGATCTCGACGGTATCGATCTCGACACAAATGGCAGTATTCATC
CACAATTTTAAAAGAAAAGGGGGGATTGGGGGGTACAGTGCAGGGGAAAGAATAGTAGACATAATAGCAATAGAGCATACAAACTAAAGAA
TTACAAAAACAAATTACAAAAATTCAAAATTTTCGGGTTTATTACAGGGACAGCAGACATGAGGACAGCTAAAACAATAAGTAATGTAAA
ATACAGCATAGCAAAACTTTAACCTCCAAATCAAGCCTCTACTTGAATCCTTTTCTGAGGGATGAATAAGGCATAGGCATCAGGGGCTGT
TGCCAATGTGCATTAGCTGTTTGCAGCCTCACCTTCTTTCATGGAGTTTAAGATATAGTGTATTTTCCCAAGGTTTGAACTAGCTCTTCA
TTTCTTTATGTTTTAAATGCACTGACCTCCCACATTCCCTTTTTAGTAAAATATTCAGAAATAATTTAAATACATCATTGCAATGAAAAT
AAATGTTTTTTATTAGGCAGAATCCAGATGCTCAAGGCCCTTCATAATATCCCCCAGTTTAGTAGTTGGACTTAGGGAACAAAGGAACCT
TTAATAGAAATTGGACAGCAAGAAAGCGAGCTTAGTGATACTTGTGGGCCAGGGCATTAGCCACACCAGCCACCACTTTCTGATAGGCAG
CCTGCACTGGTGGGGTGAATTCTTTGCCAAAGTGATGGGCCAGCACACAGACCAGCACGTTGCCCAGGAGCTGTGGGAGGAAGATAAGAG
GTATGAACATGATTAGCAAAAGGGCCTAGCTTGGACTCAGAATAATCCAGCCTTATCCCAACCATAAAATAAAAGCAGAATGGTAGCTGG
ATTGTAGCTGCTATTAGCAATATGAAACCTCTTACATCAGTTACAATTTATATGCAGAAATACCCTGTTACTTCTCCCCTTCCTATGACA
TGAACTTAACCATAGAAAAGAAGGGGAAAGAAAACATCAAGGGTCCCATAGACTCACCCTGAAGTTCTCAGGATCCACGTGCAGCTTGTC
GCAGTGCAGCTCGCTCAGCTGGGCGAAGGTGCCCTTCAGGTTGTCCAGGTGGGCCAGGCCGTCGCTGAAGGCGCCCAGCACCTTCTTGCC
GTGGGCCTTCACCTTGGGGTTGCCCATCACGGCGTCGGGGGTGCTCAGGTCGCCGAAGCTCTCGAAGAAGCGCTGGGTCCAGGGGTACAC
CACCAGCAGCCTAAGGGTGGGAAAATAGACCAATAGGCAGAGAGAGTCAGTGCCTATCAGAAACCCAAGAGTCTTCTCTGTCTCCACATG
CCCAGTTTCTATTGGTCTCCTTAAACCTGTCTTGTAACCTTGATACCAACCTGCCCAGGGCCTCACCACCAACGGCATCCACGTTCACCT
TGTCCCACAGGGCAGTAACGGCAGACTTCTCCTCAGGAGTCAGGTGCACCATGGTGTCTGTTTGAGGTTGCTAGTGAACACAGTTGTGTC
AGAAGCAAATGTAAGCAATAGATGGCTCTGCCCTGACTTTTATGCCCAGCCCTGGCTCCTGCCCTCCCTGCTCCTGGGAGTAGATTGGCC
AACCCTAGGGTGTGGCTCCACAGGGTGAGGTCTAAGTGATGACAGCCGTACCTGTCCTTGGCTCTTCTGGCACTGGCTTAGGAGTTGGAC
TTCAAACCCTCAGCCCTCCCTCTAAGATATATCTCTTGGCCCCATACCATCAGTACAAATTGCTACTAAAAACATCCTCCTTTGCAAGTG
TATTTACCATCAATAATTCTAGCCCCACAGGAGTTTGTTCTGAAAGTAAACTTCCACAACCGCAAGCTTATTGAGGCTAAGGCATCTGTG
AAGGAAAGAAACATCTCCTCTAAACCACTATGCTGCTAGAGCCTCTTTTCTGTACTCAAGCCTCATTCAGACACTAGTGTCACCAGTCTC
CTCATATACCTATTGTATTTTCTTCTTGCTGGTTTAGTCATGTTTTCTGGGAGCTTAGGGGCTTATTTTATTTTGTTTTGTTTTCTA
ATCAACAGAGATGGGCAAACCCATTATTTTTTTCTTTAGACTTGGGATGGTGATAGCTGGGCAGCGTCAGAAACTGTGTGTGGATATAGA
TAAGAGCTCAGGACTATGCTGAGCTGTGATGAGGGAGGGGCCTAGCTAAAGGCAGTGAGAGTCAGAATGCTCCTGCTATTGCCTTCTCAG
TCCCCACGCTTGGTTTCTACACAAGTAGATACATAGAAAAGGCTATAGGTTAGTGTTTGAGAGTCCTGCATGATTAGTTGCTCAGAAATG
CCCGATAAATATGTTATGTGTGTTTATGTATATATATGTTTTATATGTGTGTGTGTGTGTGTTGTGTTTACAAATATGTGATTATCATCA
AAACGTGAGGGTACGTATATGTGTATATATATATATATTCAGGAAATAATATATTCTAGAATATGTCACATTCTGTCTCAGGCATCCA
TTTTCTTTATGATGCCGTTTGAGGTGGAGTTTTAGTCAGGTGGTCAGCTTCTCCTTTTTTTTTGCCATCTGCCCTGTAAGCATCCTGCTGG
GGACCCAGATAGGAGTCATCACTCTAGGCTGAGAACATCTGGGCACACACCCTAAGCCTCAGCATGACTCATCATGACTCAGCATTGCTG
TGCTTGAGCCAGAAGGTTTGCTTAGAAGGTTACACAGAACCAGAAGGCGGGGTGGGGCACTGACCCCGACAGGGGCCTGGCCAGAACTG
CTCATGCTTGGACTATGGGAGGTCACTAATGGAGACACACAGAAATGTAACAGGAACTAAGGAAAAACTGAAGCTTTGGGGGTATAGGGG
AGCAGTCCCATGTAGTAGTAGAATGAAAAATGCTGCTATGCTGTGCCTCCCCCACCTTTCCCATGTCTGCCCTCTACTCATGGTCTATCT
CTCCTGGCTCCTGGGAGTCATGGACTCCACCCAGCACCACCAACCTGACCTAACCACCTATCTGAGCCTGCCAGCCTATAACCCATCTGG
GCCCTGATAGCTGGTGGCCAGCCCTGACCCCACCCCACCCTCCCTGGAACCTCTGATAGACACATCTGGCACCAGCTCGCAAAGTCAC
CGTGAGGGTCTTGTGTTTGCTGAGTCAAAATTCCTTGAAATCCAAGTCCTTAGAGACTCCCAGGCTTGGATTCAAAGCTCCTGACTTTCT
GTCTAGTGTATGTGCAGTGAGCCCCTTTTCCTCTAACTGAAAGAAGGAAAAAAAATGGAACCCAAAATATTCTACATAGTTTCCATGTC
ACAGCCAGGGCTGGGCAGTCTCCTGTTATTTCTTTTAAAATAAATATATCATTTAAATGCATAAATAAGCAAACCCTGCTCGGGAATGGG
AGGGAGAGTCTCTGGAGTCCAACCCTTCTCGGCCCTGGCTCTGCAGATAGTGCTAATCAAAGCCCTGACAGAGCCCTGCCCATTGCTGGG
CTTGGAGTGAGTCAGCCTAGTAGAGAGGCAGGGCAAGCCATCTCATAGCTGCTGAGTGGGAGAGAGAAAAGGGCTCATTGTCTATAAACT
CAGGTCATGGCTATTCTTATTAAAAGAAAAGGGGGGACTGGAAGGGCTAATTCACTCCCAACGAAGACAAGATCTGCTTTTTGCTTGTAC
TGGGTCTCTCTGGTTAGACCAGATCTGAGCCTGGGAGCTCTCTGGCTAACTAGGGAACCCACTGCTTAAGCCTCAATAAAGCTTGCCTTG
AGTGCTTCAAGTAGTGTGTTGGTTTTTTGTGTGTGCATTGTCTGAGTAGGTGTCATTCTATTCTGGGGGGTGGGGTGGGGCAGCACAGCA
AGGGGGAGGATTGGGAAGACAATAGCAGGCATGCTGGGGATGCGGTGGGCTCTATGGAGTAGTAGTTCATGTCATCTTATTATTCAGTAT
TTATAACTTGCAAAGAAATGAATATCAGAGAGTGAGAGGAACTTGTTTATTGCAGCTTATAATGGTTACAAATAAAGCAATAGCATCACA
AATTTCACAAATAAAGCATTTTTTTCACTGCATTCTAGTTGTGGTTTGTCCAAACTCATCAATGTATCTTATCATGTCTGGCTCTAGCTA
TCCCGCCCCTAACTCCGCCCATCCCGCCCCTAACTCCGCCCAGTTCCGCCCATTCTCCGCCCCATGGCTCTCACTACTTCTGGAATAGCT
CAGAGGCCGAGGCGGCCTCGGCCTCTGCATAAATAAAAAAAATTAGTCGAGGCTTTTTTGGAGGCCTAGGGACGTACCCAATTCGCCCTA
TAGTGAGTCGTATTACGCGCGCTCACTGGCCGTCGTTTTACAACGTCGTGACTGGGAAAACCCTGGCGTTACCCAACTTAATCGCCTTGC
AGCACATCCCCCTTTCGCCAGCTGGCGTAATAGCGAAGAGGCCCGCACCGATCGCCCTTCCCAACAGTTGCGCAGCCTGAATGGCGAATG
GG
```

What is claimed is:

1. A recombinant lentiviral vector (LV) comprising:
an expression cassette comprising a nucleic acid construct comprising:
a human β-globin locus control region (LCR) comprising an HS1 ENCODE core (EC1) sequence set forth in SEQ ID NO:1, and a combination of an HS2 core sequence (ecHS2) set forth in SEQ ID NO: 2, an HS3 core sequence (ecHS3) set forth in SEQ ID NO:3, and an HS4 core sequence (ecHS4) set forth in SEQ ID NO:4, or a combination of a full length HS2, a full length HS3 and a full length HS4; and
a heterologous gene to be expressed by the construct operably linked to the human β-globin LCR.

2. The vector of claim 1, wherein said vector comprises the LCR shown in SEQ ID NO:6.

3. The vector of claim 1, wherein said heterologous gene comprises a recombinant human beta globin gene encoding a beta globin polypeptide.

4. The vector of claim 3, wherein said human beta globin gene comprises a wild-type beta globin gene.

5. The vector of claim 3, wherein said human beta globin gene comprises an anti-sickling human beta globin gene encoding an anti-sickling beta globin polypeptide.

6. The vector of claim 5, wherein said anti-sickling human beta globin gene encoding an anti-sickling-beta globin polypeptide comprises one or more mutations selected from the group consisting of Gly16Asp, Glu22Ala and Thr87Gln.

7. The vector of claim 1, wherein:
said vector comprises a human Ankyrin insulator element; and/or
said vector comprises an insulator in the 3' LTR; and/or
said vector comprises a Ψ region vector genome packaging signal; and/or
said vector comprises a 5' LTR comprising a CMV enhancer/promoter; and/or
said vector comprises a Rev Responsive Element (RRE); and/or
said vector comprises a central polypurine tract; and/or
said vector comprises a post-translational regulatory element.

8. The vector of claim 1, wherein said vector comprises the nucleic acid sequence of SEQ ID NO:6.

9. The vector of claim 1, wherein:
said vector comprises the nucleotide sequence of pUV-AS3 set forth in SEQ ID NO: 13; or
said vector comprises the nucleotide sequence of pUV-HS1-AS3 as set forth in SEQ ID NO:15.

10. A host cell transduced with a vector of claim 1.

11. The vector of claim 7, wherein said insulator comprises FII/BEAD-A, a 77 bp insulator element, which contains the minimal CTCF binding site enhancer-blocking components of the chicken β-globin 5' DnaseI-hypersensitive site 4 (5' HS4).

12. The vector of claim 7, wherein said posttranscriptional regulatory element is modified Woodchuck Post-transcriptional Regulatory Element (WPRE).

* * * * *